US012788809B2

(12) United States Patent
Wei et al.

(10) Patent No.: US 12,788,809 B2
(45) Date of Patent: Nov. 10, 2026

(54) CIRCULAR RNA VACCINES AND METHODS OF USE THEREOF

(71) Applicant: Peking University, Beijing (CN)

(72) Inventors: Wensheng Wei, Beijing (CN); Liang Qu, Beijing (CN); Zongyi Yi, Beijing (CN)

(73) Assignee: Peking University, Beijing (CN)

(*) Notice: Subject to any disclaimer, the term of this patent is extended or adjusted under 35 U.S.C. 154(b) by 626 days.

(21) Appl. No.: 18/022,488

(22) PCT Filed: Aug. 20, 2021

(86) PCT No.: PCT/CN2021/113865
§ 371 (c)(1),
(2) Date: Feb. 21, 2023

(87) PCT Pub. No.: WO2022/037692
PCT Pub. Date: Feb. 24, 2022

(65) Prior Publication Data
US 2023/0346921 A1 Nov. 2, 2023

(30) Foreign Application Priority Data
Aug. 21, 2020 (WO) ................ PCT/CN2020/110486
Feb. 3, 2021 (WO) ................ PCT/CN2021/074998

(51) Int. Cl.
*C07H 21/02* (2006.01)
*A61K 39/215* (2006.01)
(Continued)

(52) U.S. Cl.
CPC ........ *A61K 39/215* (2013.01); *A61K 48/0066* (2013.01); *C12N 15/85* (2013.01);
(Continued)

(58) Field of Classification Search
None
See application file for complete search history.

(56) References Cited

U.S. PATENT DOCUMENTS

| | | | |
|---|---|---|---|
| 5,766,903 | A | 6/1998 | Sarnow et al. |
| 8,241,610 | B2 | 8/2012 | Agger et al. |

(Continued)

FOREIGN PATENT DOCUMENTS

| | | | |
|---|---|---|---|
| CN | 108165549 | A | 6/2018 |
| CN | 108251424 | A | 7/2018 |

(Continued)

OTHER PUBLICATIONS

Lu et al., "Circularing circular RNAs as biomarkers of cancer," Non-coding RNA Investig 3:8 (Year: 2019).*

(Continued)

*Primary Examiner* — M Franco G Salvoza
(74) *Attorney, Agent, or Firm* — MORRISON & FOERSTER LLP

(57) ABSTRACT

The present application provides circular RNAs (circRNAs) encoding therapeutic polypeptides (e.g., an antigenic polypeptide, a functional protein, a receptor protein, or a targeting protein). In some embodiments, the present application provides circRNA vaccines against a coronavirus such as SARS-COV-2. In some embodiments, the circRNA vaccine comprises a circRNA comprising a nucleic acid sequence encoding an antigenic polypeptide comprising a Spike(S) protein or a fragment thereof of a coronavirus. Also provided are methods of treating or preventing a disease or condition using the circRNAs or compositions thereof.

33 Claims, 18 Drawing Sheets

Specification includes a Sequence Listing.

(51) Int. Cl.
*A61K 48/00* (2006.01)
*C12N 15/85* (2006.01)
*A61K 39/00* (2006.01)

(52) U.S. Cl.
CPC ..................... *A61K 2039/53* (2013.01); *C12N 2770/20022* (2013.01); *C12N 2770/20034* (2013.01); *C12N 2830/42* (2013.01); *C12N 2840/203* (2013.01)

(56) References Cited

U.S. PATENT DOCUMENTS

| | | | | |
|---|---|---|---|---|
| 8,399,007 | B2 | 3/2013 | Taft et al. | |
| 8,506,966 | B2 | 8/2013 | Podda et al. | |
| 8,603,457 | B2 | 12/2013 | Yu | |
| 10,407,683 | B2 | 9/2019 | Nelson et al. | |
| 11,981,909 | B2 | 5/2024 | Anderson | |
| 2010/0137407 | A1 | 6/2010 | Abe et al. | |
| 2010/0303850 | A1 | 12/2010 | Lipford et al. | |
| 2011/0293700 | A1 | 12/2011 | Bratzler et al. | |
| 2011/0293701 | A1 | 12/2011 | Bratzler et al. | |
| 2011/0293723 | A1 | 12/2011 | Bratzler et al. | |
| 2012/0027806 | A1 | 2/2012 | Ilyinskii et al. | |
| 2012/0027813 | A1 | 2/2012 | Podda et al. | |
| 2018/0117126 | A1* | 5/2018 | Loibner | A61K 38/4813 |
| 2019/0022247 | A1 | 1/2019 | Ansell et al. | |
| 2020/0080106 | A1 | 3/2020 | Anderson et al. | |
| 2020/0121809 | A1 | 4/2020 | Hope et al. | |
| 2020/0163878 | A1 | 5/2020 | Baumhof et al. | |
| 2022/0135963 | A1 | 5/2022 | Wei et al. | |
| 2022/0177908 | A1 | 6/2022 | Sun et al. | |
| 2024/0247265 | A1 | 7/2024 | Wei | |
| 2025/0051816 | A1 | 2/2025 | Wei et al. | |
| 2025/0082746 | A1 | 3/2025 | Wei et al. | |
| 2025/0108134 | A1 | 4/2025 | Wei et al. | |

FOREIGN PATENT DOCUMENTS

| | | | | |
|---|---|---|---|---|
| CN | 109554368 | A | 4/2019 | |
| CN | 109666744 | B | 4/2019 | |
| CN | 111057764 | A | 4/2020 | |
| CN | 111217917 | A | 6/2020 | |
| CN | 111321143 | A | 6/2020 | |
| CN | 111378686 | A | 7/2020 | |
| CN | 112574997 | A | 3/2021 | |
| CN | 112725378 | A | 4/2021 | |
| WO | 2010138192 | A2 | 12/2010 | |
| WO | 2010138192 | A3 | 6/2011 | |
| WO | 2011068810 | A1 | 6/2011 | |
| WO | 2011150240 | A1 | 12/2011 | |
| WO | 2011150249 | A1 | 12/2011 | |
| WO | 2011150258 | A1 | 12/2011 | |
| WO | 2011150264 | A2 | 12/2011 | |
| WO | 2012170930 | A1 | 12/2012 | |
| WO | 2011150264 | A3 | 4/2013 | |
| WO | WO-2016170176 | A1 * | 10/2016 | A61P 35/00 |
| WO | WO-2016187583 | A1 * | 11/2016 | A41C 3/0064 |
| WO | 2016197121 | A1 | 12/2016 | |
| WO | 2017222911 | A1 | 12/2017 | |
| WO | 2018237372 | A1 | 12/2018 | |
| WO | 2019008001 | A1 | 1/2019 | |
| WO | WO-2019077001 | A1 * | 4/2019 | C12N 15/67 |
| WO | 2019/094486 | A1 | 5/2019 | |
| WO | 2019118919 | A1 | 6/2019 | |
| WO | 2019189722 | A1 | 10/2019 | |
| WO | 2019223293 | A1 | 11/2019 | |
| WO | WO-2019236673 | A1 * | 12/2019 | C12N 15/85 |
| WO | 2020181013 | A1 | 9/2020 | |
| WO | 2020237227 | A1 | 11/2020 | |
| WO | WO-2020252436 | A1 * | 12/2020 | A61K 40/4211 |
| WO | 2021008447 | A1 | 1/2021 | |
| WO | 2021030701 | A1 | 2/2021 | |
| WO | WO-2021147025 | A1 * | 7/2021 | C07K 14/005 |
| WO | 2021156267 | A1 | 8/2021 | |
| WO | 2021196268 | A1 | 10/2021 | |
| WO | 2021236855 | A1 | 11/2021 | |
| WO | 2022088953 | A1 | 5/2022 | |
| WO | 2022105825 | A1 | 5/2022 | |
| WO | 2022150974 | A1 | 7/2022 | |
| WO | 2022261490 | A2 | 12/2022 | |
| WO | 2023020574 | A1 | 2/2023 | |
| WO | 2023024500 | A1 | 3/2023 | |
| WO | 2023115732 | A1 | 6/2023 | |
| WO | 2023133684 | A1 | 7/2023 | |
| WO | 2023134611 | A1 | 7/2023 | |
| WO | 2023143541 | A1 | 8/2023 | |

OTHER PUBLICATIONS

Accession ID: EPI-ISL-402124. (2019). Abstract, 2 pages.
Bai, Y. et al. (Jan. 12, 2023). "Research Progress on Circular RNA Vaccines," Front. Immunol. 13:1091797, 12 pages.
Qu, L. et al. (May 12, 2022). "Circular RNA Vaccines Against SARS-CoV-2 and Emerging Variants," Cell. 185:1728-1744, 34 pages.
Altschul, S.F. et al. (1990). "Basic Local Alignment Search Tool," J. Mol. Biol. 215:403-410.
Amanat, F. et al. (Apr. 14, 2020). "SARS-CoV-2 Vaccines: Status Report," Immunity 52:583-589.
Baird, S.D. et al. (Oct. 2006). "Searching for IRES," RNA 12(10):1755-1785.
Barnes, C.O. et al. (Dec. 24-31, 2020, e-pub. Oct. 12, 2020). "SARS-CoV-2 Neutralizing Antibody Structures Inform Therapeutic Strategies," Nature 588:682-687, 22 pages.
Bringmann, A. et al. (2010). "RNA Vaccines in Cancer Treatment," Journal of Biomedicine and Biotechnology 2010 (623687):1-13.
Carrillo, H. et al. (Oct. 1988). "The Multiple Sequence Alignment Problem in Biology," SIAM J Applied Math 48(5):1073-1082.
Chen, X. et al. (Oct. 15, 2013). "Fusion Protein Linkers: Property, Design and Functionality," Adv. Drug Deli Rev. 65(10):1357-1369, 32 pages.
ClinicalTrials.gov (Apr. 6, 2020). NCT04335136—Recombinant Human Angiotensin-converting Enzyme 2 (rhACE2) as a Treatment for Patients With COVID-19 (APN01-COVID-19), 9 pages.
Devereux, J. et al. (1984). "A Comprehensive Set of Sequence Analysis Programs for the VAX," Nucleic Acids Research 12(1):387-395.
Edgar, R.C. (Aug. 19, 2004). "MUSCLE: A Multiple Sequence Alignment Method With Reduced Time and Space Complexity," BMC Bioinformatics 5:113, pp. 1-19.
Edgar, R.C. (Mar. 19, 2004). "MUSCLE: Multiple Sequence Alignment With High Accuracy and High Throughput," Nucleic Acids Research 32(5):1792-1797.
Forster, P. et al. (Apr. 28, 2020). "Phylogenetic Network Analysis of SARS-CoV-2 Genomes," PNAS 117(17) 9241-9243.
Genbank Accession Number (Jul. 21, 2004). AAT74874—Spike Protein [SARS Coronavirus HHS-2004], 3 pages.
Glasgow, A et al. (Nov. 10, 2020). "Engineered ACE2 Receptor Traps Potently Neutralize SARS-CoV-2," PNAS 117(45):28046-28055.
Haschke, M. et al. (Sep. 2013, e-pub. May 17, 2013). "Pharmacokinetics and Pharmacodynamics of Recombinant Human Angiotensin-Converting Enzyme 2 in Healthy Human Subjects," Clin. Pharmacokinet. 52(9):783-792.
Higuchi, Y. et al. (Dec. 14, 2020). "High Affinity Modified ACE2 Receptors Protect from SARSSARS-CoVCoV-2 Infection in Hamsters," bioRxiv, 37 pages.
Hofacker, I.L. (2003). "Vienna RNA Secondary Structure Server," Nucleic Acids Res. 31(13):3429-3431.
Ickenstein, L.M. et al. (Nov. 2019, Sep. 17, 2019). "Lipid-Based Nanoparticle Formulations for Small Molecules and RNA Drugs," Expert Opin. Drug Deliv. 77 pages.
International Search Report and Written Opinion, mailed Jun. 27, 2022, for PCT Application No. PCT/CN2022/082225, filed Mar. 22, 2022, 11 pages.
International Search Report and Written Opinion, mailed Nov. 25, 2021, for PCT Application No. PCT/CN2021/113865, filed Aug. 20, 2021, 14 pages.

(56) References Cited

OTHER PUBLICATIONS

International Search Report and Written Opinion, mailed Oct. 12, 2022, for PCT Application No. PCT/CN2022/071347, Jan. 11, 2022, 15 pages.
International Search Report and Written Opinion, mailed Sep. 27, 2022, for PCT Application No. PCT/CN2022/082224, filed Mar. 22, 2022, 11 pages.
Ke, S. et al. (2017). "m6A mRNA Modifications are Deposited in Nascent Pre-mRNA and are Not Required for Splicing but do Specify Cytoplasmic Turnover," Genes & Dev. 31:990-1006.
Meyers, E. et al. (1988). "Optimal Alignments in Linear Space," Comput. Appl. Biosci., 4(1):11-17.
NCBI Reference (Aug. 8, 2020). YP 009047204.1—Spike Protein [Middle East Respiratory Syndrome-Related Coronavirus], 3 pages.
NCBI Reference (Jul. 18, 2020). YP 009724390—Surface Glycoprotein [Severe Acute Respiratory Syndrome Coronavirus 2], 3 pages.
Petkovic, S. et al. (Feb. 27, 2015, e-pub. Feb. 6, 2015). "RNA Circularization Strategies in vivo and in vitro," Nucleic Acids Res. 43(4):2454-2465.
Qu, L. et al. (Mar. 16, 2021). "Circular RNA Vaccines Against SARS-CoV-2 and Emerging Variants," bioRxiv 56 pages.
Qu, L. et al. (Sep. 30, 2019, e-pub. Jul. 15, 2019). "Programmable RNA Editing by Recruiting Endogenous ADAR Using Engineered RNAs," Nature Biotechnology 37:1059-1069, 16 pages.
Remington's Pharmaceutical Sciences. (1980). 16th edition, Osol, A. Ed, pp. 1-2, (Table of Contents Only).
Semple, S.C. et al. (Feb. 2010, e-pub. Jan. 17, 2010). "Rational Design of Cationic Lipids for siRNA Delivery," Nat. Biotechnol. 28(2):172-176.
Sliepen, K. et al. (Mar. 20, 2015). "Immunosilencing a Highly Immunogenic Protein Trimerization Domain," The Journal of Biol. Chem. 290(12):7436-7442.
Vazquez-Lombardi, R. et al. (Oct. 2015). "Challenges and Opportunities for Non-Antibody Scaffold Drugs," Drug Discovery Today 20(10):1271-1283.
Vigneron, N. et al. (Jul. 15, 2013). "Database of T Cell-Defined Human Tumor Antigens: The 2013 Update," Cancer Immunity 13(15):1-6.
Wesselhoeft, R.A. et al. (2019, e-pub. May 2, 2019). "RNA Circularization Diminishes Immunogenicity and Can Extend Translation Duration In Vivo," Mol. Cell 74(3):508-520, 18 pages.
Yang, X. et al. (2009; e-published on Dec. 19, 2008). "An Introduction to Epitope Prediction Methods and Software" Rev. Med. Virol. 19(2):77-96.
Zhang, M.L. et al. (Mar. 31, 2018, e-pub. Jan. 18, 2018). "A Novel Protein Encoded by the Circular Form of the SHPRH Gene Suppresses Glioma Tumorigenesis," Oncogene 37(13):1805-1814, 10 pages.
Zuker, M. (2003). "Mfold Web Server for Nucleic Acid Folding and Hybridization Prediction," Nucleic Acids Res. 31(13):3406-3415.
Bangaru, S. et al. (Nov. 27, 2020). "Structural Analysis of Full-Length SARS-CoV-2 Spike Protein from an Advanced Vaccine Candidate," Science 370:1089-1094.
Boutros, C. et al. (Aug. 2016). "Safety Profiles of Anti-CTLA-4 and Anti-PD-1 Antibodies Alone and in Combination," Nat. Rev. Clin. Oncol. 13:473-486.
Bouwman, K.M. et al. (Feb. 8, 2021). "Multimerization- and Glycosylation-Dependent Receptor Binding of SARS-CoV-2 Spike Proteins," PLoS Pathog. 17:e1009282, 20 pages.
Cao, Y. et al. (Jul. 9, 2020). "Potent Neutralizing Antibodies Against SARS-CoV-2 Identified by High-Throughput Single-Cell Sequencing of Convalescent Patients' B Cells," Cell 182:73-84, 29 pages.
Cele, S. et al. (May 2021). "Escape of SARS-CoV-2 501Y.V2 from Neutralization by Convalescent Plasma," Nature 593(7857):142-146, 24 pages.
Chan, K. K. et al. (Sep. 4, 2020). "Engineering Human ACE2 to Optimize Binding to the Spike Protein of SARS Coronavirus 2," Science 369:1261-1265.
Chen, C.Y. et al. (Apr. 21, 1995). "Initiation of Protein Synthesis by the Eukaryotic Translational Apparatus on Circular RNAs," Science 268:415-417.
Chen, L.L. (Apr. 2016). "The Biogenesis and Emerging Roles of Circular RNAs," Nat. Rev. Mol. Cell Biol. 17(4):205-211, 7 pages.
Chen, R. E. et al. (Apr. 2021). "Resistance of SARS-CoV-2 Variants to Neutralization by Monoclonal and Serum-Derived Polyclonal Antibodies," Nat. Med. 27(4):717-726, 35 pages.
Chen, Y.G. et al. (Oct. 3, 2019). "N6-Methyladenosine Modification Controls Circular RNA Immunity," Mol. Cell 76(1):96-109, 42 pages.
Corbett, K.S. et al. (Jul. 28, 2020). "Evaluation of the mRNA-1273 Vaccine Against SARS-CoV-2 in Nonhuman Primates," N. Engl. J. Med. 383:1544-1555.
Corbett, K.S. et al. (Oct. 2020). "SARS-CoV-2 mRNA Vaccine Design Enabled by Prototype Pathogen Preparedness," Nature 586(7830):567-571, 26 pages.
Dai, L. et al. (Aug. 6, 2020). "A Universal Design of Betacoronavirus Vaccines against COVID-19, MERS, and SARS," Cell 182:722-733, 24 pages.
Davies, N. G. et al. (2021). "Increased Hazard of Death in Community-Tested Cases of SARS-CoV-2 Variant of Concern 202012/01," medRxiv, 49 pages.
Du, S. et al. (2020). "Structurally Resolved SARS-CoV-2 Antibody Shows High Efficacy in Severely Infected Hamsters and Provides a Potent Cocktail Pairing Strategy," Cell 183:1013-1023, 26 pages.
Durymanov, M. et al. (Aug. 21, 2018). "Non-Viral Delivery of Nucleic Acids: Insight into Mechanisms of Overcoming Intracellular Barriers," Front Pharmacol. 9(971):1-15.
Enuka, Y. et al. (2016, e-pub. Dec. 10, 2015). "Circular RNAs Are Long-Lived and Display Only Minimal Early Alterations in Response to a Growth Factor," Nucleic Acids Res. 44(3):1370-1383.
Fenton, O.S. et al. (Apr. 20, 2016). "Bioinspired Alkenyl Amino Alcohol Ionizable Lipid Materials for Highly Potent In Vivo mRNA Delivery," Adv. Mater. 28(15):2939-2943, 11 pages.
Fischer, J. W. et al. (Apr. 2017). "CircRNAs: A Regulator of Cellular Stress," Crit. Rev. Biochem. Mol. Biol. 52(2):220-233, 27 pages.
Focosi, D. et al. (2021). "Neutralising Antibody Escape of SARS-CoV-2 Spike Protein: Risk Assessment for Antibody-Based Covid-19 Therapeutics and Vaccines," Rev. Med. Virol. 31:e2231, 21 pages.
Ford, E. et al. (Apr. 1994). "Synthesis of Circular RNA in bacteria and Yeast Using RNA Cyclase Ribozymes Derived from a Group I Intron of Phage T4," Proc. Natl Acad. Sci. 91:3117-3121.
Gao, Q. et al. (Jul. 3, 2020, e-pub. May 6, 2020). "Development of an Inactivated Vaccine Candidate for SARS-CoV-2," Science 369(6499):77-81, 5 pages.
Gao, X. et al. (Mar. 2021). "Circular RNA-Encoded Oncogenic E-Cadherin Variant Promotes Glioblastoma Tumorigenicity Through Activation of EGFR-STAT3 Signalling," Nat. Cell Biol. 23:278-291.
Garcia-Beltran, W.F. et al. (Apr. 29, 2021). "Multiple SARS-CoV-2 Variants Escape Neutralization by Vaccine-Induced Humoral Immunity," Cell 184:2372-2383.
Gu, H. et al. (Sep. 25, 2020). "Adaptation of SARS-CoV-2 in BALB/c Mice for Testing Vaccine Efficacy," Science 369:1603-1607.
Gupta, R.K. (Jun. 2021). "Will SARS-CoV-2 Variants of Concern Affect the Promise of Vaccines?" Nat. Rev. Immunol. 21:340-341.
Hacisuleyman, E. et al. (Apr. 21, 2021). "Vaccine Breakthrough Infections with SARS-CoV-2 Variants," N. Engl. J. Med., 7 pages.
He, X. et al. (2020, e-pub. May 28, 2020). "Immune Checkpoint Signaling and Cancer Immunotherapy," Cell Res. 30:660-669.
Hoffmann, M. et al. (Apr. 16, 2020). "SARS-CoV-2 Cell Entry Depends on ACE2 and TMPRSS2 and Is Blocked by a Clinically Proven Protease Inhibitor," Cell 181(2):271-280.
Hoffmann, M. et al. (Apr. 29, 2021). "SARS-CoV-2 Variants B.1. 351 and P.1 Escape from Neutralizing Antibodies," Cell 184:2384-2393.
Hsieh, C. L. et al. (2020, e-pub. Jul. 23, 2020). "Structure-Based Design of Prefusion-Stabilized SARS-CoV-2 Spikes," Science 369:1501-1505, 9 pages.

(56) References Cited

OTHER PUBLICATIONS

Huang, Q. et al. (2021). "A Single-Dose mRNA Vaccine Provides a Long-Term Protection for hACE2 Transgenic Mice From SARS-CoV-2," Nat. Commun. 12: 776, 10 pages.
International Preliminary Report on Patentability, issued Feb. 16, 2023, for PCT Application No. PCT/CN2021/113865, filed Aug. 20, 2021, 8 pages.
International Preliminary Report on Patentability, issued Feb. 27, 2024, for PCT Application No. PCT/CN2022/082225, filed Mar. 22, 2022, 4 pages.
International Preliminary Report on Patentability, issued Jul. 30, 2024, for PCT Application No. PCT/CN2023/073619, Jan. 28, 2023, 6 pages.
International Preliminary Report on Patentability, issued Jun. 20, 2024, for PCT Application No. PCT/CN2022/071347, Jan. 11, 2022, 7 pages.
International Preliminary Report on Patentability, issued Jun. 20, 2024, for PCT Application No. PCT/CN2022/082224, filed Mar. 22, 2022, 6 pages.
International Preliminary Report on Patentability, issued Jun. 20, 2024, for PCT Application No. PCT/CN2023/071196, filed Jan. 9, 2023, 6 pages.
International Search Report and Written Opinion, mailed Mar. 31, 2023, for PCT Application No. PCT/CN2023/071196, filed Jan. 9, 2023, 13 pages.
International Search Report and Written Opinion, mailed May 17, 2023, for PCT Application No. PCT/CN2023/073619, Jan. 28, 2023, 14 pages.
Jackson, N.A.C. et al. (2020). "The Promise of mRNA Vaccines: A Biotech and Industrial Perspective," NPJ Vaccines 5:11, 6 pages.
Kim, D. et al. (May 14, 2020). "The Architecture of SARS-CoV-2 Transcriptome," Cell 181:914-921.
Koenig, P.A. et al. (Feb. 12, 2021). "Structure-Guided Multivalent Nanobodies Block SARS-CoV-2 Infection and Suppress Mutational Escape," Science 371:eabe6230, 16 pages.
Kou, Y. et al. (2017). "Tissue Plasminogen Activator (tPA) Signal Sequence Enhances Immunogenicity of MVA-Based Vaccine Against Tuberculosis," Immunol. Lett. 190:51-57.
Krammer, F. (Oct. 22, 2020, e-pub. Sep. 23, 2020). "SARS-CoV-2 Vaccines in Development," Nature 586:516-527.
Kristensen, L.S. et al. (Nov. 2019, e-pub. Aug. 8, 2019). "The Biogenesis, Biology and Characterization of Circular RNAs," Nat. Rev. Genet. 20:675-691.
Laczkó, D. et al. (Oct. 13, 2020). "Single Immunization with Nucleoside-Modified mRNA Vaccines Elicits Strong Cellular and Humoral Immune Responses Against SARS-CoV-2 in Mice," Immunity 53:724-732.
Lauring, A. S. et al. (Feb. 9, 2021). "Genetic Variants of SARS-CoV-2-What Do They Mean?" JAMA 325(6):529-531.
Legnini, I. et al. (Apr. 6, 2017). "Circ-ZNF609 Is a Circular RNA that Can Be Translated and Functions in Myogenesis," Mol Cell 66:22-37.
Li, Q. et al. (Apr. 29, 2021). "SARS-CoV-2 501Y.V2 Variants Lack Higher Infectivity but do Have Immune Escape," Cell 184:2362-2371.
Linsky, T.W. et al. (Dec. 4, 2020). "De Novo Design of Potent and Resilient hACE2 Decoys to Neutralize SARS-CoV-2," Science 370:1208-1214.
Madhi, S.A. et al. (Mar. 16, 2021). "Efficacy of the ChAdOx1 nCoV-19 Covid-19 Vaccine Against the B.1.351 Variant," N. Engl. J. Med., 14 pages.
Memczak, S. et al. (Mar. 21, 2013, e-pub. Feb. 27, 2013). "Circular RNAs Are a Large Class of Animal RNAs With Regulatory Potency," Nature 495(7441):333-338, 10 pages.
Montagutelli, X. et al. (2021). "The B1.351 and P.1 Variants Extend SARS-CoV-2 Host Range to Mice," bioRxiv, 16 pages.
Muik, A. et al. (Mar. 12, 2021). "Neutralization of SARS-CoV-2 Lineage B.1.1.7 Pseudovirus by BNT162b2 Vaccine-Elicited Human Sera," Science 371:1152-1153.
Mukhopadhyay, S. et al. (Mar. 2021). "The Metabolic Landscape of RAS-Driven Cancers from Biology to Therapy," Nat. Cancer 2(3):271-283, 29 pages.
Mullard, A. (Jun. 6, 2020). "COVID-19 Vaccine Development Pipeline Gears Up," Lancet 395:1751-1752.
Ou, X. et al. (2020). "Characterization of Spike Glycoprotein of SARS-CoV-2 on Virus Entry and its Immune Cross-Reactivity with SARS-CoV," Nat. Commun. 11:1620, 12 pages.
Papanikolopoulou, K. et al. (2008). "Creation of Hybrid Nanorods from Sequences of Natural Trimeric Fibrous Proteins Using the Fibritin Trimerization Motif," in Methods Mol. Biol. 474:15-33, 270 pages.
Pardi, N. et al. (Apr. 2018). "mRNA Vaccines—A New Era in Vaccinology," Nat. Rev. Drug Discov. 17(4):261-279, 43 pages.
Pardi, N. et al. (Mar. 9, 2017). "Zika Virus Protection by a Single Low-Dose Nucleoside-Modified mRNA Vaccination," Nature 543(7644):248-251, 21 pages.
Pinto, D. et al. (Jul. 9, 2020, e-pub. May 18, 2020). "Cross-Neutralization of SARS-CoV-2 by a Human Monoclonal SARS-CoV Antibody," Nature 583:290-295, 22 pages.
Planas, D. et al. (May 2021). "Sensitivity of Infectious SARS-CoV-2 B.1.1.7 and B.1.351 Variants to Neutralizing Antibodies," Nat. Med. 27:917-924.
Puttaraju, M. et al. (1992). "Group I Permuted Intron-Exon (PIE) Sequences Self-Splice to Produce Circular Exons," Nucleic Acids Res. 20(20):5357-5364.
Richner, J.M. et al. (Mar. 9, 2017). "Modified mRNA Vaccines Protect Against Zika Virus Infection," Cell 168:1114-1125, 1 page.
Sabapathy, K. et al. (Jan. 2018). "Therapeutic Targeting of p53: All Mutants are Equal, but Some Mutants are More Equal Than Others," Nat. Rev. Clin. Oncol. 15:13-30.
Sahin, U. et al. (Oct. 22, 2020, e-pub. Sep. 30, 2020). "COVID-19 Vaccine BNT162b1 Elicits Human Antibody and TH1T Cell Responses," Nature 586:594-599.
Sanchez-Felipe, L. et al. (Feb. 11, 2021, e-pub. Dec. 1, 2020). "A Single-Dose Live-Attenuated YF17D-Vectored SARS-CoV-2 Vaccine Candidate," Nature 590:320-325.
Schoof, M. et al. (Dec. 18, 2020). "An Ultrapotent Synthetic Nanobody Neutralizes SARS-CoV-2 by Stabilizing Inactive Spike," Science 370:1473-1479.
Sette, A. et al. (Feb. 18, 2021). "Adaptive Immunity to SARS-CoV-2 and COVID-19," Cell 184:861-880.
Shang, J. et al. (May 26, 2020, e-pub. May 6, 2020). "Cell Entry Mechanisms of SARS-CoV-2," Proc. Natl. Acad. Sci. USA 117:11727-11734.
Tai, W. et al. (2020, e-pub. Aug. 2020). "A Novel Receptor-Binding Domain (RBD)-Based mRNA Vaccine Against SARS-CoV-2," Cell Res. 30:932-935.
Tan, C.W. et al. (Sep. 2020). "A SARS-CoV-2 Surrogate Virus Neutralization Test Based on Antibody-Mediated Blockage of ACE2-Spike Protein-Protein Interaction," Nat. Biotechnol. 38:1073-1078.
V'Kovski, P. et al. (Mar. 2021). "Coronavirus Biology and Replication: Implications for SARS-CoV-2," Nat. Rev. Microbiol. 19:155-170.
Van Doremalen, N. et al. (Oct. 2020). "ChAdOx1 nCoV-19 Vaccine Prevents SARS-CoV-2 Pneumonia in Rhesus Macaques," Nature 586(7830):578-582, 21 pages.
Vicens, Q. et al. (2008). "Toward Predicting Self-Splicing and Protein-Facilitated Splicing of Group I Introns," RNA 14:2013-2029.
Vogel, A.B. et al. (Apr. 8, 2021, e-pub. Feb. 1, 2021). "BNT162b Vaccines Protect Rhesus Macaques from SARS-CoV-2," Nature 592:283-289, 35 pages.
Walls, A. C. et al. (Apr. 16, 2020). "Structure, Function, and Antigenicity of the SARS-CoV-2 Spike Glycoprotein," Cell 180(2):281-292, 38 pages.
Wang, G. L. et al. (2021). "Susceptibility of Circulating SARS-CoV-2 Variants to Neutralization," N. Engl. J. Med., 3 pages.
Wang, P. et al. (May 6, 2021, e-pub. Mar. 8, 2021). "Antibody Resistance of SARS-CoV-2 Variants B.1.351 and B.1.1.7," Nature 593:130-135, 18 pages.

(56) References Cited

OTHER PUBLICATIONS

Wang, Z. et al. (Apr. 2021). "mRNA Vaccine-Elicited Antibodies to SARS-CoV-2 and Circulating Variants," Nature 592(7855):616-622, 30 pages.
Wesselhoeft, R.A. et al. (2018, e-pub. Jul. 6, 2018). "Engineering Circular RNA for Potent and Stable Translation in Eukaryotic Cells," Nat. Commun. 9:2629, 10 pages.
Wibmer, C.K. et al. (Apr. 2021). "SARS-CoV-2 501Y.V2 Escapes Neutralization by South African COVID-19 Donor Plasma," Nat. Med. 27:622-625.
Wrapp, D. et al. (Mar. 13, 2020, e-pub. Feb. 19, 2020). "Cryo-EM Structure of the 2019-nCoV Spiked in the Prefusion Conformation," Science 367:1260-1263.
Wu, F. et al. (Mar. 12, 2020, e-pub. Feb. 3, 2020). "A New Coronavirus Associated with Human Respiratory Disease in China," Nature 579:265-269.
Xiang, Y. et al. (Dec. 18, 2020). "Versatile and Multivalent Nanobodies Efficiently Neutralize SARS-CoV-2," Science 370:1479-1484.
Yan, R. et al. (Mar. 27, 2020). "Structural Basis for the Recognition of SARS-CoV-2 by Full-Length Human ACE2," Science 367:1444-1448.
Yang, J. et al. (Oct. 22, 2020, e-pub. Jul. 29, 2020). "A Vaccine Targeting the RBD of the S Protein of SARS-CoV-2 Induces Protective Immunity," Nature 586:572-577, 21 pages.
Yang, Y. et al. (2017, e-pub. Mar. 10, 2017). "Extensive Translation of Circular RNAs Driven by N6-Methyladenosine," Cell Res 27:626-641.
Yu, J. et al. (Aug. 14, 2020). "DNA Vaccine Protection Against SARS-CoV-2 in Rhesus Macaques," Science 369:806-811.
Zhang, M. et al. (2018). "A Peptide Encoded by Circular Form of LINC-PINT Suppresses Oncogenic Transcriptional Elongation in Glioblastoma," Nat. Commun. 9:4475, 17 pages.
Zhang, N. N. et al. (Sep. 3, 2020). "A Thermostable mRNA Vaccine Against COVID-19," Cell 182:1271-1283, 30 pages.
Zhang, X.O. et al. (Sep. 25, 2014). "Complementary Sequence-Mediated Exon Circularization," Cell 159:134-147.
Zhou, P. et al. (Mar. 12, 2020, e-pub. Feb. 3, 2020). "A Pneumonia Outbreak Associated With a New Coronavirus of Probable Bat Origin," Nature, 579:270-273, 20 pages.
Zhu, F.C. et al. (Jun. 13, 2020, e-pub. May 22, 2020). "Safety, Tolerability, and Immunogenicity of a Recombinant Adenovirus Type-5 Vectored COVID-19 vaccine: A Dose-Escalation, Open-Label, Non-Randomised, First-In-Human Trial," Lancet 395:1845-1854.
Chen, H. et al. (2020, e-pub. Mar. 30, 2020). "Preferential Production of RNA Rings T4 RNA Ligase 2 Without Any Splint Through Rational Design of Precursor Strand," Nucleic Acids Research 48(9):e54, 12 pages.
Cheng, K. et al. (Jan. 1, 2019). "RNA Ligation of Very Small Pseudo Nick Structures by T4 RNA Ligase 2, Leading to Efficient Production of Versatile RNA Rings," RSC Advances 9(15):8620-8627.
Maloney, A. et al. (Jan. 2, 2024, e-pub. Dec. 11, 2023). "Validating the EMCV IRES Secondary Structure with Structure-Function Analysis," Biochemistry 63(1):107-115, 18 pages.
Sean, P. et al. (2009, e-pub. May 14, 2009). "Altered Interactions Between Stem-Loop IV Withing the 5' Noncoding Region of Coxsackievirus RNA and Poly(rC) Binding Protein 2: Effects on IRES-Mediated Translation and Viral Infectivity," Virology 389(1-2):45-58.
Costello, A. et al. (2019). "Continuous Translation of Circularized mRNA Improves Recombinant Protein Titer," Metabolic Engineering 52:284-292.

* cited by examiner

CIRCULAR RNA VACCINES AND METHODS OF USE THEREOF

CROSS REFERENCE TO RELATED APPLICATIONS

This application is a national stage application under 35 U.S.C. § 371 of International Application No. PCT/CN2021/113865, filed internationally on Aug. 20, 2021, which claims priority benefit of International Patent Application No. PCT/CN2021/074998 filed Feb. 3, 2021, and International Patent Application No. PCT/CN2020/110486 filed Aug. 21, 2020, the contents of which are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165392000200SEQLIST.TXT, date recorded: Feb. 10, 2023, size: 249,927 bytes).

FIELD

The present application relates to circular RNA (circRNA) encoding a therapeutic polypeptide, such as circRNA vaccines against a coronavirus, and methods of use thereof.

BACKGROUND

COVID-19 is a serious worldwide public health emergency caused by a coronavirus infection with the SARS-Cov-2 virus. Currently, no effective drugs or vaccines are available. Thus, there is an urgent need for the development of safe and effective vaccines for coronavirus infections, such as SARS-COV-2. Vaccines typically fall into two broad categories: vaccines comprising a complete virus (live attenuated vaccines or inactivated vaccines), or vaccines comprising a part of a virus, which can be recombinant protein or DNA or RNA-based vaccines. Vaccines based on a complete virus are subject to several disadvantages, including the need to handle large amounts of an infectious virus during vaccine production for an inactivated vaccine, and the need for extensive safety testing of live attenuated vaccines. Vaccines based on recombinant protein are also limited by global production capacity of recombinant proteins, while DNA-based vaccines suffer from difficulties related to safe delivery of DNA and effectiveness to generate immune responses (Amanat, F. & Krammer, F. SARS-COV-2 Vaccines: Status Report. (2020) Immunity 52, 583-589).

The development of RNA-based vaccines provides a potential pathway to an immunogenic vaccine without requiring handling of infectious virus during production. RNA molecules are considered to be significantly safer than DNA vaccines, as RNAs are more easily degraded. They are cleared quickly out of the organism and cannot integrate into the genome and influence the cell's gene expression in an uncontrollable manner. It is also less likely for RNA vaccines to cause severe side effects like the generation of autoimmune disease or anti-DNA antibodies (Bringmann A. et al., Journal of Biomedicine and Biotechnology (2010), vol. 2010, article ID623687). Transfection with RNA requires only insertion into the cell's cytoplasm, which is easier to achieve than into the nucleus.

BRIEF SUMMARY

The present application provides circRNAs encoding polypeptides, such as therapeutic polypeptides, and methods of treatment using the circRNAs. In some embodiments, the present application provides novel vaccines against a coronavirus (e.g., SARS-COV-2) based on circular RNAs (circRNA). Optionally the SARS-COV-2 infection is caused by a SARS-COV-2 variant (e.g., B.1.351 or B.1.617.2 variant). Also provided are methods of producing the circRNA vaccines and methods of treating or preventing a coronavirus infection using the circRNA vaccines.

One aspect of the present application provides a circular RNA (circRNA) comprising a nucleic acid sequence encoding a therapeutic polypeptide, wherein therapeutic polypeptide is selected from the group consisting of an antigenic polypeptide, a functional protein, a receptor protein, and a targeting protein. In some embodiments, the circRNA further comprises a Kozak sequence operably linked to the nucleic acid sequence encoding therapeutic polypeptide.

In some embodiments according to any one of the circRNAs described above, the circRNA further comprises an in-frame 2A peptide coding sequence operably linked to the 3' end of the nucleic acid sequence encoding therapeutic polypeptide.

In some embodiments according to any one of the circRNAs described above, the circRNA further comprises an internal ribosomal entry site (IRES) sequence operably linked to the nucleic acid sequence encoding therapeutic polypeptide. In some embodiments, the IRES sequence is a CVB3 virus, EV71 virus, EMCV virus, PV virus, or CSFV virus IRES sequence. In some embodiments, the circRNA comprises a nucleic acid sequence comprising from the 5' end to the 3' end: the IRES sequence, the Kozak sequence, and the nucleic acid sequence encoding therapeutic polypeptide. In some embodiments according to any one of the circRNAs comprising an IRES sequence described above, the circRNA further comprises a polyAC or polyA sequence disposed at the 5' end of the IRES.

In some embodiments according to any one of the circRNAs described above, the circRNA further comprises an m6A modification motif sequence operably linked to the nucleic acid sequence encoding therapeutic polypeptide. In some embodiments, the circRNA comprises a nucleic acid sequence comprising from the 5' to the 3' end: the m6A modification motif sequence, the Kozak sequence, and the nucleic acid sequence encoding therapeutic polypeptide.

In some embodiments according to any one of the circRNAs described above, the nucleic acid further encodes a signal peptide (SP) fused to the N-terminus of therapeutic polypeptide. In some embodiments, the SP is an SP of a human tissue plasminogen activator (tPA) or an SP of a human IgE immunoglobulin (e.g., the sequence shown in SEQ ID NO: 16). In some embodiments, the SP is an SP of a human IgE immunoglobulin, (e.g., the sequence shown in SEQ ID NO: 17).

In some embodiments according to any one of the circRNAs described above, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence comprises the nucleic acid sequence of SEQ ID NO: 21, and the 5' exon sequence comprises the nucleic acid sequence of SEQ ID NO: 22.

In some embodiments according to any one of the circRNAs described above, the circRNA is circularized in vitro.

In some embodiments according to any one of the circRNAs described above, therapeutic polypeptide is for treating or preventing an infection. In some embodiments, the infection is an infection by a virus, such as a coronavirus. In some embodiments, the coronavirus is selected from the group consisting of SARS-COV, MERS-COV, and SARS-COV-2. In some embodiments, the coronavirus is SARS-COV-2.

One aspect of the present application provides a circRNA comprising a nucleic acid sequence encoding a therapeutic polypeptide, wherein therapeutic polypeptide is an antigenic polypeptide. In some embodiments, the circRNA is according to any one of the circRNAs described above.

One aspect of the present application provides a circRNA comprising a nucleic acid sequence encoding a therapeutic polypeptide, wherein therapeutic polypeptide is a receptor protein. In some embodiments, the circRNA is according to any one of the circRNAs described above. In some embodiments, therapeutic polypeptide is a soluble receptor comprising an extracellular domain of a naturally occurring receptor. In some embodiments, the receptor is an ACE2 receptor. In some embodiments, the receptor is a high-affinity mutant ACE2 receptor.

In some embodiments, there is provided a composition comprising a plurality of circRNAs according to any one of the circRNAs encoding a receptor protein described above, wherein the receptor proteins corresponding to the plurality of circRNAs are different with respect to each other. In some embodiments, the plurality of circRNAs target a plurality of strains of a coronavirus, e.g., SARS-COV-2.

One aspect of the present application provides a circRNA comprising a nucleic acid sequence encoding a therapeutic polypeptide, wherein therapeutic polypeptide is a targeting protein. In some embodiments, the circRNA is according to any one of the circRNAs described above. In some embodiments, the targeting protein is an antibody. In some embodiments, the antibody is a neutralizing antibody, e.g., a neutralizing antibody targeting a coronavirus such as SARS-COV-2. In some embodiments, the targeting protein is a therapeutic antibody.

In some embodiments, there is provided a composition comprising a plurality of circRNAs according to any one of the circRNAs encoding a targeting proteins described above, wherein the targeting proteins corresponding to the plurality of circRNAs are different with respect to each other. In some embodiments, the targeting proteins are neutralizing antibodies. In some embodiments, the plurality of circRNAs target a plurality of strains of a coronavirus, e.g., SARS-CoV-2.

One aspect of the present application provides a circRNA comprising a nucleic acid sequence encoding a therapeutic polypeptide, wherein therapeutic polypeptide is a functional protein. In some embodiments, the circRNA is according to any one of the circRNAs described above. In some embodiments, the functional protein is a tumor suppressor, such as p53 or PTEN. In some embodiments, the functional protein is an enzyme, such as OTC, FAH, or IDUA. In some embodiments, the functional protein is selected from the group consisting of DMD, COL3A1, BMPR2, AHI1, FANCC, MYBPC3, and IL2RG. In some embodiments, therapeutic polypeptide comprises a sequence having at least about 80% (e.g., at least about 85%, 90%, 95%, 98%, or more, or 100%) identity to an amino acid sequence selected from the group consisting of SEQ ID NOs: 18-25.

One aspect of the present application provides a circular RNA (circRNA) comprising a nucleic acid sequence encoding an antigenic polypeptide comprising a Spike(S) protein or a fragment thereof of a coronavirus. In some embodiments, the circRNA is according to any one of the circRNAs described above. In some embodiments, the coronavirus is SARS-COV, MERS-CoV, or SARS-COV-2. In some embodiments, the coronavirus is SARS-COV-2. In some embodiments, the S protein or fragment thereof comprises a D614G mutation.

In some embodiments according to any one of the circRNAs encoding an antigenic polypeptide described above, the antigenic polypeptide comprises an amino acid sequence having at least about 80% (e.g., at least about 85%, 90%, 95%, 98%, or more, or 100%) sequence identity to an amino acid sequence selected from the group consisting of SEQ ID NOs: 8-10 and 62-63. In some embodiments, the circRNA comprises a nucleic acid sequence having at least about 80% (e.g., at least about 85%, 90%, 95%, 98%, or more, or 100%) sequence identity to a nucleic acid sequence selected from the group consisting of SEQ ID NOs: 11-15 and 64.

In some embodiments according to any one of the circRNAs encoding an antigenic polypeptide described above, the antigenic polypeptide comprises a receptor-binding domain (RBD) of the S protein. In some embodiments, the RBD comprises amino acid residues 319 to 542 of a full-length S protein of SARS-COV-2, wherein the numbering is based on SEQ ID NO: 1. In some embodiments, the RBD comprises an amino acid sequence having at least about 80% identity (e.g., at least about 85%, 90%, 95%, 98%, or more, or 100% identity) to the amino acid sequence of SEQ ID NO: 2.

In some embodiments according to any one of the circRNAs encoding an antigenic polypeptide described above, the antigenic polypeptide comprises a receptor-binding domain (RBD) of the S protein, wherein the RBD comprises an amino acid sequence having at least about 80% identity (e.g., at least about 85%, 90%, 95%, 98%, 99% or more, or 100% identity) to the amino acid sequence of SEQ ID NO: 63.

In some embodiments according to any one of the circRNAs comprising an RBD described above, the antigenic polypeptide further comprises a multimerization domain. In some embodiments, the multimerization domain is a C-terminal Foldon (Fd) domain of a T4 fibritin protein or a GCN4-based isoleucine zipper domain. In some embodiments, the multimerization domain comprises an amino acid sequence having at least about 80% (e.g., at least about 85%, 90%, 95%, 98%, or more, or 100%) to the amino acid sequence of SEQ ID NO: 3 or SEQ ID NO: 4. In some embodiments, the RBD is fused to the multimerization domain via a peptide linker. In some embodiments, the peptide linker comprises the amino acid sequence of SEQ ID NO: 5.

In some embodiments according to any one of the circRNAs encoding an antigenic polypeptide described above, the antigenic polypeptide comprises an S2 region of the S protein. In some embodiments, the S2 region comprises amino acid residues 686 to 1273 of a full-length S protein of SARS-COV-2, wherein the numbering is based on SEQ ID NO: 1. In some embodiments, the S2 region comprises one or more mutations that stabilize a pre-fusion conformation of the S protein. In some embodiments, the one or more mutations comprise K986P and V987P. In some embodiments, the S2 region comprises an amino acid sequence having at least about 80% (e.g., at least about 85%, 90%, 95%, 98%, or more, or 100%) to the amino acid sequence of SEQ ID NO: 6 or SEQ ID NO: 7.

In some embodiments according to any one of the circRNAs encoding an antigenic polypeptide described above, the antigenic polypeptide comprises amino acid residues 2-1273 of a full-length S protein of SARS-COV-2, wherein the numbering is based on SEQ ID NO: 1. In some embodiments, the antigenic polypeptide comprises one or more mutations that inhibit cleavage of the S protein. In some embodiments, the one or more mutations that inhibit cleavage of the S protein comprise deletion of amino acid residues 681-684, wherein the numbering is based on SEQ ID NO: 1.

In some embodiments, there is provided a composition comprising a plurality of circRNAs according to any one of the circRNAs encoding an antigenic polypeptides described above, wherein the antigenic polypeptides corresponding to the plurality of circRNAs are different with respect to each other. In some embodiments, the plurality of circRNAs target a plurality of strains of a coronavirus, e.g., SARS-COV-2.

In some embodiments, there is provided a circRNA vaccine comprising a circRNA or a plurality of circRNAs according to any one of the circRNAs encoding an antigenic polypeptide described above.

In some embodiments, there is provided a pharmaceutical composition comprising the circRNA according to any one of the circRNAs described above, and a pharmaceutically acceptable carrier.

In some embodiments according to any one of the circRNA vaccines or pharmaceutical compositions described above, the circRNA vaccine or the pharmaceutical composition further comprises a transfection agent. In some embodiments, the transfection reagent is polethylenimine (PEI) or a lipid nanoparticle (LNP). In some embodiments, the LNP comprises MC3-lipid, DSPC, cholesterol, and PEG2000-DMG. In some embodiments, the circRNA or the pharmaceutical composition is not formulated with a transfection agent.

Other aspects of the present application provide methods of treating or preventing a coronavirus infection in an individual, comprising administering to the individual an effective amount of any one of the circRNA vaccines described above. In some embodiments, the infection is SARS-COV-2 infection. In some embodiments, the circRNA is subject to rolling circle translation by a ribosome in the individual.

Another aspect of the present application provides a method of treating or preventing a disease or condition in an individual, comprising administering to the individual an effective amount of any one of the circRNAs described above or any one of the pharmaceutical compositions described above. In some embodiments, wherein the circRNA encodes an antigenic polypeptide, a receptor or a targeting protein (e.g., antibody), the disease or condition is an infection, such as a viral infection. In some embodiments, the disease or condition is a disease or condition associated with insufficient levels and/or activity of a naturally-occurring protein corresponding to the therapeutic polypeptide. In some embodiments, the disease or condition is a hereditary genetic disease associated with one or more mutations in the protein corresponding to the therapeutic polypeptide. In some embodiments, therapeutic polypeptide is TP53 or PTEN, and the disease or condition is cancer. In some embodiments, therapeutic polypeptide is OTC, and the disease is ornithine transcarbamylase deficiency. In some embodiments, therapeutic polypeptide is FAH, and the disease is tyrosinemia. In some embodiments, therapeutic polypeptide is DMD, and the disease is Duchenne and Becker muscular dystrophy, X-linked dilated cardiomyopathy, or familial dilated cardiomyopathy. In some embodiments, therapeutic polypeptide is IDUA, and the disease or condition is Mucopolysaccharidosis type I (MPS I). In some embodiments, therapeutic polypeptide is COL3A1, and the disease or condition is Ehlers-Danlos syndrome. In some embodiments, therapeutic polypeptide is AHI1, and the disease or condition is Joubert syndrome. In some embodiments, therapeutic polypeptide is BMPR2, and the disease or condition is pulmonary arterial hypertension, or pulmonary veno-occlusive disease. In some embodiments, therapeutic polypeptide is FANCC, and the disease or condition is Fanconi anemia. In some embodiments, therapeutic polypeptide is MYBPC3, and the disease or condition is primary familial hypertrophic cardiomyopathy. In some embodiments, therapeutic polypeptide is IL2RG, and the disease or condition is X-linked severe combined immunodeficiency. In some embodiments, the circRNA is subject to rolling circle translation by a ribosome in the individual.

Other aspects of the present application provide a linear RNA capable of forming the circRNA of any one of the circRNAs provided herein.

In some embodiments, the linear RNA can be circularized by autocatalysis of a Group I intron comprising a 5' catalytic Group I intron fragment and a 3' catalytic Group I intron fragment. In some embodiments, the linear RNA comprises a 3' catalytic Group I intron fragment flanking the 5' end of a 3' exon sequence recognizable by a Group I intron, and a 5' catalytic Group I intron fragment flanking the 3' end of a 5' exon sequence recognizable by a Group I intron. In some embodiments, the 3' catalytic Group I intron fragment comprises the sequence of SEQ ID NO: 28, and the 5' catalytic Group I intron fragment comprises the sequence of SEQ ID NO: 29. In some embodiments, the linear RNA further comprises a 5' homology sequence flanking the 5' end of the 3' catalytic Group I intron fragment, and a 3' homology sequence flanking the 3' end of the 5' catalytic Group I intron fragment. In some embodiments, the 5' homology sequence comprises the nucleic acid sequence of SEQ ID NO: 23, and the 3' homology sequence comprises the nucleic acid sequence of SEQ ID NO: 24.

In some embodiments, the linear RNA can be circularized by a ligase (e.g., an RNA ligase). In some embodiments, the ligase is selected from the group consisting of a T4 DNA ligase (T4 Dnl), a T4 RNA ligase 1 (T4 Rnl1) and a T4 RNA ligase 2 (T4 Rnl2). In some embodiments, the linear RNA comprises a 5' ligation sequence at the 5' end of the nucleic acid sequence encoding the circRNA, and a 3' ligation sequence at the 3' end of the nucleic acid sequence encoding the circRNA, wherein the 5' ligation sequence and the 3' ligation sequence can be ligated to each other via the ligase.

One aspect of the present application provides a nucleic acid construct comprising a nucleic acid sequence encoding any one of the linear RNAs described above. In some embodiments, the nucleic acid construct comprises a T7 promoter operably linked to the nucleic acid sequence encoding the linear RNA.

One aspect of the present application provides a method of producing a circRNA, comprising: (a) subjecting any one of the linear RNAs described above, wherein the linear RNA comprises a 3' catalytic Group I intron fragment flanking the 5' end of a 3' exon sequence recognizable by a Group I intron, and a 5' catalytic Group I intron fragment flanking the 3' end of a 5' exon sequence recognizable by a Group I intron, to a condition that activates autocatalysis of the 5' catalytic Group I intron fragment and the 3' catalytic Group I intron fragment to provide a circularized RNA product; and (b) isolating the circularized RNA product, thereby providing the circRNA vaccine.

One aspect of the present application provides a method of producing a circRNA, comprising: (a) contacting any one of the linear RNAs described above, wherein the linear RNA comprises a 5' ligation sequence at the 5' end of the nucleic acid sequence encoding the circRNA, and a 3' ligation sequence at the 3' end of the nucleic acid sequence encoding the circRNA, with a single-stranded adaptor nucleic acid comprising from the 5' end to the 3' end: a first sequence complementary to the 3' ligation sequence and a second sequence complementary to the 5' ligation sequence, and wherein the 5' ligation sequence and the 3' ligation sequence hybridize to the single-stranded adaptor nucleic acid to provide a duplex nucleic acid intermediate comprising a single strand break between the 3' end of the 5' ligation sequence and the 5' end of the 3' ligation sequence; (b) contacting the intermediate with an RNA ligase under a condition that allows ligation of the 5' ligation sequence to the 3' ligation sequence to provide a circularized RNA product; and (c) isolating the circularized RNA product, thereby providing the circRNA vaccine.

One aspect of the present application provides a method of producing a circRNA, comprising: (a) contacting any one of the linear RNAs described above, wherein the linear RNA comprises a 5' ligation sequence at the 5' end of the nucleic acid sequence encoding the circRNA, and a 3' ligation sequence at the 3' end of the nucleic acid sequence encoding the circRNA, with an RNA ligase under a condition that allows ligation of the 5' ligation sequence to the 3' ligation sequence to provide a circularized RNA product; and (b) isolating the circularized RNA product, thereby providing the circular RNA.

In some embodiments according to any one of the methods of producing a circRNA vaccine described above, the method further comprises obtaining the linear RNA by in vitro transcription of a nucleic acid construct comprising a nucleic acid sequence encoding the linear RNA.

In some embodiments according to any one of the methods of producing a circRNA vaccine described above, the method further comprises purifying the circularized RNA product.

Also provided are compositions, kits and articles of manufacture for use in any one the methods described above.

BRIEF DESCRIPTION OF THE DRAWINGS

FIG. 11A shows a schematic representation of an LNP-circRNA complex. FIG. 11B shows a representative of concentration-size graph of LNP-circRNA$^{RBD}$ measured by dynamic light scattering method. FIG. 11C shows a schematic diagram of the LNP-circRNA$^{RBD}$ vaccination process in BALB/c mice and serum collection schedule for specific antibodies analysis. FIG. 11D shows results of measuring the SARS-COV-2 specific IgG antibody titer with ELISA. The data were shown as the mean±S.E.M. (n=4 or 5). Each symbol represented an individual mouse. FIG. 11E shows a sigmoidal curve diagram of the inhibition rate by sera of immunized mice with surrogate virus neutralization assay. Sera from circRNA$^{RBD}$ (10 μg) and circRNA$^{RBD}$ (50 μg) immunized mice were collected at 2 weeks post the second dose. The data were shown as the mean±S.E.M. (n=4). FIG. 11F shows a sigmoldal curve diagram of the inhibition rate by sera of immunized mice with surrogate virus neutralization assay. Sera from circRNA$^{RBD}$ (10 μg) and circRNA$^{RBD}$ (50 μg) immunized mice were collected at 5 weeks post boost. The data were shown as the mean±S.E.M. (n=5). FIG. 11G shows the NT50 of circRNA$^{RBD}$, calculated using lentivirus-based SARS-COV-2 pseudovirus. The data were shown as the mean±S.E.M. (n 336=5). Each symbol represented an individual mouse. FIG. 11H shows the NT50 of circRNA$^{RBD}$, determined using infectious SARS-COV-2 authentic virus. Sera from circRNA$^{RBD}$ (50 μg) immunized mice were collected at 5 weeks post the second dose. The data were shown as the mean±S.E.M. (n=4 or 5). Each symbol represented an individual mouse.

FIG. 12A shows FACS analysis results showing the percentages of cytokine positive cells evaluated among single and viable CD44$^{+}$ CD62L$^{-}$CD4$^{+}$ T cells. FIG. 12B shows an intracellular staining assay for cytokines (IFN-γ, TNF-α, and IL-2) production among SARS-COV-2 specific CD4$^{+}$ effector memory T cells (CD44$^{+}$CD62L$^{-}$) in splenocytes. Results were pooled from two independent experiments. Data were presented as the mean±S.E.M. (n=3 or 4). Each symbol represented an individual mouse. FIG. 12C shows FACS analysis results showing the percentages of cytokine positive cells evaluated among single and viable CD44$^{+}$CD62L$^{-}$ CD8$^{+}$ T. FIG. 12D shows an intracellular staining assay for cytokines (IFN-γ, TNF-α, and IL-2) production among SARS-COV-2 specific CD8$^{+}$ effector memory T cells (CD44$^{+}$CD62L$^{-}$) in splenocytes. Results were pooled from two independent experiments. Data were presented as the mean±S.E.M. (n=3 or 4). Each symbol represented an individual mouse.

FIG. 13A shows the schematic diagram of circRNA$^{RBD\text{-}501Y.V2}$ circularization by the Group I ribozyme autocatalysis. SP, signal peptide sequence of human tPA protein. T4, the trimerization domain from bacteriophage T4 fibritin protein. RBD-501Y.V2, the RBD antigen harboring the K417N-E484K-N501Y mutations in SARS-COV-2 501Y.V2 variant. FIG. 13B shows the SARS-COV-2 specific IgG antibody titer with ELISA. The data were shown as the mean±S.E.M. Each symbol represented an individual mouse. FIG. 13C shows the Sigmodal curve diagram of the inhibition rate by sera of immunized mice with surrogate virus neutralization assay. Sera from circRNA$^{RBD\text{-}501Y.V2}$ (50 μg) immunized mice were collected at 1 week or 2 weeks post boost. The data were shown as the mean±S.E.M. FIG. 13D shows the neutralizating results of VSV-based D614G, B.1.1.7 or B.1.351 pseudovirus with the serum of mice immunized with circRNA$^{RBD}$ vaccines. The serum samples were collected at 5 weeks post boost. The data were shown as the mean±S.E.M. (n=5). FIG. 13E shows the neutralizating results of VSV-based D614G, B.1.1.7 or B.1.351 pseudovirus with the serum of mice immunized with circRNA$^{RBD\text{-}501Y.V2}$ vaccines. The serum samples were collected at 1 week post boost. The data were shown as the mean±S.E.M. (n=5). FIG. 13F-13G shows the NT50 determined using authentic SARS-COV-2 B.1.351/501Y.V2 strain (FIG. 13F) or D614G strain (FIG. 13G). Sera from circRNA$^{RBD\text{-}501Y.V2}$ (50 μg) immunized mice were collected at 2 weeks post the second dose. The data were shown as the mean±S.E.M. Each symbol represented an individual mouse.

FIG. 14A shows a schematic of the dosing regimen and serum collection. At seven weeks post the second immunization with circRNA$^{RBD\text{-}501Y.V2}$ vaccine, the BALB/c mice were challenged with $5\times10^{4}$ PFU of authentic SARS-COV-2 B.1.351/501Y.V2 strain via the intranasal (i.n.) route, and the lung tissues were collected at 3 days after challenge for detecting the viral loads. FIG. 14B shows measurement of the SARS-COV-2 specific IgG antibody titers with ELISA. The data were shown as the mean±S.E.M. (n=5). Each symbol represented an individual mouse. FIG. 14C shows a sigmoidal curve diagram of the inhibition rate by sera of immunized mice with surrogate virus neutralization assay. In FIG. 14B and FIG. 14C, the sera from circRNARBD-501Y.V2 (50 μg) immunized mice were collected at 3 days before challenge with authentic SARS-COV-2 B.1.351/501Y.V2 strain. FIG. 14D shows the weight change of immunized mice after virus challenge. FIG. 14E show viral loads in the lung tissues of challenged mice. The data were shown as the mean±S.E.M. (n≥5). Each symbol represented an individual mouse. The statistical test was performed by unpaired two-sided Student's t-test.

DETAILED DESCRIPTION

The present application provides circRNAs encoding a therapeutic polypeptide, such as an antigenic polypeptide, a functional protein, a receptor protein, or a targeting protein (e.g., antibody). In some embodiments, the present application provides a novel vaccine against a coronavirus such as the SARS-COV-2 virus based on circular RNAs (circRNA). In some embodiments, the circRNA vaccine encodes an antigenic polypeptide comprising a Spike protein or fragment thereof of the coronavirus such as SARS-COV-2. Unlike other types of coronavirus vaccines, the circRNA vaccines described herein do not require the handling of large amounts of infectious particles during production. Furthermore, the circRNA vaccines described herein may provide enhanced stability and efficacy compared to linear RNA vaccines. For example, given their circular nature, circRNAs are particularly stable compared to many linear RNAs because they are resistant to exonucleolytic decay by the cellular exosome ribonuclease complex. In some embodiments, the circRNA in the circRNA vaccines disclosed herein can be subject to rolling circle translation by a ribosome in an individual, to whom the vaccine has been administered, giving rise to high amounts of antigenic polypeptides. The production of this circRNA vaccine could be performed using various methods, such as chemical ligation, enzyme catalysis, or ribozyme autocatalysis. The circRNA vaccines described herein provide a platform for rapid development of vaccines against emerging coronavirus strains. Moreover, circular RNAs could be quickly generated in large quantities in vitro, and they do not require any nucleotide modification, strikingly different from canonical mRNA vaccines. Our data demonstrated that an exemplary circRNA and encapsulated circRNA-LNP complex were highly thermostable at 4° C. or room temperature for 7 to 14 days. Owing to their specific properties, circRNAs hold potentials in biomedical applications.

I. Definitions

Terms are used herein as generally used in the art, unless otherwise defined as follows.

The terms "polynucleotide," "nucleic acid," "nucleotide sequence," and "nucleic acid sequence" are used interchangeably. They refer to a polymeric form of nucleotides of any length, either deoxyribonucleotides or ribonucleotides, or analogs thereof.

The term "vaccine" is understood as being directed to an immunoactive pharmaceutical preparation. In certain embodiments, the vaccine induces adaptive immunity when administered to a host. The vaccine preparation may further contain a pharmaceutical carrier, which may be designed for the particular mode by which the vaccine is intended to be administered.

Figure 1A:
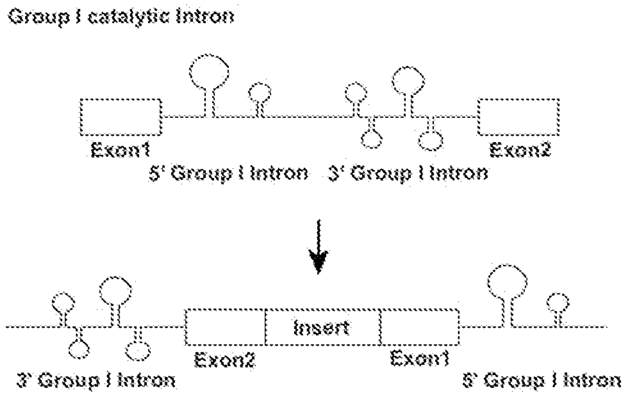
FIG. 1A shows an exemplary method of generating a circRNA vaccine in vitro based on a Group I catalytic intron. A typical Group I catalytic intron comprises, from the 5' end to the 3' end: a 5' exon comprising a 5' exon sequence recognizable by a 5' catalytic Group I intron fragment (Exon 1), 5' catalytic Group I intron fragment, 3' catalytic Group I intron fragment, and a 3' exon comprising a 3' exon sequence recognizable by the 3' catalytic Group I intron fragment (Exon 2). A linear RNA construct with an insert sequence can be made to allow auto-catalysis of the Group I intron fragments in order to join the two ends of the insert sequence and obtain a circular RNA after self-splicing by the Group I intron. The linear construct comprises, from 5' to 3', 3' catalytic Group I intron fragment, a 3' exon (Exon 2), an insert sequence, a 5' exon (Exon 1), and 5' Group I intron. The insert sequence may comprise the nucleic acid sequence encoding the antigenic polypeptide.

The terms "Group I intron" and "Group I catalytic intron" are used interchangeably to refer to a self-splicing ribozyme that can catalyze its own excision from an RNA precursor. Group I introns comprise two fragments, the 5' catalytic Group I intron fragment and the 3' catalytic Group I intron fragment, which retain their folding and catalytic function (i.e., self-splicing activity). In its native environment, the 5' catalytic Group I intron fragment is flanked at its 5' end by a 5' exon, which comprises a 5' exon sequence that is recognized by the 5' catalytic Group I intron fragment; and the 3' catalytic Group I intron fragment is flanked at its 3' end by a 3' exon, which comprises a 3' exon sequence that is recognized by the 3' catalytic Group I intron fragment. The terms "5' exon sequence" and "3' exon sequence" used herein are labeled according to the order of the exons with respect to the Group I intron in its natural environment, e.g., as shown in FIG. 1A.

The term "therapeutic polypeptide" refers to a polypeptide having a therapeutic effect. A therapeutic polypeptide may be a naturally-occurring protein or an engineered functional variant thereof, including functional fragments, derivatives having one or more mutations (e.g., insertion, deletion, substitution, etc.) to the amino acid sequence of the naturally-occurring protein, and fusion proteins comprising a naturally-occurring protein or fragment thereof. A therapeutic polypeptide may also be an engineered protein that does not have a naturally-occurring counterpart. Therapeutic polypeptide may have a single polypeptide chain or multiple polypeptide chains.

The term "antigenic polypeptide" refers to a polypeptide that can be used to trigger the immune system of a mammal to develop antibodies specific to the polypeptide or a portion thereof. Antigenic polypeptides described herein include naturally-occurring proteins, protein domains, and short peptide fragments derived from a naturally-occurring protein. An antigenic polypeptide may contain one or more known epitopes of a naturally-occurring protein. The antigenic polypeptide may comprise a carrier protein or multimerization protein that improves immunogenicity.

The term "functional protein" refers to a naturally-occurring protein, functional variants thereof, or an engineered derivative thereof that is functional in treating a genetic disease or condition. The disease or condition may be caused in whole or in part by a change, such as a mutation, in the wildtype, naturally-occurring protein corresponding to the functional protein.

The term "targeting protein" refers to a polypeptide that specifically binds to a target molecule. Targeting proteins described herein include both antibody-based and non-antibody based binding proteins or target-binding portions thereof.

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure.

As use herein, the terms "specifically binds," "specifically recognizing," and "is specific for" refer to measurable and reproducible interactions, such as binding between a target and a targeting moiety. For example, a targeting moiety that specifically recognizes a target (which can be an epitope) is a targeting moiety (e.g., antibody) that binds this target with greater affinity, avidity, more readily, and/or with greater duration than its bindings to other molecules. In some embodiments, the extent of binding of a targeting moiety to an unrelated molecule is less than about 10% of the binding of the targeting moiety to the target as measured, e.g., by a radioimmunoassay (RIA). In some embodiments, a targeting moiety that specifically binds a target has a dissociation constant (KD) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, specific binding can include, but does not require exclusive binding. Binding specificity of the targeting moiety can be determined experimentally by methods known in the art. Such methods comprise, but are not limited to Western blots, ELISA, RIA, ECL, IRMA, EIA, BIACORE™ and peptide scans.

The term "functional variant" of a reference protein refers to a variant polypeptide derived from the reference protein or a portion thereof, and the variant has substantially the same activity (e.g., binding to a target or enzymatic activity) as the reference protein. "Substantially the same activity" means an activity level that is at least about any one of 20%, 30%, 40%, 50%, 60%, 70%, 80%, 90%, or more as the activity of the reference protein.

The term "introducing" or "introduction" used herein means delivering one or more polynucleotides, such as circRNAs or one or more constructs including vectors as described herein, one or more transcripts thereof, to a host cell. The methods of the present application can employ many delivery systems, including but not limited to, viral, liposome, electroporation, microinjection and conjugation, to achieve the introduction of the circRNA or construct as described herein into a host cell. Conventional viral and non-viral based gene transfer methods can be used to introduce nucleic acids into mammalian cells or target tissues. Such methods can be used to administer nucleic acids encoding the circRNA of the present application to cells in culture, or in a host organism. Non-viral vector delivery systems include DNA plasmids, RNA (e.g. a transcript of a construct described herein), naked nucleic acid, and nucleic acid complexed with a delivery vehicle, such as a liposome. Viral vector delivery systems include DNA and RNA viruses, which have either episomal or integrated genomes for delivery to the host cell.

As used herein, "operably linked," when referring to a first nucleic acid sequence that is operably linked with a second nucleic acid sequence, means a situation when the first nucleic acid sequence is placed in a functional relationship with the second nucleic acid sequence. For instance, a promoter is operably linked to a coding sequence if the promoter effects the transcription of the coding sequence. Likewise, the coding sequence of a signal peptide is operably linked to the coding sequence of a polypeptide if the signal peptide effects the extracellular secretion of that polypeptide. Generally, operably linked nucleic acid sequences are contiguous and, where necessary to join two protein coding regions, the open reading frames are aligned.

As used herein, "complementarity" refers to the ability of a nucleic acid to form hydrogen bond(s) with another nucleic acid by traditional Watson-Crick base-pairing. A percent complementarity indicates the percentage of residues in a nucleic acid molecule which can form hydrogen bonds (i.e., Watson-Crick base pairing) with a second nucleic acid (e.g., about 5, 6, 7, 8, 9, 10 out of 10, being about 50%, 60%, 70%, 80%, 90%, and 100% complementary respectively). "Perfectly complementary" means that all the contiguous residues of a nucleic acid sequence form hydrogen bonds with the same number of contiguous residues in a second nucleic acid sequence. "Substantially complementary" as used herein refers to a degree of complementarity that is at least about any one of 70%, 75%, 80%, 85%, 90%, 95%, 97%, 98%, 99%, or 100% over a region of about 40, 50, 60, 70, 80, 100, 150, 200, 250 or more nucleotides, or refers to two nucleic acids that hybridize under stringent conditions.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

The terms "individual," "subject" and "patient" are used interchangeably herein to describe a mammal, including humans. In some embodiments, the individual is human. In some embodiments, the individual is a rodent, such as a mouse. In some embodiments, the individual suffers from a genetic disease or condition. In some embodiments, the individual suffers from a coronavirus infection. In some embodiments, the individual is at risk of contracting a coronavirus infection. In some embodiments, the individual is in need of treatment.

As is understood in the art, an "effective amount" refers to an amount of a composition sufficient to produce a desired therapeutic outcome (e.g., stimulating the production of antibodies and improving immunity against one or more coronaviruses, reducing the severity or duration of, stabilizing the severity of, or eliminating one or more symptoms of a coronavirus infection). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients. In some embodiments, an effective amount of the therapeutic agent may extend survival (including overall survival and progression free survival); result in an objective response (including a complete response or a partial response); relieve to some extent one or more signs or symptoms of the disease or condition; and/or improve the quality of life of the subject. In some embodiments, an effective amount is a prophylactically effective amount, which is an amount of a composition sufficient to prevent or reduce the severity of one or more future symptoms of a coronavirus infection when administered to an individual who is susceptible and/or who may develop the coronavirus infection. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotypes presenting during future development of the disease).

As used herein the term "wild type" is a term of the art understood by skilled persons and means the typical form of an organism, strain, gene or characteristic as it occurs in nature as distinguished from mutant or variant forms.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular, the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM 120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12 (1), 387 (1984)), BLASTP, BLASTN, and FASTA Altschul, S. F. et al., J. Molec. Biol., 215, 403 (1990)).

"Percent (%) amino acid sequence identity" with respect to the polypeptide sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R.C., Nucleic Acids Research 32 (5): 1792-1797, 2004; Edgar, R.C., BMC Bioinformatics 5 (1): 113, 2004, each of which are incorporated herein by reference in their entirety for all purposes).

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide" or "peptide" are used herein to encompass all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to one or more ingredients in a pharmaceutical formulation, other than an active ingredient, which is nontoxic to a subject. A pharmaceutically acceptable carrier includes, but is not limited to, a buffer, excipient, stabilizer, cryoprotectant, tonicity agent, preservative, and combinations thereof. Pharmaceutically acceptable carriers or excipients have preferably met the required standards of toxicological and manufacturing testing and/or are included on the Inactive Ingredient Guide prepared by the U.S. Food and Drug administration or other state/federal government or listed in the U.S. Pharmacopeia or other generally recognized pharmacopeia for use in mammals, and more particularly in humans.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or condition (e.g., coronavirus infection), or a probe for specifically detecting a biomarker described herein. In certain embodiments, the manufacture or kit is promoted, distributed, or sold as a unit for performing the methods described herein.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat disease of type X means the method is used to treat disease of types other than X.

The term "about X-Y" used herein has the same meaning as "about X to about Y."

As used herein and in the appended claims, the singular forms "a," "an," or "the" include plural referents unless the context clearly dictates otherwise.

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Therapeutic Circular RNA

The present application provides circular RNAs (circRNAs) encoding polypeptides, such as therapeutic polypeptides, including any one of therapeutic polypeptides described in Section A. "Therapeutic polypeptides" below.

In some embodiments, there is provided a circRNA comprising a nucleic acid sequence encoding a therapeutic polypeptide, wherein therapeutic polypeptide is selected from the group consisting of an antigenic polypeptide, a functional protein, a receptor protein, and a targeting protein.

In some embodiments, the circRNA is stable for at least 7, 8, 9, 10, 11, 12, 13, 14, 15, 16, 17, 18, 19, 20, or 20 days when stored at 4° C. or at room temperature. In some embodiments, the circRNA is stable for at least 7 days when stored at 4° C. or at room temperature. In some embodiments, the circRNA is stable for at least 14 days when stored at 4° C. or at room temperature. In some embodiments, the circRNA is stable for at least 30 days when stored at 4° C. In some embodiments, the circRNA is less than 40% degraded after storage at room temperature for 14 days.

In some embodiments, the present application provides a circRNA comprising: (a) a nucleic acid sequence encoding a therapeutic polypeptide, wherein therapeutic polypeptide is selected from the group consisting of an antigenic polypeptide, a functional protein, a receptor protein, and a targeting protein, and (b) an internal ribosomal entry site (IRES) sequence, wherein the IRES sequence is operably linked to the nucleic acid sequence encoding therapeutic polypeptide. In some embodiments, the nucleic acid sequence further encodes a SP (e.g., human tPA or IgE SP) fused to the N-terminus of therapeutic polypeptide. In some embodiments, the circRNA further comprises a Kozak sequence operably linked to the nucleic acid sequence encoding therapeutic polypeptide. In some embodiments, the circRNA comprises a nucleic acid sequence comprising from the 5' end to the 3' end: the IRES sequence, the Kozak sequence, and the nucleic acid sequence encoding therapeutic polypeptide. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding therapeutic polypeptide, and a 5' exon sequence recognizable by a 5' catalytic Group I intron fragment flanking the 3' end of the nucleic acid sequence encoding therapeutic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase).

In some embodiments, the present application provides a circRNA comprising: (a) a nucleic acid sequence encoding a therapeutic polypeptide, wherein therapeutic polypeptide is selected from the group consisting of an antigenic polypeptide, a functional protein, a receptor protein, and a targeting protein; (b) an IRES sequence, wherein the IRES sequence is operably linked to the nucleic acid sequence encoding therapeutic polypeptide; and (c) an in-frame 2A peptide coding sequence operably linked to the 3' end of the nucleic acid sequence encoding therapeutic polypeptide. In some embodiments, the nucleic acid sequence further encodes a SP (e.g., human tPA or IgE SP) fused to the N-terminus of therapeutic polypeptide. In some embodiments, the circRNA further comprises a Kozak sequence operably linked to the nucleic acid sequence encoding therapeutic polypeptide. In some embodiments, the circRNA comprises a nucleic acid sequence comprising from the 5' end to the 3' end: the IRES sequence, the Kozak sequence, the nucleic acid sequence encoding therapeutic polypeptide, and the in-frame 2A peptide coding sequence. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding therapeutic polypeptide, and a 5' exon sequence recognizable by a 5' catalytic Group I intron fragment flanking the 3' end of the nucleic acid sequence encoding therapeutic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase).

In some embodiments, the present application provides a circRNA comprising: (a) a nucleic acid sequence encoding a therapeutic polypeptide, wherein therapeutic polypeptide is selected from the group consisting of an antigenic polypeptide, a functional protein, a receptor protein, and a targeting protein; and (b) an m6A modification motif sequence operably linked to the nucleic acid sequence encoding therapeutic polypeptide. In some embodiments, the nucleic acid sequence further encodes a SP (e.g., human tPA or IgE SP) fused to the N-terminus of therapeutic polypeptide. In some embodiments, the circRNA further comprises a Kozak sequence operably linked to the nucleic acid sequence encoding therapeutic polypeptide. In some embodiments, the circRNA comprises a nucleic acid sequence comprising from the 5' end to the 3' end: the m6A modification motif sequence, the Kozak sequence, and the nucleic acid sequence encoding therapeutic polypeptide. In some embodiments, the circRNA further comprises a 3' exon sequence recognizable by a 3' catalytic Group I intron fragment flanking the 5' end of the nucleic acid sequence encoding therapeutic polypeptide, and a 5' exon sequence recognizable by a 5' catalytic Group I intron fragment flanking the 3' end of the nucleic acid sequence encoding therapeutic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase).

In some embodiments; the present application provides a circRNA comprising a nucleic acid sequence encoding an antigenic polypeptide. In some embodiments, the antigenic polypeptide is a protein or fragment thereof of an infectious agent. In some embodiments, the infectious agent is a virus. In some embodiments, the virus is a coronavirus. In some embodiments, the coronavirus is selected from the group consisting of SARS-COV, MERS-COV, and SARS-COV-2. In some embodiments, the coronavirus is SARS-COV-2. The circRNA may comprise any one of the circRNA expression and/or circularization elements described in Section B, "Additional circRNA expression and circularization elements" below.

In some embodiments, the present application provides a circRNA comprising a nucleic acid sequence encoding a receptor protein. In some embodiments, the receptor protein is a soluble receptor comprising an extracellular domain of a naturally occurring receptor. In some embodiments, the receptor protein is a receptor of an infectious agent (e.g., a virus such as a coronavirus). In some embodiments, the receptor is an ACE2 receptor, such as a soluble ACE2 receptor. In some embodiments, the receptor is a high-affinity mutant ACE2 receptor. The circRNA may comprise any one of the circRNA expression and/or circularization elements described in Section B, "Additional circRNA expression and circularization elements" below.

In some embodiments, the present application provides a circRNA comprising a nucleic acid sequence encoding a targeting protein. In some embodiments, the targeting protein is an antibody. In some embodiments, the antibody is a neutralizing antibody, e.g., a neutralizing antibody targeting a coronavirus such as SARS-COV-2. In some embodiments, the targeting protein is a therapeutic antibody. The circRNA may comprise any one of the circRNA expression and/or circularization elements described in Section B, "Additional circRNA expression and circularization elements" below.

In some embodiments, the present application provides circular RNA vaccines for treatment or prevention of coronavirus.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., SARS-CoV, MERS-COV, or SARS-COV-2).

In some embodiments, the present application provides a circular RNA (circRNA) vaccine comprising a circRNA comprising a nucleic acid sequence encoding an antigenic polypeptide comprising an S protein or a fragment thereof of SARS-COV-2.

In some embodiments, the present application provides a circular RNA (circRNA) vaccine comprising a circRNA comprising a nucleic acid sequence encoding an antigenic polypeptide comprising: (a) an S protein or a fragment thereof of a coronavirus (e.g., SARS-COV, MERS-COV, or SARS-COV-2); and (b) a multimerization domain. In some embodiments, the multimerization domain is a C-terminal Foldon (Fd) domain of a T4 fibritin protein that mediates trimerization of the T4 fibritin protein. In some embodiments, the multimerization domain is a GCN-4 based isoleucine zipper domain. In some embodiments, the multimerization domain comprises an amino acid sequence set forth in SEQ ID NOs: 3-4. In some embodiments, the multimerization domain is fused to the RBD domain of the S protein via a peptide linker, e.g., a peptide linker comprising the amino acid sequence of SEQ ID NO: 5.

In some embodiments, the present application provides a circular RNA (circRNA) vaccine comprising a circRNA comprising a nucleic acid sequence encoding an antigenic polypeptide comprising a receptor-binding domain (RBD) of an S protein of a coronavirus (e.g., SARS-COV2). In some embodiments, the RBD comprises amino acid residues 319 to 542 of a full-length S protein of SARS-COV-2, wherein the numbering is based on SEQ ID NO: 1. In some embodiments, the RBD comprises the amino acid sequence of SEQ ID NO: 2. In some embodiments, the RBD comprises the amino acid sequence of SEQ ID NO: 63.

In some embodiments, the present application provides a circular RNA (circRNA) vaccine comprising a circRNA comprising a nucleic acid sequence encoding an antigenic polypeptide comprising: (a) a RBD of an S protein fragment of a coronavirus (e.g., SARS-COV, MERS-COV, or SARS-COV-2) and (b) a multimerization domain. In some embodiments, the RBD comprises amino acid residues 319 to 542 of a full-length S protein of SARS-COV-2, wherein the numbering is based on SEQ ID NO: 1. In some embodiments, the RBD comprises the amino acid sequence of SEQ ID NO: 2. In some embodiments, the RBD comprises the amino acid sequence of SEQ ID NO: 63. In some embodiments, the multimerization domain is a C-terminal Foldon (Fd) domain of a T4 fibritin protein that mediates trimerization of the T4 fibritin protein. In some embodiments, the multimerization domain is a GCN-4 based isoleucine zipper domain. In some embodiments, the multimerization domain comprises an amino acid sequence set forth in SEQ ID NOs: 3-4. In some embodiments, the multimerization domain is fused to the RBD domain of the S protein via a peptide linker, e.g., a peptide linker comprising the amino acid sequence of SEQ ID NO: 5.

In some embodiments, the present application provides a circular RNA (circRNA) vaccine comprising a circRNA comprising a nucleic acid sequence encoding an antigenic polypeptide comprising an S2 region of an S protein of a coronavirus (e.g., SARS-COV2). In some embodiments, the S2 region comprises amino acid residues 686 to 1273 of a full-length S protein of SARS-COV-2, wherein the numbering is based on SEQ ID NO: 1. In some embodiments, the S2 region comprises one or more mutations (e.g., K986P and V987P) that stabilize a pre-fusion conformation of the S protein. In some embodiments, the S2 region comprises the amino acid sequence of SEQ ID NO: 6 or 7.

In some embodiments, the present application provides a circular RNA (circRNA) vaccine comprising a circRNA comprising a nucleic acid sequence encoding an antigenic polypeptide comprising amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the antigenic polypeptide comprises an amino acid sequence selected from the group consisting of SEQ ID NOs: 8-10 and 62-63.

In some embodiments, the present application provides a circular RNA (circRNA) vaccine comprising a circRNA comprising: (a) a nucleic acid sequence encoding an antigenic polypeptide comprising an S protein or a fragment thereof of a coronavirus (e.g., SARS-COV-2), and (b) an internal ribosomal entry site (IRES) sequence, wherein the IRES sequence is operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a Kozak sequence operably linked to the nucleic acid sequence encoding the antigenic polypeptide. In some embodiments, the circRNA comprises a nucleic acid sequence comprising from the 5' end to the 3' end: the IRES sequence, the Kozak sequence, the SP, and the nucleic acid sequence encoding the antigenic polypeptide. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the circRNA comprises a nucleic acid sequence selected from the group consisting of SEQ ID NOs: 11-15.

In some embodiments, the present application provides a circular RNA (circRNA) vaccine comprising a circRNA comprising: (a) a nucleic acid sequence encoding an antigenic polypeptide comprising an S protein or a fragment thereof of a coronavirus (e.g., SARS-COV-2); (b) an IRES sequence, wherein the IRES sequence is operably linked to the nucleic acid sequence encoding the antigenic polypeptide; and (c) an in-frame 2A peptide coding sequence operably linked to the 3' end of the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a Kozak sequence operably linked to the nucleic acid sequence encoding the antigenic polypeptide. In some embodiments, the circRNA comprises a nucleic acid sequence comprising from the 5' end to the 3' end: the IRES sequence, the Kozak sequence, the SP, the nucleic acid sequence encoding the antigenic polypeptide, and the in-frame 2A peptide coding sequence. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the circRNA comprises a nucleic acid sequence selected from the group consisting of SEQ ID NOs: 11-15.

In some embodiments, the present application provides a circular RNA (circRNA) vaccine comprising a circRNA comprising: (a) a nucleic acid sequence encoding an antigenic polypeptide comprising an S protein or a fragment thereof of a coronavirus (e.g., SARS-COV-2), and (b) an m6A modification motif sequence operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a Kozak sequence operably linked to the nucleic acid sequence encoding the antigenic polypeptide. In some embodiments, the circRNA comprises a nucleic acid sequence comprising from the 5' end to the 3' end: the m6A modification motif sequence, the Kozak sequence, the SP, and the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the circRNA comprises a nucleic acid sequence selected from the group consisting of SEQ ID NOs: 11-15.

The present application further provides a cocktail composition comprising a plurality of circRNAs each comprising a nucleic acid sequence encoding an antigenic polypeptide, a receptor protein of an infectious agent, or a targeting protein (e.g., an antibody such as a neutralizing antibody). In some embodiments, the plurality of circRNA encode antigenic polypeptides that are different with respect to each other, such as different mutants of an antigenic polypeptide (e.g., S protein or fragment thereof). In some embodiments, the plurality of circRNA encode receptor proteins that are different with respect to each other, such as different mutants of a receptor protein (e.g., ACE2). In some embodiments, the plurality of circRNA encode targeting proteins that are different with respect to each other, such as different antibodies (e.g., neutralizing antibodies).

A. Therapeutic Polypeptides

In some aspects, provided herein is a circRNA comprising a therapeutic polypeptide. In some embodiments, the therapeutic polypeptide is an antigenic polypeptide, a functional protein, a receptor protein or a targeting protein (e.g., an antibody).

In some embodiments, the nucleic acid sequence may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

i. Antigenic Polypeptides

The circRNA vaccines described herein comprise circular RNAs (circRNA) encoding an antigenic polypeptide. In some embodiments, the antigenic polypeptide comprises a Spike(S) protein or a fragment thereof of a coronavirus, such as any one of the S proteins or fragments thereof as described in the "Spike protein or fragment thereof" subsection below. In some embodiments, the antigenic polypeptide comprises a multimerization domain, such as a native multimerization domain of the S protein, or an exogenous multimerization domain. Suitable multimerization domains are described in the "Multimerization domain" subsection below. The S protein or fragment thereof may be fused to the multimerization domain via a peptide linker, such as any one of the peptide linkers described in the "peptide linker" subsection below.

An antigenic polypeptide comprises at least one epitope recognizable by a T cell receptor (TCR). In some embodiments, the antigenic polypeptide is a full-length protein or a fragment thereof, or an antigenic fusion protein that can trigger an immune response in a subject. In some embodiments, the antigenic polypeptide is a short peptide of no more than 100 amino acids long. The antigenic polypeptide can be a naturally derived peptide fragment from a protein antigen containing one or more epitopes, or an artificially designed peptide with one or more natural epitope sequences, wherein a peptide linker may optionally be placed in between adjacent epitope sequences. In some embodiments, the antigenic polypeptide comprises a single epitope of an antigenic protein. In some embodiments, the antigenic polypeptide comprises about any one of 1, 2, 3, 4, 5, 10 or more epitopes from a single antigenic protein. In some embodiments, the antigenic polypeptide comprises epitopes from a plurality (e.g., 2, 3, 4, 5, 10 or more) of different antigenic proteins. In some embodiments, the antigenic polypeptide comprises a Major Histocompatibility Complex (MHC) class I-restricted epitope. In some embodiments, the antigenic polypeptide comprises a MHC class II-restricted epitope. In some embodiments, the antigenic polypeptide comprises both MHC class I-restricted and MHC class II-restricted epitopes.

In some embodiments, the antigenic polypeptide is an antigenic protein or fragment thereof or a variant thereof from a pathogenic agent, such as a bacterium or a virus. In some embodiments, the antigenic polypeptide is an antigenic protein or fragment of a coronavirus, such as SARS-COV2, including variants thereof.

In some embodiments, the antigenic polypeptide is an antigenic protein or fragment thereof or a variant thereof of a self antigen, such as an antigen involved in a disease or condition. In some embodiments, the antigenic polypeptide is a tumor antigen peptide. Tumor antigen peptide sequences are known in the art and can be found at public databases, such as the Cancer Antigenic Peptide Database (van der Bruggen P et al. (2013) "Peptide database: T cell-defined tumor antigens." Cancer Immunity. URL: caped.icp.ucl.ac.be). The coding RNA sequence in the linear RNA or circRNA described herein may encode any of the known tumor antigen peptides or combinations thereof. In some embodiments, the antigenic polypeptide comprises an epitope of a tumor associated antigen (TAA). In some embodiments, the antigenic polypeptide comprises an epitope of a tumor specific antigen. In some embodiments, the antigenic polypeptide comprises an epitope of a neoantigen, i.e., newly acquired and expressed antigens present in tumor cells of an individual.

In some embodiments, the amino acid sequences of one or more epitope peptides are predicted based on the sequence of the antigen protein (including neoantigens) using a bioinformatics tool for T cell epitope prediction. Exemplary bioinformatics tools for T cell epitope prediction are known in the art, for example, see Yang X. and Yu X. (2009) "An introduction to epitope prediction methods and software" *Rev. Med. Virol.* 19 (2): 77-96. In some embodiments, the sequence of the antigen protein is known in the art or available in public databases. In some embodiments, the sequence of the antigen protein (including neoantigens) is determined by sequencing a sample (such as a tumor sample) of the individual being treated.

In some embodiments, the antigenic polypeptide comprises a Spike(S) protein or a fragment thereof of a coronavirus, such as a SARS-COV, MERS-COV, or SARS-COV-2 virus. In some embodiments, the antigenic polypeptide is a full-length S protein. In some embodiments, the antigenic polypeptide is a fragment of a naturally occurring S protein. In some embodiments, the antigenic polypeptide comprises a Spike(S) protein or a fragment thereof of SARS-COV-2.

In some embodiments, the antigenic polypeptide comprises a variant of an S protein or fragment thereof of a coronavirus. In some embodiments, the antigenic polypeptide comprises a naturally occurring variant of an S protein or fragment thereof of a coronavirus (e.g., SARS-COV-2). Variants of the SARS-COV-2 genome have been described. See, for example, Forster et al. (2020). Phylogenetic network analysis of SARS-COV-2 genomes. PNAS 117 (17) 9241-9243, which is incorporated herein by reference in its entirety. In some embodiments, the antigenic polypeptide comprises a variant of an S protein or fragment thereof that confers a fitness advantage to a coronavirus, such as enhanced infectivity. In some embodiments, the antigenic polypeptide comprises an S protein or fragment thereof of SARS-COV-2 having a D614G mutation. In some embodiments, the antigenic polypeptide is capable of eliciting an immune response in an individual against different strains and variants of a coronavirus, such as SARS-COV-2 variants. In some embodiments, the antigenic polypeptide is capable of eliciting an immune response in an individual against a specific strain or variant of a coronavirus.

In some embodiments, the antigenic polypeptide comprises a receptor-binding domain (RBD) of an S protein of a coronavirus (e.g., SARS-COV2). In some embodiments, the RBD comprises amino acid residues 319 to 542 of a full-length S protein of SARS-COV-2, wherein the numbering is based on SEQ ID NO: 1 In some embodiments, the RBD comprises an amino acid sequence having at least about 80% (e.g., at least about 85%, 90%, 95%, 98% or more, or 100%) sequence identity to the amino acid sequence of SEQ ID NO: 2. In some embodiments, the RBD comprises an amino acid sequence having at least about 80% (e.g., at least about 85%, 90%, 95%, 98% or more, or 100%) sequence identity to the amino acid sequence of SEQ ID NO: 63.

In some embodiments, the antigenic polypeptide comprises an S2 region of an S protein of a coronavirus (e.g., SARS-COV2). In some embodiments, the S2 region comprises amino acid residues 686 to 1273 of a full-length S protein of SARS-COV-2, wherein the numbering is based on SEQ ID NO: 1. In some embodiments, the S2 region comprises an amino acid sequence having at least about 80% (e.g., at least about 85%, 90%, 95%, 98% or more, or 100%) sequence identity to the amino acid sequence of SEQ ID NO: 6. In some embodiments, the S2 region comprises one or more mutations that stabilize a pre-fusion conformation of the S protein. In some embodiments, the S2 region comprises K986P and V987P mutations. In some embodiments, the S2 region comprises an amino acid sequence having at least about 80% (e.g., at least about 85%, 90%, 95%, 98% or more, or 100%) sequence identity to the amino acid sequence of SEQ ID NO: 7.

In some embodiments, the antigenic polypeptide comprises both an RBD and an S2 region of an S protein of a coronavirus (e.g., SARS-COV2). In some embodiments, the antigenic polypeptide comprises an amino acid sequence having at least about 80% (e.g., at least about 85%, 90%, 95%, 98% or more, or 100%) sequence identity to the amino acid sequence of SEQ ID NO: 1.

In some embodiments, the antigenic polypeptide comprises a Spike(S) protein fragment of a coronavirus (e.g., SARS-COV, MERS-COV, or SARS-COV-2) and a multimerization domain, which can be operably linked to the S protein fragment. In some embodiments, the multimerization domain is a C-terminal Foldon (Fd) domain of a T4 fibritin protein that mediates trimerization of the T4 fibritin protein. In some embodiments, the multimerization domain is a GCN-4 based isoleucine zipper domain. In some embodiments, the multimerization domain comprises the amino acid sequence as set forth in SEQ ID NO: 3 or 4. In some embodiments, the multimerization domain is fused to the S protein fragment via a peptide linker. In some embodiments, the antigenic polypeptide comprises a RBD domain of an S protein fused to a multimerization domain via a peptide linker. In some embodiments, the peptide linker comprises the amino acid sequence of SEQ ID NO: 5.

In some embodiments, the antigenic polypeptide comprises a Spike(S) protein or a fragment thereof of SARS-COV-2 fused to a multimerization domain. In some embodiments, the antigenic polypeptide comprises an S protein fragment fused to a C-terminal Foldon (Fd) domain (e.g., SEQ ID NO: 3) of a T4 fibritin protein that mediates trimerization of the T4 fibritin protein (e.g., SEQ ID NO: 4). In some embodiments, the antigenic polypeptide comprises an S protein fragment fused to a GCN-4 based isoleucine zipper domain. In some embodiments, the antigenic polypeptide comprises a receptor-binding domain (RBD) of an S protein of SARS-COV-2 fused to a multimerization domain via a peptide linker. In some embodiments, the peptide linker comprises the amino acid sequence of SEQ ID NO: 5.

The antigenic polypeptide may comprise a signal peptide (SP). In some embodiments, the SP is fused to the N-terminus of the S protein or fragment thereof. In non-limiting examples, the signal peptide is the signal sequence and propeptide from human tissue plasminogen activator (tPA), the signal sequence from human IgE Immunoglobulin, or the signal peptide sequence of MHC I. In some embodiments; the signal peptide can facilitate secretion of the antigenic polypeptide encoded by the circRNA vaccine.

In some embodiments, the circRNA comprises an in-frame 2A peptide coding sequence operably linked to the 3' end of the nucleic acid sequence encoding the antigenic polypeptide. In some embodiments, the circRNA does not comprise a stop codon at the 3' end of the nucleic acid sequence encoding the antigenic polypeptide. In some embodiments, the in-frame 2A peptide coding sequence replaces the stop codon. In some embodiments, the circRNA contains no stop codon and the number of nucleotides composing the RNA is a multiple of three. In some embodiments, the circRNA having no stop codon and the number of nucleotides composing the RNA being a multiple of three allows for rolling circle translation of the circRNA. In some embodiments, the 2A peptide coding sequence allows for rolling circle translation of the circRNA. In some embodiments, the 2A peptide allows cleavage of a polypeptide generated by rolling circle translation into monomeric polypeptide sequences. In non-limiting examples, the 2A peptide coding sequence encodes a P2A or T2A peptide, such as the sequence set forth in SEQ ID NO: 44 or 45.

Also provided is a circRNA comprising a nucleic acid sequence encoding any one of the antigenic polypeptides described herein. The nucleic acid sequences encoding the antigenic polypeptides may be codon-optimized. In some embodiments, the circRNA comprises a nucleic acid sequence having at least about 80% (e.g., at least about 85%, 90%, 95%, 98% or more, or 100%) sequence identity to a nucleic acid sequence selected from the group consisting of SEQ ID NOs: 11-15 and SEQ ID NOs: 48-49.

Spike Protein or Fragment Thereof.

The circRNA vaccines described herein comprise a circRNA comprising a nucleic acid sequence encoding an antigenic polypeptide comprising a Spike(S) protein or a fragment thereof of a coronavirus (e.g., SARS-COV-2, MERS-COV, or SARS-COV). Sequences of S proteins of coronaviruses are known in the art, including, for example, NCBI RefSeq ID: YP_009047204.1 (MERS-COV), GenBank Accession number: AAT74874 (SARS-COV), or NCBI RefSeq ID: YP_009724390 (SARS-COV-2, provided as SEQ ID NO: 1 of the present application).

In some embodiments, the S protein or fragment thereof comprises amino acid residues 2-1273 of a full-length S protein of SARS-COV-2, wherein the numbering is based on SEQ ID NO: 1. In some embodiment, the S protein or fragment thereof comprises a deletion of amino acid residues 681-684. In some embodiments, the S protein or fragment thereof comprises at least one point mutation in the S2 region, for example, a K986P, V987P, F817P, A892P, A899P, or A942P mutation or combinations thereof. In some embodiments, the S protein of fragment thereof comprises at least one mutation selected from A222V, E406W, K417N, K417T, N439K, L452R, L452Q, L455N, L478K, E484K, Q493F, F490S, N501Y, A570D, D614G, P681H, A701V, T716I, S982A, or combinations thereof. In some embodiments, the S protein or fragment thereof comprises a N501Y point mutation. In some embodiments, the S protein or fragment thereof comprises K417N, E484K, and/or N501Y point mutations. In some embodiments, the S protein or fragment thereof comprises an E484K point mutation. In some embodiments, the S protein or fragment thereof comprises K417T, E484K, and N501Y point mutations. In some embodiments, the S Protein or fragment thereof of SARS-COV-2 comprises K986P and V987P point mutations, either alone or in combination with a deletion of amino acid residues 681-684. In some embodiments, the S protein or fragment thereof comprises an amino acid sequence set forth in any one of SEQ ID NO: 1-2, SEQ ID NO: 6-10, or SEQ ID NO: 63. In some embodiments, the S protein or fragment thereof comprises an amino acid sequence set forth SEQ ID NO: 2. In some embodiments, the S protein or fragment thereof comprises an amino acid sequence set forth SEQ ID NO: 63.

In some embodiments, the S protein or fragment thereof is an Alpha (B.1.1.7), Beta (B.1.351, B.1.351.2, B.1.351.3), Delta (B.1.617.2, AY.1, AY.2, AY.3), or Gamma (P.1, P.1.1, P.1.2) S protein or fragment thereof. In some embodiments, the S protein or fragment thereof comprises two, three, four, five, or more mutations selected from the group consisting of T19R, V70F, T95I, G142D, E156-, F157-, R158G, A222V, W258L, K417N, LA52R, T478K, D614G, P681R, and D950N, wherein the amino acid numbering is based on SEQ ID NO. 1. In some embodiments, the S protein or fragment thereof comprises an RBD comprising the S protein or fragment thereof comprises one, two, or three of the or more mutations selected from the group K417N, L452R, and T478K, wherein the amino acid numbering is based on SEQ ID NO: 1. In some embodiments, the S protein or fragment thereof comprises two, three, four, five, or more mutations selected from the group consisting of residue 69 deletion, residue 70 deletion, residue 144 deletion, E484K, S494P, N501Y, A570D, D614G, P681H, T716I, S982A, D1118H, and K1191N, wherein the amino acid numbering is based on SEQ ID NO: 1. In some embodiments, the S protein or fragment thereof comprises an RBD domain comprising one, two, or three of the mutations selected from the group consisting of E484K, S494P, and N501Y, wherein the amino acid numbering is based on SEQ ID NO: 1. In some embodiments, the S protein or fragment thereof comprises one, two, three, four, five, or more mutations selected from the group consisting of D80A, D215G, 241del, 242del, 243del, K417N, E484K, N501Y, D614G, and A701V, wherein the amino acid numbering is based on SEQ ID NO: 1. In some embodiments, the S protein or fragment thereof comprises an RBD comprising one, two, or three of the mutations selected from the group consisting of K417N, E484K, and N501Y, wherein the amino acid numbering is based on SEQ ID NO: 1. In some embodiments, the S protein or fragment thereof comprises one, two, three, four, five, or more mutations selected from the group consisting of L18F, T20N, P26S, D138Y, R190S, K417T, E484K, N501Y, D614G, H655Y, and T1027I, wherein the amino acid numbering is based on SEQ ID NO: 1. In some embodiments, the S protein or fragment thereof comprises an RBD domain comprising one, two, or three of the mutations selected from the group consisting of K417T, E484K, and N501Y, wherein the amino acid numbering is based on SEQ ID NO. 1. In some embodiments, the S protein or fragment thereof comprises an RBD domain comprising one, two, or three of the mutations selected from the group consisting of E484K, N501Y, and L452R mutations, wherein the amino acid numbering is based on SEQ ID. NO: 1.

In some embodiments, the S protein or fragment thereof comprises an N-terminal domain (NTD) of an S protein of a coronavirus (e.g., SARS-COV-2, MERS-COV, or SARS-COV).

In some embodiments, the S protein or fragment thereof comprises an amino acid sequence having about 80%, at least 85%, at least about 90%, at least about 95%, at least about 98% or more sequence identity to a wild-type S protein or a fragment thereof of a coronavirus, or with any one of the sequences set forth in SEQ ID NOs: 1-2, SEQ ID NOs: 6-10, and SEQ ID NOs: 62-63.

RBD Domain

In some embodiments, the S protein or fragment thereof comprises a receptor-binding domain (RBD) of the S protein: In some embodiments, the RBD comprises amino acid residues 319 to 542 of a full-length S protein of SARS-COV-2, wherein the numbering is based on SEQ ID NO: 1 In some embodiments, the RBD comprises the amino acid sequence of SEQ ID NO: 2. In some embodiments, the RBD comprises a sequence having about 80%, at least 85%, at least about 90%, at least about 95%, at least about 98% or more sequence identity with the amino acid sequence of SEQ ID NO: 2. In some embodiments, the RBD comprises a sequence having about 80%, at least 85%, at least about 90%, at least about 95%, at least about 98% or more sequence identity with the amino acid sequence of SEQ ID NO: 63. In some embodiments, the RBD is linked to a multimerization domain. In some embodiments, the RBD is fused to a multimerization domain by a flexible peptide linker.

S2 Region

In some embodiments, the S protein or fragment thereof comprises an S2 region of the S protein. In some embodiments, the S2 region comprises amino acid residues 686 to 1273 of a full-length S protein of SARS-COV-2, wherein the numbering is based on SEQ ID NO: 1. In some embodiments, the S2 region comprises the amino acid sequence of SEQ ID NO: 6. In some embodiments, the S2 region comprises one or more mutations that stabilize a pre-fusion conformation of the S protein. In some embodiments, the S2 region comprises K986P and V987P mutations, for example, as in the sequence set forth in SEQ ID NO: 7. In some embodiments, the S2 region comprises a single point mutation, for example, a K986P, V987P, F817P, A892P, A899P or A942P mutation. In some embodiments, the S2 region comprises a combination of point mutations including K986P, V987P, F817P, A892P, A899P or A942P. In some embodiments, the S2 region comprises the wild type sequence of an S protein of a coronavirus, such as the sequence of SEQ ID NO: 6, or a sequence having about 80%, at least 85%, at least about 90%, at least about 95%, at least about 98% or more sequence identity with the amino acid sequence of SEQ ID NO: 6.

Multimerization Domain

In some embodiments, the antigenic polypeptide further comprises a multimerization domain, such as a dimerization domain, a trimerization domain, or a domain that mediates formation of higher order multimers. In some embodiments, the multimerization domain is a trimerization domain. In non-limiting examples, the multimerization domain comprises a C-terminal Foldon (Fd) domain of a T4 fibritin protein, wherein the C-terminal Foldon domain is the domain that mediates trimerization of the T4 fibritin protein, such as the amino acid sequence set forth in SEQ ID NO: 3. In another example, the multimerization domain comprises a GCN4-based isoleucine zipper (IZ) domain based on the trimerization domain of the GCN4 transcriptional activator from *Saccharomyces cerevisiae*, such as the amino acid sequence set forth in SEQ ID NO: 4. In some embodiments, the multimerization domain has about 80%, at least 85%, at least about 90%, at least about 95%, at least about 98% or more sequence identity with the amino acid sequence of SEQ ID NO: 3 or SEQ ID NO: 4. In some embodiments, the GCN4 IZ domain or T4 fibritin Fd domain can be modified to reduce their immunogenicity according to known techniques in the art. For example, the GCN4.IZ domain can be modified with N-linked glycosylation sites to reduce its immunogenicity (Sliepen et al. Immunosilencing a Highly Immunogenic Protein Trimerization Domain. The Journal of Biol. Chem. Vol. 290, No. 12, pp. 7436-7442). In some embodiments, the multimerization domain is fused to the N-terminus of the S protein or fragment thereof. In some embodiments, the multimerization domain is fused to the C-terminus of the S protein or fragment thereof.

ii. Targeting Proteins

In some embodiments, the therapeutic polypeptide is a targeting protein. In some embodiments, the targeting protein is an antibody or an antigen-binding fragment thereof.

In some embodiments, the therapeutic polypeptide is an antibody. In some embodiments, the therapeutic polypeptide is a neutralizing antibody, i.e., an antibody that blocks an interaction between a protein and its binding partner. In some embodiments, the antibody inhibits activity of a protein, e.g., by blocking binding of the protein to a binding partner. In some embodiments, the targeting protein is a therapeutic antibody. In some embodiments, the antibody is a checkpoint inhibitor, e.g., an antibody inhibitor of CTLA-4, PD-1, or PD-L1. In some embodiments, the antibody can be an antibody against a viral protein or a receptor that binds to a viral protein.

The antibody can be an antigen-binding fragment of an antibody, e.g., a portion or fragment of an intact or complete antibody having fewer amino acid residues than the intact or complete antibody, which is capable of binding to an antigen or competing with the intact antibody (i.e., the intact antibody from which the antigen-binding fragment is derived) for binding to an antigen. Antigen-binding fragments can be prepared by recombinant DNA techniques, or by enzymatic or chemical cleavage of intact antibodies. Antigen binding fragments include, but are not limited to, Fab', F(ab')2Fv, single chain Fv (scFv), single chain Fab, diabody (diabody), single domain antibody (sdAb, nanobody), camel Ig, Ig NAR, F(ab)'3Fragment, bis-scFv, (scFv)2Minibodies, diabodies, triabodies, tetradiabodies, disulfide stabilized Fv proteins ("dsFv"). In some embodiments, the neutralizing antibody can be a genetically engineered antibody, such as a chimeric antibody (e.g., humanized murine antibodies), heteroconjugate antibody (e.g., bispecific antibodies), or antigen-binding fragments thereof.

In some embodiments, the antibody is a neutralizing antibody that binds to a viral protein. In some embodiments, the antibody is a neutralizing antibody that binds to a receptor for a viral protein. In some embodiments, the antibody binds to a receptor that is required for viral entry into a cell (e.g., an ACE2 receptor). In some embodiments, the antibody is a neutralizing antibody (nAb) that binds to the S protein of a coronavirus and prevents or reduces its ability to infect cells. In some embodiments, the coronavirus is SARS-COV-2. In some embodiments the nAb is a monoclonal antibody (mAb), a functional antigen-binding fragment (Fab), a single-chain variable region fragment (scFv), or a single-domain antibody (a VHH or nanobody).

In some embodiments the nAb binds to the RBD of a S protein of a coronavirus. In some embodiments, the nAb binds to the NTD of a S protein of a coronavirus. In some embodiments, the nAB binds to the S2 region of a S protein of a coronavirus. In some embodiments, the nAb binds the S1/S2 proteolytic cleavage site of a S protein of a coronavirus. In some embodiments, the coronavirus is SARS-COV-2. In some embodiments, binding of the nAb to the S protein interferes with interaction of the RBD of the S protein with an ACE2 receptor. In some embodiments the nAb binds to the ACE2 binding site of the RBD. In some embodiments, binding of the nAb to the S protein interferes with S2-mediated membrane fusion. In some embodiments, binding of the nAb to the S protein interferes with viral entry into the host cell.

In some embodiments, the nAb binds to a S protein comprising one or more mutations. In some embodiments, the nAb binds to a S protein or fragment thereof that comprises at least one point mutation in the S2 region, for example, a K986P, V987P, F817P, A892P, A899P or A942P mutation or combinations thereof. In some embodiments, the nAb binds to a S protein or fragment thereof that comprises at least one point mutation selected from A222V, E406W, K417N, K417T, N439K, L452R, L452Q, L455N, L478K, E484K, Q493F, F490S, N501Y, A570D, D614G, P681H, A701V, T716I, S982A, or combinations thereof. In some embodiments, the nAb binds to a S protein or fragment thereof that comprises a N501Y point mutation. In some embodiments, the nAb binds to a S protein or fragment thereof that comprises K417N, E484K, and N501Y point mutations. In some embodiments, the nAb binds to a S protein or fragment thereof that comprises an E484K point mutation. In some embodiments, the nAb binds to a S protein or fragment thereof that comprises K417T, E484K, and N501Y point mutations. In some embodiments, the nAb binds to a S Protein or fragment thereof of SARS-COV-2 that comprises K986P and V987P point mutations, either alone or in combination with a deletion of amino acid residues 681-684. In some embodiments, binding of the nAb to an S protein having any of the combinations of mutations described above (e.g., K417N, K417T, E484K, and/or N501Y) interferes with interaction of the RBD of the S protein with an ACE2 receptor. In some embodiments, binding of the nAb to an S protein any of the combinations of mutations described above (e.g., K417N, K417T, E484K, and/or N501Y) interferes with S2-mediated membrane fusion. In some embodiments, binding of the nAb to an S protein any of the combinations of mutations described above (e.g., K417N, K417T, E484K, and/or N501Y) interferes with viral entry into the host cell.

Exemplary nAbs for binding and neutralization of the S protein of SARS-COV-2 have been described, for example, in Barnes, C.O. et al. SARS-COV-2 neutralizing antibody structures inform therapeutic strategies. Nature 588, 682-687 (2020), and Chinese Patent Application No. CN111690058A, the contents of which are herein incorporated by reference in their entirety.

In some embodiments, the nAb comprises a sequence selected from SEQ ID NOs: 26-33. In some embodiments, the nAb comprises a sequence having at least 80% (e.g., at least 85%, at least 90%, at least 91%, at least 92%, at least 93%, at least 94%, at least 95%, at least 96%, at least 97%, or at least 99%) amino acid sequence identity to a sequence selected from SEQ ID NOs: 26-33.

In some embodiments, the antibody is an antibody against the S protein of SARS-COV-2. In some embodiments, the antibody comprises a sequence having at least 80% (e.g., at least 85%, at least 90%, at least 91%, at least 92%, at least 93%, at least 94%, at least 95%, at least 96%, at least 97%, or at least 99%, or 100%) amino acid sequence identity to SEQ ID NO: 26. In some embodiments, the antibody comprises a sequence having at least 80% (e.g., at least 85%, at least 90%, at least 91%, at least 92%, at least 93%, at least 94%, at least 95%, at least 96%, at least 97%, or at least 99%, or 100%) amino acid sequence identity to SEQ ID NO: 27. In some embodiments, the antibody comprises a sequence having at least 80% (e.g., at least 85%, at least 90%, at least 91%, at least 92%, at least 93%, at least 94%, at least 95%, at least 96%, at least 97%, or at least 99%, or 100%) amino acid sequence identity to SEQ ID NO: 30.

In some embodiments, the targeting protein is not an antibody. Examples of non-antibody-based targeting proteins include, but are not limited to, a lipocalin, an anticalin (artificial antibody mimetic proteins that are derived from human lipocalins), "T-body", a peptide (e.g., a BICYCLE™ peptide), an affibody (antibody mimetics composed of alpha helices, e.g. an three-helix bundle), a peptibody (peptide-Fc fusion), a DARPin (designd ankyrin repeat proteins, engineered antibody mimetic proteins consisting repeat motifs), an affimer, an avimer, a knottin (a protein structural motif containing 3 disulfide bridges), a monobody, an affinity clamp, an ectodomain, a receptor ectodomain, a receptor, a cytokine, a ligand, an immunocytokine, and a centryin. See, for example, Vazquez-Lombardi, Rodrigo, et al. Drug discovery today 20.10 (2015): 1271-1283.

iii. Soluble Receptors

In some embodiments, the therapeutic polypeptide is a soluble receptor. Soluble receptors (sometimes referred to as soluble receptor decoys or "traps") can comprise all or a portion of the extracellular domain of a receptor protein. In some embodiments, a nucleotide sequence encoding all or a portion of the extracellular domain of a receptor protein is operably linked to a signal peptide for secretion from cells.

In some embodiments, the soluble receptor comprises an extracellular domain of a naturally occurring receptor. In some embodiments, the soluble receptor variant comprises an engineered variant of an extracellular domain of a naturally occurring receptor, such as a variant comprising one or more mutations in the extracellular domain. In some embodiments, the soluble receptor comprises one or more mutations that increase the affinity of the soluble receptor for its ligand compared to the affinity of the naturally occurring receptor for its ligand.

In some embodiments, the soluble receptor is a fusion protein comprising one or more additional protein domains operably linked to the extracellular domain of the receptor or a variant thereof. In some embodiments, the soluble receptor comprises an Fc domain of an immunoglobulin (Ig), e.g., a human immunoglobulin. In some embodiments, the soluble receptor comprises an Fc domain of a human IgG1.

In some embodiments, the soluble receptor comprises the extracellular domain of a signaling receptor, and the soluble receptor can reduce or inhibit activity of the signaling pathway by blocking binding between the endogenous receptor and its ligand.

In some embodiments, the soluble receptor is a receptor that binds to a viral protein and/or that mediates viral entry. In some embodiments, soluble receptor is a soluble ACE2 receptor. In some embodiments, the therapeutic polypeptide is a soluble ACE2 receptor variant capable of binding to a S protein of a coronavirus. In some embodiments, the soluble ACE2 can have a great advantage over antibodies due to resistance to escape mutations. The virus with escape mutation from sACE2 should have limited binding affinity to cell surface native ACE2 receptors, leading to a diminished or eliminated virulence.

In some embodiments, the ACE2 receptor fragment is engineered to have higher affinity to a S protein of a coronavirus. In some embodiments, the soluble ACE2 receptor variant is capable of binding to a S protein of a coronavirus and blocking or reducing binding of the S protein to an endogenous ACE2 receptor. In some embodiments, the soluble ACE2 receptor variant binds to the receptor binding domain (RBD) of the S protein. In some embodiments, the ACE2 receptor variant is enzymatically active. In other embodiments, the ACE2 receptor variant is enzymatically inactive.

In some embodiments, the soluble ACE2 receptor variant comprises the soluble extracellular domain of wild-type (WT) human recombinant ACE2 (APN01). APNO1 has been found to be safe in healthy volunteers and in a small cohort of patients with acute respiratory distress syndrome by virtue of ACE2's intrinsic angiotensin-converting activity, which is not required for viral entry. APNO1 is currently in phase 2 clinical trials in Europe for treatment of SARS-COV-2 (NCT04335136). In some embodiments, the soluble ACE2 receptor variant comprises one or more mutations in the extracellular domain of human ACE2. In some embodiments, the soluble ACE2 receptor variant is engineered via affinity maturation to have increased binding affinity to the RBD of the S protein. For example, a nucleotide sequence encoding a wild-type extracellular domain of ACE2 may be subjected to one or more cycles of random mutation and cell sorting to identify ACE2 variants having a higher affinity for the RBD of the S protein wild-type ACE2.

In some embodiments, the soluble ACE2 receptor variant comprises a sequence having at least 80% (e.g., at least 85%, at least 90%, at least 91%, at least 92%, at least 93%, at least 94%, at least 95%, at least 96%, at least 97%, or at least 99%, or 100%) amino acid sequence identity to SEQ ID NO: 34 or 35.

In some embodiments, the soluble ACE2 receptor variant is a fusion protein, e.g., a fusion of the extracellular ACE2 receptor domain to the Fc region of the human IgG1.

In some embodiments, the $K_D$ of the soluble ACE2 receptor variant for the RBD of the S protein is about 15-20 nM. In some embodiments, the $K_D$ of the soluble ACE2 receptor variant for the RBD of the S protein is less than 15 nM, less than 10 nM, less than 5 nM, less than 1 nM, less than 500 pM, less than 250 pM, less than 200 pM, or less than 150 pM.

Soluble ACE2 receptor variants have been described, for example in Haschke M et al., Clin Pharmacokinet. 2013 Sep; 52 (9): 783-92; Glasgow A et al., Proceedings of the National Academy of Sciences November 2020, 117 (45) 28046-28055; and Higuchi Y. et al., bioRxiv 2020. 09.16.299891, the contents of which are herein incorporated by reference in their entirety.

iv. Functional Proteins

In some embodiments, the therapeutic polypeptide can be any polypeptide that is capable of being expressed by target cells (e.g., human or mouse cells) for the production (and in certain instances, the excretion) of a functional enzyme or protein as disclosed, for example, in International Application No. PCT/US2010/058457 and WO2020237227, the contents of which are herein incorporated by reference in their entirety. In some embodiments, the therapeutic polypeptide can be engineered for secretion by operably linking a signal peptide to the amino terminus of the therapeutic polypeptide. For example, in some embodiments, upon the expression of one or more therapeutic polynucleotides by target cells, the production of a functional enzyme or protein in which a subject is deficient (e.g., a urea cycle enzyme or an enzyme associated with a lysosomal storage disorder) may be observed.

In some embodiments, the therapeutic polypeptide comprises a protein such as IDUA, OTC, FAH, miniDMD, DMD, p53, PTEN, COL3A1, BMPR2, AHI1, FANCC, MYBPC3, ILRG2, or ARG1, wherein deficiency of functional protein is associated with a disease or disorder.

In some embodiments, the therapeutic polypeptide comprises a protein (e.g., a lysosomal enzyme) wherein deficiency of the protein is associated with a lysosomal storage disorder.

In some embodiments, the therapeutic polypeptide comprises a protein (e.g., an enzyme), wherein deficiency of the protein is associated with a metabolic disorder. In some embodiments, the therapeutic polypeptide comprises a urea cycle enzyme (e.g., ARG1).

In some embodiments, the therapeutic polypeptide comprises a protein (e.g., p53 or PTEN), wherein deficiency of the protein is associated with a cancer. In some embodiments, the therapeutic polypeptide comprises a tumor suppressor.

In some embodiments, the therapeutic polypeptide comprises an amino acid sequence having at least about 80% (e.g., at least about 85%, 90%, 95%, 98%, or more, or 100%) to the amino acid sequence of a wildtype mouse IDUA protein (e.g., SEQ ID NO: 18).

In some embodiments, the therapeutic polypeptide comprises an amino acid sequence having at least about 80% (e.g., at least about 85%, 90%, 95%, 98%, or more, or 100%) to the amino acid sequence of a wildtype human IDUA protein (e.g., SEQ ID NO: 19).

In some embodiments, the therapeutic polypeptide comprises an amino acid sequence having at least about 80% (e.g., at least about 85%, 90%, 95%, 98%, or more, or 100%) to the amino acid sequence of a wildtype mouse OTC protein (e.g., SEQ ID NO: 20).

In some embodiments, the therapeutic polypeptide comprises an amino acid sequence having at least about 80% (e.g., at least about 85%, 90%, 95%, 98%, or more, or 100%) to the amino acid sequence of a wildtype mouse FAH protein (e.g., SEQ ID NO: 21).

In some embodiments, the therapeutic polypeptide comprises an amino acid sequence having at least about 80% (e.g., at least about 85%, 90%, 95%, 98%, or more, or 100%) to the amino acid sequence of a human miniDMD protein (e.g., SEQ ID NO: 22).

In some embodiments, the therapeutic polypeptide comprises an amino acid sequence having at least about 80% (e.g., at least about 85%, 90%, 95%, 98%, or more, or 100%) to the amino acid sequence of a wildtype human DMD protein (e.g., SEQ ID NO: 23).

In some embodiments, the therapeutic polypeptide comprises an amino acid sequence having at least about 80% (e.g., at least about 85%, 90%, 95%, 98%, or more, or 100%) to the amino acid sequence of a wildtype human p53 protein (e.g., SEQ ID NO: 24).

In some embodiments, the therapeutic polypeptide comprises an amino acid sequence having at least about 80% (e.g., at least about 85%, 90%, 95%, 98%, or more, or 100%) to the amino acid sequence of a wildtype human PTEN protein (e.g., SEQ ID NO: 25).

In some embodiments, the therapeutic polypeptide comprises an amino acid sequence having at least about 80% (e.g., at least about 85%, 90%, 95%, 98%, or more, or 100%) to the amino acid sequence of a wildtype human COL3A1 protein (e.g., SEQ ID NO: 56).

In some embodiments, the therapeutic polypeptide comprises an amino acid sequence having at least about 80% (e.g., at least about 85%, 90%, 95%, 98%, or more, or 100%) to the amino acid sequence of a wildtype human BMPR2 protein (e.g., SEQ ID NO: 57).

In some embodiments, the therapeutic polypeptide comprises an amino acid sequence having at least about 80% (e.g., at least about 85%, 90%, 95%, 98%, or more, or 100%) to the amino acid sequence of a wildtype human AHI1 protein (e.g., SEQ ID NO: 58).

In some embodiments, the therapeutic polypeptide comprises an amino acid sequence having at least about 80% (e.g., at least about 85%, 90%, 95%, 98%, or more, or 100%) to the amino acid sequence of a wildtype human FANCC protein (e.g., SEQ ID NO: 59).

In some embodiments, the therapeutic polypeptide comprises an amino acid sequence having at least about 80% (e.g.; at least about 85%, 90%, 95%, 98%, or more, or 100%) to the amino acid sequence of a wildtype human MYBPC3 protein (e.g., SEQ ID NO: 60).

In some embodiments, the therapeutic polypeptide comprises an amino acid sequence having at least about 80% (e.g., at least about 85%, 90%, 95%, 98%, or more, or 100%) to the amino acid sequence of a wildtype human ILRG2 protein (e.g., SEQ ID NO: 61).

In some embodiments, the therapeutic polypeptide comprises an amino acid sequence having at least about 80% (e.g., at least about 85%, 90%, 95%, 98%, or more, or 100%) to the amino acid sequence of a wildtype human OTC protein (e.g., SEQ ID NO: 55).

In some embodiments, the therapeutic polypeptide comprises an amino acid sequence having at least about 80% (e.g., at least about 85%, 90%, 95%, 98%, or more, or 100%) to the amino acid sequence of a wildtype human FAH protein (e.g., SEQ ID NO: 54).

v. Peptide Linker

In some embodiments, the various domains in the therapeutic polypeptide (e.g., the various domains of a Spike protein or fragment thereof) may be fused to each other or comprises domains (e.g., an antigenic polypeptide domain and a carrier protein or a multimerization domain) that are fused to each other via a peptide linker. In some embodiments, the antigenic polypeptide a domain of an S protein of a coronavirus fused to a multimerization domain via a peptide linker. Flexible peptide linkers such as glycine linkers, glycine-serine linkers, and linkers containing other amino acids are known in the art (for example, suitable peptide linkers are described by Chen et al. in Fusion Protein Linkers: Property, Design and Functionality. Adv. Drug Deli Rev. 2013 Oct. 15; 65 (10): 1357-1369). Peptide linkers can also be designed by computation methods. The peptide linker can be of any length from 1 to 10, 10 to 20, 20 to 30, 30 to 40, 40 to 50, or greater than 50 amino acids. In some embodiments, the peptide linker comprises the amino acid sequence of SEQ ID NO: 5.

B. Additional circRNA Expression and Circularization Elements

The circRNAs of the circRNA vaccines described herein comprise one or more additional expression elements that facilitate expression and/or circularization of the circRNA.

In some embodiments, the circRNA comprises a Kozak sequence operably linked to a nucleic acid sequence encoding an antigenic polypeptide comprising a Spike(S) protein or a fragment thereof of a coronavirus (e.g., SARS-COV-2). In some embodiments, the Kozak sequence functions as a protein translation initiation site.

In some embodiments, the circRNA comprises a nucleic acid sequence encoding an antigenic polypeptide comprising a Spike(S) protein or a fragment thereof of a coronavirus (e.g., SARS-COV-2), which is operably linked to an internal ribosomal entry site (IRES). In non-limiting examples, the IRES sequence can be a CVB3 virus, EV71 virus, EMCV virus, PV virus, or a CSFV virus IRES sequence. See, for example, Searching for IRES. RNA. 2006 October; 12 (10): 1755-1785, which is incorporated herein by reference in its entirety. In some embodiments, the IRES sequence is a cellular IRES sequence. In some embodiments, the IRES sequence is followed by a Kozak sequence operably linked to the nucleic acid sequence encoding the antigenic polypeptide. In some embodiments, the circRNA further comprises a polyA or polyAC sequence disposed at the 5' end of the IRES sequence.

In some embodiments, a polyA sequence or polyAC spacer is disposed at the 5' end of an IRES. In some embodiments, the polyA or polyAC sequence is disposed between the 5' end of the IRES and the exon-exon splice junction. The internal polyA sequence or polyAC spacer may range from 1 to 500 nucleotides in length (e.g., at least 20, 30, 40, 50, 60, 70, 80, 90, 120, 140, 160, 180, 200, 250, 300, 350, 400, 450, or 500 nucleotides). In some embodiments, the polyA sequence or polyAC sequence may range from 10-70, 20-60, or 30-60 nucleotides in length. In some embodiments, the circRNA comprises the polyAC sequence set forth in SEQ ID NO: 37 disposed at the 5' end of the IRES sequence. In some embodiments, no polyA sequence or polyAC sequence is disposed at the 5' end of the IRES sequence. Without being bound by any theory or hypothesis, an internal polyA sequence or a polyAC spacer added before IRES sequences can help to keep the functional second structure of IRES elements for efficient protein translation initiated by IRES. In some embodiments, the polyA sequence or polyAC spacer increases expression of the RNA construct.

In some embodiments, the circRNA comprises a nucleic acid sequence encoding an antigenic polypeptide comprising a Spike(S) protein or a fragment thereof of a coronavirus (e.g., SARS-COV-2), which is operably linked to an m6A ($N^6$-methyladenosine) modification motif sequence. The m6A modification sequence can comprise an m6A consensus sequence. M6A consensus sequences are known in the art (for example, consensus sequences identified by Ke et al., 2017 ($m^6A$ mRNA modifications are deposited in nascent pre-mRNA and are not required for splicing but do specify cytoplasmic turnover. Genes & Dev. 2017. 31:990-1006) and available for download from GEO (GSE86336). In some embodiments, the m6A modification motif sequence comprises the sequence set forth in SEQ ID NO: 38. In some embodiments, the m6A modification motif sequence is followed by a Kozak sequence operably linked to the nucleic acid sequence encoding the antigenic polypeptide.

In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence recognizable by a 3' catalytic Group I intron fragment comprises the nucleic acid sequence of SEQ ID NO: 39. In some embodiments, the 5' exon sequence recognizable by a 5' catalytic Group I intron fragment comprises the nucleic acid sequence of SEQ ID NO: 40. In some embodiments, the 3' catalytic Group I intron fragment comprises the nucleic acid sequence of SEQ ID NO: 46, and the 5' catalytic Group I intron fragment sequence comprises the nucleic acid sequence of SEQ ID NO: 47.

In some embodiments, the Group I catalytic intron of the T4 phage Td gene is bisected in such a way to preserve structural elements critical for ribozyme folding. Exon fragment 2 is then ligated upstream of exon fragment 1, and a nucleic acid sequence comprising a sequence encoding the antigenic polypeptide comprising a Spike(S) protein or fragment thereof of a coronavirus is inserted between the exon-exon junction. In some embodiments, the sequence comprising an IRES or m6A sequence, a Kozak sequence, a signal peptide encoding sequence, an antigenic polypeptide comprising an S protein or fragment thereof of a coronavirus, and a stop codon or in-frame 2A peptide sequence is inserted between the exon-exon junction.

In some embodiments, the circRNA comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase).

C. Exemplary Therapeutic circRNAs i. Exemplary circRNAs for Expression of a Therapeutic Polypeptide

In some embodiments, the present application provides a circular RNA (circRNA) comprising a nucleic acid sequence encoding a therapeutic polypeptide (e.g., any of the therapeutic polypeptides described in Section A above) and further comprising an internal ribosomal entry site (IRES) sequence or an m6A modification motif sequence, wherein the IRES or m6A modification motif sequence is operably linked to the nucleic acid sequence encoding the therapeutic polypeptide. In some embodiments, the IRES sequence is a CVB3 virus, EV71 virus, EMCV virus, PV virus, or a CSFV virus IRES sequence. In some embodiments, the nucleic acid sequence further encodes a signal peptide (SP) fused to the N-terminus of the therapeutic polypeptide (e.g., an antigenic polypeptide, soluble receptor, or antibody). In non-limiting examples, the signal peptide is human tissue plasminogen activator (tPA) or IgE signal peptide. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding the therapeutic polypeptide, and a 5' exon sequence recognizable by a 5' catalytic Group I intron fragment flanking the 3' end of the nucleic acid sequence encoding the therapeutic polypeptide. In some embodiments, the 3' exon sequence comprises the nucleic acid sequence of SEQ ID NO: 39. In some embodiments, the 5' exon sequence comprises the nucleic acid sequence of SEQ ID NO: 40. In some embodiments, the 3' exon sequence comprises the nucleic acid sequence of SEQ ID NO: 39, and the 5' exon sequence comprises the nucleic acid sequence of SEQ ID NO: 40.

In some embodiments, the present application provides a circular RNA (circRNA) comprising a nucleic acid sequence, the nucleic acid sequence comprising from the 5' end to the 3' end: an m6A modification motif sequence, a Kozak sequence, a nucleic acid sequence encoding a therapeutic polypeptide. In some embodiments, the circRNA further comprises an in-frame 2A peptide coding sequence operably linked to the 3' end of the nucleic acid sequence encoding the therapeutic polypeptide. In some embodiments, the circRNA further comprises a 3' exon sequence recognizable by a 3' catalytic Group I intron fragment flanking the 5' end of the nucleic acid sequence encoding the therapeutic polypeptide, and a 5' exon sequence recognizable by a 5' catalytic Group I intron fragment flanking the 3' end of the nucleic acid sequence encoding the therapeutic polypeptide.

In some embodiments, the present application provides a circular RNA (circRNA) comprising a nucleic acid sequence, the nucleic acid sequence comprising from the 5' end to the 3' end: an internal ribosomal entry site (IRES) sequence, a Kozak sequence, and a nucleic acid sequence encoding a therapeutic polypeptide. In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the therapeutic polypeptide, and a 5' exon sequence recognizable by a 5' catalytic Group I intron fragment flanking the 3' end of the nucleic acid sequence encoding the therapeutic polypeptide.

In some embodiments, the present application provides a circular RNA (circRNA) comprising a nucleic acid sequence encoding a therapeutic polypeptide, further comprising an in-frame 2A peptide coding sequence operably linked to the 3' end of the nucleic acid sequence encoding the therapeutic polypeptide (e.g., instead of a stop codon). In some embodiments, the circRNA further comprises an internal ribosomal entry site (IRES) sequence or an m6A modification motif sequence operably linked to the nucleic acid sequence encoding the therapeutic polypeptide. In some embodiments, the nucleic acid sequence further encodes a SP (e.g., human tPA or IgE SP) fused to the N-terminus of the therapeutic polypeptide for secretion of the therapeutic polypeptide.

In some embodiments, the present application provides a circular RNA (circRNA) comprising a nucleic acid sequence, the nucleic acid sequence comprising from the 5' end to the 3' end: an internal ribosomal entry site (IRES) sequence or an m6A modification motif sequence, a Kozak sequence, a nucleic acid sequence encoding a therapeutic polypeptide, and an in-frame 2A peptide coding sequence. In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the therapeutic polypeptide, and a 5' exon sequence recognizable by a 5' catalytic Group I intron fragment flanking the 3' end of the nucleic acid sequence encoding the therapeutic polypeptide.

ii. Exemplary circRNA Vaccines

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., SARS-CoV2), and further comprising an internal ribosomal entry site (IRES) sequence or an m6A modification motif sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof. In non-limiting examples, the signal peptide is human tissue plasminogen activator (tPA) or IgE signal peptide. In some embodiments, the circRNA further comprises a polyA or polyAC sequence disposed at the 5' end of an IRES sequence.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., SARS-CoV-2), and an internal ribosomal entry site (IRES) sequence or an m6A modification motif sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof. In non-limiting examples, the signal peptide is human tissue plasminogen activator (tPA) or IgE signal peptide. In some embodiments, the circRNA further comprises a polyA or polyAC sequence disposed at the 5' end of an IRES sequence.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., SARS-CoV-2), and further comprising an internal ribosomal entry site (IRES) or m6A modification motif sequence, and a Kozak sequence operably linked to the nucleic acid sequence encoding the antigenic polypeptide. In some embodiments, the nucleic acid sequence further encodes a signal peptide (SP) fused to the N-terminus of the S protein or fragment thereof. In some embodiments, the signal peptide is, for example, human tissue plasminogen activator (tPA) or IgE signal peptide. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence comprises the nucleic acid sequence of SEQ ID NO: 39. In some embodiments, the 5' exon sequence comprises the nucleic acid sequence of SEQ ID NO: 40. In some embodiments, the 3' exon sequence comprises the nucleic acid sequence of SEQ ID NO: 39, and the 5' exon sequence comprises the nucleic acid sequence of SEQ ID NO: 40.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), and a nucleic acid sequence encoding an antigenic polypeptide comprising a Spike(S) protein or a fragment thereof of a coronavirus (e.g., SARS-COV-2). In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: an m6A modification motif sequence, a Kozak sequence, a nucleic acid sequence encoding a signal peptide (SP), and a nucleic acid sequence encoding an antigenic polypeptide comprising a Spike(S) protein or a fragment thereof of a coronavirus (e.g., SARS-COV-2). In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) of a Spike(S) protein of a coronavirus (e.g., SARS-COV-2) and a multimerization domain (e.g., C-terminal domain of a T4 fibritin protein that mediates trimerization of the T4 fibritin protein). In some embodiments, the circRNA further comprises an internal ribosomal entry site (IRES) sequence or an m6A modification sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof (e.g., human tPA or IgE signal peptide). In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) of a Spike(S) protein of a coronavirus (e.g., derived from the wild type or B.1.351/501Y.V2 variant of SARS-COV-2) and a multimerization domain (e.g., C-terminal domain of a T4 fibritin protein that mediates trimerization of the T4 fibritin protein). In some embodiments, the circRNA further comprises an internal ribosomal entry site (IRES) sequence or an m6A modification sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof (e.g., human tPA or IgE signal peptide). In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments the RBD domain has at least 90% (e.g., at least 95%, 96%, 97%, 98%, 99%) sequence identity to the amino acid sequence of SEQ ID NO: 2. In some embodiments, the RBD domain comprises the amino acid sequence of SEQ ID NO: 2. In some embodiments the RBD domain has at least 90% (e.g., at least 95%, 96%, 97%, 98%, 99%) sequence identity to the amino acid sequence of SEQ ID NO: 63. In some embodiments, the RBD domain comprises the amino acid sequence of SEQ ID NO: 63.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), and a nucleic acid sequence encoding an antigenic polypeptide comprising a receptor-binding domain (RBD) of a Spike(S) protein of a coronavirus (e.g., derived from the wild type SARS-COV-2 or a variant such as the B.1.351 or B.1.617.2 variant of SARS-COV-2). In some embodiments, the IRES sequence is a CVB3 virus, EV71 virus, EMCV virus, PV virus, or a CSFV virus IRES sequence. In some embodiments, the circRNA further comprises a polyAC sequence disposed at the 5' end of the IRES sequence. In some embodiments, the circRNA further comprises the polyAC sequence set forth in SEQ ID NO: 37 disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence comprises the nucleic acid sequence of SEQ ID NO: 39. In some embodiments, the 5' exon sequence comprises the nucleic acid sequence of SEQ ID NO: 40. In some embodiments, the 3' exon comprises the nucleic acid sequence of SEQ ID NO: 39, and the 5' exon sequence comprises the nucleic acid sequence of SEQ ID NO: 40.

In some embodiments, the present application provides a circular RNA (circRNA) vaccine comprising a circRNA comprising a nucleic acid sequence, the nucleic acid sequence comprising from the 5' end to the 3' end: an m6A modification motif sequence, a Kozak sequence, a nucleic acid sequence encoding a signal peptide (SP), and a nucleic acid sequence encoding an antigenic polypeptide comprising a receptor-binding domain (RBD) of a Spike(S) protein of a coronavirus (e.g., derived from the wild type SARS-COV-2 or a variant such as the B.1.351 or B.1.617.2 variant of SARS-COV-2). In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence comprises the nucleic acid sequence of SEQ ID NO: 39. In some embodiments, the 5' exon sequence comprises the nucleic acid sequence of SEQ ID NO: 40. In some embodiments, the 3' exon comprises the nucleic acid sequence of SEQ ID NO: 39, and the 5' exon sequence comprises the nucleic acid sequence of SEQ ID NO: 40.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), and a nucleic acid sequence encoding an antigenic polypeptide comprising a receptor-binding domain (RBD) of a Spike(S) protein of a coronavirus (e.g., derived from the wild type SARS-COV-2 or a variant such as the B.1.351 or B.1.617.2 variant of SARS-COV-2) and a multimerization domain (e.g., C-terminal domain of a T4 fibritin protein that mediates trimerization of the T4 fibritin protein). In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments the RBD domain has at least 90% (e.g., at least 95%, 96%, 97%, 98%, 99%) sequence identity to the amino acid sequence of SEQ ID NO: 2. In some embodiments, the RBD domain comprises the amino acid sequence of SEQ ID NO: 2. In some embodiments the RBD domain has at least 90% (e.g., at least 95%, 96%, 97%, 98%, 99%) sequence identity to the amino acid sequence of SEQ ID NO: 63. In some embodiments, the RBD domain comprises the amino acid sequence of SEQ ID NO: 63.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., SARS-COV-2) and a multimerization domain (e.g., C-terminal domain of a T4 fibritin protein that mediates trimerization of the T4 fibritin protein). In some embodiments, the circRNA further comprises an internal ribosomal entry site (IRES) or m6A modification motif sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof (e.g., human tPA or IgE signal peptide). In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), and a nucleic acid sequence encoding an antigenic polypeptide comprising a receptor-binding domain (RBD) and an S2 region of a Spike(S) protein of a coronavirus (e.g., derived from the wild type SARS-COV-2 or a variant such as the B.1.351 or B.1.617.2 variant of SARS-COV-2) and a multimerization domain (e.g., C-terminal domain of a T4 fibritin protein that mediates trimerization of the T4 fibritin protein). In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: a m6A modification motif sequence, a Kozak sequence, a nucleic acid sequence encoding a signal peptide (SP), and a nucleic acid sequence encoding an antigenic polypeptide comprising a receptor-binding domain (RBD) and an S2 region of a Spike(S) protein of a coronavirus (e.g., derived from the wild type SARS-COV-2 or a variant such as the B.1.351 or B.1.617.2 variant of SARS-COV-2) and a multimerization domain (e.g., C-terminal domain of a T4 fibritin protein that mediates trimerization of the T4 fibritin protein). In some embodiments, the IRES sequence is a CVB3 virus, EV71 virus, EMCV virus, PV virus, or a CSFV virus IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide, the antigenic polypeptide comprising amino acid residues 2-1273 of a full-length S protein of SARS-COV-2, wherein the numbering is based on SEQ ID NO: 1. In some embodiments, the circRNA further comprises an internal ribosomal entry site (IRES) or m6A modification motif sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide, the antigenic polypeptide comprising amino acid residues 2-1273 of a full-length S protein of SARS-COV-2, wherein the numbering is based on SEQ ID NO: 1. In some embodiments, the circRNA further comprises an internal ribosomal entry site (IRES) or m6A modification motif sequence, and a Kozak sequence operably linked to the nucleic acid sequence encoding the antigenic polypeptide. In some embodiments, the nucleic acid sequence further encodes a signal peptide (SP) fused to the N-terminus of the S protein or fragment thereof. In some embodiments, the signal peptide is, for example, human tissue plasminogen activator (tPA) or IgE signal peptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), and a nucleic acid sequence encoding an antigenic polypeptide, the antigenic polypeptide comprising amino acid residues 2-1273 of a full-length S protein of SARS-COV-2, wherein the numbering is based on SEQ ID NO: 1. In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: a m6A modification motif sequence, a Kozak sequence, a nucleic acid sequence encoding a signal peptide (SP), and a nucleic acid sequence encoding an antigenic polypeptide, the antigenic polypeptide comprising amino acid residues 2-1273 of a full-length S protein of SARS-COV-2, wherein the numbering is based on SEQ ID NO: 1. In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a Spike(S) protein or a fragment thereof of SARS-COV-2 wherein the antigenic polypeptide comprises an S2 region of the S protein. In some embodiments, the S2 region comprises amino acid residues 686 to 1273 of a full-length S protein of SARS-COV-2, wherein the numbering is based on SEQ ID NO: 1. In some embodiments, the S2 region comprises the amino acid sequence of SEQ ID NO: 6. In some embodiments, the S2 region comprises one or more mutations that stabilize a pre-fusion conformation of the S protein. In some embodiments, the S2 region comprises K986P and V987P mutations. In some embodiments, the S2 region comprises the amino acid sequence of SEQ ID NO: 7. In some embodiments, the circRNA further comprises an internal ribosomal entry site (IRES) or m6A modification motif sequence, wherein the IRES or m6A modification motif sequence is operably linked to the nucleic acid sequence encoding the antigenic polypeptide. In some embodiments, the nucleic acid sequence further encodes a signal peptide (SP) fused to the N-terminus of the S protein or fragment thereof (e.g., human tPA or IgE signal peptide). In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the present application provides a circular RNA (circRNA) vaccine comprising a circRNA comprising a nucleic acid sequence set forth in any one of SEQ ID NOs: 11-15 or SEQ ID NOs: 48-49.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., SARS-CoV-2), further comprising an in-frame 2A peptide coding sequence operably linked to the 3' end of the nucleic acid sequence encoding the antigenic polypeptide. In some embodiments, the circRNA further comprises an internal ribosomal entry site (IRES) sequence operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof.

In some embodiments, the present application provides a circular RNA (circRNA) vaccine comprising a circRNA comprising a nucleic acid sequence, the nucleic acid sequence comprising from the 5' end to the 3' end: an internal ribosomal entry site (IRES) sequence, a Kozak sequence, a nucleic acid sequence encoding a signal peptide (SP), a nucleic acid sequence encoding an antigenic polypeptide comprising an S protein or fragment thereof of a coronavirus, and an in-frame 2A peptide coding sequence. In some embodiments, the IRES sequence is a CVB3 virus, EV71 virus, EMCV virus, PV virus, or a CSFV virus IRES sequence. In some embodiments, the circRNA further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence, the nucleic acid sequence comprising from the 5' end to the 3' end: an m6A modification motif sequence, a Kozak sequence, a nucleic acid sequence encoding a signal peptide (SP), a nucleic acid sequence encoding an antigenic polypeptide comprising an S protein or fragment thereof of a coronavirus, and an in-frame 2A peptide coding sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., derived from the wild type SARS-COV-2 or a variant such as the B.1.351 or B.1.617.2 variant of SARS-CoV-2), further comprising an in-frame 2A peptide coding sequence operably linked to the 3' end of the nucleic acid sequence encoding the antigenic polypeptide. In some embodiments, the circRNA further comprises an m6A modification motif sequence operably linked to the nucleic acid sequence encoding the antigenic polypeptide. In some embodiments, the nucleic acid sequence further comprises a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a Spike(S) protein or a fragment thereof of a coronavirus (e.g., derived from the wild type SARS-COV-2 or a variant such as the B.1.351 or B.1.617.2 variant of SARS-CoV-2), further comprising an in-frame 2A peptide coding sequence operably linked to the 3' end of the nucleic acid sequence encoding the antigenic polypeptide. In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof, and a Kozak sequence operably linked to the nucleic acid sequence encoding) the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the 3' exon sequence comprises the nucleic acid sequence of SEQ ID NO: 39. In some embodiments, the 5' exon sequence comprises the nucleic acid sequence of SEQ ID NO: 40. In some embodiments, the 3' exon sequence comprises the nucleic acid sequence of SEQ ID NO: 39, and the 5' exon sequence comprises the nucleic acid sequence of SEQ ID NO: 40.

In some embodiments, the present application provides a circular RNA (circRNA) vaccine comprising a circRNA comprising a nucleic acid sequence encoding an antigenic polypeptide comprising a receptor-binding domain (RBD) of a Spike(S) protein of a coronavirus (e.g., derived from the wild type SARS-COV-2 or a variant such as the B.1.351 or B.1.617.2 variant of SARS-COV-2), further comprising an in-frame 2A peptide coding sequence operably linked to the 3' end of the nucleic acid sequence encoding the antigenic polypeptide. In some embodiments, the circRNA further comprises an internal ribosomal entry site (IRES) or m6A modification motif sequence, wherein the IRES or m6A modification motif sequence is operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) of a Spike(S) protein of a coronavirus (e.g., derived from the wild type SARS-COV-2 or a variant such as the B.1.351 or B.1.617.2 variant of SARS-COV-2), further comprising an in-frame 2A peptide coding sequence operably linked to the 3' end of the nucleic acid sequence encoding the antigenic polypeptide. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site (IRES) or m6A modification motif sequence, wherein the IRES or m6A modification motif sequence is operably linked to the nucleic acid sequence encoding the antigenic polypeptide. In some embodiments, the nucleic acid sequence further comprises a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., derived from the wild type SARS-COV-2 or a variant such as the B.1.351 or B.1.617.2 variant of SARS-COV-2), further comprising an in-frame 2A peptide coding sequence operably linked to the 3' end of the nucleic acid sequence encoding the antigenic polypeptide. In some embodiments, the antigenic polypeptide further comprises a multimerization domain (e.g., a C-terminal Foldon domain of a T4 fibritin protein or a GCN4-based isoleucine zipper domain). In some embodiments, the circRNA further comprises an internal ribosomal entry site (IRES) sequence (e.g., a CVB3 virus, EV71 virus, EMCV virus, PV virus, or CSFV virus IRES sequence) or an m6A modification motif sequence, wherein the IRES or m6A modification motif sequence is operably linked to the nucleic acid sequence encoding the antigenic polypeptide. In some embodiments, the nucleic acid sequence further comprises a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., derived from the wild type SARS-COV-2 or a variant such as the B.1.351 or B.1.617.2 variant of SARS-COV-2), further comprising an in-frame 2A peptide coding sequence operably linked to the 3' end of the nucleic acid sequence encoding the antigenic polypeptide. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof, and a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments the RBD domain has at least 90% (e.g., at least 95%, 96%, 97%, 98%, 99%) sequence identity to the amino acid sequence of SEQ ID NO: 2. In some embodiments, the RBD domain comprises the amino acid sequence of SEQ ID NO: 2. In some embodiments the RBD domain has at least 90% (e.g., at least 95%, 96%, 97%, 98%, 99%) sequence identity to the amino acid sequence of SEQ ID NO: 63. In some embodiments, the RBD domain comprises the amino acid sequence of SEQ ID NO: 63.

In some embodiments, the present application provides a circular RNA (circRNA) vaccine comprising a circRNA comprising a nucleic acid sequence encoding amino acid residues 2-1273 of a full-length S protein of SARS-COV-2, wherein the numbering is based on SEQ ID NO: 1, further comprising an in-frame 2A peptide coding sequence operably linked to the 3' end of the nucleic acid sequence encoding the antigenic polypeptide. In some embodiments, the antigenic polypeptide further comprises a multimerization domain. In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further comprises a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding amino acid residues 2-1273 of a full-length S protein of SARS-COV-2, wherein the numbering is based on SEQ ID NO: 1, further comprising an in-frame 2A peptide coding sequence operably linked to the 3' end of the nucleic acid sequence encoding the antigenic polypeptide. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding amino acid residues 2-1273 of a full-length S protein of SARS-COV-2, wherein the numbering is based on SEQ ID NO: 1, further comprising an in-frame 2A peptide coding sequence operably linked to the 3' end of the nucleic acid sequence encoding the antigenic polypeptide. In some embodiments, the antigenic polypeptide further comprises a multimerization domain. In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof, and a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., SARS-COV-2), further comprising an in-frame 2A peptide coding sequence operably linked to the 3' end of the nucleic acid sequence encoding the antigenic polypeptide. In some embodiments, the S2 region comprises amino acid residues 686 to 1273 of a full-length S protein of SARS-COV-2, wherein the numbering is based on SEQ ID NO: 1. In some embodiments, the S2 region comprises the amino acid sequence of SEQ ID NO: 6. In some embodiments, the S2 region comprises one or more mutations that stabilize a pre-fusion conformation of the S protein. In some embodiments, the S2 region comprises the amino acid sequence of SEQ ID NO: 7. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site (TRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further comprises a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., SARS-COV-2), further comprising an in-frame 2A peptide coding sequence operably linked to the 3' end of the nucleic acid sequence encoding the antigenic polypeptide. In some embodiments, the S2 region comprises amino acid residues 686 to 1273 of a full-length S protein of SARS-COV-2, wherein the numbering is based on SEQ ID NO: 1. In some embodiments, the S2 region comprises the amino acid sequence of SEQ ID NO: 6. In some embodiments, the S2 region comprises one or more mutations that stabilize a pre-fusion conformation of the S protein. In some embodiments, the S2 region comprises the amino acid sequence of SEQ ID NO: 7. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site (IRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the present application provides a circular RNA (circRNA) vaccine comprising a circRNA comprising a nucleic acid sequence encoding an antigenic polypeptide comprising a receptor-binding domain (RBD) and an S2 region of a Spike(S) protein of a coronavirus (e.g., SARS-COV-2), further comprising an in-frame 2A peptide coding sequence operably linked to the 3' end of the nucleic acid sequence encoding the antigenic polypeptide. In some embodiments, the S2 region comprises amino acid residues 686 to 1273 of a full-length S protein of SARS-COV-2, wherein the numbering is based on SEQ ID NO: 1. In some embodiments, the S2 region comprises the amino acid sequence of SEQ ID NO: 6. In some embodiments, the S2 region comprises one or more mutations that stabilize a pre-fusion conformation of the S protein. In some embodiments, the S2 region comprises the amino acid sequence of SEQ ID NO: 7. In some embodiments, the antigenic polypeptide further comprises a multimerization domain (e.g., C-terminal domain of a T4 fibritin protein that mediates trimerization of the T4 fibritin protein). In some embodiments, the circRNA further comprises an internal ribosomal entry site: (TRES) sequence (e.g., a CVB3 virus, EV71 virus, EMCV virus, PV virus, or CSFV virus IRES sequence) operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof, and a Kozak sequence operably linked to the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, the circRNA vaccine provided comprises a nucleic acid sequence comprising from the 5' end to the 3' end: the IRES sequence, the Kozak sequence, the SP, the nucleic acid sequence encoding the antigenic polypeptide, and the in-frame 2A peptide coding sequence. In some embodiments, the circRNA vaccine further comprises a polyA or polyAC sequence disposed at the 5' end of the IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic. Group I intron fragment flanking the 3' end of the nucleic acid sequence encoding the antigenic polypeptide.

In some embodiments, the circRNA vaccine provided comprises a nucleic acid sequence comprising from the 5' end to the 3' end: the polyA or polyAC sequence, the IRES sequence, the Kozak sequence, the SP, the nucleic acid sequence encoding the antigenic polypeptide, and the in-frame 2A peptide coding sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide.

In some embodiments, there is provided a circular RNA (circRNA) comprising a nucleic acid sequence comprising from the 5' end to the 3' end: the m6A modification motif sequence, the Kozak sequence, the SP, the nucleic acid sequence encoding antigenic polypeptide, and the in-frame 2A peptide coding sequence. In some embodiments, the antigenic polypeptide comprises a receptor-binding domain (RBD) of the S protein. In some embodiments, the antigenic polypeptide further comprises a multimesization domain (e.g., C-terminal domain of a T4 fibritin protein that mediates trimerization of the T4 fibritin protein).

In some embodiments, there is provided a circular RNA (circRNA) comprising a nucleic acid sequence comprising from the 5' end to the 3' end: the m6A modification motif sequence, the Kozak sequence, the SP, and the nucleic acid sequence encoding the antigenic polypeptide. In some embodiments, the antigenic polypeptide comprises a receptor-binding domain (RBD) and an S2 region of the S protein. In some embodiments, the antigenic polypeptide further comprises a multimerization domain (e.g., C-terminal domain of a T4 fibritin protein that mediates trimerization of the T4 fibritin protein).

In some embodiments, there is provided a circular RNA (circRNA) comprising a nucleic acid sequence comprising from the 5' end to the 3' end: the m6A modification motif sequence, the Kozak sequence, the SP, and a sequence encoding the antigenic polypeptide. In some embodiments, the antigenic polypeptide comprises amino acid residues 2-1273 of a full-length S protein of SARS-COV-2, wherein the numbering is based on SEQ ID NO: 1. In some embodiments, the antigenic polypeptide further comprises a multimerization domain (e.g., C-terminal domain of a T4 fibritin protein that mediates trimerization of the T4 fibritin protein). In some embodiments, the circRNA comprises an in-frame 2A peptide coding sequence following the antigenic polypeptide.

III. Methods of Treatment

The circRNAs and compositions derived herein may be used to treat or prevent a disease or condition in an individual, including, but not limited to genetic diseases (e.g., hereditary genetic diseases, metabolic diseases and cancer), and infections (e.g., viral infections such as coronavirus infections). In some embodiments, the circRNA is subject to rolling circle translation by a ribosome in the individual.

In some embodiments, there is provided a method of treating or preventing a disease or condition in an individual, comprising administering to the individual an effective amount of a circRNA comprising a nucleic acid sequence encoding an antigenic polypeptide. In some embodiments, the antigenic polypeptide is a protein or a fragment thereof of an infectious agent, such as a virus, e.g., a coronavirus. In some embodiments, the infectious agent is SARS-COV-2. In some embodiments, the antigenic polypeptide is an S protein or fragment thereof. In some embodiments, the disease or condition is a coronavirus infection. In some embodiments, the method comprises administering an effective amount of a cocktail composition comprising a plurality of circRNA encoding different antigenic polypeptides.

In some embodiments, there is provided a method of treating or preventing a disease or condition in an individual, comprising administering to the individual an effective amount of a circRNA comprising a nucleic acid sequence encoding a functional protein. In some embodiments, the functional protein is an enzyme, a receptor, a ligand, a signaling molecule, or a transcription factor. In some embodiments, the disease or condition is a metabolic disease. In some embodiments, the disease or condition is a lysosomal storage disorder. In some embodiments, the disease or condition is a cancer.

In some embodiments, there is provided a method of treating or preventing a disease or condition in an individual, comprising administering to the individual an effective amount of a circRNA comprising a nucleic acid sequence encoding a receptor protein. In some embodiments, the receptor protein is a recepter of an infectious agent, such as a virus, e.g., a coronavirus. In some embodiments, the receptor protein is a soluble receptor, such as a soluble ACE2 receptor.

In some embodiments, there is provided a method of treating or preventing a disease or condition in an individual, comprising administering to the individual an effective amount of a circRNA comprising a nucleic acid sequence encoding a targeting protein, such as an antibody. In some embodiments, the targeting protein is a neutralizing antibody. In some embodiments, the targeting protein is a therapeutic antibody. In some embodiments, the targeting protein specifically binds an infectious agent, such as a virus, e.g., a coronavirus.

In some embodiments, the present application provides circRNAs for use in treating or preventing a disease or condition in an individual.

In some embodiments, the present application provides circRNA vaccines for use in treating or preventing a coronavirus (e.g., SARS-COV, MERS-COV, or SARS-COV-2) infection in an individual.

In some embodiments, the present application provides use of a circRNA comprising a nucleic acid sequence encoding a therapeutic polypeptide for the manufacture of a medicament for treating or preventing a disease or condition in an individual.

In some embodiments, the present application provides use of a circRNA vaccine comprising a circRNA comprising a nucleic acid sequence encoding an antigenic polypeptide comprising a Spike(S) protein or a fragment thereof of a coronavirus (e.g., SARS-COV-2) for the manufacture of a vaccine for treating or preventing a coronavirus infection in an individual.

A. Treating a Genetic Disease or Condition

The circRNAs described herein may be used for treating a genetic disease or condition that is associated with a mutation or deficiency in a naturally-occurring protein corresponding to the therapeutic polypeptide encoded by the circRNA. In some embodiments, the disease or condition is a disease or condition associated with insufficient levels and/or activity of a naturally-occurring protein corresponding to the therapeutic polypeptide. In some embodiments, the disease or condition is a hereditary genetic disease associated with one or more mutations in naturally-occurring protein corresponding to the therapeutic polypeptide. In some embodiments, the therapeutic polypeptide is a wild-type protein, or a functional variant thereof (e.g., a functional fragment, fusion protein, or mutant).

In some aspects, the present application provides methods and compositions for treatment of a disease or condition associated with a deficiency of a functional protein, such as an enzyme (e.g., IDUA) using a circRNA expressing a therapeutic polypeptide. In some embodiments, the therapeutic polypeptide comprises a nucleotide sequence encoding the protein or a derivative thereof. In some embodiments, the circRNA is capable of expressing a functional protein or functional derivative of a protein that is capable of restoring function of the protein associated with the disease or condition. In some embodiments, the circRNA is capable of restoring 10%, 20%, 30%, 40%, 50%, 60%, 70%, 80%, 90%, or 100% of the activity of the protein as compared to the endogenous wild-type protein in a cell or organism (e.g., a mouse or a human), e.g., up to 8, 12, 16, 24, 30, 36, or 40 hours after administration of the circRNA.

In some embodiments, the therapeutic polypeptide can be any polypeptide that is capable of being expressed by target cells (e.g., human or mouse cells) for the production (and in certain instances, the excretion) of a functional enzyme or protein as disclosed, for example, in International Application No. PCT/US2010/058457. In some embodiments, the therapeutic polypeptide can be engineered for secretion by operably linking a signal peptide to the amino terminus of the therapeutic polypeptide. For example, in some embodiments, upon the expression of one or more therapeutic polynucleotides by target cells, the production of a functional enzyme or protein in which a subject is deficient (e.g., a urea cycle enzyme or an enzyme associated with a lysosomal storage disorder) may be observed.

Examples of disease-associated mutations that may be treated by the methods of the present application include, but are not limited to, TP53$^{W53X}$ (e.g., 158G>A) associated with cancer, IDUA$^{W402X}$ (e.g., TGG>TAG mutation in exon 9) associated with Mucopolysaccharidosis type I (MPS I), COL3A1$^{W1278X}$ (e.g., 3833G>A mutation) associated with Ehlers-Danlos syndrome, BMPR2$^{W298X}$ (e.g., 893G>A) associated with primary pulmonary hypertension, AHI1$^{W725X}$ (e.g., 2174G>A) associated with Joubert syndrome, FANCC$^{W506X}$ (e.g., 1517G>A) associated with Fanconi anemia, MYBPC3$^{W1098X}$ (e.g., 3293G>A) associated with primary familial hypertrophic cardiomyopathy, and IL2RG$^{W237X}$ (e.g., 710G>A) associated with X-linked severe combined immunodeficiency. In some embodiments, the disease or condition is a cancer. In some embodiments, the disease or condition is a monogenetic disease. In some embodiments, the disease or condition is a polygenetic disease.

In some embodiments, the disease or condition is a liver disease or condition. In some embodiments, the disease or condition is a disease or condition of the respiratory tract of the individual, such as a lung disease or condition.

In some embodiments, there is provided a method of treating a cancer in an individual, comprising administering to the individual an effective amount of a circRNA comprising a nucleic acid sequence encoding a tumor suppressor. In some embodiments, the tumor suppressor is TP53 (including a functional variant thereof). In some embodiments, the tumor suppressor is PTEN (including a functional variant thereof). In some embodiments, the tumor suppressor comprises an amino acid sequence having at least about 80% (e.g., at least about any one of 85%, 90%, 93%, 95%, 97%, 98%, or 99%, or 100%) to the amino acid sequence of SEQ ID NO: 24 or 25.

In some embodiments, there is provided a method of treating a lysosomal storage disorder in an individual, comprising administering to the individual an effective amount of a circRNA comprising a nucleic acid sequence encoding a lysosomal enzyme.

In some embodiments, there is provided a method of treating a liver disease or condition in an individual, comprising administering to the individual an effective amount of a circRNA comprising a nucleic acid sequence encoding a liver protein (e.g., an enzyme).

In some embodiments, there is provided a method of treating Mucopolysaccharidosis type I (MPS I) in an individual, comprising administering to the individual an effective amount of a circRNA comprising a nucleic acid sequence encoding IDUA (including a functional variant thereof). In some embodiments; the IDUA comprises an amino acid sequence having at least about 80% (e.g., at least about any one of 85%, 90%, 93%, 95%, 97%, 98%, or 99%, or 100%) to the amino acid sequence of SEQ ID NO: 18. In some embodiments, the IDUA comprises an amino acid sequence having at least about 80% (e.g., at least about any one of 85%, 90%, 93%, 95%, 97%, 98%, or 99%, or 100%) to the amino acid sequence of SEQ ID NO: 19.

In some embodiments, there is provided a method of treating ornithine transcarbamylase deficiency in an individual, comprising administering to the individual an effective amount of a circRNA comprising a nucleic acid sequence encoding OTC (including a functional variant thereof). In some embodiments, the OTC comprises an amino acid sequence having at least about 80% (e.g., at least about any one of 85%, 90%, 93%, 95%, 97%, 98%, or 99%, or 100%) to the amino acid sequence of SEQ ID NO: 20. In some embodiments, the OTC comprises an amino acid sequence having at least about 80% (e.g., at least about any one of 85%, 90%, 93%, 95%, 97%, 98%, or 99%, or 100%) to the amino acid sequence of SEQ ID NO: 56.

In some embodiments, there is provided a method of treating tyrosinemia in an individual, comprising administering to the individual an effective amount of a circRNA comprising a nucleic acid sequence encoding FAH (including a functional variant thereof). In some embodiments, the FAH comprises an amino acid sequence having at least about 80% (e.g., at least about any one of 85%, 90%, 93%, 95%, 97%, 98%, or 99%, or 100%) to the amino acid sequence of SEQ ID NO: 54. In some embodiments, the FAH comprises an amino acid sequence having at least about 80% (e.g., at least about any one of 85%, 90%, 93%, 95%, 97%, 98%, or 99%, or 100%) to the amino acid sequence of SEQ ID NO: 21.

In some embodiments, there is provided a method of treating Duchenne and Becker muscular dystrophy, X-linked dilated cardiomyopathy, or familial dilated cardiomyopathy in an individual, comprising administering to the individual an effective amount of a circRNA comprising a nucleic acid sequence encoding DMD (including a functional variant thereof, e.g., miniDMD). In some embodiments, the DMD comprises an amino acid sequence having at least about 80% (e.g., at least about any one of 85%, 90%, 93%, 95%, 97%, 98%, or 99%, or 100%) to the amino acid sequence of SEQ ID NO: 23. In some embodiments, the DMD comprises an amino acid sequence having at least about 80% (e.g., at least about any one of 85%, 90%, 93%, 95%, 97%, 98%, or 99%, or 100%) to the amino acid sequence of SEQ ID NO: 22.

In some embodiments, there is provided a method of treating Ehlers-Danlos syndrome in an individual, comprising administering to the individual an effective amount of a circRNA comprising a nucleic acid sequence encoding COL3A1 (including a functional variant thereof). In some embodiments, the COL3A1 comprises an amino acid sequence having at least about 80% (e.g., at least about any one of 85%, 90%, 93%, 95%, 97%, 98%, or 99%, or 100%) to the amino acid sequence of SEQ ID NO: 56.

In some embodiments, there is provided a method of treating Joubert syndrome in an individual, comprising administering to the individual an effective amount of a circRNA comprising a nucleic acid sequence encoding AHI1 (including a functional variant thereof). In some embodiments, the AHI1 comprises an amino acid sequence having at least about 80% (e.g., at least about any one of 85%, 90%, 93%, 95%, 97%, 98%, or 99%, or 100%) to the amino acid sequence of SEQ ID NO: 58.

In some embodiments, there is provided a method of treating pulmonary arterial hypertension, or pulmonary veno-occlusive disease in an individual, comprising administering to the individual an effective amount of a circRNA comprising a nucleic acid sequence encoding FANCC (including a functional variant thereof). In some embodiments, the FANCC comprises an amino acid sequence having at least about 80% (e.g., at least about any one of 85%, 90%, 93%, 95%, 97%, 98%, or 99%, or 100%) to the amino acid sequence of SEQ ID NO: 59.

In some embodiments; there is provided a method of treating primary familial hypertrophic cardiomyopathy in an individual, comprising administering to the individual an effective amount of a circRNA comprising a nucleic acid sequence encoding MYBPC3 (including a functional variant thereof). In some embodiments, the MYBPC3 comprises an amino acid sequence having at least about 80% (e.g., at least about any one of 85%, 90%, 93%, 95%, 97%, 98%, or 99%, or 100%) to the amino acid sequence of SEQ ID NO: 60.

In some embodiments, there is provided a method of treating X-linked severe combined immunodeficiency in an individual, comprising administering to the individual an effective amount of a circRNA comprising a nucleic acid sequence encoding IL2RG (including a functional variant thereof). In some embodiments, the IL2RG comprises an amino acid sequence having at least about 80% (e.g., at least about any one of 85%, 90%, 93%, 95%, 97%, 98%, or 99%, or 100%) to the amino acid sequence of SEQ ID NO: 61.

In some embodiments, the circRNA has a functional half-life of at least or at least about 20 hours, 24 hours, 30 hours, or 36 hours. In some embodiments, the circRNA has a duration of therapeutic effect in a human cell of at least or at least about 20 hours, 24 hours, 30 hours, or 36 hours. In some embodiments, the circRNA has a duration of therapeutic effect in a human cell greater than or equal to that of an equivalent linear RNA comprising the same expression sequence. In some embodiments, the circRNA has a functional half-life in a human cell greater than or equal to that of an equivalent linear RNA comprising the same expression sequence.

In some embodiments, the therapeutic polypeptide comprises IDUA, and the disease or condition is Hurler Syndrome. In some embodiments, administration of the circRNA restores at least 10%, at least 15%, at least 20%, at least 25%, at least 30%, at least 40%, at least 50%, at least 60%, at least 70%, at least 80%, at least 90%, or at least 100% of α-1-iduronidase in a human or an animal model with a mutation in IDUA compared to wild-type. In some embodiments, the catalytic activity of IDUA increases from 4 to 24 hours (e.g., from 4 to 8 hours, from 8 to 12 hours, from 12 to 16 hours, from 16 to 20 hours, and/or from 16 to 24 hours) following administration of the circRNA encoding IDUA. In some embodiments, the circRNA encoding IDUA has a functional half-life of at least or at least about 20 hours, 24 hours, 30 hours, or 36 hours.

B. Treating or Preventing a Coronavirus Infection

The present application provides methods of treating or preventing a coronavirus (e.g., SARS-COV-2 infection) infection in an individual, comprising administering to the individual an effective amount of the circRNAs of any one of the embodiments described herein, wherein the circRNA encodes an antigenic polypeptide or a receptor protein (e.g., soluble receptor) of the coronavirus, or a neutralizing antibody specifically binding the coronavirus. In some embodiments, the coronavirus is SARS-COV, MERS-COV, or SARS-COV-2. In some embodiments, the coronavirus is SARS-COV-2. In some embodiments, the present application provides methods of preventing or decreasing the risk of a coronavirus (e.g., SARS-COV-2 infection) infection in an individual, comprising administering to the individual an effective amount of the circRNA of anyione of the embodiments described above, wherein the circRNA encodes an antigenic polypeptide or a receptor protein (e.g., soluble receptor) of the coronavirus, or a neutralizing antibody specifically binding the coronavirus. In some embodiments, the method comprises administering a cocktail composition comprising a plurality of circRNAs encoding different antigenic polypeptides, receptor proteins, or neutralizing antibodies. In some embodiments, the circRNA is subject to rolling circle translation by a ribosome in the individual. In some embodiments, the circRNA is administered as naked circRNA, or as a pharmaceutical composition comprising a transfection agent.

In some embodiments, there is provided a method of treating or preventing a coronavirus (e.g., SARS-COV-2 infection) infection in an individual, comprising administering to the individual an effective amount of a circRNA comprising a nucleic acid sequence encoding a receptor protein of the coronavirus. In some embodiments, the coronavirus is SARS-COV-2. In some embodiments, the receptor protein is a soluble receptor, such as a soluble ACE2 receptor. In some embodiments, the method comprises administering an effective amount of a cocktail composition comprising a plurality of circRNA encoding different receptor proteins.

In some embodiments, there is provided a method of treating or preventing a coronavirus (e.g., SARS-COV-2 infection) infection in an individual, comprising administering to the individual an effective amount of a circRNA comprising a nucleic acid sequence encoding a neutralizing antibody that specifically binds the coronavirus. In some embodiments, the coronavirus is SARS-COV-2. In some embodiments, the method comprises administering an effective amount of a cocktail composition comprising a plurality of circRNA encoding different neutralizing antibodies.

In some embodiments, the present application provides methods of treating or preventing a coronavirus infection in an individual, comprising administering to the individual an effective amount of the circRNA vaccine of any one of the embodiments described herein. In some embodiments, the coronavirus is SARS-COV, MERS-COV, or SARS-COV-2. In some embodiments, the coronavirus is SARS-COV-2. In some embodiments, the present application provides methods of preventing or decreasing the risk of a coronavirus (e.g., SARS-COV-2 infection) infection in an individual, comprising administering to the individual an effective amount of the circRNA vaccine of any one of the embodiments described above. In some embodiments, the circRNA is subject to rolling circle translation by a ribosome in the individual. In some embodiments, the circRNA vaccine is administered as naked circRNA, or as a pharmaceutical composition comprising a transfection agent.

In some embodiments, the present application provides methods of treating or preventing a coronavirus infection in an individual, comprising administering to the individual an effective amount of the circRNA vaccine of any one of the embodiments described herein. In some embodiments, the coronavirus is a wild-type strain of SARS-COV-2 or a variant strain of SARS-COV-2. In some embodiments, the coronavirus is SARS-COV-2. In some embodiments, the SARS-COV-2 is an Alpha (B.1.1.7), Beta (B.1.351, B.1.351.2, B.1.351.3), Delta (B.1.617.2, AY.1, AY.2, AY.3), or Gamma. (P.1, P.1.1, P.1.2) variant of SARS-COV-2. In some embodiments, the variant can be any variant described on cdc.gov/coronavirus/2019-ncov/variants/. In some embodiments, the present application provides methods of preventing or decreasing the risk of a coronavirus (e.g., SARS-COV-2 infection, such as an infection with any of the variant SARS-COV-2 strains described herein) infection in an individual, comprising administering to the individual an effective amount of the circRNA vaccine of any one of the embodiments described above. In some embodiments, the circRNA vaccine encodes an S protein or fragment thereof comprising one, two, or three of the mutations selected from the group K417N, L452R, and T478K, wherein the amino acid numbering is based on SEQ ID NO: 1. In some embodiments, the circRNA vaccine encodes an S protein or fragment thereof comprising one, two, three, four, five, or more mutations selected from the group consisting of residue 69 deletion, residue 70 deletion, residue 144 deletion, E484K, S494P, N501Y, A570D, D614G, P681H, T716I, S982A, D1118H, and K1191N, wherein the amino acid numbering is based on SEQ ID NO: 1. In some embodiments, the circRNA vaccine encodes an S protein or fragment thereof comprising one, two, or three of the mutations selected from the group consisting of E484K, S494P, and N501Y, wherein the amino acid numbering is based on SEQ ID NO: 1. In some embodiments, the circRNA vaccine encodes an S protein or fragment thereof comprising one, two, three, four, five, or more mutations selected from the group consisting of D80A, D215G, 241del, 242del, 243del, K417N, E484K, N501Y, D614G, and A701V, wherein the amino acid numbering is based on SEQ ID NO: 1. In some embodiments, the circRNA vaccine encodes an S protein or fragment thereof comprising one, two, or three of the mutations selected from the group consisting of K417N, E484K, and N501Y, wherein the amino acid numbering is based on SEQ ID NO: 1. In some embodiments, the circRNA vaccine encodes an S protein or fragment thereof comprising one, two, three, four, five, or more mutations selected from the group consisting of L18F, T20N, P26S, D138Y, R190S, K417T, E484K, N501Y, D614G, H655Y, and T1027I, wherein the amino acid numbering is based on SEQ ID NO: 1. In some embodiments, the circRNA vaccine encodes an S protein or fragment thereof comprising one, two, or three of the mutations selected from the group consisting of K417T, E484K, and N501Y.

In some embodiments, the present application provides methods of treating or preventing a multiple strains of a coronavirus (e.g., multiple strains of SARS-COV-2) infection in an individual, comprising administering to the individual an effective amount of the circRNA vaccine of any one of the embodiments described herein. In some embodiments, the present application provides methods of treating or preventing a multiple strains of a coronavirus (e.g., multiple strains of SARS-COV-2) infection in an individual, comprising administering to the individual an effective amount of multiple different circRNA vaccines of any one of the embodiments described herein. In some embodiments, the method comprises administering to the individual a composition comprising a plurality (e.g., two or more) circRNAs, wherein a first circRNA encodes an S protein or fragment thereof of a first strain of a coronavirus, and a second circRNA encodes an S protein or fragment thereof of a second strain of a coronavirus. In some embodiments, at least one of the circRNAs of the plurality encodes an S protein or fragment thereof comprising the mutations found in the D614G, B.1.1.7/501Y.V1 variant of SARS-COV-2 or the B.1.351/501Y.V2 variant of SARS-COV-2.

In some embodiments, the present application provides methods of treating or preventing a coronavirus infection in an individual, comprising administering to the individual an effective amount of a circRNA vaccine comprising a circRNA comprising a nucleic acid sequence encoding an antigenic polypeptide comprising an S protein or a fragment thereof of the coronavirus (e.g., SARS-COV-2). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the antigenic polypeptide comprises an S protein or fragment thereof of SARS-COV-2 having a D614G mutation. In some embodiments, the circRNA comprises a nucleic acid sequence selected from the group consisting of SEQ ID NOs: 11-15. In some embodiments, the circRNA is subject to rolling circle translation by a ribosome in the individual.

In some embodiments, the present application provides methods of treating or preventing a coronavirus infection in an individual, comprising administering to the individual an effective amount of a circRNA vaccine comprising a circRNA comprising: (a) a nucleic acid sequence encoding an antigenic polypeptide comprising an S protein or a fragment thereof of a coronavirus (e.g., SARS-COV-2), and (b) an IRES sequence, wherein the IRES sequence is operably linked to the nucleic acid sequence encoding the antigenic polypeptide. In some embodiments, the circRNA further comprises an in-frame 2A peptide coding sequence operably linked to the 3' end of the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a Kozak sequence operably linked to the nucleic acid sequence encoding the antigenic polypeptide. In some embodiments, the circRNA comprises a nucleic acid sequence comprising from the 5' end to the 3' end: the IRES sequence, the Kozak sequence, the SP, and the nucleic acid sequence encoding the antigenic polypeptide. In some embodiments, the circRNA further comprises a polyA or polyAC sequence disposed at the 5' end of an IRES sequence. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the antigenic polypeptide comprises an S protein or fragment thereof of SARS-COV-2 having a D614G mutation. In some embodiments, the circRNA comprises a nucleic acid sequence selected from the group consisting of SEQ ID NOs: 11-15. In some embodiments, the circRNA is subject to rolling circle translation by a ribosome in the individual. In some embodiments, the circRNA vaccine is administered via intramuscular (i.m) injection. In some embodiments, one or more doses of the circRNA vaccine are administered. In some embodiments, the interval between doses is about 2 weeks (e.g., 12, 13, 14, 15, or 16 days). In some embodiments, the method comprises administering a first dose of the circRNA vaccine and administering a second dose of the circRNA vaccine after 2 weeks or about 2 weeks.

In some embodiments, the present application provides methods of treating or preventing a coronavirus infection in an individual, comprising administering to the individual an effective amount of a circRNA vaccine comprising a circRNA comprising: (a) a nucleic acid sequence encoding an antigenic polypeptide comprising an S protein or a fragment thereof of a coronavirus (e.g., SARS-COV-2), and (b) an m6A modification motif sequence operably linked to the nucleic acid sequence encoding the antigenic polypeptide. In some embodiments, the nucleic acid sequence further encodes a SP (e.g., human tPA or IgE SP) fused to the N-terminus of the S protein or fragment thereof. In some embodiments, the circRNA further comprises a Kozak sequence operably linked to the nucleic acid sequence encoding the antigenic polypeptide. In some embodiments, the circRNA comprises a nucleic acid sequence comprising from the 5' end to the 3' end: the m6A modification motif sequence, the Kozak sequence, the SP, and the nucleic acid sequence encoding the antigenic polypeptide. In some embodiments, the circRNA further comprises a 3' exon sequence recognizable by a 3' catalytic Group I intron fragment flanking the 5' end of the nucleic acid sequence encoding the antigenic polypeptide, and a 5' exon sequence recognizable by a 5' catalytic Group I intron fragment flanking the 3' end of the nucleic acid sequence encoding the antigenic polypeptide. In some embodiments, the circRNA further comprises a 5' ligation sequence at the 5' end of the circRNA, and a 3' ligation sequence at the 3' end of the circRNA, wherein the 5' ligation sequence and the 3' ligation sequence are ligated to each other via a ligase (e.g., T4 RNA ligase). In some embodiments, the antigenic polypeptide comprises a RBD of the S protein. In some embodiments, the antigenic polypeptide further comprises a multimerization domain (e.g., C-terminal Fd domain, or a GCN-4 based isoleucine zipper domain). In some embodiments, the antigenic polypeptide comprises an S2 region of the S protein. In some embodiments, the antigenic polypeptide comprises amino acid residues 2-1273 of a full-length S protein of SARS-COV-2, wherein the numbering is based on SEQ ID NO: 1. In some embodiments, the S2 region of the S protein comprises one or more mutations (e.g., K986P and V987P) that stabilize a pre-fusion conformation of the S protein. In some embodiments, the antigenic polypeptide comprises one or more mutations (e.g., deletion of amino acid residues 681-684) that inhibit cleavage of the S protein. In some embodiments, the antigenic polypeptide comprises an S protein or fragment thereof of SARS-COV-2 having a D614G mutation. In some embodiments, the circRNA comprises a nucleic acid sequence selected from the group consisting of SEQ ID NOs: 11-15. In some embodiments, the circRNA is subject to rolling circle translation by a ribosome in the individual. In some embodiments, the circRNA vaccine is administered via intramuscular (i.m) injection. In some embodiments, one or more doses of the circRNA vaccine are administered. In some embodiments, the interval between doses is about 2 weeks (e.g., 12, 13, 14, 15, or 16 days). In some embodiments, the method comprises administering a first dose of the circRNA vaccine and administering a second dose of the circRNA vaccine after 2 weeks or about 2 weeks.

C. Formulation and Administration

In some embodiments, the circRNA composition for administration (e.g., circRNA vaccine or pharmaceutical composition) further comprises a transfection agent. In non-limiting examples, the transfection agent is polyethylenimine (PEI) or a lipid nanoparticle (LNP). Suitable lipid nanoparticles for administration of the circRNA have been described, for example, in Ickenstein, L. M. & Garidel, P. Lipid-based nanoparticle formulations for small molecules and RNA drugs. 890 *Expert Opin Drug Deliv* 16, 1205-1226, doi: 10.1080/17425247.2019.1669558 (2019), U.S. Patent App. Pub. No. 20200121809, U.S. Patent App. Pub. No. 20200163878, U.S. Patent App. Pub. No. 20190022247, and International Patent App. Pub. No. WO2021/030701, the contents of which are herein incorporated by reference in their entirety. In some embodiments, the LNP are formed from a lipid mixture of MC3-lipid:DSPC:cholesterol:PEG2000-DMG. In some embodiments, the MC3-lipid:DSPC:cholesterol:PEG2000-DMG are mixed in molar ratios of 50:10:38.5:1.5.

Other examples of lipidosomes that can be used to administer the circRNA composition for administration (e.g., circRNA vaccine or pharmaceutical composition) include protamines, cationic nanoemulsions, modified dendrimer nanoparticles, protamine liposomes, cationic polymers, cationic polymer liposomes, polysaccharide particles, cationic lipid nanoparticles, cationic lipid-cholesterol nanoparticles, cationic lipid-cholesterol PEG nanoparticle, cationic lipid transfection reagents sold under the trademark LIPOFECTAMINE, nonliposomal transfection reagents sold under the trademark FUGENE, or any combination thereof can be used as the transfection agent.

In some embodiments, the liposome formulation may be influenced by, but not limited to, the selection of the cationic lipid component, the degree of cationic lipid saturation, the nature of the PEGylation, ratio of all components and biophysical parameters such as size. In some embodiments, the liposome formulation comprises a cationic lipid, a cholesterol and a PEGylated lipid. For example, a liposome formulation may comprise a cationic lipid, dipalmitoylphosphatidylcholine, cholesterol, and PEG-c-DMA. See, for example, Semple et al. Nature Biotech. 2010 28:172-176, herein incorporated by reference in its entirety. In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to RNA in liposomes may be from about 5:1 to about 20:1, from about 10:1 to about 25:1, from about 15:1 to about 30:1 and/or at least 30:1. Suitable liposome formulations have been described, for example, in WO2020237227, the contents of which are herein incorporated by reference in their entirety.

In some embodiments, the circRNA is not formulated with a transfection reagent. In some embodiments, the circRNA is delivered as naked RNA. In some embodiments, the circRNA is delivered by gene gun or by electroporation.

The circRNA composition for administration (e.g., circRNA vaccine or pharmaceutical composition) can be administered to a subject by systemic injection into the vasculature, systemic injection into the lymph nodes, subcutaneous injection or depots, or by local injection.

In some embodiments; a circRNA vaccine herein (e.g., encoding an S protein or fragment thereof of a coronavirus) is administered via intramuscular (i.m) injection. In some embodiments, one or more doses of the circRNA vaccine are administered. In some embodiments, two or more doses of the circRNA vaccine are administered. In some embodiments, the interval between doses is about 2 weeks (e.g., 12, 13, 14, 15, or 16 days). In some embodiments, the method comprises administering a first dose of the circRNA vaccine and administering a second dose of the circRNA vaccine after 2 weeks or about 2 weeks.

In some embodiments, the circRNA may be formulated in a lipid nanoparticle such as those described in International Publication No. WO2012170930, herein incorporated by reference in its entirety.

In some embodiments, the synthetic nanocarriers may be formulated for controlled and/or sustained release of the circRNA described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the circRNA may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one circRNA, which encode at least one antigen. As a nonlimiting example, the synthetic nanocarrier may include at least one antigen and an excipient for a vaccine dosage form (see International Pub No. WO201 1150264 and US Pub No. US201 10293723, each of which is herein incorporated by reference in their entirety). As another non-limiting example, a vaccine dosage form may include at least two synthetic nanocarriers with the same or different antigens and an excipient (see International Pub No. WO201 1150249 and US Pub No. US201 10293701, each of which is herein incorporated by reference in their entirety). The vaccine dosage form may be selected by methods described herein, known in the art and/or described in International Pub No. WO201 1150258 and US Pub No. US20120027806, each of which is herein incorporated by reference in their entirety).

In some embodiments, the synthetic nanocarrier may comprise at least one circRNA, which encodes at least one adjuvant. As non-limiting example, the adjuvant may comprise dimethyldioctadecylammonium-bromide, dimethyldioctadecylammoniumchloride, dimethyldioctadecylammonium-phosphate or dimethyldioctadecylammoniumacetate (DDA) and an apolar fraction or part of said apolar fraction of a total lipid extract of a *mycobacterium* (See e.g., U.S. Pat. No. 8,241,610; herein incorporated by reference in its entirety). In another embodiment, the synthetic nanocarrier may comprise at least one circRNA and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In some embodiments, the circRNA functions as an adjuvant. As an example, RNA-sensing in the cytoplasm can trigger innate immunity, and innate immune signaling is known to contribute to adaptive immunity by diverse routes. Thus, the circRNA comprising the antigenic polypeptide or a second circRNA (e.g., a circRNA that does not encode a polypeptide) can be used as an adjuvant for boosting the adaptive immune response to the antigenic polypeptide.

In some embodiments, the circRNA composition for administration (e.g., circRNA vaccine or pharmaceutical composition) may be administered intranasally. For example, circRNA vaccines may be administered intranasally similar to the administration of live vaccines. In some embodiments, the circRNA may be administered intramuscularly or intradermally similarly to the administration of inactivated vaccines known in the art.

In some embodiments, the circRNA vaccine comprises an adjuvant, which may enable the vaccine to elicit a higher immune response. As a non-limiting example, the adjuvant could be a sub-micron oil-in-water emulsion, which can elicit a higher immune response in human pediatric populations (see e.g., the adjuvant-containing vaccines described in US Patent Publication No. US20120027813 and US Patent No. U.S. Pat. No. 8,506,966, the contents of each of which are herein incorporated by reference in its entirety).

In some embodiments, the circRNA compositions of the present application may be administrated with other prophylactic or therapeutic compounds. As a non-limiting example, the prophylactic or therapeutic compound may be an adjuvant or a booster. As used herein, when referring to a prophylactic composition, such as a vaccine, the term "booster" refers to an extra administration of the prophylactic composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 1 1 hours, 12 hours, 13 hours, 14 hours, 15 hours, 16 hours, 17 hours, 18 hours, 19 hours, 20 hours, 2 1 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years.

IV. Method of Preparation

The present application further provides nucleic acid constructs (e.g., linear RNA and vectors, etc.) for preparation of the circRNAs described herein, and methods for preparing the circRNAs, for example, by chemical ligation, enzymatic ligation, or ribozyme autocatalysis of linear RNAs. In some embodiments, the circRNA is prepared by circularizing a linear RNA in vitro.

Linear RNA and Nucleic Acid Constructs Encoding Thereof

In some embodiments, the present application provides a linear RNA capable of forming the circRNA of any one of the embodiments described above. In some embodiments, the linear RNA can circularized by chemical circularization methods using cyanogen bromide or a similar condensing agent. In some embodiments, the linear RNA can be circularized by autocatalysis of a Group I intron comprising a 5' catalytic Group I intron fragment and a 3' catalytic Group I intron fragment. In some embodiments, the linear RNA can be circularized by a ligase. In some embodiments, the linear RNA can be circularized by a T4 RNA ligase. In some embodiments, the linear RNA can be circularized by a DNA ligase. Suitable ligases include, but are not limited to a T4 DNA ligase (T4 Dnl), a T4 RNA ligase 1 (T4 Rnl1) and a T4 RNA ligase 2 (T4 Rn12).

In some embodiments, the present application provides a linear RNA capable of forming the circRNA of any one of the embodiments described above, wherein the linear RNA can be circularized by autocatalysis of a Group I intron. In some embodiments, the Group I intron comprises a 5' catalytic Group I intron fragment and a 3' catalytic Group I intron fragment. In some embodiments, the linear RNA comprises a 3' catalytic Group I intron fragment (such as the sequence set forth in SEQ ID NO: 46) flanking the 5' end of a 3' exon sequence recognizable by the 3' catalytic Group I intron fragment (such as the sequence set forth in SEQ ID NO: 39), and the 5' catalytic Group I intron fragment (such as the sequence set forth in SEQ ID NO: 47) flanking the 3' end of a 5' exon sequence recognizable by the 5' catalytic Group I intron fragment (such as the sequence set forth in SEQ ID NO: 40).

In some embodiments, the linear RNA comprises, from 5' to 3' end, a 3'Intron-IRES-Kozak-SP-Spike-5'Intron sequence. In some embodiments, the Spike sequence comprises one of the sequences set forth in SEQ ID NOs: 11-15 and SEQ ID NOs: 48-49.

In some embodiments, the linear RNA comprises, from 5' to 3' end, a 3'Intron-IRES-Kozak-SP-RBD-5'Intron sequence. In some embodiments, the RBD sequence comprises comprises amino acid residues. 319 to 542 of a full-length S protein of SARS-COV-2, wherein the numbering is based on SEQ ID NO: 1

In some embodiments, the linear RNA comprises, from 5' to 3' end, a 3'Intron-IRES-Kozak-SP-nAb-5'Intron sequence. In some embodiments, the nAb sequence encodes the amino acid sequence of SEQ ID NO: one of SEQ ID NOS: 26-35. In some embodiments, the nAb sequence encodes the amino acid sequence of SEQ ID NO: 26. In some embodiments, the nAb sequence encodes the amino acid sequence of SEQ ID NO: 27. In some embodiments, the nAb sequence encodes the amino acid sequence of SEQ ID NO: 30.

In some embodiments, the linear RNA comprises, from 5' to 3' end, a 3'Intron-IRES-Kozak-IDUA-5'Intron sequence. In some embodiments, the IDUA sequence encodes the amino acid sequence of SEQ ID NO: 18. In some embodiments, the IDUA sequence encodes the amino acid sequence of SEQ ID NO: 19.

In some embodiments, the linear RNA further comprises a 5' homology sequence flanking the 5' end of the 3' catalytic Group I intron fragment, and a 3' homology sequence flanking the 3' end of the 5'catalytic Group I intron fragment. In some embodiments, the linear RNA comprises, from 5' to 3' end, a 5'homology arm-3'catalytic Group I Intron fragment-3' exon sequence-IRES-Kozak-SP-antigenic polypeptide (e.g., Spike protein or fragment thereof)-5' exon sequence-5' catalytic Group I Intron fragment-3'homology arm sequence. In some embodiments, the homology sequence can be between 1 and 100, between 5 and 80, between 5 and 60, between 10 and 50, or between 12 and 50 nucleotides in length. In some embodiments, the homology sequence is about 20-30 nucleotides in length. In some embodiments, the 5' homology sequence comprises the nucleic acid sequence of SEQ ID NO: 41, and the 3' homology sequence comprises the nucleic acid sequence of SEQ ID NO: 42. In some embodiments, the homology arms increase the efficiency of RNA circularization by about 0 to 20%, more than 20%, more than 30%, more than 40%, or more than 50%.

In some embodiments, there is provided a nucleic acid construct comprising a nucleic acid sequence encoding the linear RNA. In some embodiments, a T7 promoter is operably linked to the nucleic acid sequence encoding the linear RNA. In some embodiments, the T7 promoter comprises the sequence set forth in SEQ ID NO: 43. In some embodiments, the T7 promoter is capable of driving in vitro transcription.

Plasmids

In some embodiments, the present application provides plasmids comprising the nucleotide sequences described herein. In some embodiments, the plasmids are obtained by cloning the sequence encoding the linearized RNAs into a plasmid vector. Plasmids can be generated by techniques known in the art, such as Gibson cloning or cloning using restriction enzymes. In some embodiments, the plasmid vector includes an antibiotic expression cassette allowing antibiotic selection of bacteria expressing the plasmid. In some embodiments, the plasmids provided can be purified from bacteria and used for production of the linear circRNA constructs. Any plasmid vector suitable for in vitro transcription of the linear RNA may be used.

In some embodiments, the plasmids are linearized prior to in vitro transcription of the linear RNA. In some embodiments, the recombinant plasmids are linearized by restriction enzyme digestion. In some embodiments, the recombinant plasmids are linearized by PCR amplification. In some embodiments, the method further comprises performing in vitro transcription with the linearized plasmid template. In some embodiments, the in vitro transcription is driven by a T7 promoter.

Linear RNA Circularized by Chemical Ligation

In some embodiments, there is provided a method of preparing a circRNA described herein, comprising: (a) chemically ligating the 5' end and the 3' end of a linear RNA comprising a nucleic acid sequence encoding the circRNA; and (b) isolating the circularized RNA product, thereby providing the circRNA.

In some embodiments, the step of circularizing the linear RNA comprises chemical circularization methods using cyanogen bromide or a similar condensing agent.

In some embodiments, the linear RNA can be circularized by chemical methods. In some chemical methods, the 5'-end and the 3'-end of the nucleic acid (e.g., a linear circular polyribonucleotide) includes chemically reactive groups that, when close together, may form a new covalent linkage between the 5'-end and the 3'-end of the molecule. The 5'-end may contain an NHS ester reactive group and the 3'-end may contain a 3'-amino terminated nucleotide such that in an organic solvent the 3'-amino-terminated nucleotide on the 3'-end of a linear RNA molecule will undergo a nucleophilic attack on the 5'-NHS-ester moiety forming a new 5'-/3'-amide bond.

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60, at least about 70%, at least about 80%, at least about 90%, at least about 95%, or 100%. In some embodiments, the circularization efficiency of the circularization methods provided herein is at least about 40%.

Linear RNA Circularized by Ribozyme Autocatalysis

In some embodiments, the circRNA can be obtained by circularizing a linear RNA by ribozyme autocatalysis. In some embodiments, the linear RNA is circularized in vitro. In some embodiments, circularization by ribozyme autocatalysis comprises (a) subjecting the linear RNA to a condition that activates autocatalysis of the Group I intron (or 5' and 3' catalytic Group I intron fragments thereof) to provide a circularized RNA product; and (b) isolating the circularized RNA product, thereby providing the circRNA.

In some embodiments, the method comprises a step of obtaining the linear RNA by first cloning the sequence encoding the linearized RNAs into a plasmid vector, and then linearizing the recombinant plasmids. In some embodiments, the recombinant plasmids are linearized by restriction enzyme digestion. In some embodiments, the recombinant plasmids are linearized by PCR amplification. In some embodiments, the method further comprises performing in vitro transcription with the linearized plasmid template. In some embodiments, the in vitro transcription is driven by a T7 promoter. In some embodiments, the method further comprises purifying the linear RNA transcripts. In some embodiments, the linear RNAs are purified by gel purification.

In some embodiments, the present application provides a method of cyclizing a linear RNA (e.g., purified linear RNA) by ribozyme autocatalysis of the Group I intron. During splicing, the 3' hydroxyl group of a guanosine nucleotide engages in a transesterification reaction at the 5' splice site. The 5' intron half is excised, and the freed hydroxyl group at the end of the intermediate engages in a second transesterification at the 3' splice site, resulting in circularization of the intervening region and excision of the 3' intron. In some embodiments, the condition that activates autocatalysis of the Group I intron or 5' and 3' catalytic Group I intron fragments is the addition of GTPs and $Mg^{2+}$. In some embodiments, there is provided a step of cyclizing the linear RNAs by adding GTPs and $Mg^{2+}$ at 55° C. for 15 min: In some embodiments, the method further comprises treating with RNase R to digest the linear RNA transcripts. In some embodiments, the method further comprises isolating the circular RNA (circRNA). In some embodiments, the step of isolating the circRNA comprises gel-purifying the circRNA. In some embodiments, the purified circRNA can be stored at −80° C.

In some embodiments, the circularization has an efficiency of at least 2%, at least 5%, at least 10%, at least 15%, at least 20%, at least 25%, at least 30%, at least 32%, at least 34%, at least 36%, at least 38%, at least 40%, at least 42%, at least 44%, at least 46%, at least 48%, or at least 50%. In some embodiments, the circularization has an efficiency of about 40% to about 50% or more than 50%.

Linear RNA Circularized by Ligation

In some embodiments, the circRNA can be obtained by circularizing a linear RNA using a ligase such as a RNA ligase. In some embodiments, the linear RNA is circularized in vitro. In some embodiments, the linear RNA can be circularized by a T4 RNA ligase. In some embodiments, the linear RNA comprises a 5' ligation sequence at the 5' end of the nucleic acid sequence encoding the circRNA, and a 3' ligation sequence at the 3' end of the nucleic acid sequence encoding the circRNA, wherein the 5' ligation sequence and the 3' ligation sequence can be ligated to each other via the RNA ligase. In non-limiting examples, the linear RNA can be circularized by a ligase such as a T4 DNA ligase (T4 Dnl), T4 RNA ligase 1 (T4 Rnl1), and T4 RNA ligase 2 (T4 Rnl2). The linear RNA may be circularized with or without the presence of a single stranded nucleic acid adaptor, e.g., a splint DNA.

In some embodiments, the present application provides a method of producing any one of the circRNAs described above, comprising: (a) contacting any one of the linear RNAs comprising a 5' ligation sequence at the 5' end of the nucleic acid sequence encoding the circRNA, and a 3' ligation sequence at the 3' end of the nucleic acid sequence encoding the circRNA described above with a single-stranded adaptor nucleic acid comprising from the 5' end to the 3' end: a first sequence complementary to the 3' ligation sequence and a second sequence complementary to the 5' ligation sequence, and wherein the 5' ligation sequence and the 3' ligation sequence hybridize to the single-stranded adaptor nucleic acid to provide a duplex nucleic acid intermediate comprising a single strand break between the 3' end of the 5' ligation sequence and the 5' end of the 3' ligation sequence; (b) contacting the intermediate with an RNA ligase under a condition that allows ligation of the 5' ligation sequence to the 3' ligation sequence to provide a circularized RNA product; and (c) isolating the circularized RNA product, thereby providing the circRNA.

In some embodiments, the method described herein comprises circularizing a linear RNA in vitro, comprising: (a) contacting any one of the linear RNAs comprising a 5' ligation sequence at the 5' end of the nucleic acid sequence encoding the circular RNA, and a 3' ligation sequence at the 3' end of the nucleic acid sequence encoding the circular RNA described above with an RNA ligase under a condition that allows ligation of the 5' ligation sequence to the 3' ligation sequence to provide a circularized RNA product; and (b) isolating the circularized RNA product, thereby providing the circular RNA.

In some embodiments, the method further comprises treating with RNase R to digest the linear RNA transcripts. In some embodiments, the method further comprises isolating the circular RNA (circRNA). In some embodiments, the step of isolating the circRNA comprises gel-purifying the circRNA. In some embodiments, the purified circRNA can be stored at −80° C.

In some embodiments, a DNA or RNA ligase may be used to enzymatically link a 5'-phosphorylated nucleic acid molecule (e.g., a linear RNA) to the 3'-hydroxyl group of a nucleic acid (e.g., a linear nucleic acid) forming a new phosphorodiester linkage. In an example reaction, a linear circular RNA is incubated at 37° C. for 1 hour with 1-10 units of T4 RNA ligase (New England Biolabs, Ipswich, Mass.) according to the manufacturer's protocol. The ligation reaction may occur in the presence of a linear nucleic acid capable of base-pairing with both the 5'- and 3'-region in juxtaposition to assist the enzymatic ligation reaction. In some embodiments, the ligation is splint ligation. For example, a splint ligase, like SPLINTR® ligase, can be used for splint ligation. For splint ligation, a single stranded polynucleotide (splint), like a single stranded RNA, can be designed to hybridize with both termini of a linear polyribonucleotide, so that the two termini can be juxtaposed upon hybridization with the single-stranded splint. Splint ligase can thus catalyze the ligation of the juxtaposed two termini of the linear polyribonucleotide, generating a circular polyribonucleotide.

In some embodiments, a DNA or RNA ligase may be used in the synthesis of the circular RNA. As a non-limiting example, the ligase may be a circ ligase or circular ligase.

Purification of circRNA

In some embodiments, the method provided herein of producing a circRNA further comprises a step of purifying the circularized RNA product. In non-limiting examples, the circRNA is purified by gel-purification or by high-performance liquid chromatography (HPLC). In some embodiments, agarose gel electrophoresis allows for simple and effective separation of circular splicing products from linear precursor molecules, nicked circles, splicing intermediates, and excised introns. In some embodiments, the method comprises purifying the circular RNA by chromatography, such as HPLC. In some embodiments, the purified circular RNA can be stored at −80° C.

V. Pharmaceutical Compositions, Kits and Articles of Manufacture

Further provided by the present application are pharmaceutical compositions comprising any one of circRNAs described herein, and a pharmaceutically acceptable carrier. Pharmaceutical compositions can be prepared by mixing the therapeutic agents described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

The present application further provides kits and articles of manufacture for use in any embodiment of the treatment methods described herein. The kits and articles of manufacture may comprise any one of the formulations and pharmaceutical compositions described herein.

In some embodiments, there is provided a kit comprising any one of the circRNAs described herein and instructions for treating or preventing a disease or condition (e.g., coronavirus infection).

In some embodiments, there is provided a kit comprising any one of the circRNA described herein and instructions for treating or preventing a coronavirus infection.

In some embodiments, there is provided a kit comprising any one of the plasmids or linear RNAs described herein, and instructions for preparing any one of the circRNAs. In some embodiments, there is provided a kit comprising any one of the plasmids, linear RNAs, or circRNAs described herein, and instructions for administering the circRNA.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the circRNA as disclosed herein to provide effective treatment of an individual or of many individuals. Additionally, kits may be provided that contain sufficient dosages of the circRNA to allow for multiple administrations to an individual (e.g., initial vaccine; administration and subsequent booster administration, in the case of a circRNA vaccine). Kits may also include multiple unit doses of the pharmaceutical compositions and instructions for use and packaged in quantities sufficient for storage and use in pharmacies, for example, hospital pharmacies and compounding pharmacies.

In some embodiments, the kit comprises a delivery system. The delivery system may be a unit dose delivery system. The volume of solution or suspension delivered per dose can be anywhere from about 5 to about 2000 microliters, from about 10 to about 1000 microliters, or from about 50 to about 500 microliters. Delivery systems for these various dosage forms can be syringes, dropper bottles, plastic squeeze units, atomizers, nebulizers or pharmaceutical aerosols in either unit dose or multiple dose packages. In some embodiments, there is provided a delivery system of any one of the circRNAs described herein, comprising the circRNA and a device for delivering the circRNA.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

VI. Exemplary Embodiments

In some aspects, the present application provides the following exemplary embodiments.

Embodiment 1. A circular RNA (circRNA) comprising a nucleic acid sequence encoding a therapeutic polypeptide, wherein the therapeutic polypeptide is selected from the group consisting of an antigenic polypeptide, a functional protein, a receptor protein, and a targeting protein.

Embodiment 2. The circRNA of embodiment 1, further comprising a Kozak sequence operably linked to the nucleic acid sequence encoding the therapeutic polypeptide.

Embodiment 3. The circRNA of embodiment 1 or 2, further comprising an in-frame 2A peptide coding sequence operably linked to the 3' end of the nucleic acid sequence encoding the therapeutic polypeptide.

Embodiment 4. The circRNA of any one of embodiments 1-3, further comprising an internal ribosomal entry site. (IRES) sequence operably linked to the nucleic acid sequence encoding the therapeutic polypeptide.

Embodiment 5. The circRNA of embodiment 4, wherein the IRES sequence is an IRES sequence selected from the group consisting of CVB3 virus, EV71 virus, EMCV virus, PV virus, and CSFV virus IRES sequences.

Embodiment 6. The circRNA of embodiment 4 or 5, comprising a nucleic acid sequence comprising from the 5' end to the 3' end: the IRES sequence, the Kozak sequence, and the nucleic acid sequence encoding the therapeutic polypeptide.

Embodiment 7. The circRNA of any one of embodiments 4-6, further comprising a polyAC or polyA sequence disposed at the 5' end of the IRES sequence.

Embodiment 8. The circRNA of any one of embodiments 1-3, further comprising an m6A modification motif sequence operably linked to the nucleic acid sequence encoding the therapeutic polypeptide.

Embodiment 9. The circRNA of embodiment 8, comprising a nucleic acid sequence comprising from the 5' end to the 3' end: the m6A modification motif sequence, the Kozak sequence, and the nucleic acid sequence encoding the therapeutic polypeptide.

Embodiment 10. The circRNA of any one of embodiments 1-9, wherein the nucleic acid sequence further encodes a signal peptide (SP) fused to the N-terminus of the therapeutic polypeptide.

Embodiment 11. The circRNA of embodiment 10, wherein the SP is an SP of a human tissue plasminogen activator (tPA) or a human IgE immunoglobulin.

Embodiment 12. The circRNA of any one of embodiments 1-11, further comprising a 3' exon sequence recognizable by a 3' catalytic Group I intron fragment flanking the 5' end of the nucleic acid sequence encoding the therapeutic polypeptide, and a 5' exon sequence recognizable by a 5' catalytic Group I intron fragment flanking the 3' end of the nucleic acid sequence encoding the therapeutic polypeptide.

Embodiment 13. The circRNA of embodiment 12, wherein the 3' exon sequence comprises the nucleic acid sequence of SEQ ID NO: 40, and the 5' exon sequence comprises the nucleic acid sequence of SEQ ID NO: 41.

Embodiment 14. The circRNA of any one of embodiments 1-13, wherein the therapeutic protein is for treating or preventing an infection.

Embodiment 15. The circRNA of embodiment 14, wherein the infection is an infection by a virus.

Embodiment 16. The circRNA of embodiment 15, wherein the virus is a coronavirus.

Embodiment 17. The circRNA of embodiment 16, wherein the coronavirusis selected from the group consisting of SARS-COV, MERS-COV, and SARS-COV-2.

Embodiment 18. The circRNA of embodiment 17, wherein the coronavirus is SARS-CoV-2.

Embodiment 19. The circRNA of any one of embodiments 1-18, wherein the therapeutic polypeptide is an antigenic polypeptide.

Embodiment 20. The circRNA of embodiment 19, wherein the antigenic polypeptide comprises a Spike (S) protein or a fragment thereof of a coronavirus.

Embodiment 21. The circRNA of embodiment 20, wherein the antigenic polypeptide comprises a receptor-binding domain (RBD) of the S protein.

Embodiment 22. The circRNA of embodiment 21, wherein the RBD comprises amino acid residues 319 to 542 of a full-length S protein of SARS-COV-2, wherein the numbering is based on SEQ ID NO: 1.

Embodiment 23. The circRNA of embodiment 22, wherein the RBD comprises the amino acid sequence of SEQ ID NO: 2.

Embodiment 24. The circRNA of any one of embodiments 21-23, wherein the antigenic polypeptide further comprises a multimerization domain.

Embodiment 25. The circRNA of embodiment 24, wherein the multimerization domain is a C-terminal Foldon (Fd) domain of a T4 fibritin protein that mediates trimerization of the T4 fibritin protein, or a GCN-4 based isoleucine zipper domain.

Embodiment 26. The circRNA of embodiment 24, wherein the multimerization domain comprises the amino acid sequence of SEQ ID NO: 3 or 4.

Embodiment 27. The circRNA of any one of embodiments 24-26, wherein the RBD is fused to the multimerization domain via a peptide linker.

Embodiment 28. The circRNA of embodiment 27, wherein the peptide linker comprises the amino acid sequence of SEQ ID NO: 5.

Embodiment 29. The circRNA of any one of embodiments 20-28, wherein the antigenic polypeptide comprises an S2 region of the S protein.

Embodiment 30. The circRNA of embodiment 29, wherein the S2 region comprises amino acid residues 686 to 1273 of a full-length S protein of SARS-COV-2, wherein the numbering is based on SEQ ID NO: 1.

Embodiment 31. The circRNA of embodiment 29, wherein the S2 region comprises one or more mutations that stabilize a pre-fusion conformation of the S protein.

Embodiment 32. The circRNA of embodiment 31, wherein the one or more mutations comprise K986P and V987P.

Embodiment 33. The circRNA of any one of embodiments 29-32, wherein the S2 region comprises the amino acid sequence of SEQ ID NO: 6 or 7.

Embodiment 34. The circRNA of any one of embodiments 20-23 and 29-33, wherein the antigenic polypeptide comprises amino acid residues 2-1273 of a full-length S protein of SARS-CoV-2, wherein the numbering is based on SEQ ID NO: 1.

Embodiment 35. The circRNA of embodiment 34, wherein the antigenic polypeptide comprises one or more mutations that inhibit cleavage of the S protein.

Embodiment 36. The circRNA of embodiment 35, wherein the one or more mutations comprise deletion of amino acid residues 681-684.

Embodiment 37. The circRNA of embodiment 20, wherein the antigenic polypeptide comprises an amino acid sequence selected from the group consisting of SEQ ID NOs: 8-10 and 62-63.

Embodiment 38. The circRNA of embodiment 20, wherein the circRNA comprises a nucleic acid sequence selected from the group consisting of SEQ ID NOs: 11-15 and 64.

Embodiment 39. The circRNA of any one of embodiments 1-18, wherein the therapeutic protein is a receptor protein.

Embodiment 40. The circRNA of embodiment 39, wherein the therapeutic protein is a soluble receptor comprising an extracellular domain of a naturally occurring receptor.

Embodiment 41. The circRNA of embodiment 39 or 40, wherein the receptor is an ACE2 receptor.

Embodiment 42. The circRNA of embodiment 41, wherein the receptor is a high-affinity mutant ACE2 receptor.

Embodiment 43. The circRNA of any one of embodiments 1-18, wherein the therapeutic protein is a targeting protein.

Embodiment 44. The circRNA of embodiment 43, wherein the targeting protein is an antibody.

Embodiment 45. The circRNA of embodiment 44, wherein the antibody is a neutralizing antibody.

Embodiment 46. The circRNA of embodiment 44, wherein the targeting protein is a therapeutic antibody.

Embodiment 47. The circRNA of any one of embodiments 1-13, wherein the therapeutic protein is a functional protein.

Embodiment 48. The circRNA of embodiment 47, wherein the functional protein is a tumor suppressor.

Embodiment 49. The circRNA of embodiment 48, wherein the tumor suppressor is selected from the group consisting of p53 and PTEN.

Embodiment 50. The circRNA of embodiment 47, wherein the functional protein is an enzyme.

Embodiment 51. The circRNA of embodiment 50, wherein the enzyme is selected from the group consisting of OTC, FAH and IDUA.

Embodiment 52. The circRNA of embodiment 47, wherein the functional protein is selected from the group consisting of DMD, COL3A1, BMPR2, AHI1, FANCC, MYBPC3, and IL2RG.

Embodiment 53. A composition comprising a plurality of circRNAs of any one of embodiments 20-38, wherein the antigenic polypeptides corresponding to the plurality of circRNAs are different with respect to each other.

Embodiment 54. A composition comprising a plurality of circRNAs of any one of embodiments 39-42, wherein the receptor proteins corresponding to the plurality of circRNAs are different with respect to each other.

Embodiment 55. A composition comprising a plurality of circRNAs of any one of embodiments 43-46, wherein the targeting proteins corresponding to the plurality of circRNAs are different with respect to each other.

Embodiment 56. The composition of any one of embodiments 53-55, wherein the plurality of circRNAs target a plurality of strains of a coronavirus.

Embodiment 57. A circRNA vaccine comprising the circRNA of any one of embodiments 20-38 or the composition of embodiment 53 or 56.

Embodiment 58. A pharmaceutical composition comprising the circRNA of any one of embodiments 1-52 and a pharmaceutically acceptable carrier.

Embodiment 59. The circRNA vaccine of embodiment 57 or the pharmaceutical composition of embodiment 58, further comprising a transfection agent.

Embodiment 60. The circRNA vaccine or the pharmaceutical composition of embodiment 59, wherein the transfection agent is polyethylenimine (PEI) or a lipid nanoparticle (LNP), optionally wherein the LNP comprises MC3-lipid, DSPC, cholesterol, and PEG2000-DMG.

Embodiment 61. The circRNA vaccine of embodiment 57 or the pharmaceutical composition of embodiment 58, wherein the circRNA is not formulated with a transfection agent.

Embodiment 62. A method of treating or preventing an infection in an individual, comprising administering to the individual an effective amount of the circRNA of any one of embodiments 20-46, the composition of any one of embodiments 53-56, or the circRNA vaccine of any one of embodiments 57 and 59-61.

Embodiment 63. The method of embodiment 62, wherein the infection is a coronavirus infection.

Embodiment 64. The method of embodiment 63, wherein the infection is SARS-COV-2 infection, optionally the SARS-COV-2 infection is caused by a SARS-COV-2 variant (e.g., B.1.351 variant).

Embodiment 65. A method of treating or preventing a disease or condition in an individual, comprising administering to the individual an effective amount of the circRNA of any one of embodiments 1-52, or the pharmaceutical composition of any one of embodiments 58-61.

Embodiment 66. The method of embodiment 65, wherein the disease or condition is a disease or condition associated with insufficient levels and/or activity of a protein corresponding to the therapeutic protein.

Embodiment 67. The method of embodiment 66, wherein the disease or condition is a hereditary genetic disease associated with one or more mutations in the protein corresponding to the therapeutic protein.

Embodiment 68. The method of any of embodiments 65-67, wherein:
(i) the therapeutic polypeptide is TP53 or PTEN, and the disease or condition is cancer;
(ii) the therapeutic polypeptide is OTC, and the disease is ornithine transcarbamylase deficiency;
(iii) the therapeutic polypeptide is FAH, and the disease is tyrosinemia;
(iv) the therapeutic polypeptide is DMD, and the disease is Duchenne and Becker muscular dystrophy, X-linked dilated cardiomyopathy, or familial dilated cardiomyopathy;
(v) the therapeutic polypeptide is IDUA, and the disease or condition is Mucopolysaccharidosis type I (MPS I);
(vi) the therapeutic polypeptide is COL3A1, and the disease or condition is Ehlers-Danlos syndrome;
(vii) the therapeutic polypeptide is AHI1, and the disease or condition is Joubert syndrome;
(viii) the therapeutic polypeptide is BMPR2, and the disease or condition is pulmonary arterial hypertension, or pulmonary veno-occlusive disease;
(ix) the therapeutic polypeptide is FANCC, and the disease or condition is Fanconi anemia;
(x) the therapeutic polypeptide is MYBPC3, and the disease or condition is primary familial hypertrophic cardiomyopathy; or
(xi) the therapeutic polypeptide is IL2RG, and the disease or condition is X-linked severe combined immunodeficiency.

Embodiment 69. The method of any one of embodiments 62-68, wherein the circRNA is subject to rolling circle translation by a ribosome in the individual.

Embodiment 70. The method of embodiment 66, wherein the disease or condition is a hereditary genetic disease associated with one or more mutations in the protein corresponding to the therapeutic protein.

Embodiment 71. A linear RNA capable of forming the circRNA of any one of embodiments 1-52.

Embodiment 72. The linear RNA of embodiment 71, wherein the linear RNA comprises a Group I intron comprising a 5' catalytic Group I intron fragment and a 3' catalytic Group I intron fragment, wherein the linear RNA can be circularized by autocatalysis of the Group I intron.

Embodiment 73. The linear RNA of embodiment 72, comprising the 3' catalytic Group I intron fragment flanking the 5' end of a 3' exon sequence recognizable by the 3' catalytic Group I intron fragment, and the 5' catalytic Group I intron fragment flanking the 3' end of a 5' exon sequence recognizable by the 5' catalytic Group I intron fragment.

Embodiment 74. The linear RNA of embodiment 73, comprising a 5' homology sequence flanking the 5' end of the 3' catalytic Group I intron fragment, and a 3' homology sequence flanking the 3' end of the 5' catalytic Group I intron fragment.

Embodiment 75. The linear RNA of embodiment 74, wherein the 5' homology sequence comprises the nucleic acid sequence of SEQ ID NO: 41, and the 3' homology sequence comprises the nucleic acid sequence of SEQ. ID NO: 42.

Embodiment 76. The linear RNA of embodiment 71, wherein the linear RNA can be circularized by a ligase.

Embodiment 77. The linear RNA of embodiment 76, wherein the ligase is selected from the group consisting of a T4 DNA ligase (T4 Dnl), a T4 RNA ligase 1 (T4 Rnl1) and a T4 RNA ligase 2 (T4 Rnl2).

Embodiment 78. The linear RNA of embodiment 76 or 77, comprising a 5' ligation sequence at the 5' end of the nucleic acid sequence encoding the circRNA, and a 3' ligation sequence at the 3' end of the nucleic acid sequence encoding the circRNA, wherein the 5' ligation sequence and the 3' ligation sequence can be ligated to each other via the RNA ligase.

Embodiment 79. A nucleic acid construct comprising a nucleic acid sequence encoding the linear RNA of any one of embodiments 70-78.

Embodiment 80. The nucleic acid construct of embodiment 79, comprising a T7 promoter operably linked to the nucleic acid sequence encoding the linear RNA.

Embodiment 81. A method of producing a circRNA, comprising:
(a) subjecting the linear RNA of any one ofembodiments 71-75 to a condition that activates autocatalysis of the 5' catalytic Group I intron fragment and the 3' catalytic Group I intron fragment to provide a circularized RNA product; and
(b) isolating the circularizad RNA product, thereby providing the circRNA.

Embodiment 82. A method of producing a circRNA, comprising:
(a) contacting the linear RNA of any one of embodiments 76-78 with a single-stranded adaptor nucleic acid comprising from the 5' end to the 3' end: a first sequence complementary to the 3' ligation sequence and a second sequence complementary to the 5' ligation sequence, and wherein the 5' ligation sequence and the 3' ligation sequence hybridize to the single-stranded adaptor nucleic acid to provide a duplex nucleic acid intermediate comprising a single strand break between the 3' end of the 5' ligation sequence and the 5' end of the 3' ligation sequence;
(b) contacting the intermediate with an RNA ligase under a condition that allows ligation of the 5' ligation sequence to the 3' ligation sequence to provide a circularized RNA product; and
(c) isolating the circularized RNA product, thereby providing the circRNA.

Embodiment 83. A method of producing a circRNA, comprising:
(a) contacting the linear RNA of any one of embodiments 76-78 with an RNA ligase under a condition that allows ligation of the 5' ligation sequence to the 3' ligation sequence to provide a circularized RNA product; and
(b) isolating the circularized RNA product, thereby providing the circular RNA.

Embodiment 84. The method of any one of embodiments80-82, further comprising obtaining the linear RNA by in vitro transcription of a nucleic acid construct comprising a nucleic acid sequence encoding the linear RNA.

Embodiment 85. The method of any one of embodiments 80-84, further comprising purifying the circularized RNA product.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended embodiments.

Example 1. In Vitro circRNA Production by Ligation

This example demonstrates in vitro production of a circular RNA (circRNA) by ligation.

Figure 2A:
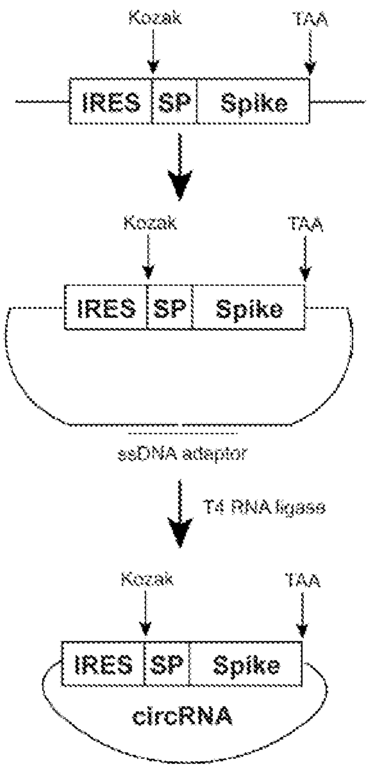
FIG. 2A shows a schematic of an exemplary nucleotide sequence having an IRES, and an exemplary method of circularizing linear RNAs by enzyme catalysis using T4 RNA ligases by supplying ssDNA adaptors.

A linear RNA is designed that can be circularized to produce a circRNA comprising, from 5' to 3', an IRES-Kozak-SP-Spike sequence, as shown in FIG. 2A. The linear RNA is designed with, from 5' to 3', an IRES sequence (SEQ ID NO: 53), a Kozak sequence (SEQ ID NO: 36), a signal peptide coding sequence (SEQ ID NO: 16 or SEQ ID NO: 17), and a Spike protein coding sequence having K986P/V987P and A681-684 modifications (SEQ ID NO: 15) followed by a TAA stop codon, Linear RNAs that can be circularized to produce the circular RNA (circRNAs) disclosed herein may be made using standard laboratory methods and materials. The cDNA sequence encoding the linear RNA may be synthesized by de novo DNA synthesis. The synthetic nucleic acid can be ordered from a synthetic nucleotide service such as GBLOCKS® (Integrated DNA Technologies). The nucleic acid sequence encoding the linear RNA sequence can be cloned into a plasmid vector containing a T7 promoter, the multiple cloning site flanked by restriction sites such as Xba1 restriction sites. The resulting plasmid may be transformed into chemically competent *E. coli.*

For the present example, NEB DH5-alpha Competent *E. coli* cells are used. Transformations are performed according to NEB instructions using 100 ng of plasmid. The protocol is as follows:

1. Thaw a tube of NEB 5-alpha Competent *E. coli* cells on ice for 10 minutes.
2. Add 1-5 μL containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 μL of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.

Spread 50-100 μL of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions. To isolate the plasmid (up to 850 mg), a maxi prep is performed using the Invitrogen PURELINK™ HiPure Maxiprep Kit (Carlsbad, CA), following the manufacturer's instructions.

Figure 2B:
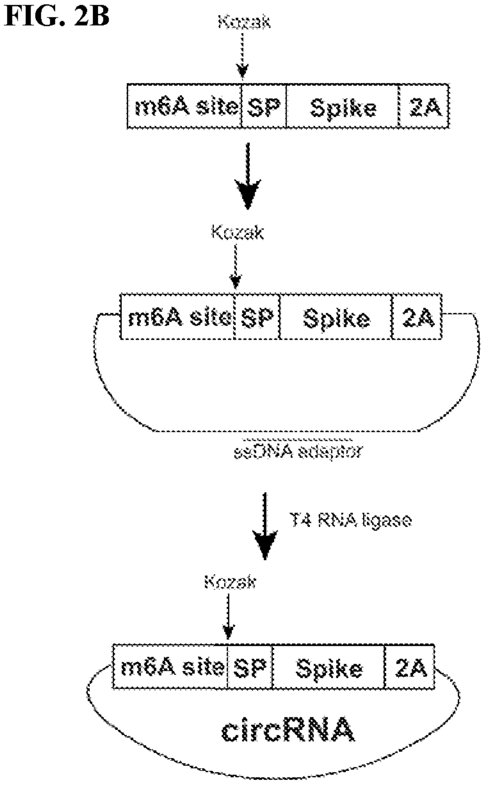
FIG. 2B shows a schematic of an exemplary nucleotide sequence wherein the IRES sequence is replaced with an m6A modification motif and the TAA stop codon is replaced with a 2A peptide coding sequence (in non-limiting examples, a T2A, P2A or other 2A peptide-coding sequence). Also shown is an exemplary method of circularizing linear RNAs by enzyme catalysis using T4 RNA ligases by supplying ssDNA adaptors.
Figure 2C:
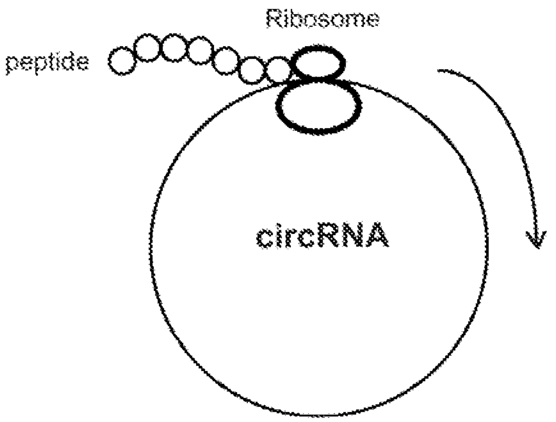
FIG. 2C shows a schematic illustration of the ribosome rolling circle translation of the circRNA vaccine. The translation factors can be recruited and translation initiated by either the IRES site or the m6A modification motifs.

In order to generate a linearized plasmid DNA template for In Vitro Transcription (IVT), the plasmid (an Example of which is shown in FIG. 2) is first linearized using a restriction enzyme such as Xbal. A typical restriction digest with Xbal will comprise the following: Plasmid 1.0 mg 10× Buffer 1.0 mL; Xbal 1.5 mL; dH20 up to 10 mL; incubated at 37° C. for 1 hr. If performing at lab scale (<5), the reaction is cleaned up using Invitrogen's PURELINK™ PCR Micro Kit (Carlsbad, CA) per manufacturer's instructions. Larger scale purifications may need to be done with a product that has a larger load capacity such as Invitrogen's standard PURELINK™ PCR Kit (Carlsbad, CA). Following the cleanup, the linearized vector is quantified using the NanoDrop and analyzed to confirm linearization using agarose gel electrophoresis.

Unmodified linear RNA is synthesized by in vitro transcription using T7 RNA polymerase from the linearized plasmid. Transcribed RNA is purified with an RNA purification system (QIAGEN), treated with alkaline phosphatase (ThermoFisher Scientific, EF0652) following the manufacturer's instructions, and purified again with the RNA purification system.

Splint ligation circular RNA is generated by treatment of the transcribed linear RNA and a DNA splint using T4 DNA ligase (New England Bio, Inc., M0202M), and the circular RNA is isolated following enrichment with RNase R treatment. RNA quality is assessed by agarose gel or through automated electrophoresis (Agilent).

Example 2. In Vitro circRNA Production by Group I Ribozyme Autocatalysis

This example demonstrates in vitro production of a circular RNA (circRNA) by Group I ribozyme autocatalysis.

Figure 1B:
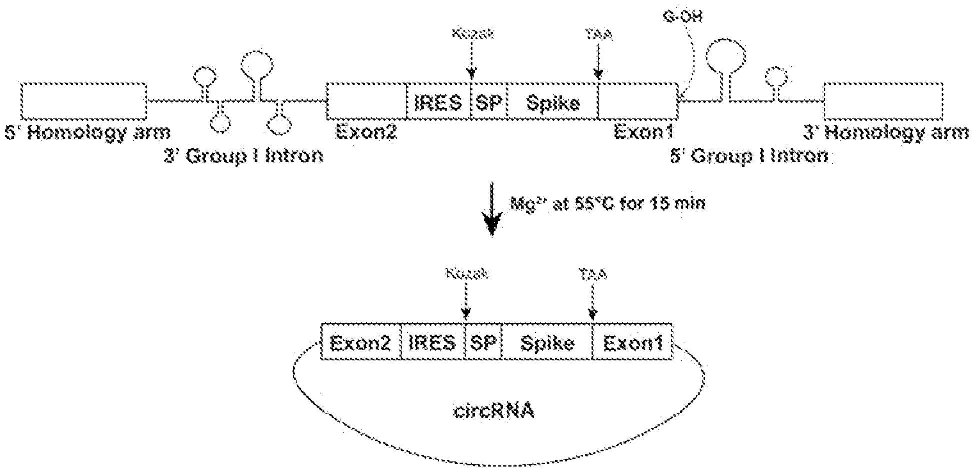
FIG. 1B shows a schematic of an exemplary nucleotide sequence having an IRES, and an exemplary method of circularizing purified linear RNAs by ribozyme autocatalysis of the Group I catalytic Intron.
Figure 1C:
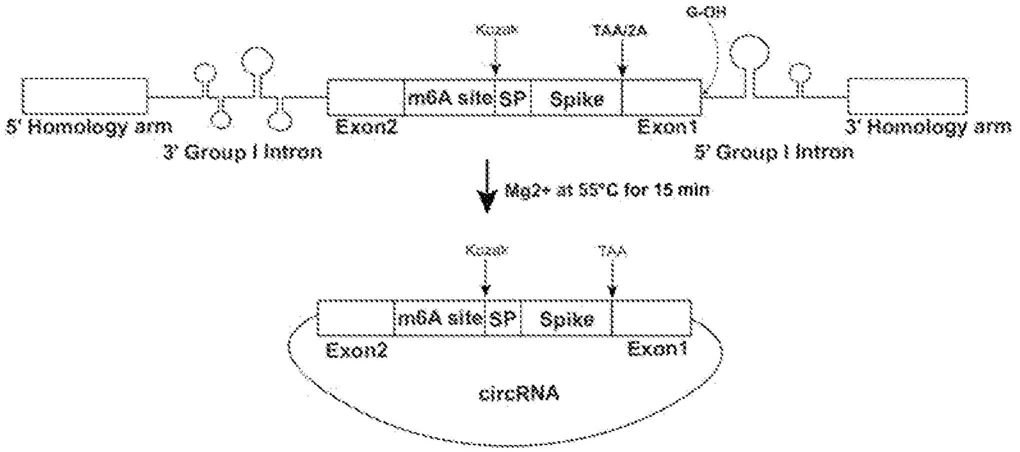
FIG. 1C shows a schematic of an exemplary nucleotide sequence having an m6A modification motif sequence before the start codon, and an exemplary method of circularizing purified linearized RNAs by ribozyme autocatalysis of the Group I catalytic intron.

A linear RNA is designed that can be circularized to produce a circRNA comprising, from 5' to 3', a 5'Homology arm-3' catalytic Group I intron fragment-3' exon sequence recognizable by the 3' catalytic Group I intron fragment (i.e., Exon 2)-m6A modification motif-Kozak-SP-Spike-2A peptide-5' exon sequence recognizable by the 5' catalytic Group I intron fragment (i.e., Exon 1)-5' catalytic Group I intron fragment-3'Homology arm, as shown in FIG. 1C. The linear RNA is designed with, from 5' to 3', a 5' homology arm (SEQ ID NO: 41), a 3' catalytic Group I intron sequence (SEQ ID NO: 46), a 3' exon sequence recognizable by a 3' catalytic Group I intron fragment (SEQ ID NO: 39), a m6A modification motif sequence (SEQ ID NO: 38), a Kozak sequence (SEQ ID NO: 37), a signal peptide coding sequence (SEQ ID NO: 16 or SEQ ID NO: 17), a Spike protein coding sequence having K986P/V987P and A681-684 modifications (SEQ ID NO: 15), a 2A peptide coding sequence (SEQ ID NO: 44 or SEQ ID NO: 45), a 5' exon sequence recognizable by a 5' catalytic Group I intron fragment (SEQ ID NO: 40), a 5' catalytic Group I intron fragment (SEQ ID NO: 47), and a 3' homology arm (SEQ ID NO: 43).

Linear RNAs that can be circularized to produce the circular RNA (circRNAs) disclosed herein may be made by the same methods described in Example 1 above.

Circularized RNA is generated by ribozyme autocatalysis of the Group I intron. During splicing, the 3' hydroxyl group of a guanosine nucleotide engages in a transesterification reaction at the 5' splice site. The 5' intron half is excised, and the freed hydroxyl group at the end of the intermediate engages in a second transesterification at the 3' splice site, resulting in circularization of the intervening region and excision of the 3' intron.

Unmodified linear mRNA or circRNA precursors are synthesized by in-vitro transcription from a linearized plasmid DNA template using a T7 High Yield RNA Synthesis Kit (New England Biolabs). After in vitro transcription, reactions are treated with DNase I (New England Biolabs) for 20 min. After DNase treatment, unmodified linear mRNA is column purified using a MEGAclear Transcription Clean-up kit (Ambion). RNA is then heated to 70° C. for 5 min and immediately placed on ice for 3 min, after which the RNA is capped using mRNA cap-2'-O-methyltransferase (NEB) and Vaccinia capping enzyme (NEB) according to the manufacturer's instructions. Polyadenosine tails are added to capped linear transcripts using *E. coli* PolyA Polymerase (NEB) according to manufacturer's instructions, and fully processed mRNA is column purified. For circRNA, after DNase treatment additional GTP is added to a final concentration of 2 mM, and then reactions are heated at 55° C. for 15 min. RNA is then column purified. In some cases, purified RNA is recircularized: RNA is heated to 70° C. for 5 min and then immediately placed on ice for 3 min, after which GTP is added to a final concentration of 2 mM along with a buffer including magnesium (50 mM Tris-HCl, 10 mM MgCl2, 1 mM DTT, pH 7.5; New England Biolabs). RNA is then heated to 55° C. for 8 min, and then column purified. To enrich for circRNA, 20 μg of RNA is diluted in water (86 μL final volume) and then heated at 65° C. for 3 min and cooled on ice for 3 min. 20U. RNase R and 10 μL of 10× RNase R buffer (Epicenter) is added, and the reaction is incubated at 37° C. for 15 min; an additional 10U RNase R is added halfway through the reaction. RNase R-digested RNA is column purified. RNA is separated on precast 2% E-gel EX agarose gels (Invitrogen) on the E-gel iBase (Invitrogen) using the E-gel EX 1-2% program; ssRNA Ladder (NEB) is used as a standard.

For gel extractions, bands corresponding to the circRNA are excised from the gel and then extracted using a Zymoclean Gel RNA Extraction Kit (Zymogen). For high-performance liquid chromatography, 30 μg of RNA is heated at 65° C. for 3 min and then placed on ice for 3 min. RNA was run through a 4.6×300 mm size-exclusion column with particle size of 5 μm and pore size of 200 Å (Sepax Technologies; part number: 215980P-4630) on an Agilent 1100 Series HPLC (Agilent). RNA is run in RNase-free TE ss (10 mM Tris, 1 mM EDTA, pH: 6) at a flow rate of 0.3 mL/minute. RNA is detected by UV absorbance at 260 nm. Resulting RNA fractions are precipitated with 5 M ammonium acetate, resuspended in water, and then in some cases treated with RNase R as described above.

The resulting circRNA is shown in FIG. 1C.

Example 3. Gel-Electrophoresis and RNase R Resistance of circRNA

This example demonstrates that the purity and endonuclease resistance of the purified circRNA.

First, circRNA a circRNA construct was designed comprising a nucleotide sequence encoding an RBD of a SARS-COV-2 Spike protein, using the circRNA backbone as described in Examples 1 and 2 above.

Briefly, linear RNAs were designed that can be circularized to produce a circRNA, the linear RNAs comprising, from 5' to 3', a 5'Homology arm-3' catalytic Group I intron fragment-3' exon sequence recognizable by the 3' catalytic Group I intron fragment (i.e., Exon 2)-IRES-Kozak-SP-RBD-TAA stop codon-5' exon sequence recognizable by the 5' catalytic Group I intron fragment (i.e., Exon 1)-5' catalytic Group I intron fragment-3'Homology arm. The linear RNA is designed with, from 5' to 3', a 5' homology arm (SEQ ID NO: 41), a 3' catalytic Group I intron sequence (SEQ ID NO: 46), a 3' exon sequence recognizable by a 3' catalytic Group I intron fragment (SEQ ID NO: 39), an IRES sequence (SEQ ID NO: 53), a Kozak sequence (SEQ ID NO: 37), a signal peptide coding sequence (SEQ ID NO: 16 or SEQ ID NO: 17), a Spike protein RBD sequence encoding the amino acid sequence shown in SEQ ID NO: 2 or a Spike protein sequence encoding the amino acid sequence set forth in SEQ ID NO: 63, a stop codon, a 5' exon sequence recognizable by a 5' catalytic Group I intron fragment (SEQ ID NO: 40), a 5' catalytic Group I intron fragment (SEQ ID NO: 47), and a 3' homology arm (SEQ ID NO: 43). The circularized RNA produced from this linear RNA were termed circRNA$^{RBD}$ and circRNA$^{Spike}$, respectively. As a control, the 3'Intron sequence was mutated to a random sequence to prevent circularization of the RNA, and the resulting construct was termed LinRNA$^{RBD}$.

Figure 3A:
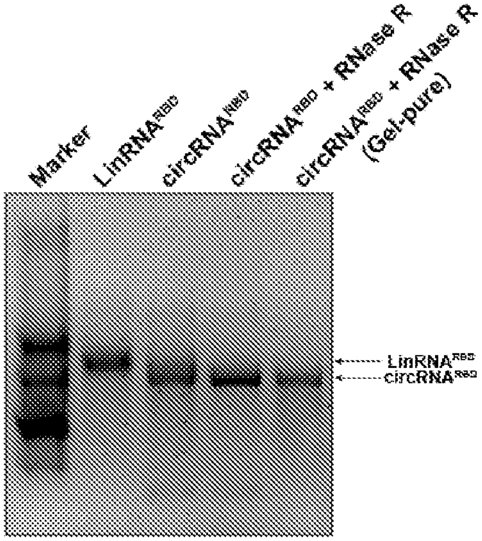
FIG. 3A shows the results of agarose gel electrophoresis of an exemplary purified circRNA$^{RBD}$ and precursor RNA (LinRNA$^{RBD}$, wherein the 3'Intron sequence was mutated to random sequence), demonstrating that the circRNA$^{RBD}$ ran faster than LinRNA$^{RBD}$, indicating circularization of the RNA.

A circRNA was generated and purified as described in Example 2. The purified circRNA$^{RBD}$ and precursor linear RNA (LinRNA$^{RBD}$, wherein the 3'Intron sequence was mutated to random sequence) were resolved in agarose gel electrophoresis. The gel electrophoresis results showed that the circRNA$^{RBD}$ ran faster than LinRNA-RBD (FIG. 3A), indicating that the RNA was circularized. The circRNA$^{RBD}$ is a circRNA that encodes the RBD domain of the Spike protein of SARS-COV-2. The RBD domain is the amino acid residues 319 to 542 of a full-length Spike protein of SARS-COV-2, as shown in SEQ ID NO: 2. The circularization of circRNA$^{RBD}$ was 101 verified (FIG. 1*b*) by reverse transcription and RT-PCR analysis using specific primers (FIG. 3C) using the primers shown in FIG. 3E.

Figure 3B:
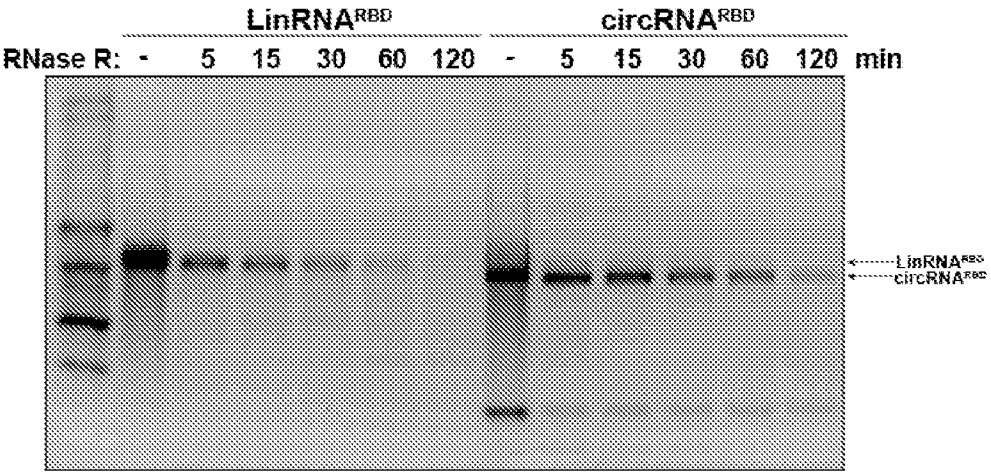
FIG. 3B shows the results of an endonuclease RNase R digestion assay of an exemplary circRNA (circRNA$^{RBD}$) or LinRNA (LinRNA$^{RBD}$). Following incubation with RNAse R for the indicated time periods, the reaction products were resolved in agarose gel electrophoresis, indicating that the circRNA, which lacks a 5' or 3' end, was more resistant to RNase R compared to the LinRNA.
Figure 3C:
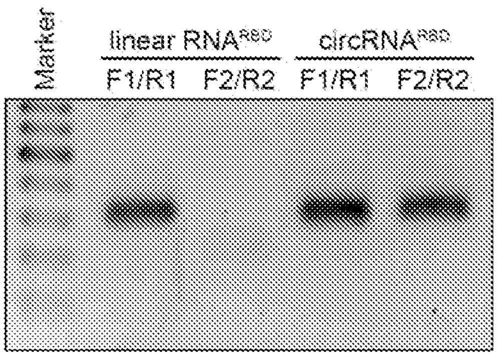
FIG. 3C shows the agarose gel electrophoresis result of the PCR products of linear RNA$^{RBD}$ and circRNA$^{RBD}$, using the primers shown in FIG. 3E.

Next, the endonuclease resistance of the purified circRNA construct was tested. Because the circRNA has no 5' or 3' end, the circRNA is resistant to endonuclease. The endonuclease RNase R was used to digest the circRNA$^{RBD}$ or LinRNA$^{RBD}$ for different times, and the reaction products were resolved in agarose gel electrophoresis. The gel electrophoresis results showed than the circRNA$^{RBD}$ was more resistant to RNase R compared to the LinRNA$^{RBD}$ (FIG. 3B).

Example 4. Expression of SARS-COV-2 RBD Antigen Via circRNA Transfection in Human HEK293T Cells and Mouse NIH3T3 Cells This example demonstrates the ability of the circRNA to express a protein (e.g., a SARS-COV-2 RBD of a S protein) in eukaryotic cells. Additionally, this example demonstrates the surprising stability of the circRNA for two weeks at room temperature. After two weeks incubation of the circRNA at room temperature, the protein could still be expressed and secreted in cells transfected with the circRNA.

Figure 3D:
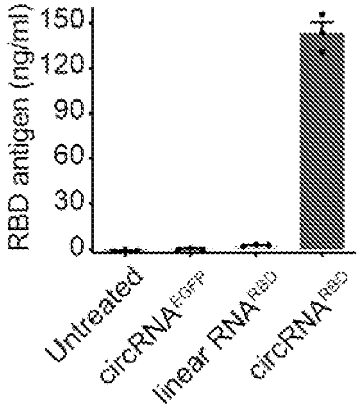
FIG. 3D shows the results of a quantitative ELISA assay to measure the concentration of RBD antigens in the supernatant. The data were shown as the mean±S.E.M. (n=3).
Figure 3E:
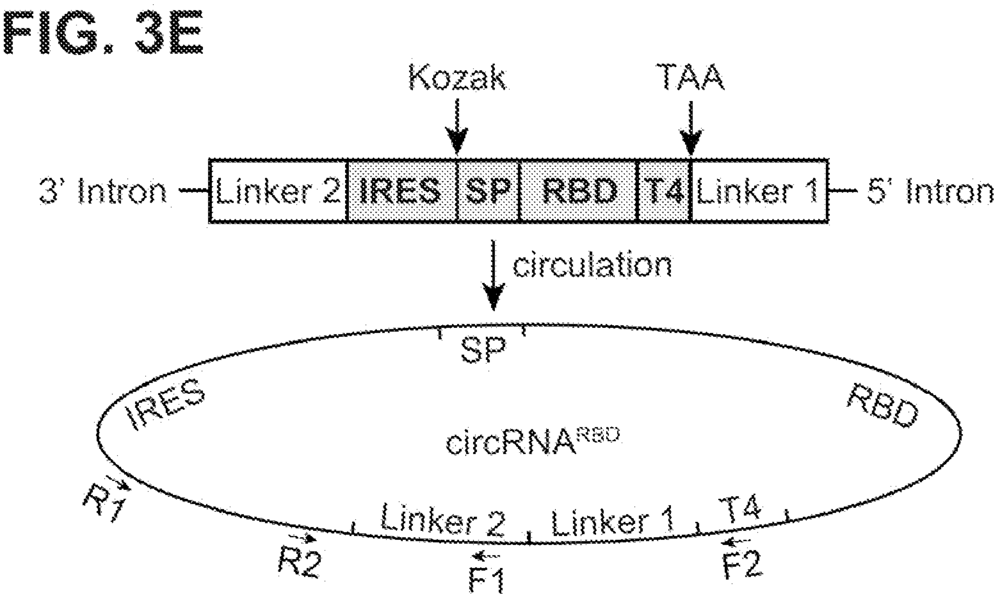
FIG. 3E shows a schematic diagram of circRNA$^{RBD}$ circularization by the Group I ribozyme autocatalysis. SP, signal peptide sequence of human tPA protein. T4, the trimerization domain from bacteriophage T4 fibritin protein. RBD, the receptor binding domain of SARS-COV-2 Spike protein. The arrows indicate the the design of primers for PCR analysis shown in FIG. 3C.

After purification of the circRNA (RNase R treatment and HPLC), the circRNA$^{RBD}$ was transfected into human HEK293T cells and mouse NIH3T3 cells with the Lipofectamine MessengerMAX Transfection Reagent (Thermo LMRNA003). The circRNA-EGFP and precursor linear RNA named LinRNA-RBD were used as controls. Quantitative ELISA assay showed that the RBD protein reached ~143 ng/ml in the supernatant, 50-fold more than the linear RNA$^{RBD}$ group (FIG. 3D).

Figure 4A:
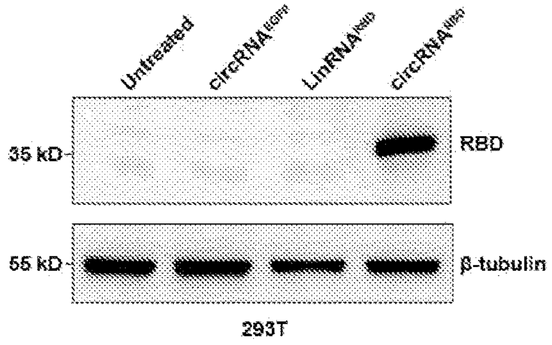
FIGS. 4A-4B show Western Blot analysis demonstrating expression and secretion of an exemplary protein from eukaryotic cells after transfection with an exemplary circRNA. Human HEK293T cells (FIG. 4A) and mouse NIH3T3 (FIG. 4B) cells were transfected with circRNA$^{RBD}$, or circRNA$^{EGFP}$ or the precursor RNA named LinRNA$^{RBD}$ as controls. After 48 hours, the culture supernatant of transfected cells was collected for Western Blot analysis. Using the SARS-COV-2 Spike RBD antibody (ABclonal, A20135) for detection, the Western Blot results showed that the circRNA$^{RBD}$ could express and secret the SARS-COV-2 RBD antigen to the cellular supernatant efficiently.
Figure 4B:
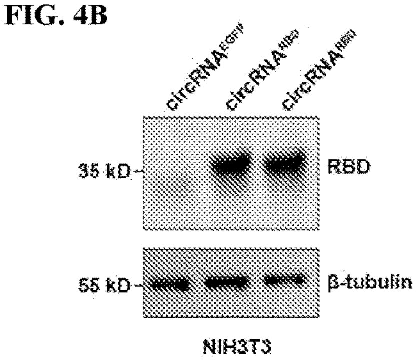

After 48 hours, the culture supernatant of transfected cells was collected for Western Blot analysis. Using the SARS-COV-2 Spike RBD antibody (ABclonal, A20135) for detection, the Western Blot results showed that the circRNA$^{RBD}$ could express and secret the SARS-COV-2 RBD antigen to the cellular supernatant efficiently. The Western Blot results are shown in FIG. 4A and FIG. 4B.

Figure 4C:
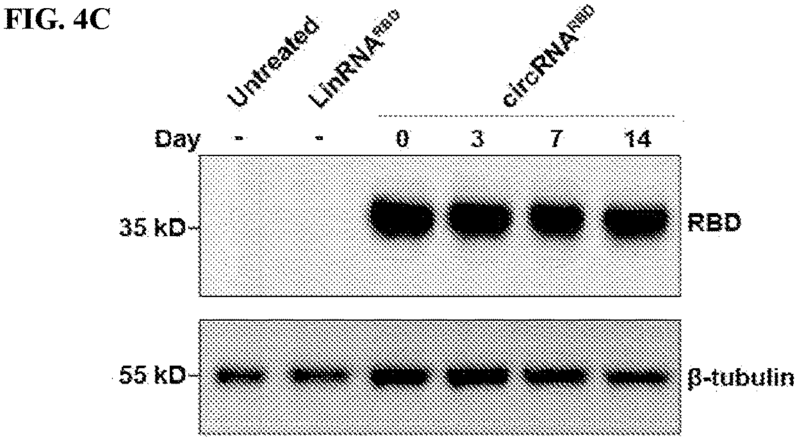
FIG. 4C shows results demonstrating the stability of an exemplary circRNA after extended incubation at room temperature. Purified circRNA$^{RBD}$ was kept at room temperature about 25° C. for 3, 7 or 14 days, and then transfected into human HEK293T cells. The Western Blot results showed that the SARS-COV-2 RBD antigen could be expressed by the circRNA$^{RBD}$ and secreted to the cellular supernatant efficiently, even when the circRNA$^{RBD}$ was kept at room temperature for 14 days.

The circRNA was stable at room temperature about 25° C. The purified circRNA$^{RBD}$ was kept at room temperature about 25° C. for 3, 7 or 14 days, and then were transfected into human HEK293T cells. The Western Blot results showed that the circRNA$^{RBD}$ could express and secret the SARS-COV-2 RBD antigen to the cellular supernatant efficiently, even when the circRNA$^{RBD}$ had been kept at room temperature for 14 days. The results are shown in FIG. 4C.

Figure 4D:
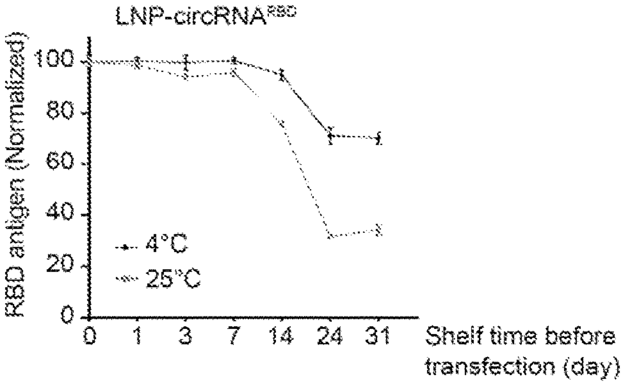
FIG. 4D shows the results of ELISA analysis measuring the expression level of RBD antigens in the supernatant of HEK293T cells transfected with circRNA$^{RBD}$-LNP formulations for different shelf time (1, 3, 7, 14, 24 and 31 days) at 4° C. or room temperature (~25° C.). The data were shown as the mean±S.E.M. (n=3 or 4).

Moreover, to test the thermostability of circRNA-LNP formulations, the encapsulated circRNA$^{RBD}$_LNP was stored at 4° C. or room temperature (~25° C.) for 1, 3, 7, 14, 24, and 31 days before transfection. The sequentially collected circRNA$^{RBD}$-LNPs were transfected into cells and the abundance of RBD antigen production was quantified by ELISA. No reduction of RBD antigens could be detected from circRNA$^{RBD}$-LNPs after storage for 7 days at either 4° C. or room temperature (~25° C.) (FIG. 4D). The expression levels dropped to ~95% and ~75% after 14-day storage of circRNA$^{RBD}$-LNP at 4° C. and room temperature, respectively (FIG. 4D). Deterioration effects did occur with extended shelf life and high temperature.

The stability of the circRNA at room temperature holds advantages for applications including vaccines and gene therapy, including for storage and transportation of the therapeutic circRNA (e.g., the circRNA vaccine).

Example 5. The SARS-COV-2 RBD Antigen was Functional and could Block the Infection of SARS-COV-2 Pseudovirus This example demonstrates that a secreted SARS-COV-2 RBD antigen expressed from an exemplary circRNA can directly interfere with infection of ACE2-expressing cells by a SARS-COV-2 pseudovirus.

To evaluate whether the secreted SARS-COV-2 RBD antigen produced by circRNA was functional, the cellular supernatant of HEK293T cells transfected with circRNA$^{RBD}$ or control circRNA were incubated with the lentivirus-based SARS-COV-2 pseudovirus encoding EGFP at 37° C. for 2 hours, and then the resulting SARS-COV-2 pseudovirus/supernatant mixtures were added into the culture medium of ACE2-overexpressing cells named HEK293-ACE2. After 48 hours, the cells were collected for FACS analysis, as the SARS-COV-2 pseudovirus expressed EGFP fluorescence marker. Cellular expression of EGFP indicated infection of cells by the SARS-COV-2 pseudovirus. The commercial SARS-COV-2 neutralizing antibody (ABclonal, A19215) was used as a positive control for neutralization of the SARS-COV-2 S protein.

Figure 5A:
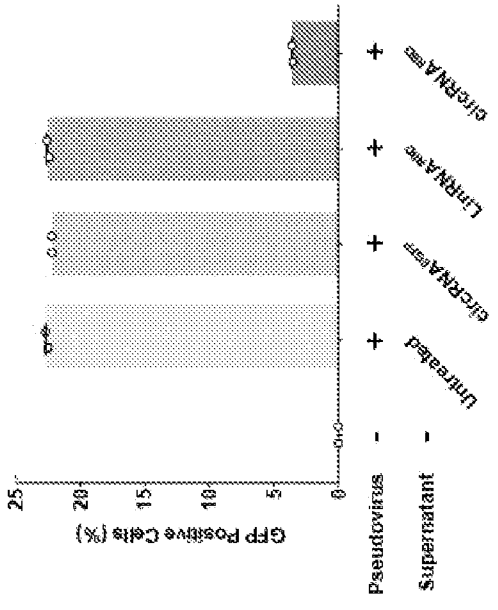
FIGS. 5A-5B show results of a pseudovirus competition experiment demonstrating that the secreted SARS-COV-2 RBD antigen produced by circRNA effectively interfered with infection of cells by a SARS-COV-2 pseudovirus. Collected supernatant from HEK293T cells transfected with circRNA$^{RBD}$ or controls was incubated with a lentivirus-based SARS-COV-2 pseudovirus expressing an EGFP fluorescence marker at 37° C. for 2 hours. The resulting supernatant was then added into the culture medium of ACE2-overexpressing cells named HEK293-ACE2. After 48 hours, the cells were collected for FACS analysis for the EGFP marker, indicating infection of the cells by the pseudovirus. The results are shown as a bar graph in FIG. 5A, and the FACS plots are shown in FIG. 5B.
Figure 5B:
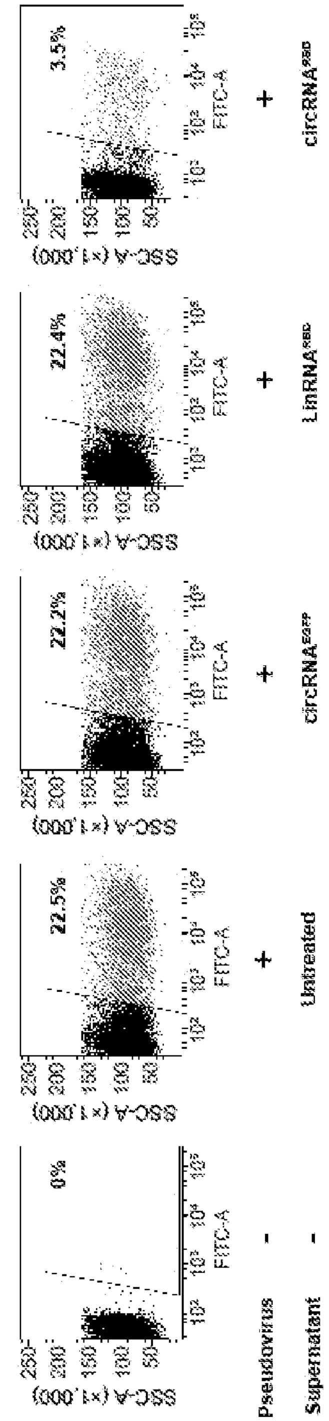

This pseudovirus competition experiment demonstrated that the secreted SARS-CoV-2 RBD antigen in supernatant produced by cells transfected with the circRNA$^{RBD}$ could block the infection of SARS-COV-2 pseudovirus efficiently, indicating that the circRNA-produced SARS-COV-2 RBD antigen was functional at the cellular level. The secreted RBD antigen was able to interfere with binding between the RBD of the SARS-COV-2 pseudovirus, thus blocking infection of the cells. The results are shown in FIG. 5A and FIG. 5B.

Example 6. The circRNA Vaccine could Induce SARS-COV-2 Specific Immune Response and Generate High-Level Neutralizing Antibody As demonstrated in Example 5 above, an RBD antigen expressed from an exemplary circRNA can directly interfere with binding of the SARS-COV-2 S protein with the ACE2 receptor, thereby preventing or reducing infection of cells by a SARS-COV-2 pseudovirus. This example demonstrates that an antigenic polypeptide (e.g., an RBD of a coronavirus S protein) expressed from a circRNA administered in vivo stimulates a specific immune response and generates a high level of neutralizing antibodies. Based on these results, the circRNAs described herein encoding antigenic polypeptides can serve as effective vaccines against viruses such as coronaviruses (e.g., SARS-COV-2).

Figure 6A:
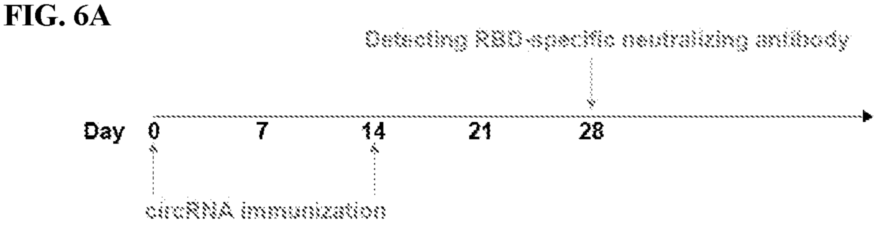
FIGS. 6A-6E show results demonstrating that immunization of mice with the circRNA$^{RBD}$ or the circRNA$^{Spike}$ results in the production of RBD-specific neutralizing antibodies. The circRNA$^{RBD}$ or the circRNA$^{Spike}$ was used to immunize BALB/c mice, respectively. The first immunization was conducted via intramuscular injection at day 0, and a second dose was adopted to boost the immune response at day 14 (FIG. 6A). At day 28, the serum of the immunized mice was collected for the following detection (FIG. 6A). Firstly, the RBD specific IgG titer was measured with ELISA, and the ELISA result showed that the IgG titer of circRNA$^{RBD}$ (10 μg) group was about 32000, and the IgG titer of circRNA$^{RBD}$ (50 μg) group was about 64000, while the Placebo group had almost no RBD-specific IgG signal (FIG. 6B). Meanwhile, an in vitro surrogate neutralizing assay was used to measure the neutralization activity of immunized mouse serum, and the result showed that circRNA$^{RBD}$ (10 μg) group had about 70% neutralization activity, and the circRNA$^{RBD}$ (50 μg) group had over 95% neutralization activity (FIG. 6C). Finally, the lentivirus-based SARS-COV-2 pseudovirus coated with SARS-COV-2 spike protein was used to determine the neutralizing activity at the cell level. The serum of immunized mice was incubated with SARS-COV-2 pseudovirus, and then incubation system was added into the culture of ACE2-over-expression HEK293T cells. 48 hours later, the reporter-luciferase activity of pseudovirus was measured. And the luciferase assay results showed that both the circRNA$^{RBD}$ and circRNA$^{Spike}$ could induce SARS-COV-2 spike specific neutralizing antibody to block the infection of pseudovirus (FIG. 6D and FIG. 6E, respectively).

The purified circRNA$^{RBD}$ (the circRNA backbone as shown in FIG. 1B comprising a nucleotide sequence encoding the amino acid sequence shown in SEQ ID NO: 2 as the "Spike" in FIG. 1B) and circRNA$^{Spike}$ (the circRNA backbone as shown in FIG. 1B comprising a nucleotide sequence encoding the amino acid sequence shown in SEQ ID NO: 62 as the "Spike" in FIG. 1B) were used to immunize BALB/c mice, respectively. The first immunization was conducted via intramuscular injection at day 0, and a second dose was adopted to boost the immune response at day 14 (FIG. 6A). At day 28, the serum of the immunized mice was collected for the following detection (FIG. 6A).

Figure 6B:
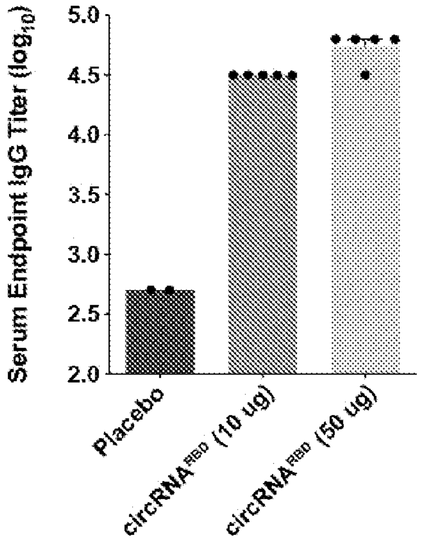
Figure 6C:
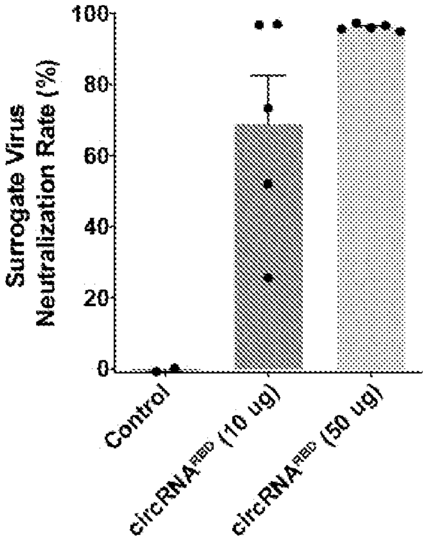
Figure 6D:
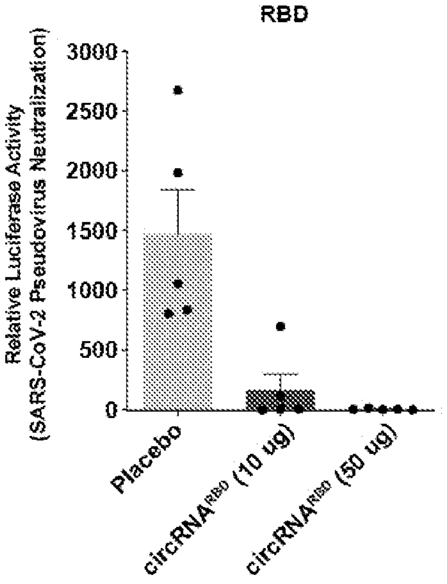
Figure 6E:
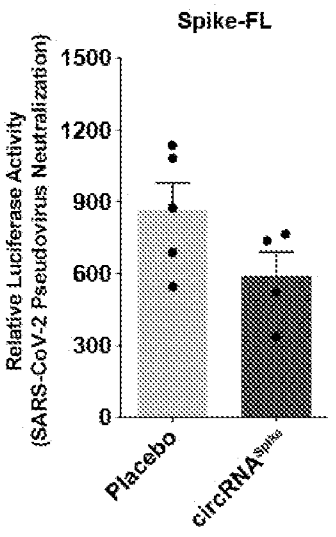

Firstly, the RBD specific IgG titer was measured with ELISA, and the ELISA result showed that the IgG titer of circRNA$^{RBD}$ (10 μg) group was about 32000, and the IgG titer of circRNA$^{RBD}$ (50 μg) group was about 64000, while the Placebo group nearly had no RBD-specific IgG signal (FIG. 6B). Meanwhile, the in vitro surrogate neutralizing assay was used to measure the neutralization activity of immunized mouse serum, and the result showed that circRNA$^{RBD}$ (10 μg) group had about 70% neutralization activity, and the circRNA$^{RBD}$ (50 μg) group had over 95% neutralization activity (FIG. 6C). Finally, the lentivirus-based SARS-COV-2 pseudovirus coated with SARS-COV-2 spike protein was used to value the neutralizing activity at the cell level. The serum of immunized mice was incubated with SARS-COV-2 pseudovirus, and then incubation system was added into the culture of ACE2-over-expression HEK293T cells. 48 hours later, the reporter-luciferase activity of pseudovirus was measured. The luciferase assay results showed that both the circRNA$^{RBD}$ and circRNA$^{Spike}$ could induce SARS-COV-2 spike specific neutralizing antibody to block the infection of pseudovirus (FIG. 6D and FIG. 6E).

The above results proved that the circRNA vaccine could induce SARS-COV-2 specific immune response and generate a high level of SARS-COV-2 spike specific neutralizing antibody.

Example 7. Measuring the Weight of Mouse Spleen after Two-Dose Immunization

This example demonstrates the effect of immunization with an exemplary circRNA encoding an antigenic polypeptide (circRNA$^{RBD}$) on the weight of the spleen in mice following two-dose immunization.

Figure 7B:
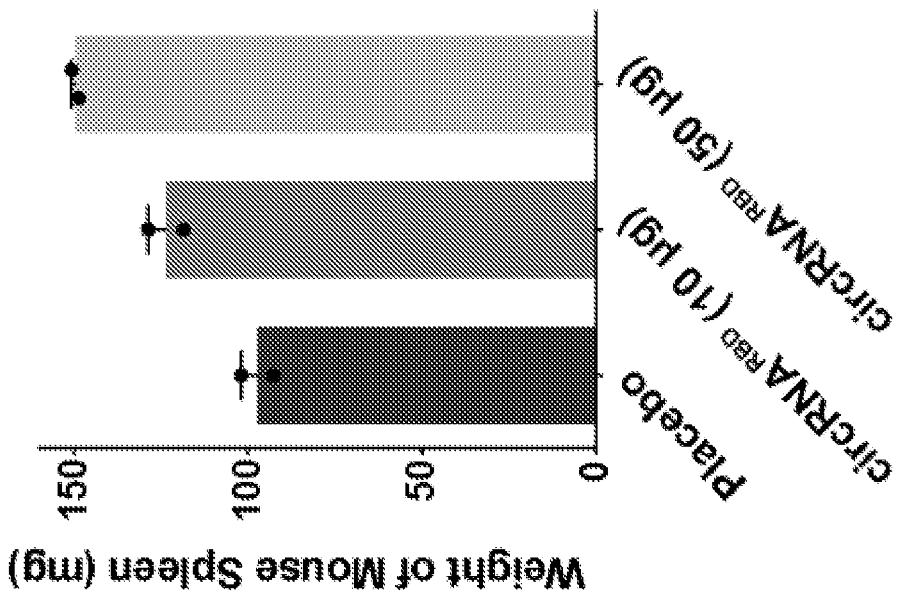
FIGS. 7A-7B show results demonstrating increased spleen weight following immunization of mice with circRNA$^{RBD}$ (10 μg) or circRNA$^{RBD}$ (50 μg) compared to placebo. Four weeks post the second dose of circRNA vaccine or placebo the mice were sacrificed and the spleens of immunized mice were isolated (FIG. 7A). Then the weight of each mouse were measured and the weight of spleen from circRNA$^{RBD}$ (10 μg) or circRNA$^{RBD}$ (50 μg) was significantly higher than the placebo group (FIG. 7B).
Figure 7A:
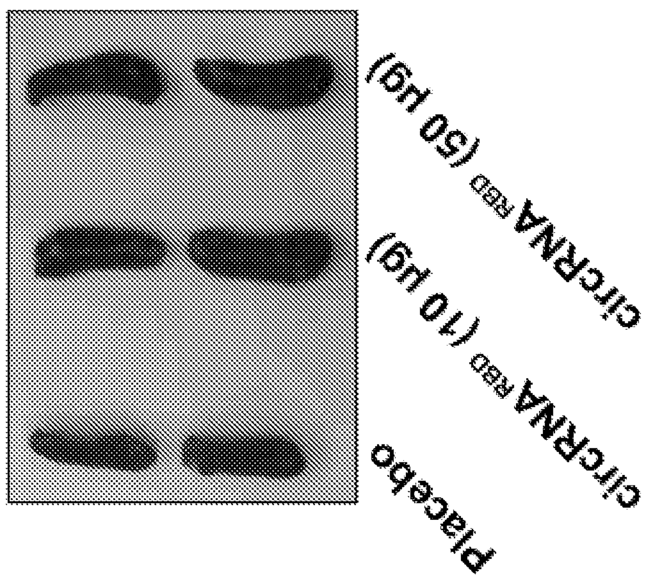

The circRNA dosing scheme is shown in FIG. 6A. Four weeks after the second dose of circRNA vaccine or placebo, the mice were sacrificed and the spleens of immunized mice were isolated (FIG. 7A). Then the weight of each mouse were measured and the weight of spleen from circRNA$^{RBD}$ (10 μg) or circRNA$^{RBD}$ (50 μg) was significantly higher than the placebo group (FIG. 7B).

Example 8. Expression of SARS-COV-2 Neutralizing Antibody Via circRNA

This example demonstrates expression of a secreted virus neutralizing antibody using exemplary circRNAs. Neutralizing antibodies expressed and secreted from cells transfected with the circRNAs described herein could effectively block infection by a SARS-CoV-2 pseudovirus.

Figure 8A:
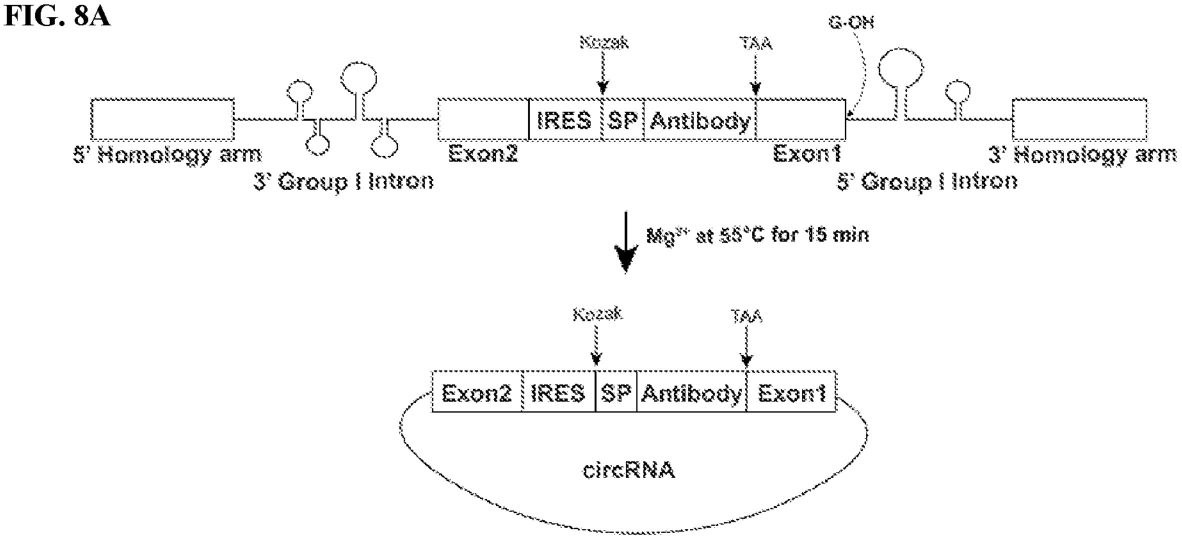
FIG. 8A shows an exemplary method of generating a circRNA and a schematic of an exemplary circRNA construct for expression of a neutralizing antibody, such as a SARS-COV-2 neutralizing antibody. Although the construct shown comprises an IRES sequence, it will be appreciated that any of the exemplary circRNA constructs described herein can be used for expression of a secreted neutralizing antibody (e.g., a variation of the construct comprising an m6A site and/or a 2A peptide instead of a stop codon, as shown in FIG. 1C).

The circRNA could also be used to express SARS-COV-2 neutralizing antibody. Similar to the above RBD antigen, the SARS-COV-2 neutralizing antibody-coding sequence was also circularized via the above circularization method (FIG. 8A).

Linear RNAs were designed that can be circularized to circRNAs, the linear RNA comprising, from 5' to 3', a 5'Homology arm-3' catalytic Group I intron fragment-3' exon sequence recognizable by the 3' catalytic Group I intron fragment (i.e., Exon 2)-IRES-Kozak-SP-RBD-TAA stop codon-5' exon sequence recognizable by the 5' catalytic Group I intron fragment (i.e., Exon 1)-5' catalytic Group I intron fragment-3'Homology arm. The linear RNA is designed with, from 5' to 3', a 5' homology arm (SEQ ID NO: 41), a 3' catalytic Group I intron sequence (SEQ ID NO: 46), a 3' exon sequence recognizable by a 3' catalytic Group I intron fragment (SEQ ID NO: 39), an IRES sequence (SEQ ID NO: 53), a Kozak sequence (SEQ ID NO: 37), a signal peptide coding sequence (SEQ ID NO: 16 or SEQ ID NO: 17), a nucleotide sequence encoding a nAb (nAb-1 (the amino acid sequence shown in SEQ ID NO: 27), nAb-2 (the amino acid sequence shown in SEQ ID NO: 28), or nAb-5 (the amino acid sequence shown in SEQ ID NO: 30)), a stop codon, a 5' exon sequence recognizable by a 5' catalytic Group I intron fragment (SEQ ID NO: 40), a 5' catalytic Group I intron fragment (SEQ ID NO: 47), and a 3' homology arm (SEQ ID NO: 43). The circularized RNAs produced from these linear RNAs were termed circRNA$^{nAb\text{-}1}$ circRNA$^{nAb\text{-}2}$, and circRNA$^{nAB\text{-}5}$, respectively. As a control, the 3'Intron sequence of the linear construct designed to generate circRNA$^{nAB\text{-}5}$ was mutated to a random sequence to prevent circularization of the RNA, and the resulting construct was termed LinRNA$^{nAB\text{-}5}$.

Circular RNAs were generated comprising a nucleotide sequence encoding nAb-1, nAb-2, nAb-3, nAb-4, nAb-5, nAb-6, nAb-7H, or nAb-7L. The amino acid sequences of the neutralizing antibodies are shown in SEQ ID NOs: 26-33, respectively. Alternatively, an antibody that binds to ACE2 and blocks binding of the S protein can be used, such as the amino acid sequences shown in SEQ ID NO: 34 or 35.

Exemplary circRNAs encoding nAbs (circRNA$^{nAb\text{-}1}$, circRNA$^{nAb\text{-}2}$, and circRNA$^{nAB\text{-}5}$) were transfected into HEK293T cells, and 48 hours later the supernatant was collected and used to conduct the with SARS-COV-2 pseudovirus neutralization assay. A circRNA encoding luciferase (circRNA$^{Luc}$) and a linear precursor RNA LinRNA$^{nAB\text{-}5}$ were used as negative controls, and the commercial SARS-COV-2 neutralizing antibody (ABclonal, A19215) was used as the positive control.

Figure 8B:
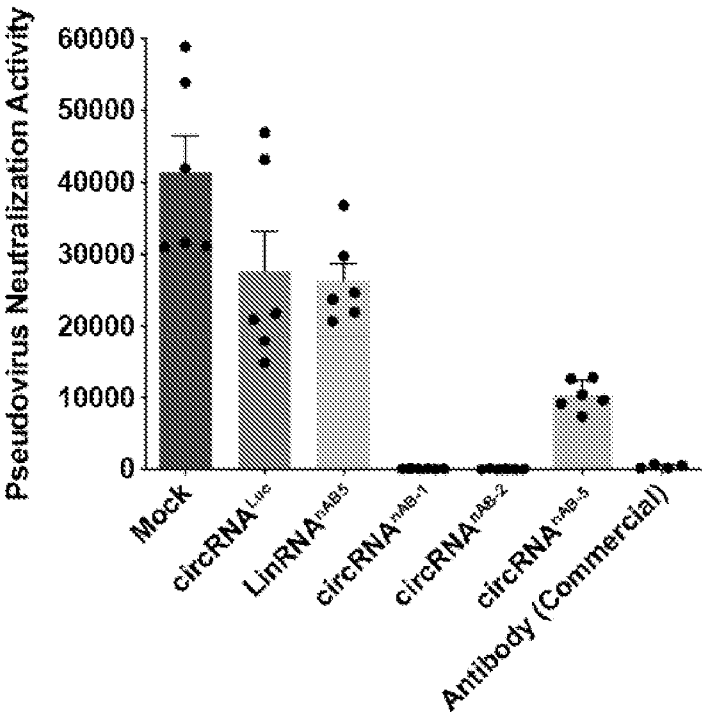
FIG. 8B shows the pseudovirus neutralization activity of a secreted nAb produced by exemplary circRNA-nAb constructs (circRNA$^{nAb-1}$, comprising a nucleotide sequence encoding nAb-1 (amino acid sequence shown in SEQ ID NO: 27), circRNA$^{nAb-2}$, comprising a nucleotide sequence encoding nAb-2 (amino acid sequence shown in SEQ ID NO: 28), and, and circRNA$^{nAB-5}$, comprising a nucleotide sequence encoding nAb-5 (amino acid sequence shown in SEQ ID NO: 31). A circRNA expressing Luciferase (circRNA$^{Luc}$) and a linear RNA encoding nAb-5 (LinRNA$^{nAB-5}$) were used as negative controls and a commercial SARS-COV-2 neutralizing antibody (ABclonal, A19215) was used as the positive control.
Figure 8C:
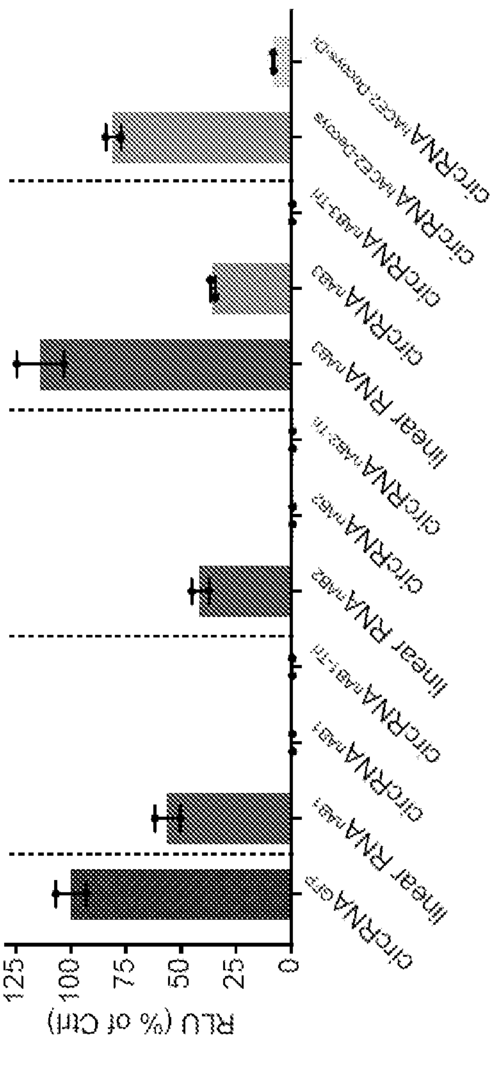
FIG. 8C shows the results of lentivirial-based pseudovirus neutralization assay with the supernatant from cells transfected with circRNA encoding neutralizing nanobodies nAB1, nAB1-Tri, nAB2, nAB2-Tri, nAB3 and nAB3-Tri or ACE2 decoys. The luciferase value was normalized to the circRNA$^{EGFP}$ control. The data were shown as the mean±S.E.M. (n=2).

The pseudovirus neutralization assay results demonstrated that circRNA$^{nAb\text{-}1}$, circRNA$^{nAb\text{-}2}$, and circRNA$^{nAB\text{-}5}$ could neutralize the infection of SARS-COV-2 pseudovirus compared to negative controls (FIG. 8B). These results indicate that the circRNA can be utilized to expressing neutralizing antibodies for therapeutic purposes, such as to treat a coronavirus (e.g., SARS-COV-2) infection. Pseudovirus neutralization assays showed that supernatants of HEK293T cells transfected with circRNA$^{nAB}$ or circRNA-$^{hACE2}$ decoys could effectively inhibit wild SARS-COV-2 S-protein based pseudovirus infection (FIG. 8C).

Figure 8D:
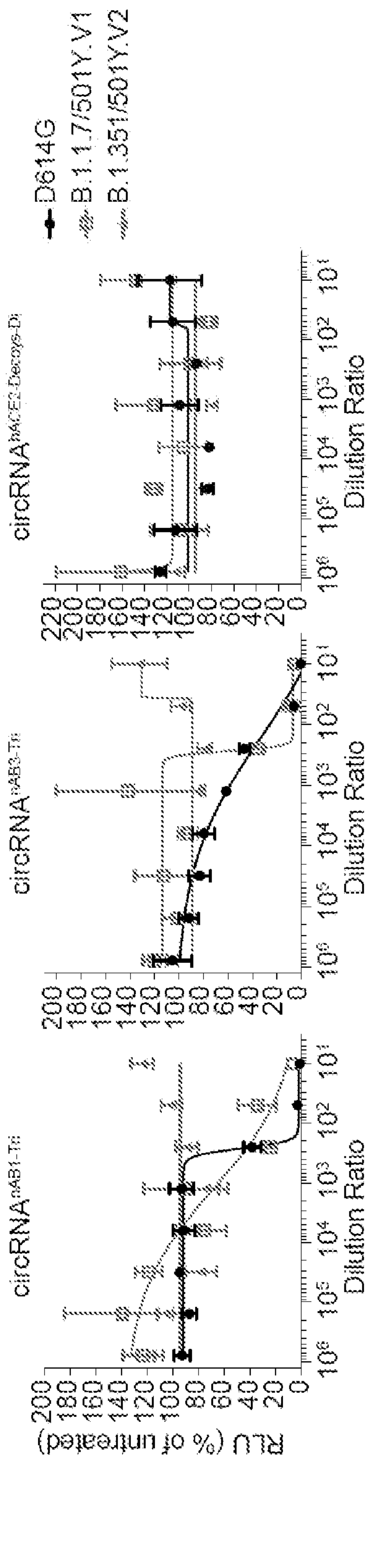
FIG. 8D shows the results of a neutralization assay of VSV-based D614G, B.1.1.7 or B.1.351 pseudovirus by the supernatant from cells transfected with neutralizing nanobodies nAB1-Tri, nAB3-Tri or ACE2 decoys expressed through the circRNA platform. The data were shown as the mean±S.E.M. (n=3).

Next, we tested neutralizing antibodies against the recently emerged SARS-COV-2 variants, including B.1.1.7/501Y.V1 and B.1.351/501Y.V2, by pseudovirus assays. The supernatants of circRNA$^{nAB1\text{-}Tri}$ and circRNA$^{nAB3\text{-}Tr}$i transfected cells effectively blocked B1.1.7/501Y.V1 and D614G pseudovirus infection (FIG. 8D). However, both nanobodies showed markedly decreased neutralizing activity against B.1.351/501Y.V2 variant (FIG. 8D). The hACE2 decoys showed no inhibition activity against B1.1.7/501Y.V1 and B.1.351/501Y.V2 variants (FIG. 8D).

In this example, circRNA-encoded SARS-COV-2 nanobodies showed strong neutralizing ability against the SARS-COV-2 native, D614G and B.1.1.7/501Y.V1 strains in vitro, but they were completely escaped by B.1.351/501Y.V2 variant (FIG. 8D). Beyond viral receptors, this circRNA expression platform hold the potential to become therapeutic drugs, encoding therapeutic antibodies in vivo, e.g. anti-PD1/PD-L1 antibodies. Compared to the antibodies protein drugs, the circRNAs could target intracellular targets, such as TP5383 and KRAS84, because they encoded therapeutic antibodies in the cytoplasm, bypassing the cytomembrane barrier.

Example 9. A circRNA Encoding IDUA could Restore the Catalytic Activity of α-1-Iduronidase (IDUA) in Primary Cells from Hurler Syndrome Mouse Models The above examples describe exemplary circRNA backbones, generation and purification of circRNAs, use of circRNAs to produce antigenic polypeptides that can effectively generate an immune response in vivo for use as vaccines, and circRNA expression of neutralizing antibodies to treat an infection (e.g., a SARS-COV-2 infection). However, the circRNAs described herein can also be applied to therapy of other diseases that would benefit from expression of a therapeutic polypeptide, such as genetic diseases associated with a deficiency in a protein or functional protein. This example provides results demonstrating that the circRNA can be used to express a functional protein such as an enzyme (e.g., IDUA). Therefore, the circRNAs provided herein can be used for production of functional therapeutic polypeptides for gene therapy applications.

Figure 9A:
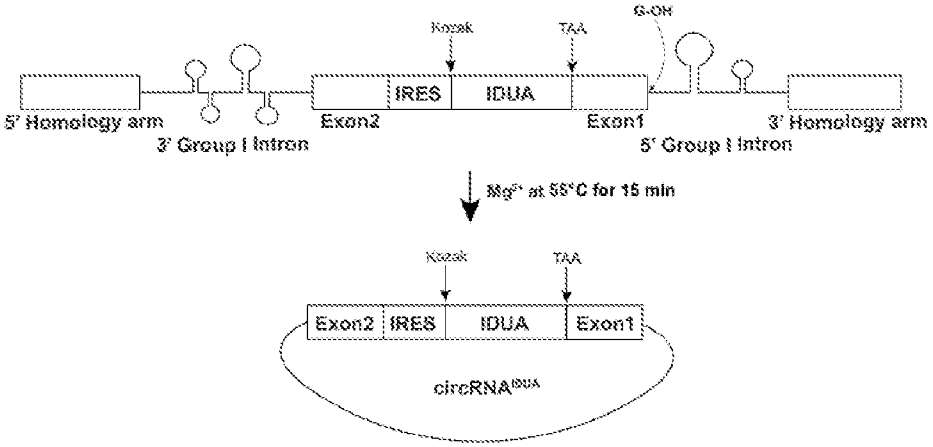
FIG. 9A shows an exemplary method of generating a circRNA and a schematic of an exemplary circRNA construct for expression of a therapeutic polypeptide, such as IDUA. A mouse α-1-iduronidase (IDUA) coding sequence was inserted into the circRNA backbone. Although the construct shown comprises an IRES sequence, and a nucleotide sequence coding for IDUA, it will be appreciated that any of the exemplary circRNA constructs described herein can be used for expression of any of the therapeutic polypeptides described herein (e.g., a variation of the construct comprising an m6A site and/or a 2A peptide instead of a stop codon, as shown in FIG. 1C).

Instead of the SARS-COV-2 RBD/Spike antigen, the functional wildtype disease-related proteins can also be expressed and function via the circRNAs and methods described herein. In an example, the mouse α-1-iduronidase (IDUA) coding sequence was inserted into the circRNA backbone to generate circRNA$^{IDUA}$ (FIG. 9A).

Briefly, a linear RNA was designed that can be circularized to produce a circRNA, the linear RNAs comprising, from 5' to 3', a 5'Homology arm-3' catalytic Group I intron fragment-3' exon sequence recognizable by the 3' catalytic Group I intron fragment (i.e., Exon 2)-IRES-Kozak-SP-RBD-TAA stop codon-5' exon sequence recognizable by the 5' catalytic Group I intron fragment (i.e., Exon 1)-5' catalytic Group I intron fragment-3'Homology arm. The linear RNA is designed with, from 5' to 3', a 5' homology arm (SEQ ID NO: 41), a 3' catalytic Group I intron sequence (SEQ ID NO: 46), a 3' exon sequence recognizable by a 3' catalytic Group I intron fragment (SEQ ID NO: 39), an IRES sequence (SEQ ID NO: 53), a Kozak sequence (SEQ ID NO: 37), a signal peptide coding sequence (SEQ ID NO: 16 or SEQ ID NO: 17), a nucleotide sequence encoding IDUA (amino acid sequence set forth in SEQ ID NO: 18), a stop codon, a 5' exon sequence recognizable by a 5' catalytic Group I intron fragment (SEQ ID NO: 40), a 5' catalytic Group I intron fragment (SEQ ID NO: 47), and a 3' homology arm (SEQ ID NO: 43). The circularized RNA produced from this linear RNA was termed circRNA$^{IDUA}$. As a control, the 3'Intron sequence was mutated to a random sequence to prevent circularization of the RNA, and the resulting construct was termed LinRNA$^{IDUA}$.

The circRNA$^{IDUA}$ was circularized and purified according to the method described in Example 2, and then was transfected into primary MEF cells from Hurler Syndrome Mouse models or human HEK293T/IDUA$^{-/-}$ cells with a cationic-lipid transfection reagent, Lipofectamine™ MessengerMAX™ Transfection Reagent (Thermo LMRNA003).

Figure 9B:
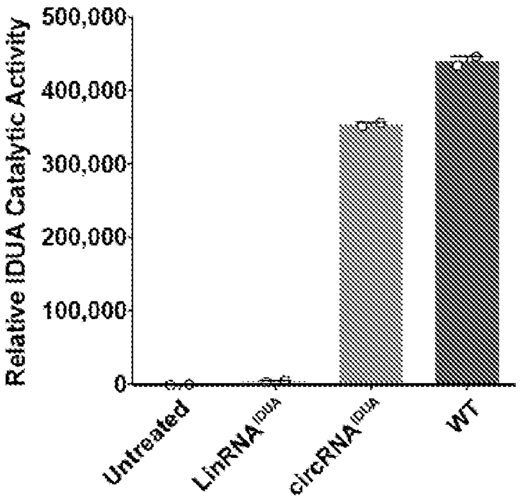
FIGS. 9B-9C show the results of an α-1-iduronidase assay demonstrating that the circRNA-IDUA, but not a linear RNA control (LinRNA-IDUA), could recover the catalytic activity of α-1-iduronidase efficiently in primary MEF cells from Hurler Syndrome mouse models (FIG. 9B) and as well as human HEK293T/IDUA$^{-/-}$ cells (FIG. 9C).
Figure 9C:
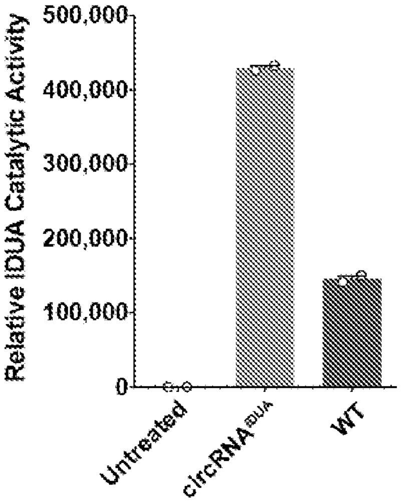

After 48 hours, the catalytic activity of α-1-iduronidase was detected with the reported α-1-iduronidase assay (Qu et al., Nature Biotechnology, vol 37, September 2019, 1059-1069). The α-1-iduronidase assay showed the circRNA$^{IDUA}$ could recover the catalytic activity of α-1-iduronidase efficiently in the primary MEF cells from Hurler Syndrome mouse models and as well as the human HEK293T/IDUA$^{-/-}$ cells, indicating that the circRNA$^{IDUA}$ was functional in Hurler Syndrome Mouse-derived primary cells. The results are shown in FIG. 9B and FIG. 9C.

Example 10. In Vivo Restoration of the Catalytic Activity of α-1-Iduronidase in Hurler Syndrome Mouse Models Example 8 above demonstrated an exemplary circRNA could express a functional enzyme protein in mouse or human cells deficient for the enzyme, thereby restoring the protein function in those cells. The present example demonstrates that an exemplary circRNA can be used to restore function of a protein in vivo. Moreover, the protein expressed from the circRNA can restore protein function for an extended period (e.g., at least 24 hours).

The purified circRNA$^{IDUA}$ (30 μg per dose) was encapsulated and delivered into Hurler Syndrome (IDUA deficient) mice via tail-vein injection. After 4 hours or 24 hours, the Hurler Syndrome mice were sacrificed to isolate the liver tissues, and α-1-iduronidase activity was assayed in the isolated liver tissues.

Figure 10:
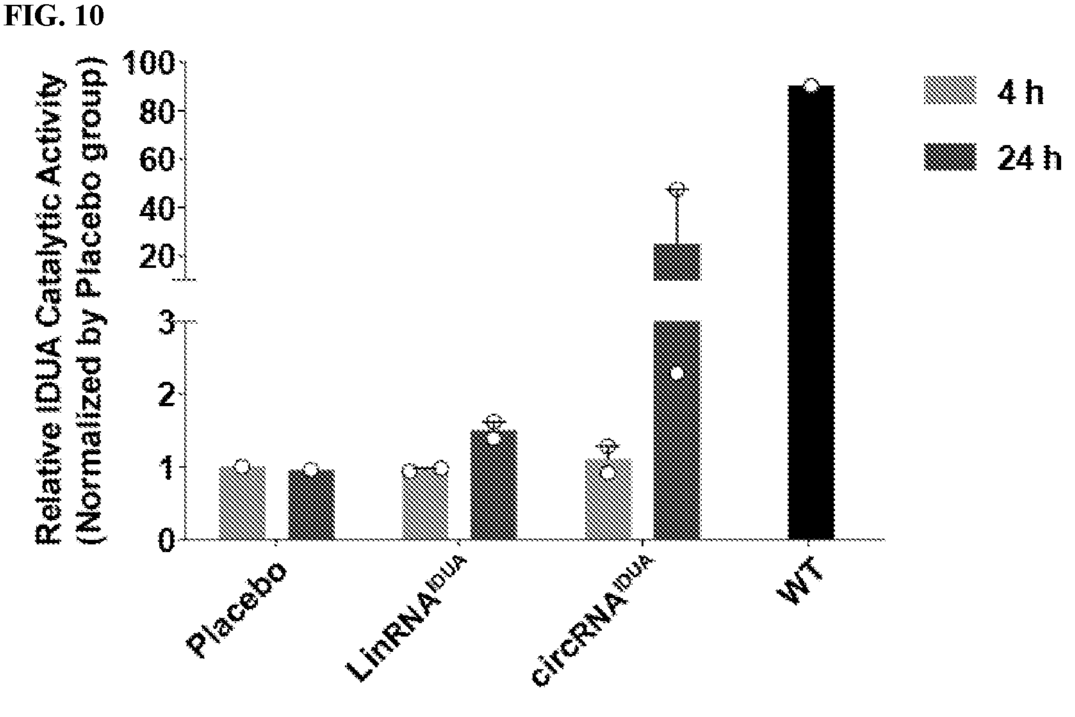
FIG. 10 shows results demonstrating in vivo restoration of the catalytic activity of α-1-iduronidase in Hurler Syndrome mouse models by injection of encapsulated circRNA-IDUA. The purified circRNA-IDUA (30 μg) was encapsulated and delivered into Hurler Syndrome mouse via tail-vein injection with the 30 μg each mouse dosage. After 4 or 24 hours, the Hurler Syndrome mice were sacrificed to isolate the liver tissues and assay α-1-iduronidase activity. The results demonstrated that circRNA-IDUA could efficiently restore the catalytic activity of α-1-iduronidase in Hurler Syndrome mouse models, reaching to nearly 20% activity of the wildtype mouse, and that the catalytic activity increased from 4 hours to 24 hours, indicating that the circRNA-IDUA could be utilized in the therapy of genetic diseases.

The α-1-iduronidase assay from the livers of mice injected with circRNA$^{IDUA}$ or control showed that circRNA$^{IDUA}$ could efficiently restore the catalytic activity of α-1-iduronidase in Hurler Syndrome mouse models, reaching to nearly 20% activity of the wildtype mouse (FIG. 10). Moreover, the catalytic activity increased from 4 hours to 24 hours, indicating that the effect of circRNA$^{IDUA}$ is long lasting and could be utilized for the therapy of genetic diseases.

Figure 11A:
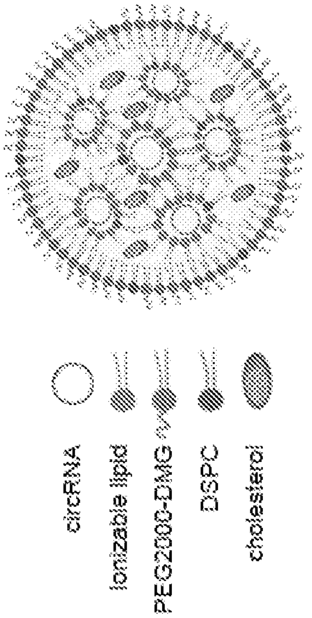
FIGS. 11A-11H provide results demonstrating humoral immune responses in mice immunized with SARS-COV-2 circRNA$^{RBD}$ vaccines.
Figure 11B:
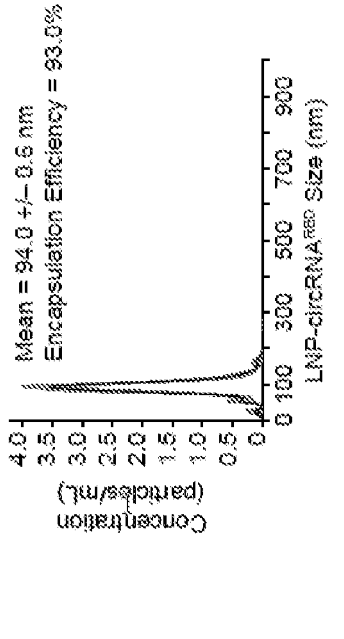
Figure 11C:
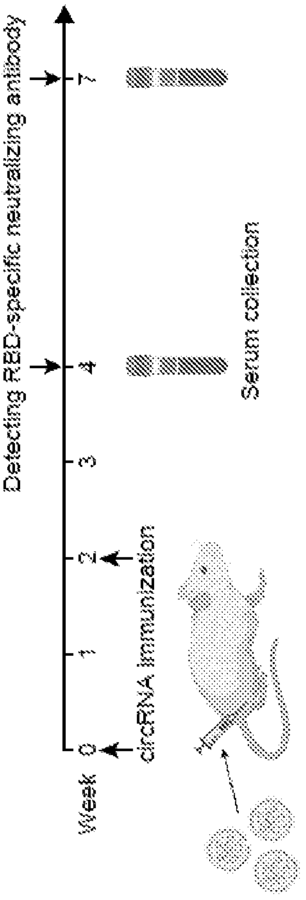

Example 11. SARS-COV-2 circRNA Vaccines Elicit Sustained Humoral Immune Responses with High-Level Neutralizing Antibodies With its stability and immunogen-coding capability, we reasoned that circRNA could be developed into a new type of vaccine. We then attempted to assess the immunogenicity of circRNA$^{RBD}$ encapsulated with lipid nanoparticle in BALB/c mice (FIG. 11A). The circRNA$^{RBD}$ encapsulation efficiency was greater than 93%, with an average size of 100 nm in diameter (FIG. 11B). Animals were immunized with LNP-circRNA$^{RBD}$ through intramuscular injection twice, using a dose of 10 μg or 50 μg per mouse at a two-week interval, while empty LNP was used as the placebo (FIG. 11C). The amount of RBD-specific IgG and pseudovirus neutralization activity were evaluated at two or five weeks post LNP-circRNA$^{RBD}$ boost.

The circRNAs were encapsulated with lipid nanoparticle (LNP) through a previously described process (Ickenstein, L. M. & Garidel, P. Lipid-based nanoparticle formulations for small molecules and RNA drugs. 890 *Expert Opin Drug Deliv* 16, 1205-1226, doi: 10.1080/17425247.2019.1669558 (2019), the contents of which are herein incorporated by reference). Briefly, the circRNAs were diluted in the 50 mM citrate buffer (pH 3.0) and the lipids were dissolved and mixed in ethanol at molar ratios of 50:10:38.5:1.5 (MC3-lipid:DSPC:cholesterol:PEG2000-DMG). The lipids mixture was then mixed with the circRNA solution at the volume ratio of 1:3 in the NANOASSEMBLR® BENCHTOP (PRECISION, #NIT0046). Then the LNP-circRNA formulations were diluted 40-fold with the 1×PBS buffer (pH 7.2~7.4) and concentrated by ultrafiltration with Amicon® Ultra Centrifugal Filter Unit (Millipore). The concentration and encapsulation rate of circRNAs were measured by the Quant-iT™ RiboGreen™ RNA Assay Kit (Invitrogen™ #R11490). The size of LNP-circRNA particles was measured using dynamic light scattering on a Malvern® Zetasizer® Nano-ZS 300 (Malvern). Samples were irradiated with red laser (1=632.8 nm) and scattered light were detected at a backscattering angle of 173. Results were analyzed to obtain an autocorrelation function using the software (Zetasizer® V7.13).

Figure 11D:
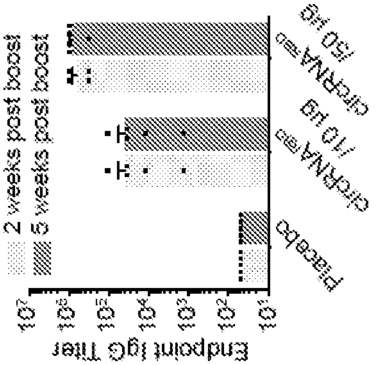

High titers of RBD-specific IgG were elicited by circRNA$^{RBD}$ in a dose-dependent manner, ~3×10$^4$ and ~1×10$^6$ for each dose and for both 2- and 5-weeks post boost, indicating that circRNA$^{RBD}$ could induce long-lasting antibodies against SARS-COV-2 RBD (FIG. 11D).

Figure 11G:
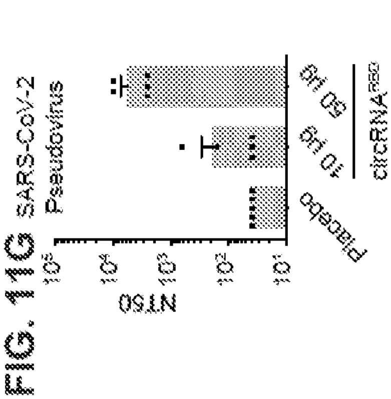
Figure 11H:
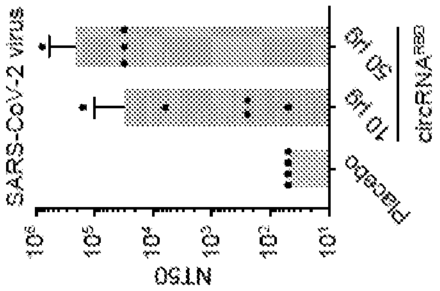
Figure 11F:
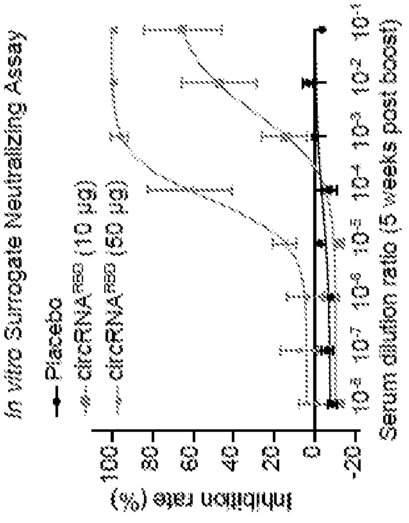
Figure 11E:
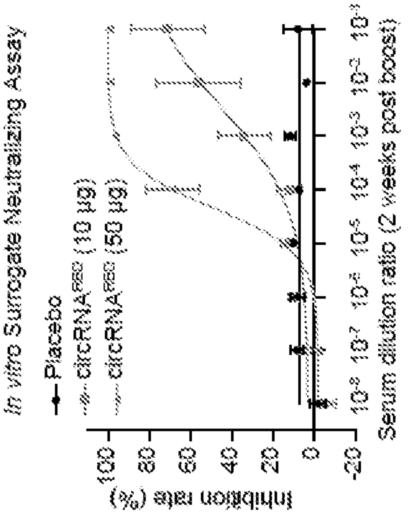

To test the antigen-specific binding capability of IgG from vaccinated animals, we performed a surrogate neutralization assay. In line with the amount of RBD-specific IgG (FIG. 11D), antibodies elicited by circRNA$^{RBD}$ vaccines showed evident neutralizing capacity in dose-dependent manner, with an NT50 of ~2×10$^4$ for the dose of 50 μg (FIG. 11E, FIG. 11F).

We further demonstrated that sera from circRNA$^{RBD}$-vaccinated mice could neutralize both SARS-COV-2 pseudovirus (FIG. 11G) and authentic SARS-COV-2 virus (FIG. 11H), with an NT50 of ~5.6×10$^3$ (FIG. 11G) and an NT50 of ~2.2×10$^5$ (FIG. 11H) in mice immunized with 50 μg of circRNA$^{RBD}$, respectively. The large amount of RBD-specific IgG, potent RBD antigen neutralization, and sustained SARS-COV-2 neutralizing capacity suggest that circRNA$^{RBD}$ vaccines did induce a long-lasting humoral immune response in mice.

Example 12. SARS-COV-2 circRNA Vaccines Induce Strong T Cell Immune Responses in the Spleen B cells (the source of antibodies), CD4$^+$ T cells, and CD8$^+$ T cells are three pillars of adaptive immunity, and they mediated effector functions that have been associated with the control of SARS-COV-2 in both non-hospitalized and hospitalized cases of COVID-19.

Figures 12A, 12B:
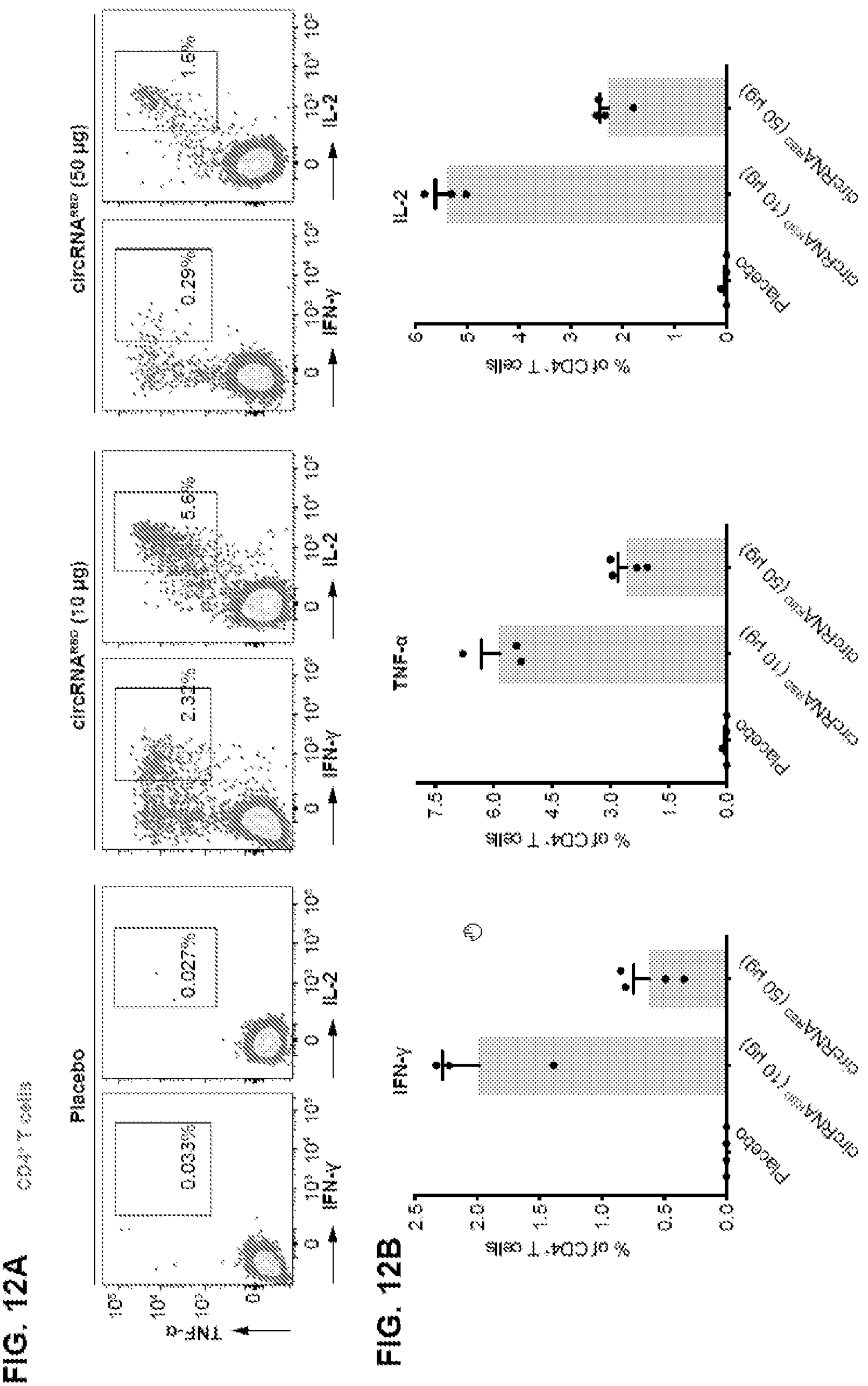
FIGS. 12A-12D provide results demonstrating SARS-COV-2 specific T cell immune responses in mice immunized with SARS-COV-2 circRNA$^{RBD}$ vaccines.

To probe CD4$^+$ and CD8$^+$ T cell immune responses in circRNA$^{RBD}$ vaccinated mice (5 weeks post-boost), splenocytes were stimulated with SARS-COV-2 Spike RBD pooled peptides (Table E1 below), and cytokine-producing T cells were quantified by intracellular cytokine staining among effector memory T cells (Tem, CD44$^+$CD62L$^-$). Stimulated with RBD peptide pools, CD4$^+$ T cells of mice immunized with circRNA$^{RBD}$ vaccines exhibited Th1-biased responses, producing interferon-γ (IFN-γ), tumor necrosis factor (TNF-α), and interleukin-2 (IL-2) (FIG. 12A, FIG.

Figures 12C, 12D:
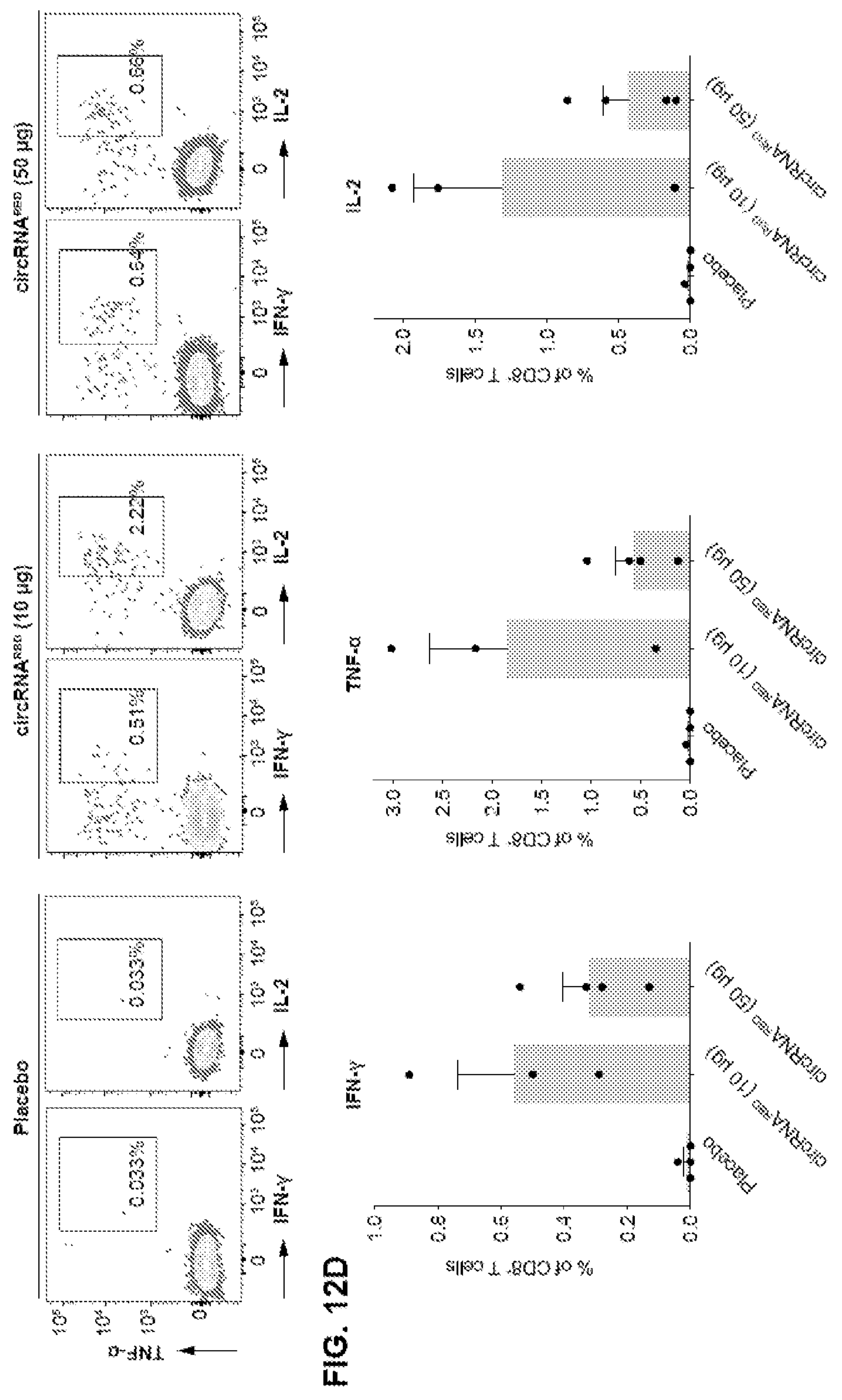

12B), but not interleukin-4 (IL-4), indicating that circRNA$^{RBD}$ vaccines mainly induced the Th1- but not the Th2-biased immune responses. In addition, multiple cytokine-producing CD8$^{+}$ were detected in circRNA$^{RBD}$ vaccinated mice (FIG. 12C, FIG. 12D). For unknown reasons, 10 μg of circRNA$^{RBD}$ elicited stronger immune responses in both CD4+ and CD8$^{+}$ effector memory T cells than 50 μg (FIGS. 12A-12D), while the latter induced higher potency of neutralizing antibodies in the B cell responses (FIG. 11G and FIG. 11H).

TABLE E1

Peptide sequences of RBD antigens

| Name | Sequence | SEQ ID NO |
|---|---|---|
| S-45 | GIYQTSNFRVQPTESIVR | 65 |
| S-46 | RVQPTESIVRFPNITNL | 66 |
| S-47 | IVRFPNITNLCPFGEVF | 67 |
| S-48 | TNLCPFGEVFNATRFASV | 68 |
| S-49 | VFNATRFASVYAWNRKRI | 69 |
| S-50 | SVYAWNRKRISNCVADY | 70 |
| S-51 | KRISNCVADYSVLYNSA | 71 |
| S-52 | ADYSVLYNSASFSTFKCY | 72 |
| S-53 | SASFSTFKCYGVSPTKL | 73 |
| S-54 | KCYGVSPTKLNDLCFTNV | 74 |
| S-55 | KLNDLCFTNVYADSFVIR | 75 |
| S-56 | NVYADSFVIRGDEVRQIA | 76 |
| S-57 | IRGDEVRQIAPGQTGKIA | 77 |
| S-58 | IAPGQTGKIADYNYKL | 78 |
| S-59 | GKIADYNYKLPDDFTGCV | 79 |
| S-60 | KLPDDFTGCVIAWNSNNL | 80 |
| S-61 | CVIAWNSNNLDSKVGGNY | 81 |
| S-62 | NLDSKVGGNYNYLYRLFR | 82 |
| S-63 | NYNYLYRLFRKSNLKPF | 83 |
| S-64 | LFRKSNLKPFERDISTEI | 84 |
| S-65 | PFERDISTEIYQA | 85 |
| S-66 | RDISTEIYQAGSTPCNGV | 86 |
| S-67 | YQAGSTPCNGVEGFNCYF | 87 |
| S-68 | NGVEGFNCYFPLQSYGF | 88 |
| S-69 | CYFPLQSYGFQPTNGVGY | 89 |
| S-70 | GFQPTNGVGYQPYRVVVL | 90 |
| S-71 | GYQPYRVVVLSFELLHA | 91 |
| S-72 | VVLSFELLHAPATVCGPK | 92 |
| S-73 | HAPATVCGPKKSTNLVK | 93 |
| S-74 | GPKKSTNLVKNKCVNFNF | 94 |
| S-75 | VKNKCVNFNFNGLTGTGV | 95 |

Collectively, these results demonstrated that SARS-COV-2 circRNA$^{RBD}$ vaccines could induce high level of humoral and cellular immune responses in mice. In this report, circRNA$^{RBD\text{-}501Y.V2}$ immunized mice produced high titers of neutralizing antibodies. Given that K417N-E484K-N501Y mutant in RBD reduces its interactions with certain neutralizing antibodies as shown in Example 8, we also demonstrated that neutralizing antibodies produced by mice immunized with circRNA$^{RBD}$ or circRNA$^{RBD\text{-}501Y.V2}$ had preferential neutralizing abilities to their corresponding virus strains. Recent studies suggested that 501Y.V2 showed no higher infectivity but had immune escape capability, and varieties of vaccines were reported to be less effective against SARS-COV-2 variants. There have also been reported vaccine breakthrough infections with SARS-COV-2 variants. Thus, it is important to develop and implement vaccines against emerging variants, and the cricRNA vaccine is such a platform that could be rapidly tailored for specific variants. For example, a vaccine contains E484K, N501Y, and L452R mutations in the RBD can be developed quickly via the circRNA platform to deal with a potential outbreak caused by the SARS-COV-2 variants (L452R being found in the recently reported B.1.617 276 variant emerging in India and in the B.1.429 variant that has emerged in the USA).

We highlight this generalizable strategy for designing immunogens. The coding sequence of circular RNA can be quickly adapted to deal with any emerging SARS-COV-2 variants, such as the recently reported B.1.1.7/501Y.V1, B.1.351/501Y.V2, P.1/501Y.V3 and B.1.671 variants. Moreover, circular RNAs could be quickly generated in large quantities in vitro, and they do not require any nucleotide modification.

Figure 13A:
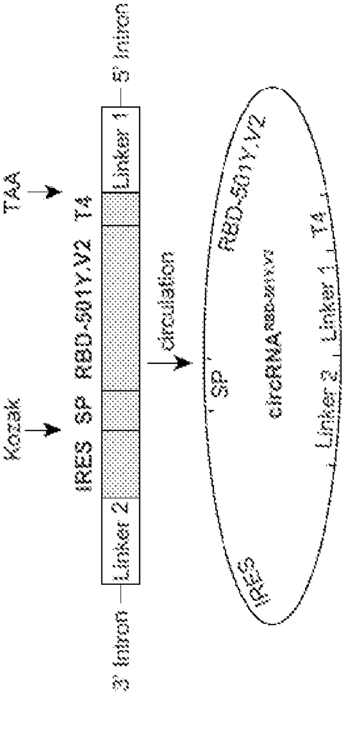
FIGS. 13A-13G provide results demonstrating the susceptibility of SARS-COV-2 D614G, B.1.1.7 or B.1.351variants to neutralizing antibodies elicited by the circRNA$^{RBD}$ or circRNA$^{RBD\text{-}501Y.V2}$ vaccines in mice.
Figure 13B:
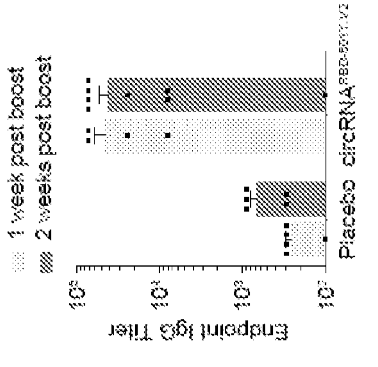
Figure 13C:
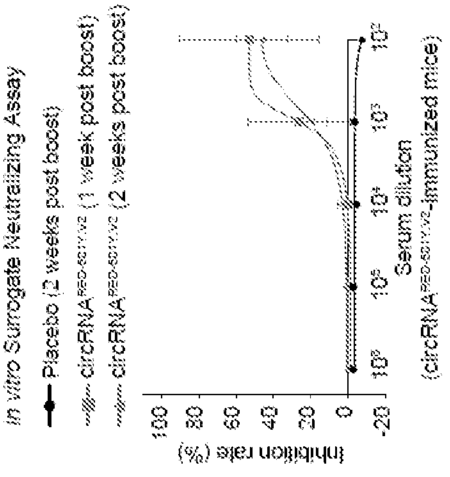
Figure 13D:
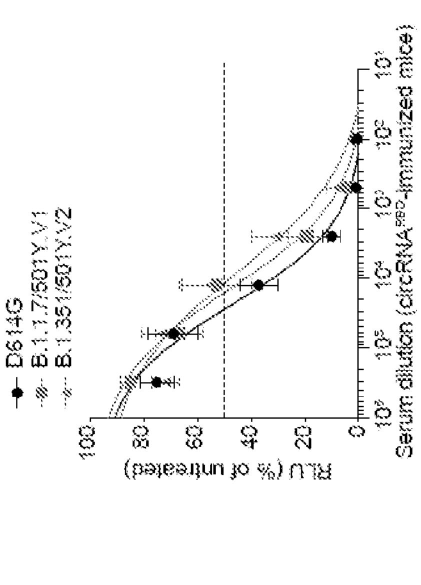
Figure 13E:
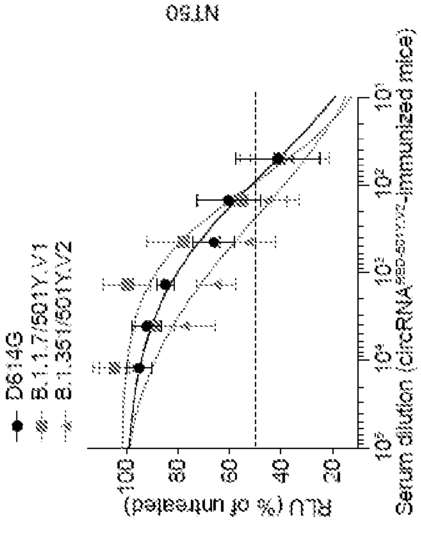

Example 13. SARS-COV-2 circRNA RBD-501Y.V2 Vaccines Elicited Antibodies Show Preferential Neutralizing Activity Against B.1.351 Variant Next, we evaluated the efficacy of a circRNA vaccine encoding RBD/K417N-E484K-N501Y derived from the B.1.351/501Y.V2 variant, termed as circRNA$^{RBD\text{-}501Y.V2}$ (FIG. 13A). BALB/c mice were immunized with an i.m. injection of the circRNA$^{RBD\text{-}501Y.V2}$ vaccine, followed by a boost at a two-week interval. The immunized mice's sera were collected at 1 and 2 weeks post the boost. The ELISA showed that the RBD-501Y.V2-specific IgG titer reached $7\times10^{4}$ at 2 weeks post boost (FIG. 13B). The surrogate neutralization assay showed that sera of circRNA$^{RBD\text{-}501Y.V2}$ immunized mice effectively neutralized RBD antigens (FIG. 13C). We then went on to assess the neutralization activity of the sera from mice immunized with circRNARBD or circRNA$^{RBD\text{-}501Y.V2}$ vaccines against D614G, B.1.1.7/501Y.V1, or B.1.351/501Y.V2 variants. VSV-based pseudovirus neutralization assay revealed that antibodies elicited by circRNARBD vaccines, which encode the native RBD sequence, effectively neutralized all three viral strains, with the highest activity against the D614G strain (FIG. 13D). The circRNA$^{RBD\text{-}501Y.V2}$ immunized mouse serum could also neutralize all three pseudoviruses, with the highest neutralizing activity against its corresponding variant, 501Y.V2 (FIG. 13E).

Figure 13F:
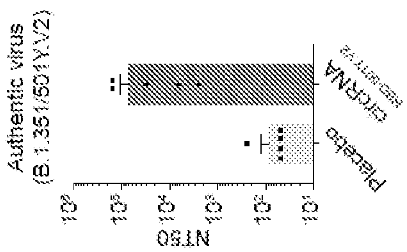
Figure 13G:
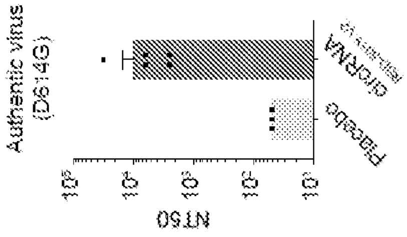

We further tested the neutralizing capacity of the circRNA$^{RBD\text{-}501Y.V2}$ immunized mouse serum against authentic SARS-COV-2 strains. In line with pseudovirus neutralization assay, the serum could effectively neutralize authentic SARS-COV-2 B.1.351/501Y.V2 strain with an NT50 of $7.1\times10^{4}$ (FIG. 13F), and could neutralize authentic SARS- COV-2 D164G strain less effectively with an NT50 of $9.8\times10^{3}$ (FIG. 13G). Collectively, circRNA vaccines-elicited antibodies showed the best neutralizing activity against their corresponding variant strains. It's worth noting that both vaccines could neutralize all three strains albeit with variable efficacies. Nevertheless, the updated vaccines for corresponding variant strains or multivalent vaccines might provide better protection for both native SARS-COV-2 strain and its circulating variants.

Figures 14A, 14B, 14C, 14D, 14E:
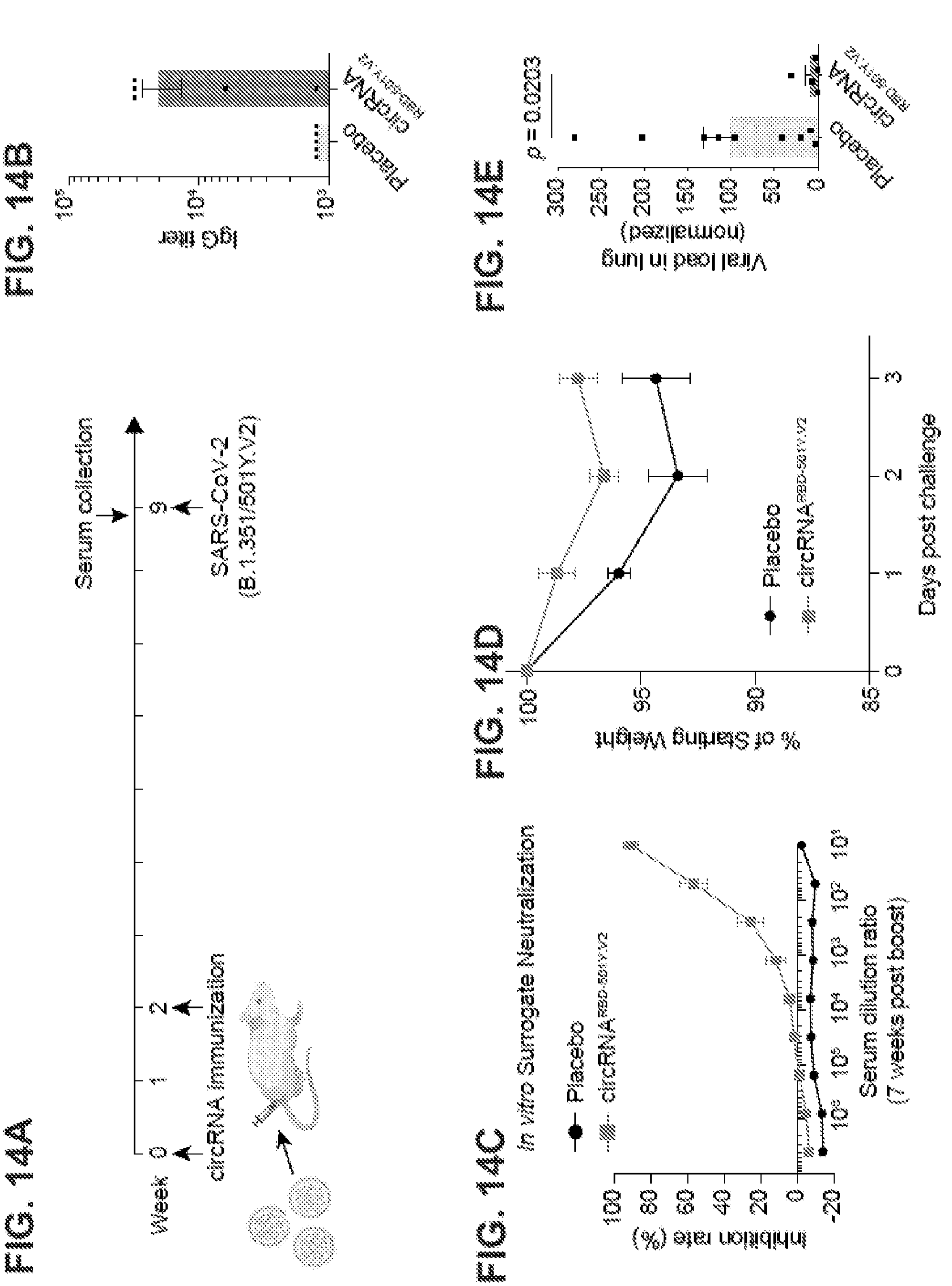
FIGS. 14A-14E provide results demonstrating protection of circRNA$^{RBD\text{-}501Y.V2}$ vaccines against SARS-COV-2 (B.1.351 strain) challenge in mice.

Example 14. Long-Lasting Protection of circRNA$^{RBD\text{-}501Y.V2}$ Vaccines Against Authentic B.1.351 Strain in a Novel Mouse Model To further evaluate the protective efficacy of SARS-COV-2 circRNA$^{RBD\text{-}501Y.V2}$ vaccines in vivo, we employed the B.1.351/501Y.V2 strain for authentic virus challenge experiments due to its severe antibody escape capability. Consistent with a recent report, the B.1.351/501Y.V2 variant could infect BALB/c mice and replicate in their lungs, possibly due to the mutations in spike protein, especially in the RBD domain, such as K417N, E484K and N501Y. We then employed BALB/c mice for accessing the protective efficacy of SARS-COV-2 circRNA$^{RBD\text{-}501Y.V2}$ vaccines: The BALB/c mice were received two-dose immunization of 50 μg circRNA$^{RBD\text{-}501Y.V2}$ vaccine or placebo via the i.m. route, at a two-week interval (FIG. 14A). To evaluate the long-term protection of circRNA vaccines, each immunized mouse was challenged with $5\times10^{4}$ PFU of authentic SARS-COV-2 B.1.351/501Y.V2 strain via the intranasal (i.n.) route at 7 weeks post the boost dose, and the lung tissues were collected 3 days after challenge for detecting viral RNA (FIG. 14A). Three days before virus challenge, the sera of immunized mice were collected to detect the RBD-501Y.V2-specific IgG (FIG. 14A). Near two months after the immunization, the titer of RBD-501Y.V2-specific IgG is around $2\times10^{4}$ (FIG. 14B), and the serum showed significant neutralizing capacity against RBD-501Y.V2 antigens (FIG. 14C).

Moreover, we found that the mice in the placebo group underwent increased weight loss compared with vaccinated mice (FIG. 14D). Consistently, virus titers in the lungs of vaccinated mice were significantly decreased compared with those who received placebos (FIG. 14E). These results indicated that the circRNA$^{RBD\text{-}501Y.V2}$ vaccine could effectively protect the mice from infection by SARS-COV-2 B.1.351/501Y.V2 variants.

EXEMPLARY SEQUENCES

```
SEQ ID NO: 1 Full-length S protein sequence of SARS-CoV-2
MFVFLVLLPLVSSQCVNLTTRTQLPPAYTNSFTRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMD
LEGKQGNFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSET
KCTLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGKIA
DYNYKLPDDFTGCVIAWNSNNLDSKVGGNYNYLYRLFRKSNLKPFERDISTEIYQAGST
PCNGVEGFNCYFPLQSYGFQPTNGVGYQPYRVVVLSFELLHAPATVCGPKKSTNLVKN
KCVNFNFNGLTGTGVLTESNKKFLPFQQFGRDIADTTDAVRDPQTLEILDITPCSFGGVS
VITPGTNTSNQVAVLYQDVNCTEVPVAIHADQLTPTWRVYSTGSNVFQTRAGCLIGAEH
VNNSYECDIPIGAGICASYQTQTNSPRRARSVASQSIIAYTMSLGAENSVAYSNNSIAIPT
NFTISVTTEILPVSMTKTSVDCTMYICGDSTECSNLLLQYGSFCTQLNRALTGIAVEQDK
NTQEVFAQVKQIYKTPPIKDFGGFNFSQILPDPSKPSKRSFIEDLLFNKVTLADAGFIKQY
GDCLGDIAARDLICAQKFNGLTVLPPLLTDEMIAQYTSALLAGTITSGWTFGAGAALQIP
FAMQMAYRFNGIGVTQNVLYENQKLIANQFNSAIGKIQDSLSSTASALGKLQDVVNQN
AQALNTLVKQLSSNFGAISSVLNDILSRLDKVEAEVQIDRLITGRLQSLQTYVTQQLIRAA
EIRASANLAATKMSECVLGQSKRVDFCGKGYHLMSFPQSAPHGVVFLHVTYVPAQEKN
FTTAPAICHDGKAHFPREGVFVSNGTHWFVTQRNFYEPQIITTDNTFVSGNCDVVIGIVN
NTVYDPLQPELDSFKEELDKYFKNHTSPDVDLGDISGINASVVNIQKEIDRLNEVAKNLN
ESLIDLQELGKYEQYIKWPWYIWLGFIAGLIAIVMVTIMLCCMTSCCSCLKGCCSCGSCC
KFDEDDSEPVLKGVKLHYT

SEQ ID NO: 2 RBD amino acid residues 319-542 of S protein
RVQPTESIVRFPNITNLCPFGEVFNATRFASVYAWNRKRISNCVADYSVLYNSASFSTFK
CYGVSPTKLNDLCFTNVYADSFVIRGDEVRQIAPGQTGKIADYNYKLPDDFTGCVIAWN
SNNLDSKVGGNYNYLYRLFRKSNLKPFERDISTEIYQAGSTPCNGVEGFNCYFPLQSYGF
QPTNGVGYQPYRVVVLSFELLHAPATVCGPKKSTNLVKNKCVNF

SEQ ID NO: 3 C-terminal Foldon domain of a T4 fibritin domain
GSGYIPEAPRDGQAYVRKDGEWVLLSTFLGRS

SEQ ID NO: 4 GCN4-based leucine zipper domain
RMKQIEDKIEEILSKIYHIENEIARIKKLIGER

SEQ ID NO: 5 Exemplary peptide linker
GGGGSGGGGS

SEQ ID NO: 6 wildtype S2 region of SARS-CoV-2 S protein
SVASQSIIAYTMSLGAENSVAYSNNSIAIPTNFTISVTTEILPVSMTKTSVDCTMYICGDST
ECSNLLLQYGSFCTQLNRALTGIAVEQDKNTQEVFAQVKQIYKTPPIKDFGGFNFSQILP
DPSKPSKRSFIEDLLFNKVTLADAGFIKQYGDCLGDIAARDLICAQKFNGLTVLPPLLTDE
MIAQYTSALLAGTITSGWTFGAGAALQIPFAMQMAYRFNGIGVTQNVLYENQKLIANQF
NSAIGKIQDSLSSTASALGKLQDVVNQNAQALNTLVKQLSSNFGAISSVLNDILSRLDKV
EAEVQIDRLITGRLQSLQTYVTQQLIRAAEIRASANLAATKMSECVLGQSKRVDFCGKG
YHLMSFPQSAPHGVVFLHVTYVPAQEKNFTTAPAICHDGKAHFPREGVFVSNGTHWFV
TQRNFYEPQUITTDNTFVSGNCDVVIGIVNNTVYDPLQPELDSFKEELDKYFKNHTSPDV
```

-continued

| EXEMPLARY SEQUENCES |
| --- |
| DLGDISGINASVVNIQKEIDRLNEVAKNLNESLIDLQELGKYEQYIKWPWYIWLGFIAGLI<br>AIVMVTIMLCCMTSCCSCLKGCCSCGSCCKFDEDDSEPVLKGVKLHYT |
| SEQ ID NO: 7 K986P/V987P S2 region sequence of SARS-CoV-2 S protein<br>SVASQSIIAYTMSLGAENSVAYSNNSIAIPTNFTISVTTEILPVSMTKTSVDCTMYICGDST<br>ECSNLLLQYGSFCTQLNRALTGIAVEQDKNTQEVFAQVKQIYKTPPIKDFGGFNFSQILP<br>DPSKPSKRSFIEDLLFNKVTLADAGFIKQYGDCLGDIAARDLICAQKFNGLTVLPPLLTDE<br>MIAQYTSALLAGTITSGWTFGAGAALQIPFAMQMAYRFNGIGVTQNVLYENQKLIANQF<br>NSAIGKIQDSLSSTASALGKLQDVVNQNAQALNTLVKQLSSNFGAISSVLNDILSRLDPPE<br>AEVQIDRLITGRLQSLQTYVTQQLIRAAEIRASANLAATKMSECVLGQSKRVDFCGKGY<br>HLMSFPQSAPHGVVFLHVTYVPAQEKNFTTAPAICHDGKAHFPREGVFVSNGTHWFVT<br>QRNFYEPQUITTDNTFVSGNCDVVIGIVNNTVYDPLQPELDSFKEELDKYFKNHTSPDVD<br>LGDISGINASVVNIQKEIDRLNEVAKNLNESLIDLQELGKYEQYIKWPWYIWLGFIAGLIA<br>IVMVTIMLCCMTSCCSCLKGCCSCGSCCKFDEDDSEPVLKGVKLHYT |
| SEQ ID NO: 8 wildtype amino acid residues 2-1273 sequence of S<br>protein of SARS-CoV-2<br>FVFLVLLPLVSSQCVNLTTRTQLPPAYTNSFTRGVYYPDKVFRSSVLHSTQDLFLPFFSN<br>VTWFHAIHVSGTNGTKRFDNPVLPFNDGVYFASTEKSNIIRGWIFGTTLDSKTQSLLIVN<br>NATNVVIKVCEFQFCNDPFLGVYYHKNNKSWMESEFRVYSSANNCTFEYVSQPFLMDL<br>EGKQGNFKNLREFVFKNIDGYFKIYSKHTPINLVRDLPQGFSALEPLVDLPIGINITRFQTL<br>LALHRSYLTPGDSSSGWTAGAAAYYVGYLQPRTFLLKYNENGTITDAVDCALDPLSETK<br>CTLKSFTVEKGIYQTSNFRVQPTESIVRFPNITNLCPFGEVFNATRFASVYAWNRKRISNC<br>VADYSVLYNSASFSTFKCYGVSPTKLNDLCFTNVYADSFVIRGDEVRQIAPGQTGKIAD<br>YNYKLPDDFTGCVIAWNSNNLDSKVGGNYNYLYRLFRKSNLKPFERDISTEIYQAGSTP<br>CNGVEGFNCYFPLQSYGFQPTNGVGYQPYRVVVLSFELLHAPATVCGPKKSTNLVKNK<br>CVNFNFNGLTGTGVLTESNKKFLPFQQFGRDIADTTDAVRDPQTLEILDITPCSFGGVSVI<br>TPGTNTSNQVAVLYQDVNCTEVPVAIHADQLTPTWRVYSTGSNVFQTRAGCLIGAEHV<br>NNSYECDIPIGAGICASYQTQTNSPRRARSVASQSIIAYTMSLGAENSVAYSNNSIAIPTNF<br>TISVTTEILPVSMTKTSVDCTMYICGDSTECSNLLLQYGSFCTQLNRALTGIAVEQDKNT<br>QEVFAQVKQIYKTPPIKDFGGFNFSQILPDPSKPSKRSFIEDLLFNKVTLADAGFIKQYGD<br>CLGDIAARDLICAQKFNGLTVLPPLLTDEMIAQYTSALLAGTITSGWTFGAGAALQIPFA<br>MQMAYRFNGIGVTQNVLYENQKLIANQFNSAIGKIQDSLSSTASALGKLQDVVNQNAQ<br>ALNTLVKQLSSNFGAISSVLNDILSRLDKVEAEVQIDRLITGRLQSLQTYVTQQLIRAAEI<br>RASANLAATKMSECVLGQSKRVDFCGKGYHLMSFPQSAPHGVVFLHVTYVPAQEKNF<br>TTAPAICHDGKAHFPREGVFVSNGTHWFVTQRNFYEPQUITTDNTFVSGNCDVVIGIVNN<br>TVYDPLQPELDSFKEELDKYFKNHTSPDVDLGDISGINASVVNIQKEIDRLNEVAKNLNE<br>SLIDLQELGKYEQYIKWPWYIWLGFIAGLIAIVMVTIMLCCMTSCCSCLKGCCSCGSCCK<br>FDEDDSEPVLKGVKLHYT |
| SEQ ID NO: 9 amino acid residues 2-1273 sequence of S protein<br>of SARS-CoV-2, Δ681-684<br>FVFLVLLPLVSSQCVNLTTRTQLPPAYTNSFTRGVYYPDKVFRSSVLHSTQDLFLPFFSN<br>VTWFHAIHVSGTNGTKRFDNPVLPFNDGVYFASTEKSNIIRGWIFGTTLDSKTQSLLIVN<br>NATNVVIKVCEFQFCNDPFLGVYYHKNNKSWMESEFRVYSSANNCTFEYVSQPFLMDL<br>EGKQGNFKNLREFVFKNIDGYFKIYSKHTPINLVRDLPQGFSALEPLVDLPIGINITRFQTL<br>LALHRSYLTPGDSSSGWTAGAAAYYVGYLQPRTFLLKYNENGTITDAVDCALDPLSETK<br>CTLKSFTVEKGIYQTSNFRVQPTESIVRFPNITNLCPFGEVFNATRFASVYAWNRKRISNC<br>VADYSVLYNSASFSTFKCYGVSPTKLNDLCFTNVYADSFVIRGDEVRQIAPGQTGKIAD<br>YNYKLPDDFTGCVIAWNSNNLDSKVGGNYNYLYRLFRKSNLKPFERDISTEIYQAGSTP<br>CNGVEGFNCYFPLQSYGFQPTNGVGYQPYRVVVLSFELLHAPATVCGPKKSTNLVKNK<br>CVNFNFNGLTGTGVLTESNKKFLPFQQFGRDIADTTDAVRDPQTLEILDITPCSFGGVSVI<br>TPGTNTSNQVAVLYQDVNCTEVPVAIHADQLTPTWRVYSTGSNVFQTRAGCLIGAEHV<br>NNSYECDIPIGAGICASYQTQTNSRSVASQSIIAYTMSLGAENSVAYSNNSIAIPTNFTISV<br>TTEILPVSMTKTSVDCTMYICGDSTECSNLLLQYGSFCTQLNRALTGIAVEQDKNTQEVF<br>AQVKQIYKTPPIKDFGGFNFSQILPDPSKPSKRSFIEDLLFNKVTLADAGFIKQYGDCLGDI<br>AARDLICAQKFNGLTVLPPLLTDEMIAQYTSALLAGTITSGWTFGAGAALQIPFAMQMA<br>YRFNGIGVTQNVLYENQKLIANQFNSAIGKIQDSLSSTASALGKLQDVVNQNAQALNTL<br>VKQLSSNFGAISSVLNDILSRLDKVEAEVQIDRLITGRLQSLQTYVTQQLIRAAEIRASAN<br>LAATKMSECVLGQSKRVDFCGKGYHLMSFPQSAPHGVVFLHVTYVPAQEKNFTTAPAI<br>CHDGKAHFPREGVFVSNGTHWFVTQRNFYEPQUITTDNTFVSGNCDVVIGIVNNTVYDP<br>LQPELDSFKEELDKYFKNHTSPDVDLGDISGINASVVNIQKEIDRLNEVAKNLNESLIDLQ<br>ELGKYEQYIKWPWYIWLGFIAGLIAIVMVTIMLCCMTSCCSCLKGCCSCGSCCKFDEDD<br>SEPVLKGVKLHYT |
| SEQ ID NO: 10 amino acid residues 2-1273 sequence of S protein<br>of SARS-CoV-2, K986P V987P Δ681-684 sequence<br>FVFLVLLPLVSSQCVNLTTRTQLPPAYTNSFTRGVYYPDKVFRSSVLHSTQDLFLPFFSN<br>VTWFHAIHVSGTNGTKRFDNPVLPFNDGVYFASTEKSNIIRGWIFGTTLDSKTQSLLIVN<br>NATNVVIKVCEFQFCNDPFLGVYYHKNNKSWMESEFRVYSSANNCTFEYVSQPFLMDL<br>EGKQGNFKNLREFVFKNIDGYFKIYSKHTPINLVRDLPQGFSALEPLVDLPIGINITRFQTL<br>LALHRSYLTPGDSSSGWTAGAAAYYVGYLQPRTFLLKYNENGTITDAVDCALDPLSETK<br>CTLKSFTVEKGIYQTSNFRVQPTESIVRFPNITNLCPFGEVFNATRFASVYAWNRKRISNC<br>VADYSVLYNSASFSTFKCYGVSPTKLNDLCFTNVYADSFVIRGDEVRQIAPGQTGKIAD<br>YNYKLPDDFTGCVIAWNSNNLDSKVGGNYNYLYRLFRKSNLKPFERDISTEIYQAGSTP<br>CNGVEGFNCYFPLQSYGFQPTNGVGYQPYRVVVLSFELLHAPATVCGPKKSTNLVKNK<br>CVNFNFNGLTGTGVLTESNKKFLPFQQFGRDIADTTDAVRDPQTLEILDITPCSFGGVSVI |

-continued

| EXEMPLARY SEQUENCES |
| --- |
| TPGTNTSNQVAVLYQDVNCTEVPVAIHADQLTPTWRVYSTGSNVFQTRAGCLIGAEHV<br>NNSYECDIPIGAGICASYQTQTNSRSVASQSIIAYTMSLGAENSVAYSNNSIAIPTNFTISV<br>TTEILPVSMTKTSVDCTMYICGDSTECSNLLLQYGSFCTQLNRALTGIAVEQDKNTQEVF<br>AQVKQIYKTPPIKDFGGFNFSQILPDPSKPSKRSFIEDLLFNKVTLADAGFIKQYGDCLGDI<br>AARDLICAQKFNGLTVLPPLLTDEMIAQYTSALLAGTITSGWTFGAGAALQIPFAMQMA<br>YRFNGIGVTQNVLYENQKLIANQFNSAIGKIQDSLSSTASALGKLQDVVNQNAQALNTL<br>VKQLSSNFGAISSVLNDILSRLDPPEAEVQIDRLITGRLQSLQTYVTQQLIRAAEIRASANL<br>AATKMSECVLGQSKRVDFCGKGYHLMSFPQSAPHGVVFLHVTYVPAQEKNFTTAPAIC<br>QPELDSFKEELDKYFKNHTSPDVDLGDISGINASVVNIQKEIDRLNEVAKNLNESLIDLQE<br>LGKYEQYIKWPWYIWLGFIAGLIAIVMVTIMLCCMTSCCSCLKGCCSCGSCCKFDEDDS<br>EPVLKGVKLHYT |
| SEQ ID NO: 11 Nucleic acid sequence of the wildtype S2 region sequence<br>AGTGTGGCTTCTCAAAGCATTATAGCATACACTATGTCTCTTGGTGCCGAAAATTCC<br>GTGGCCTATTCTAACAATTCAATCGCCATCCCAACCAACTTCACAATTAGCGTGACT<br>ACCGAAATACTGCCTGTGAGCATGACGAAAACCAGCGTAGACTGCACTATGTATAT<br>CTGTGGAGACTCCACTGAGTGCTCCAACCTTCTCCTGCAGTACGGTAGCTTCTGTAC<br>CCAATTGAACCGCGCCCTTACAGGCATCGCTGTTGAGCAAGATAAGAATACCCAGG<br>AAGTTTTTGCCCAGGTTAAGCAGATATACAAAACACCGCCCATTAAGGACTTCGGAG<br>GCTTCAACTTCTCTCAGATACTGCCTGACCCCTCCAAGCCATCAAAACGCAGCTTCA<br>TTGAGGACCTCTTGTTCAACAAAGTGACTCTGGCTGATGCTGGCTTCATTAAGCAGT<br>ACGGAGATTGCCTGGGAGATATTGCTGCCAGGGACCTCATCTGCGCCCAGAAGTTTA<br>ATGGCCTGACAGTCTTGCCCCCACTTCTGACAGACGAGATGATTGCTCAGTACACAT<br>CTGCCCTCCTCGCTGGCACCATAACATCCGGATGGACATTTGGTGCTGGTGCTGCCC<br>TCCAGATTCCCTTCGCAATGCAGATGGCGTATCGCTTTAACGGCATCGGTGTCACAC<br>AAAACGTGTTGTATGAGAACCAAAAGCTCATCGCTAACCAGTTTAATTCTGCTATTG<br>GTAAGATTCAGGACAGCCTGTCATCAACCGCGTCTGCCCTTGGTAAGTTGCAGGACG<br>TGGTGAACCAGAATGCTCAGGCTTTGAATACTCTGGTGAAGCAACTCTCTTCAAATT<br>TCGGCGCTATCTCTTCTGTGTTGAACGACATCCTGAGTCGCCTTGATAAGGTGGAAG<br>CTGAAGTTCAAATTGATAGATTGATTACTGGCAGGCTCCAGTCTTTGCAGACCTACG<br>TTACACAGCAGCTGATTAGGGCGGCTGAAATTAGAGCTTCCGCCAATCTGGCTGCAA<br>CCAAGATGTCCGAATGCGTCCTGGGTCAGTCAAAGCGCGTTGACTTTTGTGGTAAAG<br>GCTACCACCTCATGTCATTTCCCCAGTCAGCACCTCACGGAGTAGTGTTCCTCCACG<br>TCACCTACGTTCCAGCACAGGAAAAGAATTTTACCACTGCGCCGGCAATCTGTCACG<br>ACGGTAAGGCACACTTCCCCCGCGAGGGCGTATTCGTGTCTAACGGAACTCATTGGT<br>TCGTCACACAGAGAAACTTCTATGAGCCTCAGATCATTACCACCGACAATACATTTG<br>TGTCCGGTAACTGCGACGTTGTGATTGGAATCGTCAACAACACTGTGTACGATCCAC<br>TTCAGCCAGAACTGGATAGCTTCAAGGAAGAATTGGACAAATATTTCAAAAATCAC<br>ACTTCACCCGATGTGGACCTGGGTGACATTAGTGGTATCAATGCGTCCGTGGTCAAT<br>ATTCAAAAAGAGATTGACAGGCTCAACGAAGTGGCCAAGAACCTGAACGAAAGTCT<br>TATCGATCTGCAAGAATTGGGAAAGTATGAGCAGTACATCAAGTGGCCGTGGTACA<br>TTTGGTTGGGTTTTATCGCCGGTCTGATCGCCATCGTTATGGTTACCATTATGCTTTG<br>CTGCATGACGAGCTGTTGCTCCTGTCTGAAGGGATGCTGCTCTTGCGGATCATGTTG<br>CAAGTTCGATGAAGACGATAGCGAACCAGTTCTGAAGGGCGTCAAGCTGCATTACA<br>CA |
| SEQ ID NO: 12 Nucleic acid sequence of the K986P/V987P S2 region sequence<br>AGTGTGGCTTCTCAAAGCATTATAGCATACACTATGTCTCTTGGTGCCGAAAATTCC<br>GTGGCCTATTCTAACAATTCAATCGCCATCCCAACCAACTTCACAATTAGCGTGACT<br>ACCGAAATACTGCCTGTGAGCATGACGAAAACCAGCGTAGACTGCACTATGTATAT<br>CTGTGGAGACTCCACTGAGTGCTCCAACCTTCTCCTGCAGTACGGTAGCTTCTGTAC<br>CCAATTGAACCGCGCCCTTACAGGCATCGCTGTTGAGCAAGATAAGAATACCCAGG<br>AAGTTTTTGCCCAGGTTAAGCAGATATACAAAACACCGCCCATTAAGGACTTCGGAG<br>GCTTCAACTTCTCTCAGATACTGCCTGACCCCTCCAAGCCATCAAAACGCAGCTTCA<br>TTGAGGACCTCTTGTTCAACAAAGTGACTCTGGCTGATGCTGGCTTCATTAAGCAGT<br>ACGGAGATTGCCTGGGAGATATTGCTGCCAGGGACCTCATCTGCGCCCAGAAGTTTA<br>ATGGCCTGACAGTCTTGCCCCCACTTCTGACAGACGAGATGATTGCTCAGTACACAT<br>CTGCCCTCCTCGCTGGCACCATAACATCCGGATGGACATTTGGTGCTGGTGCTGCCC<br>TCCAGATTCCCTTCGCAATGCAGATGGCGTATCGCTTTAACGGCATCGGTGTCACAC<br>AAAACGTGTTGTATGAGAACCAAAAGCTCATCGCTAACCAGTTTAATTCTGCTATTG<br>GTAAGATTCAGGACAGCCTGTCATCAACCGCGTCTGCCCTTGGTAAGTTGCAGGACG<br>TGGTGAACCAGAATGCTCAGGCTTTGAATACTCTGGTGAAGCAACTCTCTTCAAATT<br>TCGGCGCTATCTCTTCTGTGTTGAACGACATCCTGAGTCGCCTTGATcctccaGAAGCTG<br>AAGTTCAAATTGATAGATTGATTACTGGCAGGCTCCAGTCTTTGCAGACCTACGTTA<br>CACAGCAGCTGATTAGGGCGGCTGAAATTAGAGCTTCCGCCAATCTGGCTGCAACC<br>AAGATGTCCGAATGCGTCCTGGGTCAGTCAAAGCGCGTTGACTTTTGTGGTAAAGGC<br>TACCACCTCATGTCATTTCCCCAGTCAGCACCTCACGGAGTAGTGTTCCTCCACGTC<br>ACCTACGTTCCAGCACAGGAAAAGAATTTTACCACTGCGCCGGCAATCTGTCACGAC<br>GGTAAGGCACACTTCCCCCGCGAGGGCGTATTCGTGTCTAACGGAACTCATTGGTTC |

-continued

| EXEMPLARY SEQUENCES |
| --- |

GTCACACAGAGAAACTTCTATGAGCCTCAGATCATTACCACCGACAATACATTTGTG
TCCGGTAACTGCGACGTTGTGATTGGAATCGTCAACAACACTGTGTACGATCCACTT
CAGCCAGAACTGGATAGCTTCAAGGAAGAATTGGACAAATATTTCAAAAATCACAC
TTCACCCGATGTGGACCTGGGTGACATTAGTGGTATCAATGCGTCCGTGGTCAATAT
TCAAAAAGAGATTGACAGGCTCAACGAAGTGGCCAAGAACCTGAACGAAAGTCTTA
TCGATCTGCAAGAATTGGGAAAGTATGAGCAGTACATCAAGTGGCCGTGGTACATTT
GGTTGGGTTTTATCGCCGGTCTGATCGCCATCGTTATGGTTACCATTATGCTTTGCTG
CATGACGAGCTGTTGCTCCTGTCTGAAGGGATGCTGCTCTTGCGGATCATGTTGCAA
GTTCGATGAAGACGATAGCGAACCAGTTCTGAAGGGCGTCAAGCTGCATTACACA

SEQ ID NO: 13 Nucleic acid sequence of the wildtype 2-1273
sequence of Spike
TTCGTTTTCCTTGTTCTGTTGCCTCTCGTTAGTAGCCAATGCGTCAACCTTACTACTA
GAACCCAGCTCCCTCCAGCATATACCAACTCTTTCACCAGGGGCGTATATTACCCGG
ACAAAGTGTTCCGCTCAAGTGTGCTGCATTCTACGCAGGACCTTTTCTTGCCCTTTTT
CAGTAATGTTACTTGGTTTCATGCTATCCATGTGTCTGGAACTAACGGAACCAAGCG
CTTTGACAACCCCGTCCTCCCTTTCAACGATGGCGTGTACTTCGCTTCCACGGAAAA
GTCAAACATAATTCGCGGCTGGATCTTTGGTACAACACTCGACTCAAAGACGCAGA
GCCTGCTGATCGTTAATAACGCTACAAATGTTGTGATAAAGGTGTGTGAATTTCAGT
TCTGCAATGATCCCTTCCTGGGTGTGTACTACCATAAGAATAACAAGAGCTGGATGG
AATCCGAATTTAGGGTTTACAGTTCCGCTAACAACTGCACATTCGAATACGTAAGCC
AGCCATTTCTTATGGATCTTGAGGGCAAGCAAGGAAACTTCAAGAACTTGAGGGAG
TTCGTGTTCAAAAATATCGACGGCTATTTTAAGATATATAGCAAGCACACTCCAATA
AACTTGGTGCGCGACCTGCCCCAGGGATTCTCTGCTCTGGAGCCCCTGGTGGATCTG
CCCATTGGAATAAACATAACTCGCTTTCAAACACTGCTCGCCCTGCATCGCAGTTAC
CTCACCCCTGGTGATAGTAGTTCAGGATGGACAGCAGGAGCCGCCGCATACTACGT
CGGCTACCTGCAGCCTAGGACCTTCTTGCTGAAGTACAACGAGAACGGTACAATAA
CTGACGCTGTGGACTGCGCTCTGGACCCTCTGTCCGAGACGAAGTGCACCCTGAAGA
GCTTTACTGTTGAAAAAGGCATTTACCAAACCAGCAACTTCCGCGTCCAGCCAACCG
AGAGCATCGTCAGATTTCCCAACATTACAAATCTGTGTCCCTTCGGCGAGGTGTTCA
ACGCCACACGCTTCGCTTCAGTGTACGCATGGAACCGCAAGCGCATATCTAACTGCG
TCGCGGATTATTCTGTCCTCTACAACTCCGCCTCTTTCTCCACCTTCAAGTGCTACGG
AGTGTCACCGACTAAGCTGAACGATCTCTGCTTTACCAACGTCTACGCGGACTCCTT
CGTGATAAGAGGTGATGAAGTGAGACAAATAGCCCCAGGTCAGACTGGTAAGATCG
CAGATTACAACTACAAATTGCCTGATGATTTCACTGGTTGCGTTATCGCGTGGAACT
CTAATAACCTCGATTCTAAGGTCGGTGGTAACTACAATTACCTGTACCGCTTGTTTA
GGAAGTCAAACCTGAAGCCTTTCGAGAGGGATATTTCAACCGAAATCTATCAAGCG
GGTTCAACACCGTGTAACGGTGTGGAAGGATTTAACTGCTACTTCCCCCTGCAGTCT
TACGGATTCCAGCCAACCAATGGCGTGGGTTACCAACCTTATCGCGTGGTGGTTCTG
AGTTTCGAACTGTTGCACGCTCCCGCCACGGTATGCGGTCCCAAGAAGAGCACTAAC
TTGGTGAAGAATAAGTGCGTGAATTTCAATTTCAATGGCCTCACTGGAACTGGAGTG
CTGACCGAATCCAATAAGAAGTTCTTGCCCTTCCAGCAGTTCGGAAGAGACATTGCT
GACACAACCGACGCGGTGCGCGATCCTCAGACTCTGGAGATATTGGACATTACACC
ATGTTCTTTCGGCGGTGTGTCTGTCATTACTCCGGGCACGAATACTAGCAACCAGGT
AGCCGTGCTGTACCAAGACGTGAATTGCACAGAGGTTCCCGTCGCAATTCACGCTGA
CCAGCTGACCCCCACGTGGAGGGTTTACAGCACTGGTAGTAACGTCTTCCAGACGA
GAGCCGGTTGCTTGATCGGAGCGGAACATGTGAATAACTCCTACGAGTGCGACATC
CCCATCGGAGCCGGTATATGCGCCTCTTATCAGACACAAACTAACTCACCCAGGAG
AGCCCGCAGTGTGGCTTCTCAAAGCATTATAGCATACACTATGTCTCTTGGTGCCGA
AAATTCCGTGGCCTATTCTAACAATTCAATCGCCATCCCAACCAACTTCACAATTAG
CGTGACTACCGAAATACTGCCTGTGAGCATGACGAAAACCAGCGTAGACTGCACTA
TGTATATCTGTGGAGACTCCACTGAGTGCTCCAACCTTCTCCTGCAGTACGGTAGCTT
CTGTACCCAATTGAACCGCGCCCTTACAGGCATCGCTGTTGAGCAAGATAAGAATAC
CCAGGAAGTTTTTGCCCAGGTTAAGCAGATATACAAAACACCGCCCATTAAGGACTT
CGGAGGCTTCAACTTCTCTCAGATACTGCCTGACCCCTCCAAGCCATCAAAACGCAG
CTTCATTGAGGACCTCTTGTTCAACAAAGTGACTCTGGCTGATGCTGGCTTCATTAA
GCAGTACGGAGATTGCCTGGGAGATATTGCTGCCAGGGACCTCATCTGCGCCCAGA
AGTTTAATGGCCTGACAGTCTTGCCCCCACTTCTGACAGACGAGATGATTGCTCAGT
ACACATCTGCCCTCCTCGCTGGCACCATAACATCCGGATGGACATTTGGTGCTGGTG
CTGCCCTCCAGATTCCCTTCGCAATGCAGATGGCGTATCGCTTTAACGGCATCGGTG
TCACACAAAACGTGTTGTATGAGAACCAAAAGCTCATCGCTAACCAGTTTAATTCTG
CTATTGGTAAGATTCAGGACAGCCTGTCATCAACCGCGTCTGCCCTTGGTAAGTTGC
AGGACGTGGTGAACCAGAATGCTCAGGCTTTGAATACTCTGGTGAAGCAACTCTCTT
CAAATTTCGGCGCTATCTCTTCTGTGTTGAACGACATCCTGAGTCGCCTTGATAAGGT
GGAAGCTGAAGTTCAAATTGATAGATTGATTACTGGCAGGCTCCAGTCTTTGCAGAC
CTACGTTACACAGCAGCTGATTAGGGCGGCTGAAATTAGAGCTTCCGCCAATCTGGC
TGCAACCAAGATGTCCGAATGCGTCCTGGGTCAGTCAAAGCGCGTTGACTTTTGTGG
TAAAGGCTACCACCTCATGTCATTTCCCCAGTCAGCACCTCACGGAGTAGTGTTCCT
CCACGTCACCTACGTTCCAGCACAGGAAAAGAATTTTACCACTGCGCCGGCAATCTG
TCACGACGGTAAGGCACACTTCCCCCGCGAGGGCGTATTCGTGTCTAACGGAACTCA
TTGGTTCGTCACACAGAGAAACTTCTATGAGCCTCAGATCATTACCACCGACAATAC
ATTTGTGTCCGGTAACTGCGACGTTGTGATTGGAATCGTCAACAACACTGTGTACGA
TCCACTTCAGCCAGAACTGGATAGCTTCAAGGAAGAATTGGACAAATATTTCAAAA
ATCACACTTCACCCGATGTGGACCTGGGTGACATTAGTGGTATCAATGCGTCCGTGG
TCAATATTCAAAAAGAGATTGACAGGCTCAACGAAGTGGCCAAGAACCTGAACGAA
AGTCTTATCGATCTGCAAGAATTGGGAAAGTATGAGCAGTACATCAAGTGGCCGTG
GTACATTTGGTTGGGTTTTATCGCCGGTCTGATCGCCATCGTTATGGTTACCATTATG -continued

| EXEMPLARY SEQUENCES |
|---|
| CTTTGCTGCATGACGAGCTGTTGCTCCTGTCTGAAGGGATGCTGCTCTTGCGGATCAT<br>GTTGCAAGTTCGATGAAGACGATAGCGAACCAGTTCTGAAGGGCGTCAAGCTGCAT<br>TACACA |
| SEQ ID NO: 14 Nucleic acid sequence of the Δ681-684 sequence of Spike<br>TTCGTTTTCCTTGTTCTGTTGCCTCTCGTTAGTAGCCAATGCGTCAACCTTACTACTA<br>GAACCCAGCTCCCTCCAGCATATACCAACTCTTTCACCAGGGGCGTATATTACCCGG<br>ACAAAGTGTTCCGCTCAAGTGTGCTGCATTCTACGCAGGACCTTTTCTTGCCCTTTTT<br>CAGTAATGTTACTTGGTTTCATGCTATCCATGTGTCTGGAACTAACGGAACCAAGCG<br>CTTTGACAACCCCGTCCTCCCTTTCAACGATGGCGTGTACTTCGCTTCCACGGAAAA<br>GTCAAACATAATTCGCGGCTGGATCTTTGGTACAACACTCGACTCAAAGACGCAGA<br>GCCTGCTGATCGTTAATAACGCTACAAATGTTGTGATAAAGGTGTGTGAATTTCAGT<br>TCTGCAATGATCCCTTCCTGGGTGTGTACTACCATAAGAATAACAAGAGCTGGATGG<br>AATCCGAATTTAGGGTTTACAGTTCCGCTAACAACTGCACATTCGAATACGTAAGCC<br>AGCCATTTCTTATGGATCTTGAGGGCAAGCAAGGAAACTTCAAGAACTTGAGGGAG<br>TTCGTGTTCAAAAATATCGACGGCTATTTTAAGATATATAGCAAGCACACTCCAATA<br>AACTTGGTGCGCGACCTGCCCCAGGGATTCTCTGCTCTGGAGCCCCTGGTGGATCTG<br>CCCATTGGAATAAACATAACTCGCTTTCAAACACTGCTCGCCCTGCATCGCAGTTAC<br>CTCACCCCTGGTGATAGTAGTTCAGGATGGACAGCAGGAGCCGCCGCATACTACGT<br>CGGCTACCTGCAGCCTAGGACCTTCTTGCTGAAGTACAACGAGAACGGTACAATAA<br>CTGACGCTGTGGACTGCGCTCTGGACCCTCTGTCCGAGACGAAGTGCACCCTGAAGA<br>GCTTTACTGTTGAAAAAGGCATTTACCAAACCAGCAACTTCCGCGTCCAGCCAACCG<br>AGAGCATCGTCAGATTTCCCAACATTACAAATCTGTGTCCCTTCGGCGAGGTGTTCA<br>ACGCCACACGCTTCGCTTCAGTGTACGCATGGAACCGCAAGCGCATATCTAACTGCG<br>TCGCGGATTATTCTGTCCTCTACAACTCCGCCTCTTTCTCCACCTTCAAGTGCTACGG<br>AGTGTCACCGACTAAGCTGAACGATCTCTGCTTTACCAACGTCTACGCGGACTCCTT<br>CGTGATAAGAGGTGATGAAGTGAGACAAATAGCCCCAGGTCAGACTGGTAAGATCG<br>CAGATTACAACTACAAATTGCCTGATGATTTCACTGGTTGCGTTATCGCGTGGAACT<br>CTAATAACCTCGATTCTAAGGTCGGTGGTAACTACAATTACCTGTACCGCTTGTTTA<br>GGAAGTCAAACCTGAAGCCTTTCGAGAGGGATATTTCAACCGAAATCTATCAAGCG<br>GGTTCAACACCGTGTAACGGTGTGGAAGGATTTAACTGCTACTTCCCCCTGCAGTCT<br>TACGGATTCCAGCCAACCAATGGCGTGGGTTACCAACCTTATCGCGTGGTGGTTCTG<br>AGTTTCGAACTGTTGCACGCTCCCGCCACGGTATGCGGTCCCAAGAAGAGCACTAAC<br>TTGGTGAAGAATAAGTGCGTGAATTTCAATTTCAATGGCCTCACTGGAACTGGAGTG<br>CTGACCGAATCCAATAAGAAGTTCTTGCCCTTCCAGCAGTTCGGAAGAGACATTGCT<br>GACACAACCGACGCGGTGCGCGATCCTCAGACTCTGGAGATATTGGACATTACACC<br>ATGTTCTTTCGGCGGTGTGTCTGTCATTACTCCGGGCACGAATACTAGCAACCAGGT<br>AGCCGTGCTGTACCAAGACGTGAATTGCACAGAGGTTCCCGTCGCAATTCACGCTGA<br>CCAGCTGACCCCCACGTGGAGGGTTTACAGCACTGGTAGTAACGTCTTCCAGACGA<br>GAGCCGGTTGCTTGATCGGAGCGGAACATGTGAATAACTCCTACGAGTGCGACATC<br>CCCATCGGAGCCGGTATATGCGCCTCTTATCAGACACAAACTAACTCACGCAGTGTG<br>GCTTCTCAAAGCATTATAGCATACACTATGTCTCTTGGTGCCGAAAATTCCGTGGCC<br>TATTCTAACAATTCAATCGCCATCCCAACCAACTTCACAATTAGCGTGACTACCGAA<br>ATACTGCCTGTGAGCATGACGAAAACCAGCGTAGACTGCACTATGTATATCTGTGGA<br>GACTCCACTGAGTGCTCCAACCTTCTCCTGCAGTACGGTAGCTTCTGTACCCAATTG<br>AACCGCGCCCTTACAGGCATCGCTGTTGAGCAAGATAAGAATACCCAGGAAGTTTTT<br>GCCCAGGTTAAGCAGATATACAAAACACCGCCCATTAAGGACTTCGGAGGCTTCAA<br>CTTCTCTCAGATACTGCCTGACCCCTCCAAGCCATCAAAACGCAGCTTCATTGAGGA<br>CCTCTTGTTCAACAAAGTGACTCTGGCTGATGCTGGCTTCATTAAGCAGTACGGAGA<br>TTGCCTGGGAGATATTGCTGCCAGGGACCTCATCTGCGCCCAGAAGTTTAATGGCCT<br>GACAGTCTTGCCCCCACTTCTGACAGACGAGATGATTGCTCAGTACACATCTGCCCT<br>CCTCGCTGGCACCATAACATCCGGATGGACATTTGGTGCTGGTGCTGCCCTCCAGAT<br>TCCCTTCGCAATGCAGATGGCGTATCGCTTTAACGGCATCGGTGTCACACAAAACGT<br>GTTGTATGAGAACCAAAAGCTCATCGCTAACCAGTTTAATTCTGCTATTGGTAAGAT<br>TCAGGACAGCCTGTCATCAACCGCGTCTGCCCTTGGTAAGTTGCAGGACGTGGTGAA<br>CCAGAATGCTCAGGCTTTGAATACTCTGGTGAAGCAACTCTCTTCAAATTTCGGCGC<br>TATCTCTTCTGTGTTGAACGACATCCTGAGTCGCCTTGATAAGGTGGAAGCTGAAGT<br>TCAAATTGATAGATTGATTACTGGCAGGCTCCAGTCTTTGCAGACCTACGTTACACA<br>GCAGCTGATTAGGGCGGCTGAAATTAGAGCTTCCGCCAATCTGGCTGCAACCAAGA<br>TGTCCGAATGCGTCCTGGGTCAGTCAAAGCGCGTTGACTTTTGTGGTAAAGGCTACC<br>ACCTCATGTCATTTCCCCAGTCAGCACCTCACGGAGTAGTGTTCCTCCACGTCACCT<br>ACGTTCCAGCACAGGAAAAGAATTTTACCACTGCGCCGGCAATCTGTCACGACGGT<br>AAGGCACACTTCCCCCGCGAGGGCGTATTCGTGTCTAACGGAACTCATTGGTTCGTC<br>ACACAGAGAAACTTCTATGAGCCTCAGATCATTACCACCGACAATACATTTGTGTCC<br>GGTAACTGCGACGTTGTGATTGGAATCGTCAACAACACTGTGTACGATCCACTTCAG<br>CCAGAACTGGATAGCTTCAAGGAAGAATTGGACAAATATTTCAAAAATCACACTTC<br>ACCCGATGTGGACCTGGGTGACATTAGTGGTATCAATGCGTCCGTGGTCAATATTCA<br>AAAAGAGATTGACAGGCTCAACGAAGTGGCCAAGAACCTGAACGAAAGTCTTATCG<br>ATCTGCAAGAATTGGGAAAGTATGAGCAGTACATCAAGTGGCCGTGGTACATTTGG<br>TTGGGTTTTATCGCCGGTCTGATCGCCATCGTTATGGTTACCATTATGCTTTGCTGCA<br>TGACGAGCTGTTGCTCCTGTCTGAAGGGATGCTGCTCTTGCGGATCATGTTGCAAGT<br>TCGATGAAGACGATAGCGAACCAGTTCTGAAGGGCGTCAAGCTGCATTACACA |
| SEQ ID NO: 15 Nucleic acid sequence of the K986P/V987P<br>Δ681-684 sequence of Spike<br>TTCGTTTTCCTTGTTCTGTTGCCTCTCGTTAGTAGCCAATGCGTCAACCTTACTACTA<br>GAACCCAGCTCCCTCCAGCATATACCAACTCTTTCACCAGGGGCGTATATTACCCGG |

-continued

| EXEMPLARY SEQUENCES |
|---|
| ACAAAGTGTTCCGCTCAAGTGTGCTGCATTCTACGCAGGACCTTTTCTTGCCCTTTTT<br>CAGTAATGTTACTTGGTTTCATGCTATCCATGTGTCTGGAACTAACGGAACCAAGCG<br>CTTTGACAACCCCGTCCTCCCTTTCAACGATGGCGTGTACTTCGCTTCCACGGAAAA<br>GTCAAACATAATTCGCGGCTGGATCTTTGGTACAACACTCGACTCAAAGACGCAGA<br>GCCTGCTGATCGTTAATAACGCTACAAATGTTGTGATAAAGGTGTGTGAATTTCAGT<br>TCTGCAATGATCCCTTCCTGGGTGTGTACTACCATAAGAATAACAAGAGCTGGATGG<br>AATCCGAATTTAGGGTTTACAGTTCCGCTAACAACTGCACATTCGAATACGTAAGCC<br>AGCCATTTCTTATGGATCTTGAGGGCAAGCAAGGAAACTTCAAGAACTTGAGGGAG<br>TTCGTGTTCAAAAATATCGACGGCTATTTTAAGATATATAGCAAGCACACTCCAATA<br>AACTTGGTGCGCGACCTGCCCCAGGGATTCTCTGCTCTGGAGCCCCTGGTGGATCTG<br>CCCATTGGAATAAACATAACTCGCTTTCAAACACTGCTCGCCCTGCATCGCAGTTAC<br>CTCACCCCTGGTGATAGTAGTTCAGGATGGACAGCAGGAGCCGCCGCATACTACGT<br>CGGCTACCTGCAGCCTAGGACCTTCTTGCTGAAGTACAACGAGAACGGTACAATAA<br>CTGACGCTGTGGACTGCGCTCTGGACCCTCTGTCCGAGACGAAGTGCACCCTGAAGA<br>GCTTTACTGTTGAAAAAGGCATTTACCAAACCAGCAACTTCCGCGTCCAGCCAACCG<br>AGAGCATCGTCAGATTTCCCAACATTACAAATCTGTGTCCCTTCGGCGAGGTGTTCA<br>ACGCCACACGCTTCGCTTCAGTGTACGCATGGAACCGCAAGCGCATATCTAACTGCG<br>TCGCGGATTATTCTGTCCTCTACAACTCCGCCTCTTTCTCCACCTTCAAGTGCTACGG<br>AGTGTCACCGACTAAGCTGAACGATCTCTGCTTTACCAACGTCTACGCGGACTCCTT<br>CGTGATAAGAGGTGATGAAGTGAGACAAATAGCCCCAGGTCAGACTGGTAAGATCG<br>CAGATTACAACTACAAATTGCCTGATGATTTCACTGGTTGCGTTATCGCGTGGAACT<br>CTAATAACCTCGATTCTAAGGTCGGTGGTAACTACAATTACCTGTACCGCTTGTTTA<br>GGAAGTCAAACCTGAAGCCTTTCGAGAGGGATATTTCAACCGAAATCTATCAAGCG<br>GGTTCAACACCGTGTAACGGTGTGGAAGGATTTAACTGCTACTTCCCCCTGCAGTCT<br>TACGGATTCCAGCCAACCAATGGCGTGGGTTACCAACCTTATCGCGTGGTGGTTCTG<br>AGTTTCGAACTGTTGCACGCTCCCGCCACGGTATGCGGTCCCAAGAAGAGCACTAAC<br>TTGGTGAAGAATAAGTGCGTGAATTTCAATTTCAATGGCCTCACTGGAACTGGAGTG<br>CTGACCGAATCCAATAAGAAGTTCTTGCCCTTCCAGCAGTTCGGAAGAGACATTGCT<br>GACACAACCGACGCGGTGCGCGATCCTCAGACTCTGGAGATATTGGACATTACACC<br>ATGTTCTTTCGGCGGTGTGTCTGTCATTACTCCGGGCACGAATACTAGCAACCAGGT<br>AGCCGTGCTGTACCAAGACGTGAATTGCACAGAGGTTCCCGTCGCAATTCACGCTGA<br>CCAGCTGACCCCCACGTGGAGGGTTTACAGCACTGGTAGTAACGTCTTCCAGACGA<br>GAGCCGGTTGCTTGATCGGAGCGGAACATGTGAATAACTCCTACGAGTGCGACATC<br>CCCATCGGAGCCGGTATATGCGCCTCTTATCAGACACAAACTAACTCACGCAGTGTG<br>GCTTCTCAAAGCATTATAGCATACACTATGTCTCTTGGTGCCGAAAATTCCGTGGCC<br>TATTCTAACAATTCAATCGCCATCCCAACCAACTTCACAATTAGCGTGACTACCGAA<br>ATACTGCCTGTGAGCATGACGAAAACCAGCGTAGACTGCACTATGTATATCTGTGGA<br>GACTCCACTGAGTGCTCCAACCTTCTCCTGCAGTACGGTAGCTTCTGTACCCAATTG<br>AACCGCGCCCTTACAGGCATCGCTGTTGAGCAAGATAAGAATACCCAGGAAGTTTTT<br>GCCCAGGTTAAGCAGATATACAAAACACCGCCCATTAAGGACTTCGGAGGCTTCAA<br>CTTCTCTCAGATACTGCCTGACCCCTCCAAGCCATCAAAACGCAGCTTCATTGAGGA<br>CCTCTTGTTCAACAAAGTGACTCTGGCTGATGCTGGCTTCATTAAGCAGTACGGAGA<br>TTGCCTGGGAGATATTGCTGCCAGGGACCTCATCTGCGCCCAGAAGTTTAATGGCCT<br>GACAGTCTTGCCCCCACTTCTGACAGACGAGATGATTGCTCAGTACACATCTGCCCT<br>CCTCGCTGGCACCATAACATCCGGATGGACATTTGGTGCTGGTGCTGCCCTCCAGAT<br>TCCCTTCGCAATGCAGATGGCGTATCGCTTTAACGGCATCGGTGTCACACAAAACGT<br>GTTGTATGAGAACCAAAAGCTCATCGCTAACCAGTTTAATTCTGCTATTGGTAAGAT<br>TCAGGACAGCCTGTCATCAACCGCGTCTGCCCTTGGTAAGTTGCAGGACGTGGTGAA<br>CCAGAATGCTCAGGCTTTGAATACTCTGGTGAAGCAACTCTCTTCAAATTTCGGCGC<br>TATCTCTTCTGTGTTGAACGACATCCTGAGTCGCCTTGATcctccaGAAGCTGAAGTTCA<br>AATTGATAGATTGATTACTGGCAGGCTCCAGTCTTTGCAGACCTACGTTACACAGCA<br>GCTGATTAGGGCGGCTGAAATTAGAGCTTCCGCCAATCTGGCTGCAACCAAGATGTC<br>CGAATGCGTCCTGGGTCAGTCAAAGCGCGTTGACTTTTGTGGTAAAGGCTACCACCT<br>CATGTCATTTCCCCAGTCAGCACCTCACGGAGTAGTGTTCCTCCACGTCACCTACGTT<br>CCAGCACAGGAAAAGAATTTTACCACTGCGCCGGCAATCTGTCACGACGGTAAGGC<br>ACACTTCCCCCGCGAGGGCGTATTCGTGTCTAACGGAACTCATTGGTTCGTCACACA<br>GAGAAACTTCTATGAGCCTCAGATCATTACCACCGACAATACATTTGTGTCCGGTAA<br>CTGCGACGTTGTGATTGGAATCGTCAACAACACTGTGTACGATCCACTTCAGCCAGA<br>ACTGGATAGCTTCAAGGAAGAATTGGACAAATATTTCAAAAATCACACTTCACCCG<br>ATGTGGACCTGGGTGACATTAGTGGTATCAATGCGTCCGTGGTCAATATTCAAAAAG<br>AGATTGACAGGCTCAACGAAGTGGCCAAGAACCTGAACGAAAGTCTTATCGATCTG<br>CAAGAATTGGGAAAGTATGAGCAGTACATCAAGTGGCCGTGGTACATTTGGTTGGG<br>TTTTATCGCCGGTCTGATCGCCATCGTTATGGTTACCATTATGCTTTGCTGCATGACG<br>AGCTGTTGCTCCTGTCTGAAGGGATGCTGCTCTTGCGGATCATGTTGCAAGTTCGAT<br>GAAGACGATAGCGAACCAGTTCTGAAGGGCGTCAAGCTGCATTACACA<br><br>SEQ ID NO: 16 tissue plasminogen activator SP<br>DAMKRGLCCVLLLCGAVFVSPSQEIHARFRR<br><br>SEQ ID NO: 17 human IgE immunoglobulin SP<br>DWTWILFLVAAATRVHS<br><br>SEQ ID NO: 18 amino acid sequence of mouse Alpha-L-iduronidase<br>(IDUA) protein<br>MLTFFAAFLAAPLALAESPYLVRVDAARPLRPLLPFWRSTGFCPPLPHDQADQYDLSWD<br>QQLNLAYIGAVPHSGIEQVRIHWLLDLITARKSPGQGLMYNFTHLDAFLDLLMENQLLP<br>GFELMGSPSGYFTDFDDKQQVFEWKDLVSLLARRYIGRYGLTHVSKWNFETWNEPDH |

-continued

| EXEMPLARY SEQUENCES |
|---|

HDFDNVSMTTQGFLNYYDACSEGLRIASPTLKLGGPGDSFHPLPRSPMCWSLLGHCANG
TNFFTGEVGVRLDYISLHKKGAGSSIAILEQEMAVVEQVQQLFPEFKDTPIYNDEADPLV
GWSLPQPWRADVTYAALVVKVIAQHQNLLFANSSSSMRYVLLSNDNAFLSYHPYPFSQ
RTLTARFQVNNTHPPHVQLLRKPVLTVMGLMALLDGEQLWAEVSKAGAVLDSNHTVG
VLASTHHPEGSAAAWSTTVLIYTSDDTHAHPNHSIPVTLRLRGVPPGLDLVYIVLYLDNQ
LSSPYSAWQHMGQPVFPSAEQFRRMRMVEDPVAEAPRPFPARGRLTLHRKLPVPSLLLV
HVCTRPLKPPGQVSRLRALPLTHGQLILVWSDERVGSKCLWTYEIQFSQKGEEYAPINRR
PSTFNLFVFSPDTAVVSGSYRVRALDYWARPGPFSDPVTYLDVPAS

SEQ ID NO: 19 amino acid sequence of human Alpha-L-iduronidase (IDUA) protein
MRPLRPRAALLALLASLLAAPPVAPAEAPHLVHVDAARALWPLRRFWRSTGFCPPLPHS
QADQYVLSWDQQLNLAYVGAVPHRGIKQVRTHWLLELVTTRGSTGRGLSYNFTHLDG
YLDLLRENQLLPGFELMGSASGHFTDFEDKQQVFEWKDLVSSLARRYIGRYGLAHVSK
WNFETWNEPDHHDFDNVSMTMQGFLNYYDACSEGLRAASPALRLGGPGDSFHTPPRSP
LSWGLLRHCHDGTNFFTGEAGVRLDYISLHRKGARSSISILEQEKVVAQQIRQLFPKFAD
TPIYNDEADPLVGWSLPQPWRADVTYAAMVVKVIAQHQNLLLANTTSAFPYALLSNDN
AFLSYHPHPFAQRTLTARFQVNNTRPPHVQLLRKPVLTAMGLLALLDEEQLWAEVSQA
GTVLDSNHTVGVLASAHRPQGPADAWRAAVLIYASDDTRAHPNRSVAVTLRLRGVPPG
PGLVYVTRYLDNGLCSPDGEWRRLGRPVFPTAEQFRRMRAAEDPVAAAPRPLPAGGRL
TLRPALRLPSLLLVHVCARPEKPPGQVTRLRALPLTQGQLVLVWSDEHVGSKCLWTYEI
QFSQDGKAYTPVSRKPSTFNLFVFSPDTGAVSGSYRVRALDYWARPGPFSDPVPYLEVP
VPRGPPSPGNP SEQ ID NO: 20 amino acid sequence of mouse Ornithine carbamoyltransferase (OTC) protein
MLSNLRILLNNAALRKGHTSVVRHFWCGKPVQSQVQLKGRDLLTLKNFTGEEIQYMLW
LSADLKFRIKQKGEYLPLLQGKSLGMIFEKRSTRTRLSTETGFALLGGHPSFLTTQDIHLG
VNESLTDTARVLSSMTDAVLARVYKQSDLDTLAKEASIPIVNGLSDLYHPIQILADYLTL
QEHYGSLKGLTLSWIGDGNNILHSIMMSAAKFGMHLQAATPKGYEPDPNIVKLAEQYA
KENGTKLSMTNDPLEAARGGNVLITDTWISMGQEDEKKKRLQAFQGYQVTMKTAKVA
ASDWTFLHCLPRKPEEVDDEVFYSPRSLVFPEAENRKWTIMAVMVSLLTDYSPVLQKPK
F SEQ ID NO: 21 amino acid sequence of mouse Fumarylacetoacetase (FAH) protein
MSFIPVAEDSDFPIQNLPYGVFSTQSNPKPRIGVAIGDQILDLSVIKHLFTGPALSKHQHVF
DETTLNNFMGLGQAAWKEARASLQNLLSASQARLRDDKELRQRAFTSQASATMHLPA
TIGDYTDFYSSRQHATNVGIMFRGKENALLPNWLHLPVGYHGRASSIVVSGTPIRRPMG
RDIQQWEYVPLGPFLGKSFGTTISPWVVPMDALMPFVVPNPKQDPKPLPYLCHSQPYTF
DINLSVSLKGEGMSQAATICRSNFKHMYWTMLQQLTHHSVNGCNLRPGDLLASGTISGS
DPESFGSMLELSWKGTKAIDVEQGQTRTFLLDGDEVIITGHCQGDGYRVGFGQCAGKVL
PALSPA SEQ ID NO: 22 amino acid sequence of human miniDMD protein
MLWWEEVEDCYEREDVQKKTFTKWVNAQFSKFGKQHIENLFSDLQDGRRLLDLLEGL
TGQKLPKEKGSTRVHALNNVNKALRVLQNNNVDLVNIGSTDIVDGNHKLTLGLIWNIIL
HWQVKNVMKNIMAGLQQTNSEKILLSWVRQSTRNYPQVNVINFTTSWSDGLALNALIH
SHRPDLFDWNSVVCQQSATQRLEHAFNIARYQLGIEKLLDPEDVDTTYPDKKSILMYITS
LFQVLPQQVSIEAIQEVEMLPRPPKVTKEEHFQLHHQMHYSQQITVSLAQGYERTSSPKP
RFKSYAYTQAAYVTTSDPTRSPFPSQHLEAPEDKSFGSSLMESEVNLDRYQTALEEVLS
WLLSAEDTLQAQGEISNDVEVVKDQFHTHEGYMMDLTAHQGRVGNILQLGSKLIGTGK
LSEDEETEVQEQMNLLNSRWECLRVASMEKQSNLHRVLMDLQNQKLKELNDWLTKTE
ERTRKMEEEPLGPDLEDLKRQVQQHKVLQEDLEQEQVRVNSLTHMVVVVDESSGDHA
TAALEEQLKVLGDRWANICRWTEDRWVLLQDILLKWQRLTEEQCLFSAWLSEKEDAV
NKIHTTGFKDQNEMLSSLQKLAVLKADLEKKKQSMGKLYSLKQDLLSTLKNKSVTQKT
EAWLDNFARCWDNLVQKLEKSTAQETEIAVQAKQPDVEEILSKGQHLYKEKPATQPVK
RKLEDLSSEWKAVNRLLQELRAKQPDLAPGLTTIGASPTQTVTLVTQPVVTKETAISKLE
MPSSLMLEVPALADFNRAWTELTDWLSLLDQVIKSQRVMVGDLEDINEMIIKQKATMQ
DLEQRRPQLEELITAAQNLKNKTSNQEARTHITDRIERIQNQWDEVQEHLQNRRQQLNE
MLKDSTQWLEAKEEAEQVLGQARAKLESWKEGPYTVDAIQKKITETKQLAKDLRQWQ
TNVDVANDLALKLLRDYSADDTRKVHMITENINASWRSIHKRVSEREAALEETHRLLQ
QFPLDLEKFLAWLTEAETTANVLQDATRKERLLEDSKGVKELMKQWQDLQGEIEAHTD
VYHNLDENSQKILRSLEGSDDAVLLQRRLDNMNFKWSELRKKSLNIRSHLEASSDQWK
RLHLSLQELLVWLQLKDDELSRQAPIGGDFPAVQKQNDVHRAFKRELKTKEPVIMSTLE
TVRIFLTEQPLEGLEKLYQEPRELPPEERAQNVTRLLRKQAEEVNTEWEKLNLHSADWQ
RKIDETLERLRELQEATDELDLKLRQAEVIKGSWQPVGDLLIDSLQDHLEKVKALRGEIA
PLKENVSHVNDLARQLTTLGIQLSPYNLSTLEDLNTRWKLLQVAVEDRVRQLHEAHRD
FGPASQHFLSTSVQGPWERAISPNKVPYYINHETQTTCWDHPKMTELYQSLADLNNVRF
SAYRTAMKLRRLQKALCLDLLSLSAACDALDQHNLKQNDQPMDILQIINCLTTIYDRLE
QEHNNLVNVPLCVDMCLNWLLNVYDTGRTGRIRVLSFKTGIISLCKAHLEDKYRYLFK
QVASSTGFCDQRRLGLLLHDSIQIPRQLGEVASFGGSNIEPSVRSCFQFANNKPEIEAALF
LDWMRLEPQSMVWLPVLHRVAAAETAKHQAKCNICKECPIIGFRYRSLKHFNYDICQS
CFFSGRVAKGHKMHYPMVEYCTPTTSGEDVRDFAKVLKNKFRTKRYFAKHPRMGYLP
VQTVLEGDNMETPVTLINFWPVDSAPASSPQLSHDDTHSRIEHYASRLAEMENSNGSYL
NDSISPNESIDDEHLLIQHYCQSLNQDSPLSQPRSPAQILISLESEERGELERILADLEEENR
NLQAEYDRLKQQHEHKGLSPLPSPPEMMPTSPQSPRDAELIAEAKLLRQHKGRLEARMQ -continued

| EXEMPLARY SEQUENCES |
| --- |
| ILEDHNKQLESQLHRLRQLLEQPQAEAKVNGTTVSSPSTSLQRSDSSQPMLLRVVGSQTS<br>DSMGEEDLLSPPQDTSTGLEEVMEQLNNSFPSSRGRNTPGKPMREDTM |
| SEQ ID NO: 23 amino acid sequence of human DMD protein<br>MLWWEEVEDCYEREDVQKKTFTKWVNAQFSKFGKQHIENLFSDLQDGRRLLDLLEGL<br>TGQKLPKEKGSTRVHALNNVNKALRVLQNNNVDLVNIGSTDIVDGNHKLTLGLIWNIIL<br>HWQVKNVMKNIMAGLQQTNSEKILLSWVRQSTRNYPQVNVINFTTSWSDGLALNALIH<br>SHRPDLFDWNSVVCQQSATQRLEHAFNIARYQLGIEKLLDPEDVDTTYPDKKSILMYITS<br>LFQVLPQQVSIEAIQEVEMLPRPPKVTKEEHFQLHHQMHYSQQITVSLAQGYERTSSPKP<br>RFKSYAYTQAAYVTTSDPTRSPFPSQHLEAPEDKSFGSSLMESEVNLDRYQTALEEVLS<br>WLLSAEDTLQAQGEISNDVEVVKDQFHTHEGYMMDLTAHQGRVGNILQLGSKLIGTGK<br>LSEDEETEVQEQMNLLNSRWECLRVASMEKQSNLHRVLMDLQNQKLKELNDWLTKTE<br>ERTRKMEEEPLGPDLEDLKRQVQQHKVLQEDLEQEQVRVNSLTHMVVVVDESSGDHA<br>TAALEEQLKVLGDRWANICRWTEDRWVLLQDILLKWQRLTEEQCLFSAWLSEKEDAV<br>NKIHTTGFKDQNEMLSSLQKLAVLKADLEKKKQSMGKLYSLKQDLLSTLKNKSVTQKT<br>EAWLDNFARCWDNLVQKLEKSTAQISQAVTTTQPSLTQTTVMETVTTVTTREQILVKH<br>AQEELPPPPPQKKRQITVDSEIRKRLDVDITELHSWITRSEAVLQSPEFAIFRKEGNFSDLK<br>EKVNAIEREKAEKFRKLQDASRSAQALVEQMVNEGVNADSIKQASEQLNSRWIEFCQLL<br>SERLNWLEYQNNIIAFYNQLQQLEQMTTTAENWLKIQPTTPSEPTAIKSQLKICKDEVNR<br>LSDLQPQIERLKIQSIALKEKGQGPMFLDADFVAFTNHFKQVFSDVQAREKELQTIFDTL<br>PPMRYQETMSAIRTWVQQSETKLSIPQLSVTDYEIMEQRLGELQALQSSLQEQQSGLYY<br>LSTTVKEMSKKAPSEISRKYQSEFEEIEGRWKKLSSQLVEHCQKLEEQMNKLRKIQNHIQ<br>TLKKWMAEVDVFLKEEWPALGDSEILKKQLKQCRLLVSDIQTIQPSLNSVNEGGQKIKN<br>EAEPEFASRLETELKELNTQWDHMCQQVYARKEALKGGLEKTVSLQKDLSEMHEWMT<br>QAEEEYLERDFEYKTPDELQKAVEEMKRAKEEAQQKEAKVKLLTESVNSVIAQAPPVA<br>QEALKKELETLTTNYQWLCTRLNGKCKTLEEVWACWHELLSYLEKANKWLNEVEFKL<br>KTTENIPGGAEEISEVLDSLENLMRHSEDNPNQIRILAQTLTDGGVMDELINEELETFNSR<br>WRELHEEAVRRQKLLEQSIQSAQETEKSLHLIQESLTFIDKQLAAYIADKVDAAQMPQE<br>AQKIQSDLTSHEISLEEMKKHNQGKEAAQRVLSQIDVAQKKLQDVSMKFRLFQKPANFE<br>QRLQESKMILDEVKMHLPALETKSVEQEVVQSQLNHCVNLYKSLSEVKSEVEMVIKTG<br>RQIVQKKQTENPKELDERVTALKLHYNELGAKVTERKQQLEKCLKLSRKMRKEMNVL<br>TEWLAATDMELTKRSAVEGMPSNLDSEVAWGKATQKEIEKQKVHLKSITEVGEALKTV<br>LGKKETLVEDKLSLLNSNWIAVTSRAEEWLNLLLEYQKHMETFDQNVDHITKWIIQADT<br>LLDESEKKKPQQKEDVLKRLKAELNDIRPKVDSTRDQAANLMANRGDHCRKLVEPQIS<br>ELNHRFAAISHRIKTGKASIPLKELEQFNSDIQKLLEPLEAEIQQGVNLKEEDFNKDMNED<br>NEGTVKELLQRGDNLQQRITDERKREEIKIKQQLLQTKHNALKDLRSQRRKKALEISHQ<br>WYQYKRQADDLLKCLDDIEKKLASLPEPRDERKIKEIDRELQKKKEELNAVRRQAEGLS<br>EDGAAMAVEPTQIQLSKRWREIESKFAQFRRLNFAQIHTVREETMMVMTEDMPLEISYV<br>PSTYLTEITHVSQALLEVEQLLNAPDLCAKDFEDLFKQEESLKNIKDSLQQSSGRIDIIHSK<br>KTAALQSATPVERVKLQEALSQLDFQWEKVNKMYKDRQGRFDRSVEKWRRFHYDIKIF<br>NQWLTEAEQFLRKTQIPENWEHAKYKWYLKELQDGIGQRQTVVRTLNATGEEIIQQSSK<br>TDASILQEKLGSLNLRWQEVCKQLSDRKKRLEEQKNILSEFQRDLNEFVLWLEEADNIA<br>SIPLEPGKEQQLKEKLEQVKLLVEELPLRQGILKQLNETGGPVLVSAPISPEEQDKLENKL<br>KQTNLQWIKVSRALPEKQGEIEAQIKDLGQLEKKLEDLEEQLNHLLLWLSPIRNQLEIYN<br>QPNQEGPFDVKETEIAVQAKQPDVEEILSKGQHLYKEKPATQPVKRKLEDLSSEWKAVN<br>RLLQELRAKQPDLAPGLTTIGASPTQTVTLVTQPVVTKETAISKLEMPSSLMLEVPALAD<br>FNRAWTELTDWLSLLDQVIKSQRVMVGDLEDINEMIIKQKATMQDLEQRRPQLEELITA<br>AQNLKNKTSNQEARTIITDRIERIQNQWDEVQEHLQNRRQQLNEMLKDSTQWLEAKEE<br>AEQVLGQARAKLESWKEGPYTVDAIQKKITETKQLAKDLRQWQTNVDVANDLALKLL<br>RDYSADDTRKVHMITENINASWRSIHKRVSEREAALEETHRLLQQFPLDLEKFLAWLTE<br>AETTANVLQDATRKERLLEDSKGVKELMKQWQDLQGEIEAHTDVYHNLDENSQKILRS<br>LEGSDDAVLLQRRLDNMNFKWSELRKKSLNIRSHLEASSDQWKRLHLSLQELLVWLQL<br>KDDELSRQAPIGGDFPAVQKQNDVHRAFKRELKTKEPVIMSTLETVRIFLTEQPLEGLEK<br>LYQEPRELPPEERAQNVTRLLRKQAEEVNTEWEKLNLHSADWQRKIDETLERLRELQEA<br>TDELDLKLRQAEVIKGSWQPVGDLLIDSLQDHLEKVKALRGEIAPLKENVSHVNDLARQ<br>LTTLGIQLSPYNLSTLEDLNTRWKLLQVAVEDRVRQLHEAHRDFGPASQHFLSTSVQGP<br>WERAISPNKVPYYINHETQTTCWDHPKMTELYQSLADLNNVRFSAYRTAMKLRRLQKA<br>LCLDLLSLSAACDALDQHNLKQNDQPMDILQIIINCLTTIYDRLEQEHNNLVNVPLCVDM<br>CLNWLLNVYDTGRTGRIRVLSFKTGIISLCKAHLEDKYRYLFKQVASSTGFCDQRRLGL<br>LLHDSIQIPRQLGEVASFGGSNIEPSVRSCFQFANNKPEIEAALFLDWMRLEPQSMVWLP<br>VLHRVAAAETAKHQAKCNICKECPIIGFRYRSLKHFNYDICQSCFFSGRVAKGHKMHYP<br>MVEYCTPTTSGEDVRDFAKVLKNKFRTKRYFAKHPRMGYLPVQTVLEGDNMETPVTLI<br>NFWPVDSAPASSPQLSHDDTHSRIEHYASRLAEMENSNGSYLNDSISPNESIDDEHLLIQH<br>YCQSLNQDSPLSQPRSPAQILISLESEERGELERILADLEEENRNLQAEYDRLKQQHEHKG<br>LSPLPSPPEMMPTSPQSPRDAELIAEAKLLRQHKGRLEARMQILEDHNKQLESQLHRLRQ<br>LLEQPQAEAKVNGTTVSSPSTSLQRSDSSQPMLLRVVGSQTSDSMGEEDLLSPPQDTSTG<br>LEEVMEQLNNSFPSSRGRNTPGKPMREDTM |
| SEQ ID NO: 24 amino acid sequence of human p53 protein<br>MEEPQSDPSVEPPLSQETFSDLWKLLPENNVLSPLPSQAMDDLMLSPDDIEQWFTEDPGP<br>DEAPRMPEAAPPVAPAPAAPTPAAPAPAPSWPLSSSVPSQKTYQGSYGFRLGFLHSGTA<br>KSVTCTYSPALNKMFCQLAKTCPVQLWVDSTPPPGTRVRAMAIYKQSQHMTEVVRRCP<br>HHERCSDSDGLAPPQHLIRVEGNLRVEYLDDRNTFRHSVVVPYEPPEVGSDCTTIHYNY<br>MCNSSCMGGMNRRPILTIITLEDSSGNLLGRNSFEVRVCACPGRDRRTEEENLRKKGEPH<br>HELPPGSTKRALPNNTSSSPQPKKKPLDGEYFTLQIRGRERFEMFRELNEALELKDAQAG<br>KEPGGSRAHSSHLKSKKGQSTSRHKKLMFKTEGPDSD |

-continued

| EXEMPLARY SEQUENCES |
|---|
| SEQ ID NO: 25 amino acid sequence of human PTEN protein<br>HKNHYKIYNLCAERHYDTAKFNCRVAQYPFEDHNPPQLELIKPFCEDLDQWLSEDDNH<br>VAAIHCKAGKGRTGVMICAYLLHRGKFLKAQEALDFYGEVRTRDKKGVTIPSQRRYVY<br>YYSYLLKNHLDYRPVALLFHKMMFETIPMFSGGTCNPQFVVCQLKVKIYSSNSGPTRRE<br>DKFMYFEFPQPLPVCGDIKVEFFHKQNKMLKKDKMFHFWVNTFFIPGPEETSEKVENGS<br>LCDQEIDSICSIERADNDKEYLVLTLTKNDLDKANKDKANRYFSPNFKVKLYFTKTVEEP<br>SNPEASSSTSVTPDVSDNEPDHYRYSDTTDSDPENEPFDEDQHTQITKV |
| SEQ ID NO: 26 amino acid sequence of SARS-CoV-2 neutralizing antibody nAB-1<br>QVQLVESGGGLVQAGGSLRLSCAVSGAGAHRVGWFRRAPGKEREFVAAIGASGGMTN<br>YLDSVKGRFTISRDNAKNTIYLQMNSLKPQDTAVYYCAARDIETAEYIYWGQGTQVTVS<br>S |
| SEQ ID NO: 27 amino acid sequence of SARS-CoV-2 neutralizing antibody nAB-2<br>QVQLVESGGGLVQAGGSLRLSCAVSGLGAHRVGWFRRAPGKEREFVAAIGANGGNTN<br>YLDSVKGRFTISRDNAKNTIYLQMNSLKPQDTAVYYCAARDIETAEYTYWGQGTQVTV<br>SS |
| SEQ ID NO: 28 amino acid sequence of SARS-CoV-2 neutralizing antibody nAB-3<br>QVQLVESGGGLVQAGGSLRLSCAVSGAGAHRVGWFRRAPGKEREFVAAIGASGGMTN<br>YLDSVKGRFTISRDNAKNTIYLQMNSLKPQDTAVYYCAARDIETAEYIYWGQGTQVTVS<br>SKLGGGGSGGGGSGGGGSGGGGSGGGGSQVQLVESGGGLVQAGGSLRLSCAVSGAGA<br>HRVGWFRRAPGKEREFVAAIGASGGMTNYLDSVKGRFTISRDNAKNTIYLQMNSLKPQ<br>DTAVYYCAARDIETAEYIYWGQGTQVTVSSGGGGSGGGGSGGGGSGGGGSGGGGSQV<br>QLVESGGGLVQAGGSLRLSCAVSGAGAHRVGWFRRAPGKEREFVAAIGASGGMTNYL<br>DSVKGRFTISRDNAKNTIYLQMNSLKPQDTAVYYCAARDIETAEYIYWGQGTQVTVSS |
| SEQ ID NO: 29 amino acid sequence of SARS-CoV-2 neutralizing antibody nAB-4<br>QVQLVESGGGLVQAGGSLRLSCAVSGLGAHRVGWFRRAPGKEREFVAAIGANGGNTN<br>YLDSVKGRFTISRDNAKNTIYLQMNSLKPQDTAVYYCAARDIETAEYTYWGQGTQVTV<br>SSKLGGGGSGGGGSGGGGSGGGGSGGGGSSQVQLVESGGGLVQAGGSLRLSCAVSGL<br>GAHRVGWFRRAPGKEREFVAAIGANGGNTNYLDSVKGRFTISRDNAKNTIYLQMNSLK<br>PQDTAVYYCAARDIETAEYTYWGQGTQVTVSSGGGGSGGGGSGGGGSGGGGSGGGGS<br>QVQLVESGGGLVQAGGSLRLSCAVSGLGAHRVGWFRRAPGKEREFVAAIGANGGNTN<br>YLDSVKGRFTISRDNAKNTIYLQMNSLKPQDTAVYYCAARDIETAEYTYWGQGTQVTV<br>SS |
| SEQ ID NO: 30 amino acid sequence of SARS-CoV-2 neutralizing antibody nAB-5<br>QVQLVESGGGLVQAGGSLRLSCAASGYIFGRNAMGWYRQAPGKERELVAGITRRGSIT<br>YYADSVKGRFTISRDNAKNTVYLQMNSLKPEDTAVYYCAADPASPAYGDYWGQGTQV<br>TVSS |
| SEQ ID NO: 31 amino acid sequence of SARS-CoV-2 neutralizing antibody nAB-6<br>QVQLVESGGGLVQAGGSLRLSCAASGYIFGRNAMGWYRQAPGKERELVAGITRRGSIT<br>YYADSVKGRFTISRDNAKNTVYLQMNSLKPEDTAVYYCAADPASPAYGDYWGQGTQV<br>TVSSGGGGSGGGGSGGGGSGGGGSQVQLVESGGGLVQAGGSLRLSCAASGYIFGRNA<br>MGWYRQAPGKERELVAGITRRGSITYYADSVKGRFTISRDNAKNTVYLQMNSLKPEDT<br>AVYYCAADPASPAYGDYWGQGTQVTVSSGGGGSGGGGSGGGGSGGGGSQVQLVESG<br>GGLVQAGGSLRLSCAASGYIFGRNAMGWYRQAPGKERELVAGITRRGSITYYADSVKG<br>RFTISRDNAKNTVYLQMNSLKPEDTAVYYCAADPASPAYGDYWGQGTQVTVSS |
| SEQ ID NO: 32 amino acid sequence of SARS-CoV-2 neutralizing antibody nAB-7H<br>EVQLLESGGGVVQPGGSLRLSCAASGFAFTTYAMNWVRQAPGRGLEWVSAISDGGGSA<br>YYADSVKGRFTISRDNSKNTLYLQMNSLRAEDTAVYYCAKTRGRGLYDYVWGSKDY<br>WGQGTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| SEQ ID NO: 33 amino acid sequence of SARS-CoV-2 neutralizing antibody nAB-7L<br>DIVMTQSPLSLPVTPGEPASISCRSSQSLLHSNGYNYLDWYLQKPGQSPQLLIYLGSNRAS<br>GVPDRFSGSGSGTDFTLKISRVEAEDVGVYYCMQALQTPGTFGQGTRLEIKRTVAAPSV<br>FIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |

-continued

| EXEMPLARY SEQUENCES |
|---|

SEQ ID NO: 34 amino acid sequence of ACE-binding-1
SAEIDLGKGDFREIRASEDAREAAEALAEAARAMKEALEIIREIAEKLRDSSRASEAAKRI
AKAIRKAADAIAEAAKIAARAAKDGDAARNAENAARKAKEFAEEQAKLADMYAELAK
NGDKSSVLEQLKTFADKAFHEMEDRFYQAALAVFEAAEAAAGGSGWGSG SEQ ID NO: 35 amino acid sequence of ACE-binding-2
SAEIDLGKGDFREIRASEDAREAAEALAEAARAMKEALEIIREIAEKLRDSSRASEAAKRI
AKAIRKAADAIAEAAKIAARAAKDGDAARNAENAARKAKEFAEEQAKLADMYAELAK
NGDKSSVLEQLKTFADKAFHEMEDRFYQAALAVFEAAEAAAGGGGSGGSGSGGSGGG
SPGSAEIDLGKGDFREIRASEDAREAAEALAEAARAMKEALEIIREIAEKLRDSSRASEAA
KRIAKAIRKAADAIAEAAKIAARAAKDGDAARNAENAARKAKEFAEEQAKLADMYAE
LAKNGDKSSVLEQLKTFADKAFHEMEDRFYQAALAVFEAAEAAAGGSGWGS SEQ ID NO: 36 Kozak nucleic acid sequence
GCCACCAUG SEQ ID NO: 37 polyAC sequence
GAAAAACAAAAAACAAAAAAAACAAAAAAAAAACCAAAAAAACAAAACACA SEQ ID NO: 38 m6A modification sequence
ACGAGTCCTGGACTGAAACGGACTTGT SEQ ID NO: 39 3' exon sequence recognizable by a 3' catalytic Group I intron fragment
AAAAUCCGUUGACCUUAAACGGUCGUGUGGGUUCAAGUCCCUCCACCCCCAC SEQ ID NO: 40 5' exon sequence recognizable by a 5' catalytic Group I intron fragment
GAGACGCUACGGACUU SEQ ID NO: 41 Exemplary 5' homology sequence
GGGAGACCCUCGACCGUCGAUUGUCCACUGGUC SEQ ID NO: 42 Exemplary 3' homology sequence
ACCAGUGGACAAUCGACGGAUAACAGCAUAUCUAG SEQ ID NO: 43 T7 Promoter
UAAUACGACUCACUAUAGG SEQ ID NO: 44 T2A peptide coding sequence
GAGGGCAGAGGAAGUCUUCUAACAUGCGGUGACGUGGAGGAGAAUCCCGGCCCU SEQ ID NO: 45 P2A peptide coding sequence
GCUACUAACUUCAGCCUGCUGAAGCAGGCUGGAGACGUGGAGGAGAACCCUGGAC
CU SEQ ID NO: 46 catalytic Group I intron fragment
AACAAUAGAUGACUUACAACUAAUCGGAAGGUGCAGAGACUCGACGGGAGCUAC
CCUAACGUCAAGACGAGGGUAAAGAGAGAGUCCAAUUCUCAAAGCCAAUAGGCA
GUAGCGAAAGCUGCAAGAGAAUG SEQ ID NO: 47 5' catalytic Group I intron fragment
AAAUAAUUGAGCCUUAAAGAAGAAAUUCUUUAAGUGGAUGCUCUCAAACUCAGG
GAAACCUAAAUCUAGUUAUAGACAAGGCAAUCCUGAGCCAAGCCGAAGUAGUAA
UUAGUAAG SEQ ID NO: 48 Nucleic acid sequence of full-length S protein sequence of SARS-CoV-2
ATGTTCGTTTTCCTTGTTCTGTTGCCTCTCGTTAGTAGCCAATGCGTCAACCTTACTA
CTAGAACCCAGCTCCCTCCAGCATATACCAACTCTTTCACCAGGGGCGTATATTACC
CGGACAAAGTGTTCCGCTCAAGTGTGCTGCATTCTACGCAGGACCTTTTCTTGCCCTT
TTTCAGTAATGTTACTTGGTTTCATGCTATCCATGTGTCTGGAACTAACGGAACCAA
GCGCTTTGACAACCCCGTCCTCCCTTTCAACGATGGCGTGTACTTCGCTTCCACGGA
AAAGTCAAACATAATTCGCGGCTGGATCTTTGGTACAACACTCGACTCAAAGACGC
AGAGCCTGCTGATCGTTAATAACGCTACAAATGTTGTGATAAAGGTGTGTGAATTTC
AGTTCTGCAATGATCCCTTCCTGGGTGTGTACTACCATAAGAATAACAAGAGCTGGA
TGGAATCCGAATTTAGGGTTTACAGTTCCGCTAACAACTGCACATTCGAATACGTAA
GCCAGCCATTTCTTATGGATCTTGAGGGCAAGCAAGGAAACTTCAAGAACTTGAGG
GAGTTCGTGTTCAAAAATATCGACGGCTATTTTAAGATATATAGCAAGCACACTCCA
ATAAACTTGGTGCGCGACCTGCCCCAGGGATTCTCTGCTCTGGAGCCCCTGGTGGAT
CTGCCCATTGGAATAAACATAACTCGCTTTCAAACACTGCTCGCCCTGCATCGCAGT
TACCTCACCCCTGGTGATAGTAGTTCAGGATGGACAGCAGGAGCCGCCGCATACTA
CGTCGGCTACCTGCAGCCTAGGACCTTCTTGCTGAAGTACAACGAGAACGGTACAAT
AACTGACGCTGTGGACTGCGCTCTGGACCCTCTGTCCGAGACGAAGTGCACCCTGAA
GAGCTTTACTGTTGAAAAAGGCATTTACCAAACCAGCAACTTCCGCGTCCAGCCAAC
CGAGAGCATCGTCAGATTTCCCAACATTACAAATCTGTGTCCCTTCGGCGAGGTGTT -continued

| EXEMPLARY SEQUENCES |
| --- |

CAACGCCACACGCTTCGCTTCAGTGTACGCATGGAACCGCAAGCGCATATCTAACTG
CGTCGCGGATTATTCTGTCCTCTACAACTCCGCCTCTTTCTCCACCTTCAAGTGCTAC
GGAGTGTCACCGACTAAGCTGAACGATCTCTGCTTTACCAACGTCTACGCGGACTCC
TTCGTGATAAGAGGTGATGAAGTGAGACAAATAGCCCCAGGTCAGACTGGTAAGAT
CGCAGATTACAACTACAAATTGCCTGATGATTTCACTGGTTGCGTTATCGCGTGGAA
CTCTAATAACCTCGATTCTAAGGTCGGTGGTAACTACAATTACCTGTACCGCTTGTTT
AGGAAGTCAAACCTGAAGCCTTTCGAGAGGGATATTTCAACCGAAATCTATCAAGC
GGGTTCAACACCGTGTAACGGTGTGGAAGGATTTAACTGCTACTTCCCCCTGCAGTC
TTACGGATTCCAGCCAACCAATGGCGTGGGTTACCAACCTTATCGCGTGGTGGTTCT
GAGTTTCGAACTGTTGCACGCTCCCGCCACGGTATGCGGTCCCAAGAAGAGCACTA
ACTTGGTGAAGAATAAGTGCGTGAATTTCAATTTCAATGGCCTCACTGGAACTGGAG
TGCTGACCGAATCCAATAAGAAGTTCTTGCCCTTCCAGCAGTTCGGAAGAGACATTG
CTGACACAACCGACGCGGTGCGCGATCCTCAGACTCTGGAGATATTGGACATTACA
CCATGTTCTTTCGGCGGTGTGTCTGTCATTACTCCGGGCACGAATACTAGCAACCAG
GTAGCCGTGCTGTACCAAGACGTGAATTGCACAGAGGTTCCCGTCGCAATTCACGCT
GACCAGCTGACCCCCACGTGGAGGGTTTACAGCACTGGTAGTAACGTCTTCCAGAC
GAGAGCCGGTTGCTTGATCGGAGCGGAACATGTGAATAACTCCTACGAGTGCGACA
TCCCCATCGGAGCCGGTATATGCGCCTCTTATCAGACACAAACTAACTCACCCAGGA
GAGCCCGCAGTGTGGCTTCTCAAAGCATTATAGCATACACTATGTCTCTTGGTGCCG
AAAATTCCGTGGCCTATTCTAACAATTCAATCGCCATCCCAACCAACTTCACAATTA
GCGTGACTACCGAAATACTGCCTGTGAGCATGACGAAAACCAGCGTAGACTGCACT
ATGTATATCTGTGGAGACTCCACTGAGTGCTCCAACCTTCTCCTGCAGTACGGTAGC
TTCTGTACCCAATTGAACCGCGCCCTTACAGGCATCGCTGTTGAGCAAGATAAGAAT
ACCCAGGAAGTTTTTGCCCAGGTTAAGCAGATATACAAAACACCGCCCATTAAGGA
CTTCGGAGGCTTCAACTTCTCTCAGATACTGCCTGACCCCTCCAAGCCATCAAAACG
CAGCTTCATTGAGGACCTCTTGTTCAACAAAGTGACTCTGGCTGATGCTGGCTTCATT
AAGCAGTACGGAGATTGCCTGGGAGATATTGCTGCCAGGGACCTCATCTGCGCCCA
GAAGTTTAATGGCCTGACAGTCTTGCCCCCACTTCTGACAGACGAGATGATTGCTCA
GTACACATCTGCCCTCCTCGCTGGCACCATAACATCCGGATGGACATTTGGTGCTGG
TGCTGCCCTCCAGATTCCCTTCGCAATGCAGATGGCGTATCGCTTTAACGGCATCGG
TGTCACACAAAACGTGTTGTATGAGAACCAAAAGCTCATCGCTAACCAGTTTAATTC
TGCTATTGGTAAGATTCAGGACAGCCTGTCATCAACCGCGTCTGCCCTTGGTAAGTT
GCAGGACGTGGTGAACCAGAATGCTCAGGCTTTGAATACTCTGGTGAAGCAACTCTC
TTCAAATTTCGGCGCTATCTCTTCTGTGTTGAACGACATCCTGAGTCGCCTTGATAAG
GTGGAAGCTGAAGTTCAAATTGATAGATTGATTACTGGCAGGCTCCAGTCTTTGCAG
ACCTACGTTACACAGCAGCTGATTAGGGCGGCTGAAATTAGAGCTTCCGCCAATCTG
GCTGCAACCAAGATGTCCGAATGCGTCCTGGGTCAGTCAAAGCGCGTTGACTTTTGT
GGTAAAGGCTACCACCTCATGTCATTTCCCCAGTCAGCACCTCACGGAGTAGTGTTC
CTCCACGTCACCTACGTTCCAGCACAGGAAAAGAATTTTACCACTGCGCCGGCAATC
TGTCACGACGGTAAGGCACACTTCCCCCGCGAGGGCGTATTCGTGTCTAACGGAACT
CATTGGTTCGTCACACAGAGAAACTTCTATGAGCCTCAGATCATTACCACCGACAAT
ACATTTGTGTCCGGTAACTGCGACGTTGTGATTGGAATCGTCAACAACACTGTGTAC
GATCCACTTCAGCCAGAACTGGATAGCTTCAAGGAAGAATTGGACAAATATTTCAA
AAATCACACTTCACCCGATGTGGACCTGGGTGACATTAGTGGTATCAATGCGTCCGT
GGTCAATATTCAAAAAGAGATTGACAGGCTCAACGAAGTGGCCAAGAACCTGAACG
AAAGTCTTATCGATCTGCAAGAATTGGGAAAGTATGAGCAGTACATCAAGTGGCCG
TGGTACATTTGGTTGGGTTTTATCGCCGGTCTGATCGCCATCGTTATGGTTACCATTA
TGCTTTGCTGCATGACGAGCTGTTGCTCCTGTCTGAAGGGATGCTGCTCTTGCGGATC
ATGTTGCAAGTTCGATGAAGACGATAGCGAACCAGTTCTGAAGGGCGTCAAGCTGC
ATTACACA

SEQ ID NO: 49 Nucleic acid sequence of the RBD amino acid residues 319-542 of S protein
CGCGTCCAGCCAACCGAGAGCATCGTCAGATTTCCCAACATTACAAATCTGTGTCCC
TTCGGCGAGGTGTTCAACGCCACACGCTTCGCTTCAGTGTACGCATGGAACCGCAAG
CGCATATCTAACTGCGTCGCGGATTATTCTGTCCTCTACAACTCCGCCTCTTTCTCCA
CCTTCAAGTGCTACGGAGTGTCACCGACTAAGCTGAACGATCTCTGCTTTACCAACG
TCTACGCGGACTCCTTCGTGATAAGAGGTGATGAAGTGAGACAAATAGCCCCAGGT
CAGACTGGTAAGATCGCAGATTACAACTACAAATTGCCTGATGATTTCACTGGTTGC
GTTATCGCGTGGAACTCTAATAACCTCGATTCTAAGGTCGGTGGTAACTACAATTAC
CTGTACCGCTTGTTTAGGAAGTCAAACCTGAAGCCTTTCGAGAGGGATATTTCAACC
GAAATCTATCAAGCGGGTTCAACACCGTGTAACGGTGTGGAAGGATTTAACTGCTAC
TTCCCCCTGCAGTCTTACGGATTCCAGCCAACCAATGGCGTGGGTTACCAACCTTAT
CGCGTGGTGGTTCTGAGTTTCGAACTGTTGCACGCTCCCGCCACGGTATGCGGTCCC
AAGAAGAGCACTAACTTGGTGAAGAATAAGTGCGTGAATTTC SEQ ID NO: 50 Nucleic acid sequence of the C-terminal Foldon domain of a T4 fibritin protein
GGAAGCGGCTACATCCCAGAAGCCCCTAGAGACGGACAGGCTTACGTGCGAAAAGA
CGGCGAGTGGGTGCTGCTGAGCACATTCCTGGGAAGGAGC SEQ ID NO: 51 Nucleic acid sequence of the GCN4-based isoleucine zipper domain
CGAATGAAGCAGATTGAGGATAAAATTGAGGAGATTCTCAGCAAAATTTACCACAT
AGAAAATGAGATCGCTCGGATTAAAAAACTGATCGGAGAAAGA -continued

| EXEMPLARY SEQUENCES |
|---|

SEQ ID NO: 52 Nucleic acid sequence of the GS peptide linker
GGCGGAGGAGGCAGCGGCGGAGGAGGCAGC SEQ ID NO: 53 CVB3 virus IRES
TTAAAACAGCCTGTGGGTTGATCCCACCCACAGGCCCATTGGGCGCTAGCACTCTGG
TATCACGGTACCTTTGTGCGCCTGTTTTATACCCCCTCCCCCAACTGTAACTTAGAAG
TAACACACACCGATCAACAGTCAGCGTGGCACACCAGCCACGTTTTGATCAAGCAC
TTCTGTTACCCCGGACTGAGTATCAATAGACTGCTCACGCGGTTGAAGGAGAAAGCG
TTCGTTATCCGGCCAACTACTTCGAAAAACCTAGTAACACCGTGGAAGTTGCAGAGT
GTTTCGCTCAGCACTACCCCAGTGTAGATCAGGTCGATGAGTCACCGCATTCCCCAC
GGGCGACCGTGGCGGTGGCTGCGTTGGCGGCCTGCCCATGGGGAAACCCATGGGAC
GCTCTAATACAGACATGGTGCGAAGAGTCTATTGAGCTAGTTGGTAGTCCTCCGGCC
CCTGAATGCGGCTAATCCTAACTGCGGAGCACACACCCTCAAGCCAGAGGGCAGTG
TGTCGTAACGGGCAACTCTGCAGCGGAACCGACTACTTTGGGTGTCCGTGTTTCATT
TTATTCCTATACTGGCTGCTTATGGTGACAATTGAGAGATCGTTACCATATAGCTATT
GGATTGGCCATCCGGTGACTAATAGAGCTATTATATATCCCTTTGTTGGGTTTATACC
ACTTAGCTTGAAAGAGGTTAAAACATTACAATTCATTGTTAAGTTGAATACAGCAAA SEQ ID NO: 54 amino acid sequence of human Fumarylacetoacetase (FAH) protein
MSFIPVAEDSDFPIHNLPYGVFSTRGDPRPRIGVAIGDQILDLSIIKHLFTGPVLSKHQDVF
NQPTLNSFMGLGQAAWKEARVFLQNLLSVSQARLRDDTELRKCAFISQASATMHLPATI
GDYTDFYSSRQHATNVGIMFRDKENALMPNWLHLPVGYHGRASSVVVSGTPIRRPMGQ
DIQKWEYVPLGPFLGKSFGTTVSPWVVPMDALMPFAVPNPKQDPRPLPYLCHDEPYTFD
INLSVNLKGEGMSQAATICKSNFKYMYWTMLQQLTHHSVNGCNLRPGDLLASGTISGP
EPENFGSMLELSWKGTKPIDLGNGQTRKFLLDGDEVIITGYCQGDGYRIGFGQCAGKVL
PALLPS SEQ ID NO: 55 amino acid sequence of human Ornithine carbamoyltransferase (OTC) protein
MLFNLRILLNNAAFRNGHNFMVRNFRCGQPLQNKVQLKGRDLLTLKNFTGEEIKYMLW
LSADLKFRIKQKGEYLPLLQGKSLGMIFEKRSTRTRLSTETGLALLGGHPCFLTTQDIHLG
VNESLTDTARVLSSMADAVLARVYKQSDLDTLAKEASIPIINGLSDLYHPIQILADYLTL
QEHYSSLKGLTLSWIGDGNNILHSIMMSAAKFGMHLQAATPKGYEPDASVTKLAEQYA
KENGTKLLLTNDPLEAAHGGNVLITDTWISMGQEEEKKKRLQAFQGYQVTMKTAKVA
ASDWTFLHCLPRKPEEVDDEVFYSPRSLVFPEAENRKWTIMAVMVSLLTDYSPQLQKPK
F SEQ ID NO: 56 amino acid sequence of human Ornithine COL3A1 protein
MMSFVQKGSWLLLALLHPTIILAQQEAVEGGCSHLGQSYADRDVWKPEPCQICVCDSG
SVLCDDIICDDQELDCPNPEIPFGECCAVCPQPPTAPTRPPNGQGPQGPKGDPGPPGIPGR
NGDPGIPGQPGSPGSPGPPGICESCPTGPQNYSPQYDSYDVKSGVAVGGLAGYPGPAGPP
GPPGPPGTSGHPGSPGSPGYQGPPGEPGQAGPSGPPGPPGAIGPSGPAGKDGESGRPGRP
GERGLPGPPGIKGPAGIPGFPGMKGHRGFDGRNGEKGETGAPGLKGENGLPGENGAPGP
MGPRGAPGERGRPGLPGAAGARGNDGARGSDGQPGPPGPPGTAGFPGSPGAKGEVGPA
GSPGSNGAPGQRGEPGPQGHAGAQGPPGPPGINGSPGGKGEMGPAGIPGAPGLMGARG
PPGPAGANGAPGLRGGAGEPGKNGAKGEPGPRGERGEAGIPGVPGAKGEDGKDGSPGE
PGANGLPGAAGERGAPGFRGPAGPNGIPGEKGPAGERGAPGPAGPRGAAGEPGRDGVP
GGPGMRGMPGSPGGPGSDGKPGPPGSQGESGRPGPPGPSGPRGQPGVMGFPGPKGNDG
APGKNGERGGPGGPGPQGPPGKNGETGPQGPPGPTGPGGDKGDTGPPGPQGLQGLPGT
GGPPGENGKPGEPGPKGDAGAPGAPGGKGDAGAPGERGPPGLAGAPGLRGGAGPPGPE
GGKGAAGPPGPPGAAGTPGLQGMPGERGGLGSPGPKGDKGEPGGPGADGVPGKDGPR
GPTGPIGPPGPAGQPGDKGEGGAPGLPGIAGPRGSPGERGETGPPGPAGFPGAPGQNGEP
GGKGERGAPGEKGEGGPPGVAGPPGKDGTSGHPGPIGPPGPRGNRGERGSEGSPGHPGQ
PGPPGPPGAPGPCCGGVGAAAIAGIGGEKAGGFAPYYGDEPMDFKINTDEIMTSLKSVN
GQIESLISPDGSRKNPARNCRDLKFCHPELKSGEYWVDPNQGCKLDAIKVFCNMETGET
CISANPLNVPRKHWWTDSSAEKKHVWFGESMDGGFQFSYGNPELPEDVLDVQLAFLRL
LSSRASQNITYHCKNSIAYMDQASGNVKKALKLMGSNEGEFKAEGNSKFTYTVLEDGC
TKHTGEWSKTVFEYRTRKAVRLPIVDIAPYDIGGPDQEFGVDVGPVCFL SEQ ID NO: 57 amino acid sequence of human BMPR2 protein
MTSSLQRPWRVPWLPWTILLVSTAAASQNQERLCAFKDPYQQDLGIGESRISHENGTILC
TDLCNVNFTENFPPPDTTPLSPPHSFNRDETIIIALASVSVLAVLIVALCFGYRMLTGDRK
QGLHSMNMMEAAASEPSLDLDNLKLLELIGRGRYGAVYKGSLDERPVAVKVFSFANRQ
NFINEKNIYRVPLMEHDNIARFIVGDERVTADGRMEYLLVMEYYPNGSLCKYLSLHTSD
WVSSCRLAHSVTRGLAYLHTELPRGDHYKPAISHRDLNSRNVLVKNDGTCVISDFGLSM
RLTGNRLVRPGEEDNAAISEVGTIRYMAPEVLEGAVNLRDCESALKQVDMYALGLIYW
EIFMRCTDLFPGESVPEYQMAFQTEVGNHPTFEDMQVLVSREKQRPKFPEAWKENSLA
VRSLKETIEDCWDQDAEARLTAQCAEERMAELMMIWERNKSVSPTVNPMSTAMQNER
NLSHNRRVPKIGPYPDYSSSSYIEDSIHHTDSIVKNISSEHSMSSTPLTIGEKNRNSINYERQ
QAQARIPSPETSVTSLSTNTTTTNTTGLTPSTGMTTISEMPYPDETNLHTTNVAQSIGPTP
VCLQLTEEDLETNKLDPKEVDKNLKESSDENLMEHSLKQFSGPDPLSSTSSSLLYPLIKL
AVEATGQQDFTQTANGQACLIPDVLPTQIYPLPKQQNLPKRPTSLPLNTKNSTKEPRLKF
GSKHKSNLKQVETGVAKMNTINAAEPHVVTVTMNGVAGRNHSVNSHAATTQYANGT
VLSGQTTNIVTHRAQEMLQNQFIGEDTRLNINSSPDEHEPLLRREQQAGHDEGVLDRLV
DRRERPLEGGRTNSNNNNSNPCSEQDVLAQGVPSTAADPGPSKPRRAQRPNSLDLSATN -continued

| EXEMPLARY SEQUENCES |
| --- |

VLDGSSIQIGESTQDGKSGSGEKIKKRVKTPYSLKRWRPSTWVISTESLDCEVNNNGSNR
AVHSKSSTAVYLAEGGTATTMVSKDIGMNCL

SEQ ID NO: 58 amino acid sequence of human AHI1 protein
MPTAESEAKVKTKVRFEELLKTHSDLMREKKKLKKKLVRSEENISPDTIRSNLHYMKET
TSDDPDTIRSNLPHIKETTSDDVSAANTNNLKKSTRVTKNKLRNTQLATENPNGDASVEE
DKQGKPNKKVIKTVPQLTTQDLKPETPENKVDSTHQKTHTKPQPGVDHQKSEKANEGR
EETDLEEDEELMQAYQCHVTEEMAKEIKRKIRKKLKEQLTYFPSDTLFHDDKLSSEKRK
KKKEVPVFSKAETSTLTISGDTVEGEQKKESSVRSVSSDSHQDDEISSMEQSTEDSMQDD
TKPKPKKTKKKTKAVADNNEDVDGDGVHEITSRDSPVYPKCLLDDDLVLGVYIHRTDR
LKSDFMISHPMVKIHVVDEHTGQYVKKDDSGRPVSSYYEKENVDYILPIMTQPYDFKQL
KSRLPEWEEQIVFNENFPYLLRGSDESPKVILFFEILDFLSVDEIKNNSEVQNQECGFRKIA
WAFLKLLGANGNANINSKLRLQLYYPPTKPRSPLSVVEAFEWWSKCPRNHYPSTLYVV
RGLKVPDCIKPSYRSMMAPQEEKGKPVHCERHHESSSVDTEPGLEESKEVIKWKRLPGQ
NIIYDLSWSKDDHYILTSSSDGTARIWKNEINNTNTFRVLPHPSFVYTAKFHPAVRELVV
TGCYDSMIRIWKVEMREDSAILVRQFDVHKSFINSLCFDTEGHHMYSGDCTGVIVVWNT
YVKINDLEHSVHHWTINKEIKETEFKGIPISYLEIHPNGKRLLIHTKDSTLRIMDLRILVAR
KFVGAANYREKIHSTLTPCGTFLFAGSEDGIVYVWNPETGEQVAMYSDLPFKSPIRDISY
HPFENMVAFCAFGQNEPILLYIYDFHVAQQEAEMFKRYNGTFPLPGIHQSQDALCTCPK
LPHQGSFQIDEFVHTESSSTKMQLVKQRLETVTEVIRSCAAKVNKNLSFTSPPAVSSQQS
KLKQSNMLTAQEILHQFGFTQTGIISIERKPCNHQVDTAPTVVALYDYTANRSDELTIHR
GDIIRVFFKDNEDWWYGSIGKGQEGYFPANHVASETLYQELPPEIKERSPPLSPEEKTKIE
KSPAPQKQSINKNKSQDFRLGSESMTHSEMRKEQSHEDQGHIMDTRMRKNKQAGRKVT
LIE SEQ ID NO: 59 amino acid sequence of human FANCC protein
MAQDSVDLSCDYQFWMQKLSVWDQASTLETQQDTCLHVAQFQEFLRKMYEALKEMD
SNTVIERFPTIGQLLAKACWNPFILA YDESQKILIWCLCCLINKEPQNSGQSKLNSWIQGV
LSHILSALRFDKEVALFTQGLGYAPIDYYPGLLKNMVLSLASELRENHLNGFNTQRRMA
PERVASLSRVCVPLITLTDVDPLVEALLICHGREPQEILQPEFFEAVNEAILLKKISLPMSA
VVCLWLRHLPSLEKAMLHLFEKLISSERNCLRRIECFIKDSSLPQAACHPAIFRVVDEMFR
CALLETDGALEIIATIQVFTQCFVEALEKASKQLRFALKTYFPYTSPSLAMVLLQDPQDIP
RGHWLQTLKHISELLREAVEDQTHGSCGGPFESWFLFIHFGGWAEMVAEQLLMSAAEP
PTALLWLLAFYYGPRDGRQQRAQTMVQVKAVLGHLLAMSRSSSLSAQDLQTVAGQGT
DTDLRAPAQQLIRHLLLNFLLWAPGGHTIAWDVITLMAHTAEITHEIIGFLDQTLYRWNR
LGIESPRSEKLARELLKELRTQV SEQ ID NO: 60 amino acid sequence of human MYBPC3 protein
MPEPGKKPVSAFSKKPRSVEVAAGSPAVFEAETERAGVKVRWQRGGSDISASNKYGLA
TEGTRHTLAVREVGPADQGSYAVIAGSSKVKFDLKVIEAEEAEPMLAPAPAPAEATGAP
GEAPAPAAELGESAPSPKGSSSAALNGPTPGAPDDPIGLFVMRPQDGEVTVGGSITFSAR
VAGASLLKPPVVKWFKGKWVDLSSKVGQHLQLHDSYDRASKVYLFELHITDAQPAFTG
SYRCEVSTKDKFDCSNFNLTVHEAMGTGDLDLLSAFRRTSLAGGGRRISDSHEDTGILDF
SSLLKKRDSFRTPRDSKLEAPAEEDVWETLRQAPPSEYERIAFQYGVTDLRGMLKRLKG
MRRDEKKSTAFQKKLEPAYQVSKGHKIRLTVELADHDAEVKWLKDGQEIQMSGSKYIF
ESIGAKRTLTISQCSLADDAAYQCVVGGEKCSTELFVKEPPVLITRPLEDQLVMVGQRVE
FECEVSEEGAQVKWLKDGVELTREETFKYRFKKDGQRHHLIINEAMLEDAGHYALCTS
GGQALAELIVQEKKLEVYQSIADLMVGAKDQAVFKCEVSDENVRGVWLKNGKELVPD
SRIKVSHIGRVHKLTIDDVTPADEADYSFVPEGFACNLSAKLHFMEVKIDFVPRQEPPKIH
LDCPGRIPDTIVVVAGNKLRLDVPISGDPAPTVIWQKAITQGNKAPARPAPDAPEDTGDS
DEWVFDKKLLCETEGRVRVETTKDRSIFTVEGAEKEDEGVYTVTVKNPVGEDQVNLTV
KVIDVPDAPAAPKISNVGEDSCTVQWEPPAYDGGQPILGYILERKKKKSYRWMRLNFDL
IQELSHEARRMIEGVVYEMRVYAVNAIGMSRPSPASQPFMPIGPPSEPTHLAVEDVSDTT
VSLKWRPPERVGAGGLDGYSVEYCPEGCSEWVAALQGLTEHTSILVKDLPTGARLLSR
VRAHNMAGPGAPVTTTEPVTVQEILQRPRLQLPRHLRQTIQKKVGEPVNLLIPFQGKPRP
QVTWTKEGQPLAGEEVSIRNSPTDTILFIRAARRVHSGTYQVTVRIENMEDKATLVLQV
VDKPSPPQDLRVTDAWGLNVALEWKPPQDVGNTELWGYTVQKADKKTMEWFTVLEH
YRRTHCVVPELIIGNGYYFRVFSQNMVGFSDRAATTKEPVFIPRPGITYEPPNYKALDFSE
APSFTQPLVNRSVIAGYTAMLCCAVRGSPKPKISWFKNGLDLGEDARFRMFSKQGVLTL
EIRKPCPFDGGIYVCRATNLQGEARCECRLEVRVPQ SEQ ID NO: 61 amino acid sequence of human IL2RG protein
MLKPSLPFTSLLFLQLPLLGVGLNTTILTPNGNEDTTADFFLTTMPTDSLSVSTLPLPEVQ
CFVFNVEYMNCTWNSSSEPQPTNLTLHYWYKNSDNDKVQKCSHYLFSEEITSGCQLQK
KEIHLYQTFVVQLQDPREPRRQATQMLKLQNLVIPWAPENLTLHKLSESQLELNWNNRF
LNHCLEHLVQYRTDWDHSWTEQSVDYRHKFSLPSVDGQKRYTFRVRSRFNPLCGSAQH
WSEWSHPIHWGSNTSKENPFLFALEAVVISVGSMGLIISLLCVYFWLERTMPRIPTLKNL
EDLVTEYHGNFSAWSGVSKGLAESLQPDYSERLCLVSEIPPKGGALGEGPGASPCNQHS
PYWAPPCYTLKPET SEQ ID NO: 62 amino acid residues 2-1273 sequence of S protein of
SARS-CoV-2, K986P V987P
FVFLVLLPLVSSQCVNLTTRTQLPPAYTNSFTRGVYYPDKVFRSSVLHSTQDLFLPFFSN
VTWFHAIHVSGTNGTKRFDNPVLPFNDGVYFASTEKSNIIRGWIFGTTLDSKTQSLLIVN
NATNVVIKVCEFQFCNDPFLGVYYHKNNKSWMESEFRVYSSANNCTFEYVSQPFLMDL
EGKQGNFKNLREFVFKNIDGYFKIYSKHTPINLVRDLPQGFSALEPLVDLPIGINITRFQTL
LALHRSYLTPGDSSSGWTAGAAAYYVGYLQPRTFLLKYNENGTITDAVDCALDPLSETK -continued

EXEMPLARY SEQUENCES

CTLKSFTVEKGIYQTSNFRVQPTESIVRFPNITNLCPFGEVFNATRFASVYAWNRKRISNC
VADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTP
CNGVEGFNCYFPLQSYGFQPTNGVGYQPYRVVVLSFELLHAPATVCGPKKSTNLVKNK
CVNFNFNGLTGTGVLTESNKKFLPFQQFGRDIADTTDAVRDPQTLEILDITPCSFGGVSVI
TPGTNTSNQVAVLYQDVNCTEVPVAIHADQLTPTWRVYSTGSNVFQTRAGCLIGAEHV
NNSYECDIPIGAGICASYQTQTNSPRRARSVASQSIIA YTMSLGAENSVAYSNNSIAIPTNF
TISVTTEILPVSMTKTSVDCTMYICGDSTECSNLLLQYGSFCTQLNRALTGIAVEQDKNT
QEVFAQVKQIYKTPPIKDFGGFNFSQILPDPSKPSKRSFIEDLLFNKVTLADAGFIKQYGD
CLGDIAARDLICAQKFNGLTVLPPLLTDEMIAQYTSALLAGTITSGWTFGAGAALQIPFA
MQMAYRFNGIGVTQNVLYENQKLIANQFNSAIGKIQDSLSSTASALGKLQDVVNQNAQ
ALNTLVKQLSSNFGAISSVLNDILSRLDPPEAEVQIDRLITGRLQSLQTYVTQQLIRAAEIR
ASANLAATKMSECVLGQSKRVDFCGKGYHLMSFPQSAPHGVVFLHVTYVPAQEKNFTT
APAICHDGKAHFPREGVFVSNGTHWFVTQRNFYEPQIITTDNTFVSGNCDVVIGIVNNTV
YDPLQPELDSFKEELDKYFKNHTSPDVDLGDISGINASVVNIQKEIDRLNEVAKNLNESLI
DLQELGKYEQYIKWPWYIWLGFIAGLIAIVMVTIMLCCMTSCCSCLKGCCSCGSCCKFD
EDDSEPVLKGVKLHYT

SEQ ID NO: 63 amino acid sequence of SARS-CoV-2 strain B.1.351 RBD
RVQPTESIVRFPNITNLCPFGEVFNATRFASVYAWNRKRISNCVADYSVLYNSASFSTFK
CYGVSPTKLNDLCFTNVYADSFVIRGDEVRQIAPGQTGNIADYNYKLPDDFTGCVIAWN
SNNLDSKVGGNYNYLYRLFRKSNLKPFERDISTEIYQAGSTPCNGVKGFNCYFPLQSYGF
QPTYGVGYQPYRVVVLSFELLHAPATVCGPKKSTNLVKNKCVNF SEQ ID NO: 64 Nucleic acid sequence encoding SARS-CoV-2 strain B.1.351 RBD
CGCGTCCAGCCAACCGAGAGCATCGTCAGATTTCCCAACATTACAAATCTGTGTCCC
TTCGGCGAGGTGTTCAACGCCACACGCTTCGCTTCAGTGTACGCATGGAACCGCAAG
CGCATATCTAACTGCGTCGCGGATTATTCTGTCCTCTACAACTCCGCCTCTTTCTCCA
CCTTCAAGTGCTACGGAGTGTCACCGACTAAGCTGAACGATCTCTGCTTTACCAACG
TCTACGCGGACTCCTTCGTGATAAGAGGTGATGAAGTGAGACAAATAGCCCCAGGT
CAGACTGGTAACATCGCAGATTACAACTACAAATTGCCTGATGATTTCACTGGTTGC
GTTATCGCGTGGAACTCTAATAACCTCGATTCTAAGGTCGGTGGTAACTACAATTAC
CTGTACCGCTTGTTTAGGAAGTCAAACCTGAAGCCTTTCGAGAGGGATATTTCAACC
GAAATCTATCAAGCGGGTTCAACACCGTGTAACGGTGTGAAAGGATTTAACTGCTAC
TTCCCCCTGCAGTCTTACGGATTCCAGCCAACCTATGGCGTGGGTTACCAACCTTAT
CGCGTGGTGGTTCTGAGTTTCGAACTGTTGCACGCTCCCGCCACGGTATGCGGTCCC
AAGAAGAGCACTAACTTGGTGAAGAATAAGTGCGTGAATTTC

What is claimed is:

1. A circular RNA (circRNA) comprising from 5' to 3': a 3' exon sequence recognizable by a 3' catalytic Group I intron fragment, an internal ribosomal entry site (IRES) sequence or a m6A modification motif sequence, a Kozak sequence, a signal peptide encoding sequence, a nucleic acid sequence encoding a therapeutic polypeptide, a TAA stop codon or in-frame 2A peptide coding sequence, and a 5' exon sequence recognizable by a 5' catalytic Group I intron fragment;
   - wherein the 3' exon sequence recognizable by a 3' catalytic Group I intron fragment comprises the nucleic acid sequence of SEQ ID NO: 39, and the 5' exon sequence recognizable by a 5' catalytic Group I intron fragment comprises the nucleic acid sequence of SEQ ID NO: 40;
   - wherein the therapeutic polypeptide is selected from the group consisting of an antigenic polypeptide, a functional protein, a receptor protein, and a targeting protein.

2. The circRNA of claim 1, wherein the circRNA comprises from 5' to 3': the 3' exon sequence recognizable by a 3' catalytic Group I intron fragment, the IRES sequence, the Kozak sequence, the signal peptide encoding sequence, the nucleic acid sequence encoding a therapeutic polypeptide, the TAA stop codon, and the 5' exon sequence recognizable by a 5' catalytic Group I intron fragment.

3. The circRNA of claim 1, wherein the circRNA comprises from 5' to 3': the 3' exon sequence recognizable by a 3' catalytic Group I intron fragment, the m6A modification motif sequence, the Kozak sequence, the signal peptide encoding sequence, the nucleic acid sequence encoding a therapeutic polypeptide, the TAA stop codon, and the 5' exon sequence recognizable by a 5' catalytic Group I intron fragment.

4. The circRNA of claim 1, wherein the circRNA comprises from 5' to 3': the 3' exon sequence recognizable by a 3' catalytic Group I intron fragment, the IRES sequence, the Kozak sequence, the signal peptide encoding sequence, the nucleic acid sequence encoding a therapeutic polypeptide, the in-frame 2A peptide coding sequence, and the 5' exon sequence recognizable by a 5' catalytic Group I intron fragment.

5. The circRNA of claim 1, wherein the circRNA comprises from 5' to 3': the 3' exon sequence recognizable by a 3' catalytic Group I intron fragment, the m6A modification motif sequence, the Kozak sequence, the signal peptide encoding sequence, the nucleic acid sequence encoding a therapeutic polypeptide, the in-frame 2A peptide coding sequence, and the 5' exon sequence recognizable by a 5' catalytic Group I intron fragment.

6. The circRNA of claim 1, further comprising a poly AC or poly A sequence disposed at the 5' end of the IRES sequence.

7. The circRNA of claim 1, wherein the therapeutic protein is for treating or preventing an infection.

8. The circRNA of claim 7, wherein the infection is an infection by a virus.

9. The circRNA of claim 8, wherein the virus is a coronavirus.

10. The circRNA of claim 9, wherein the coronavirus is SARS-COV-2.

11. The circRNA of claim 1, wherein the therapeutic polypeptide is an antigenic polypeptide.

12. The circRNA of claim 11, wherein the antigenic polypeptide comprises a Spike(S) protein or a fragment thereof of a coronavirus.

13. The circRNA of claim 12, wherein the antigenic polypeptide comprises a receptor-binding domain (RBD) of the S protein.

14. The circRNA of claim 11, wherein the antigenic polypeptide further comprises a multimerization domain.

15. The circRNA of claim 12, wherein the antigenic polypeptide comprises an S2 region of the S protein.

16. The circRNA of claim 12, wherein the antigenic polypeptide comprises amino acid residues 2-1273 of a full-length S protein of SARS-COV-2, wherein the numbering is based on SEQ ID NO: 1.

17. The circRNA of claim 13, wherein the antigenic polypeptide comprises an amino acid sequence selected from the group consisting of SEQ ID NOs: 8-10 or SEQ ID NOs: 62-63, and/or wherein the circRNA comprises a nucleic acid sequence selected from the group consisting of SEQ ID NOs: 11-15 and 64.

18. The circRNA of claim 1, wherein the therapeutic protein is a receptor protein.

19. The circRNA of claim 18, wherein the receptor is an ACE2 receptor.

20. The circRNA of claim 1, wherein the therapeutic protein is a targeting protein.

21. The circRNA of claim 20, wherein the targeting protein is an antibody.

22. A composition comprising a plurality of circRNAs of claim 1, wherein the therapeutic polypeptides corresponding to the plurality of circRNAs are different with respect to each other.

23. The composition of claim 22, wherein the plurality of circRNAs target a plurality of strains of a coronavirus.

24. A circRNA vaccine comprising the circRNA of claim 1.

25. A pharmaceutical composition comprising the circRNA of claim 1 and a pharmaceutically acceptable carrier.

26. A method of treating or preventing an infection in an individual, comprising administering to the individual an effective amount of the circRNA of claim 1.

27. The method of claim 26, wherein the infection is a coronavirus infection.

28. The method of claim 27, wherein the infection is SARS-COV-2 infection.

29. A method of treating or preventing a disease or condition in an individual, comprising administering to the individual an effective amount of the circRNA of claim 1.

30. The method of claim 29, wherein the disease or condition is a hereditary genetic disease associated with one or more mutations in the protein corresponding to the therapeutic protein.

31. The method of claim 29, wherein:

(i) the therapeutic polypeptide is TP53 or PTEN, and the disease or condition is cancer;

(ii) the therapeutic polypeptide is OTC, and the disease is ornithine transcarbamylase deficiency;

(iii) the therapeutic polypeptide is FAH, and the disease is tyrosinemia;

(iv) the therapeutic polypeptide is DMD, and the disease is Duchenne and Becker muscular dystrophy, X-linked dilated cardiomyopathy, or familial dilated cardiomyopathy;

(v) the therapeutic polypeptide is IDUA, and the disease or condition is Mucopolysaccharidosis type I (MPS I);

(vi) the therapeutic polypeptide is COL3A1, and the disease or condition is Ehlers-Danlos syndrome;

(vii) the therapeutic polypeptide is AHI1, and the disease or condition is Joubert syndrome;

(viii) the therapeutic polypeptide is BMPR2, and the disease or condition is pulmonary arterial hypertension, or pulmonary veno-occlusive disease;

(ix) the therapeutic polypeptide is FANCC, and the disease or condition is Fanconi anemia;

(x) the therapeutic polypeptide is MYBPC3, and the disease or condition is primary familial hypertrophic cardiomyopathy; or (xi) the therapeutic polypeptide is IL2RG, and the disease or condition is X-linked severe combined immunodeficiency.

32. A linear RNA capable of forming the circRNA of claim 1.

33. A nucleic acid construct comprising a nucleic acid sequence encoding the linear RNA of claim 32.

* * * * *

SEQUENCE LISTING

<160> NUMBER OF SEQ ID NOS: 95

<210> SEQ ID NO 1
<211> LENGTH: 1273
<212> TYPE: PRT
<213> ORGANISM: SARS-CoV-2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

```
Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
```

```
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975
```

```
Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270
```

<210> SEQ ID NO 2
<211> LENGTH: 223
<212> TYPE: PRT
<213> ORGANISM: Artificial Sequence
<220> FEATURE:
<223> OTHER INFORMATION: Synthetic Construct

<400> SEQUENCE: 2

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60
```

```
Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 3
<211> LENGTH: 32
<212> TYPE: PRT
<213> ORGANISM: Artificial Sequence
<220> FEATURE:
<223> OTHER INFORMATION: Synthetic Construct

<400> SEQUENCE: 3

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu Gly Arg Ser
            20                  25                  30


<210> SEQ ID NO 4
<211> LENGTH: 33
<212> TYPE: PRT
<213> ORGANISM: Artificial Sequence
<220> FEATURE:
<223> OTHER INFORMATION: Synthetic Construct

<400> SEQUENCE: 4

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg


<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Ser Gly Gly Gly Gly Ser
1               5                   10
```

<210> SEQ ID NO 6
<211> LENGTH: 588
<212> TYPE: PRT
<213> ORGANISM: SARS-CoV-2

<400> SEQUENCE: 6

```
Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
            20                  25                  30

Phe Thr Ile Ser Val Thr Thr Glu Ile Leu Pro Val Ser Met Thr Lys
        35                  40                  45

Thr Ser Val Asp Cys Thr Met Tyr Ile Cys Gly Asp Ser Thr Glu Cys
    50                  55                  60

Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
    130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
        195                 200                 205

Leu Gln Ile Pro Phe Ala Met Gln Met Ala Tyr Arg Phe Asn Gly Ile
    210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
        275                 280                 285

Ser Ser Val Leu Asn Asp Ile Leu Ser Arg Leu Asp Lys Val Glu Ala
    290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
        355                 360                 365

Gln Ser Ala Pro His Gly Val Val Phe Leu His Val Thr Tyr Val Pro
    370                 375                 380
```

```
Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
        435                 440                 445

Asn Asn Thr Val Tyr Asp Pro Leu Gln Pro Glu Leu Asp Ser Phe Lys
    450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Trp Pro
        515                 520                 525

Trp Tyr Ile Trp Leu Gly Phe Ile Ala Gly Leu Ile Ala Ile Val Met
    530                 535                 540

Val Thr Ile Met Leu Cys Cys Met Thr Ser Cys Cys Ser Cys Leu Lys
545                 550                 555                 560

Gly Cys Cys Ser Cys Gly Ser Cys Cys Lys Phe Asp Glu Asp Asp Ser
                565                 570                 575

Glu Pro Val Leu Lys Gly Val Lys Leu His Tyr Thr
            580                 585


<210> SEQ ID NO 7
<211> LENGTH: 588
<212> TYPE: PRT
<213> ORGANISM: Artificial Sequence
<220> FEATURE:
<223> OTHER INFORMATION: Synthetic Construct

<400> SEQUENCE: 7

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
            20                  25                  30

Phe Thr Ile Ser Val Thr Thr Glu Ile Leu Pro Val Ser Met Thr Lys
        35                  40                  45

Thr Ser Val Asp Cys Thr Met Tyr Ile Cys Gly Asp Ser Thr Glu Cys
    50                  55                  60

Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
    130                 135                 140

Asp Ala Gly Phe Ile Lys Gln Tyr Gly Asp Cys Leu Gly Asp Ile Ala
145                 150                 155                 160
```

```
Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
        195                 200                 205

Leu Gln Ile Pro Phe Ala Met Gln Met Ala Tyr Arg Phe Asn Gly Ile
    210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
        275                 280                 285

Ser Ser Val Leu Asn Asp Ile Leu Ser Arg Leu Asp Pro Pro Glu Ala
    290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
        355                 360                 365

Gln Ser Ala Pro His Gly Val Val Phe Leu His Val Thr Tyr Val Pro
    370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
        435                 440                 445

Asn Asn Thr Val Tyr Asp Pro Leu Gln Pro Glu Leu Asp Ser Phe Lys
    450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Trp Pro
        515                 520                 525

Trp Tyr Ile Trp Leu Gly Phe Ile Ala Gly Leu Ile Ala Ile Val Met
    530                 535                 540

Val Thr Ile Met Leu Cys Cys Met Thr Ser Cys Cys Ser Cys Leu Lys
545                 550                 555                 560

Gly Cys Cys Ser Cys Gly Ser Cys Cys Lys Phe Asp Glu Asp Asp Ser
                565                 570                 575

Glu Pro Val Leu Lys Gly Val Lys Leu His Tyr Thr
```

580 585

<210> SEQ ID NO 8
<211> LENGTH: 1272
<212> TYPE: PRT
<213> ORGANISM: SARS-CoV-2

<400> SEQUENCE: 8

Phe Val Phe Leu Val Leu Leu Pro Leu Val Ser Ser Gln Cys Val Asn
1 5 10 15

Leu Thr Thr Arg Thr Gln Leu Pro Pro Ala Tyr Thr Asn Ser Phe Thr
20 25 30

Arg Gly Val Tyr Tyr Pro Asp Lys Val Phe Arg Ser Ser Val Leu His
35 40 45

Ser Thr Gln Asp Leu Phe Leu Pro Phe Phe Ser Asn Val Thr Trp Phe
50 55 60

His Ala Ile His Val Ser Gly Thr Asn Gly Thr Lys Arg Phe Asp Asn
65 70 75 80

Pro Val Leu Pro Phe Asn Asp Gly Val Tyr Phe Ala Ser Thr Glu Lys
85 90 95

Ser Asn Ile Ile Arg Gly Trp Ile Phe Gly Thr Thr Leu Asp Ser Lys
100 105 110

Thr Gln Ser Leu Leu Ile Val Asn Asn Ala Thr Asn Val Val Ile Lys
115 120 125

Val Cys Glu Phe Gln Phe Cys Asn Asp Pro Phe Leu Gly Val Tyr Tyr
130 135 140

His Lys Asn Asn Lys Ser Trp Met Glu Ser Glu Phe Arg Val Tyr Ser
145 150 155 160

Ser Ala Asn Asn Cys Thr Phe Glu Tyr Val Ser Gln Pro Phe Leu Met
165 170 175

Asp Leu Glu Gly Lys Gln Gly Asn Phe Lys Asn Leu Arg Glu Phe Val
180 185 190

Phe Lys Asn Ile Asp Gly Tyr Phe Lys Ile Tyr Ser Lys His Thr Pro
195 200 205

Ile Asn Leu Val Arg Asp Leu Pro Gln Gly Phe Ser Ala Leu Glu Pro
210 215 220

Leu Val Asp Leu Pro Ile Gly Ile Asn Ile Thr Arg Phe Gln Thr Leu
225 230 235 240

Leu Ala Leu His Arg Ser Tyr Leu Thr Pro Gly Asp Ser Ser Ser Gly
245 250 255

Trp Thr Ala Gly Ala Ala Ala Tyr Tyr Val Gly Tyr Leu Gln Pro Arg
260 265 270

Thr Phe Leu Leu Lys Tyr Asn Glu Asn Gly Thr Ile Thr Asp Ala Val
275 280 285

Asp Cys Ala Leu Asp Pro Leu Ser Glu Thr Lys Cys Thr Leu Lys Ser
290 295 300

Phe Thr Val Glu Lys Gly Ile Tyr Gln Thr Ser Asn Phe Arg Val Gln
305 310 315 320

Pro Thr Glu Ser Ile Val Arg Phe Pro Asn Ile Thr Asn Leu Cys Pro
325 330 335

Phe Gly Glu Val Phe Asn Ala Thr Arg Phe Ala Ser Val Tyr Ala Trp
340 345 350

Asn Arg Lys Arg Ile Ser Asn Cys Val Ala Asp Tyr Ser Val Leu Tyr
355 360 365

```
Asn Ser Ala Ser Phe Ser Thr Phe Lys Cys Tyr Gly Val Ser Pro Thr
    370                 375                 380

Lys Leu Asn Asp Leu Cys Phe Thr Asn Val Tyr Ala Asp Ser Phe Val
385                 390                 395                 400

Ile Arg Gly Asp Glu Val Arg Gln Ile Ala Pro Gly Gln Thr Gly Lys
                405                 410                 415

Ile Ala Asp Tyr Asn Tyr Lys Leu Pro Asp Asp Phe Thr Gly Cys Val
            420                 425                 430

Ile Ala Trp Asn Ser Asn Asn Leu Asp Ser Lys Val Gly Gly Asn Tyr
        435                 440                 445

Asn Tyr Leu Tyr Arg Leu Phe Arg Lys Ser Asn Leu Lys Pro Phe Glu
    450                 455                 460

Arg Asp Ile Ser Thr Glu Ile Tyr Gln Ala Gly Ser Thr Pro Cys Asn
465                 470                 475                 480

Gly Val Glu Gly Phe Asn Cys Tyr Phe Pro Leu Gln Ser Tyr Gly Phe
                485                 490                 495

Gln Pro Thr Asn Gly Val Gly Tyr Gln Pro Tyr Arg Val Val Val Leu
            500                 505                 510

Ser Phe Glu Leu Leu His Ala Pro Ala Thr Val Cys Gly Pro Lys Lys
        515                 520                 525

Ser Thr Asn Leu Val Lys Asn Lys Cys Val Asn Phe Asn Phe Asn Gly
    530                 535                 540

Leu Thr Gly Thr Gly Val Leu Thr Glu Ser Asn Lys Lys Phe Leu Pro
545                 550                 555                 560

Phe Gln Gln Phe Gly Arg Asp Ile Ala Asp Thr Thr Asp Ala Val Arg
                565                 570                 575

Asp Pro Gln Thr Leu Glu Ile Leu Asp Ile Thr Pro Cys Ser Phe Gly
            580                 585                 590

Gly Val Ser Val Ile Thr Pro Gly Thr Asn Thr Ser Asn Gln Val Ala
        595                 600                 605

Val Leu Tyr Gln Asp Val Asn Cys Thr Glu Val Pro Val Ala Ile His
    610                 615                 620

Ala Asp Gln Leu Thr Pro Thr Trp Arg Val Tyr Ser Thr Gly Ser Asn
625                 630                 635                 640

Val Phe Gln Thr Arg Ala Gly Cys Leu Ile Gly Ala Glu His Val Asn
                645                 650                 655

Asn Ser Tyr Glu Cys Asp Ile Pro Ile Gly Ala Gly Ile Cys Ala Ser
            660                 665                 670

Tyr Gln Thr Gln Thr Asn Ser Pro Arg Arg Ala Arg Ser Val Ala Ser
        675                 680                 685

Gln Ser Ile Ile Ala Tyr Thr Met Ser Leu Gly Ala Glu Asn Ser Val
    690                 695                 700

Ala Tyr Ser Asn Asn Ser Ile Ala Ile Pro Thr Asn Phe Thr Ile Ser
705                 710                 715                 720

Val Thr Thr Glu Ile Leu Pro Val Ser Met Thr Lys Thr Ser Val Asp
                725                 730                 735

Cys Thr Met Tyr Ile Cys Gly Asp Ser Thr Glu Cys Ser Asn Leu Leu
            740                 745                 750

Leu Gln Tyr Gly Ser Phe Cys Thr Gln Leu Asn Arg Ala Leu Thr Gly
        755                 760                 765

Ile Ala Val Glu Gln Asp Lys Asn Thr Gln Glu Val Phe Ala Gln Val
    770                 775                 780

Lys Gln Ile Tyr Lys Thr Pro Pro Ile Lys Asp Phe Gly Gly Phe Asn
```

-continued

```
785                 790                 795                 800

Phe Ser Gln Ile Leu Pro Asp Pro Ser Lys Pro Ser Lys Arg Ser Phe
                805                 810                 815

Ile Glu Asp Leu Leu Phe Asn Lys Val Thr Leu Ala Asp Ala Gly Phe
            820                 825                 830

Ile Lys Gln Tyr Gly Asp Cys Leu Gly Asp Ile Ala Ala Arg Asp Leu
        835                 840                 845

Ile Cys Ala Gln Lys Phe Asn Gly Leu Thr Val Leu Pro Pro Leu Leu
    850                 855                 860

Thr Asp Glu Met Ile Ala Gln Tyr Thr Ser Ala Leu Leu Ala Gly Thr
865                 870                 875                 880

Ile Thr Ser Gly Trp Thr Phe Gly Ala Gly Ala Ala Leu Gln Ile Pro
                885                 890                 895

Phe Ala Met Gln Met Ala Tyr Arg Phe Asn Gly Ile Gly Val Thr Gln
            900                 905                 910

Asn Val Leu Tyr Glu Asn Gln Lys Leu Ile Ala Asn Gln Phe Asn Ser
        915                 920                 925

Ala Ile Gly Lys Ile Gln Asp Ser Leu Ser Ser Thr Ala Ser Ala Leu
    930                 935                 940

Gly Lys Leu Gln Asp Val Val Asn Gln Asn Ala Gln Ala Leu Asn Thr
945                 950                 955                 960

Leu Val Lys Gln Leu Ser Ser Asn Phe Gly Ala Ile Ser Ser Val Leu
                965                 970                 975

Asn Asp Ile Leu Ser Arg Leu Asp Lys Val Glu Ala Glu Val Gln Ile
            980                 985                 990

Asp Arg Leu Ile Thr Gly Arg Leu Gln Ser Leu Gln Thr Tyr Val Thr
        995                 1000                1005

Gln Gln Leu Ile Arg Ala Ala Glu Ile Arg Ala Ser Ala Asn Leu Ala
    1010                1015                1020

Ala Thr Lys Met Ser Glu Cys Val Leu Gly Gln Ser Lys Arg Val Asp
1025                1030                1035                1040

Phe Cys Gly Lys Gly Tyr His Leu Met Ser Phe Pro Gln Ser Ala Pro
                1045                1050                1055

His Gly Val Val Phe Leu His Val Thr Tyr Val Pro Ala Gln Glu Lys
            1060                1065                1070

Asn Phe Thr Thr Ala Pro Ala Ile Cys His Asp Gly Lys Ala His Phe
        1075                1080                1085

Pro Arg Glu Gly Val Phe Val Ser Asn Gly Thr His Trp Phe Val Thr
    1090                1095                1100

Gln Arg Asn Phe Tyr Glu Pro Gln Ile Ile Thr Thr Asp Asn Thr Phe
1105                1110                1115                1120

Val Ser Gly Asn Cys Asp Val Val Ile Gly Ile Val Asn Asn Thr Val
                1125                1130                1135

Tyr Asp Pro Leu Gln Pro Glu Leu Asp Ser Phe Lys Glu Glu Leu Asp
            1140                1145                1150

Lys Tyr Phe Lys Asn His Thr Ser Pro Asp Val Asp Leu Gly Asp Ile
        1155                1160                1165

Ser Gly Ile Asn Ala Ser Val Val Asn Ile Gln Lys Glu Ile Asp Arg
    1170                1175                1180

Leu Asn Glu Val Ala Lys Asn Leu Asn Glu Ser Leu Ile Asp Leu Gln
1185                1190                1195                1200

Glu Leu Gly Lys Tyr Glu Gln Tyr Ile Lys Trp Pro Trp Tyr Ile Trp
                1205                1210                1215
```

```
Leu Gly Phe Ile Ala Gly Leu Ile Ala Ile Val Met Val Thr Ile Met
            1220                1225                1230

Leu Cys Cys Met Thr Ser Cys Cys Ser Cys Leu Lys Gly Cys Cys Ser
        1235                1240                1245

Cys Gly Ser Cys Cys Lys Phe Asp Glu Asp Asp Ser Glu Pro Val Leu
    1250                1255                1260

Lys Gly Val Lys Leu His Tyr Thr
1265                1270


<210> SEQ ID NO 9
<211> LENGTH: 1268
<212> TYPE: PRT
<213> ORGANISM: Artificial Sequence
<220> FEATURE:
<223> OTHER INFORMATION: Synthetic Construct

<400> SEQUENCE: 9

Phe Val Phe Leu Val Leu Leu Pro Leu Val Ser Ser Gln Cys Val Asn
1               5                   10                  15

Leu Thr Thr Arg Thr Gln Leu Pro Pro Ala Tyr Thr Asn Ser Phe Thr
            20                  25                  30

Arg Gly Val Tyr Tyr Pro Asp Lys Val Phe Arg Ser Ser Val Leu His
        35                  40                  45

Ser Thr Gln Asp Leu Phe Leu Pro Phe Phe Ser Asn Val Thr Trp Phe
    50                  55                  60

His Ala Ile His Val Ser Gly Thr Asn Gly Thr Lys Arg Phe Asp Asn
65                  70                  75                  80

Pro Val Leu Pro Phe Asn Asp Gly Val Tyr Phe Ala Ser Thr Glu Lys
                85                  90                  95

Ser Asn Ile Ile Arg Gly Trp Ile Phe Gly Thr Thr Leu Asp Ser Lys
            100                 105                 110

Thr Gln Ser Leu Leu Ile Val Asn Asn Ala Thr Asn Val Val Ile Lys
        115                 120                 125

Val Cys Glu Phe Gln Phe Cys Asn Asp Pro Phe Leu Gly Val Tyr Tyr
    130                 135                 140

His Lys Asn Asn Lys Ser Trp Met Glu Ser Glu Phe Arg Val Tyr Ser
145                 150                 155                 160

Ser Ala Asn Asn Cys Thr Phe Glu Tyr Val Ser Gln Pro Phe Leu Met
                165                 170                 175

Asp Leu Glu Gly Lys Gln Gly Asn Phe Lys Asn Leu Arg Glu Phe Val
            180                 185                 190

Phe Lys Asn Ile Asp Gly Tyr Phe Lys Ile Tyr Ser Lys His Thr Pro
        195                 200                 205

Ile Asn Leu Val Arg Asp Leu Pro Gln Gly Phe Ser Ala Leu Glu Pro
    210                 215                 220

Leu Val Asp Leu Pro Ile Gly Ile Asn Ile Thr Arg Phe Gln Thr Leu
225                 230                 235                 240

Leu Ala Leu His Arg Ser Tyr Leu Thr Pro Gly Asp Ser Ser Ser Gly
                245                 250                 255

Trp Thr Ala Gly Ala Ala Ala Tyr Tyr Val Gly Tyr Leu Gln Pro Arg
            260                 265                 270

Thr Phe Leu Leu Lys Tyr Asn Glu Asn Gly Thr Ile Thr Asp Ala Val
        275                 280                 285

Asp Cys Ala Leu Asp Pro Leu Ser Glu Thr Lys Cys Thr Leu Lys Ser
    290                 295                 300
```

```
Phe Thr Val Glu Lys Gly Ile Tyr Gln Thr Ser Asn Phe Arg Val Gln
305                 310                 315                 320

Pro Thr Glu Ser Ile Val Arg Phe Pro Asn Ile Thr Asn Leu Cys Pro
                325                 330                 335

Phe Gly Glu Val Phe Asn Ala Thr Arg Phe Ala Ser Val Tyr Ala Trp
            340                 345                 350

Asn Arg Lys Arg Ile Ser Asn Cys Val Ala Asp Tyr Ser Val Leu Tyr
        355                 360                 365

Asn Ser Ala Ser Phe Ser Thr Phe Lys Cys Tyr Gly Val Ser Pro Thr
    370                 375                 380

Lys Leu Asn Asp Leu Cys Phe Thr Asn Val Tyr Ala Asp Ser Phe Val
385                 390                 395                 400

Ile Arg Gly Asp Glu Val Arg Gln Ile Ala Pro Gly Gln Thr Gly Lys
                405                 410                 415

Ile Ala Asp Tyr Asn Tyr Lys Leu Pro Asp Asp Phe Thr Gly Cys Val
            420                 425                 430

Ile Ala Trp Asn Ser Asn Asn Leu Asp Ser Lys Val Gly Gly Asn Tyr
        435                 440                 445

Asn Tyr Leu Tyr Arg Leu Phe Arg Lys Ser Asn Leu Lys Pro Phe Glu
    450                 455                 460

Arg Asp Ile Ser Thr Glu Ile Tyr Gln Ala Gly Ser Thr Pro Cys Asn
465                 470                 475                 480

Gly Val Glu Gly Phe Asn Cys Tyr Phe Pro Leu Gln Ser Tyr Gly Phe
                485                 490                 495

Gln Pro Thr Asn Gly Val Gly Tyr Gln Pro Tyr Arg Val Val Val Leu
            500                 505                 510

Ser Phe Glu Leu Leu His Ala Pro Ala Thr Val Cys Gly Pro Lys Lys
        515                 520                 525

Ser Thr Asn Leu Val Lys Asn Lys Cys Val Asn Phe Asn Phe Asn Gly
    530                 535                 540

Leu Thr Gly Thr Gly Val Leu Thr Glu Ser Asn Lys Lys Phe Leu Pro
545                 550                 555                 560

Phe Gln Gln Phe Gly Arg Asp Ile Ala Asp Thr Thr Asp Ala Val Arg
                565                 570                 575

Asp Pro Gln Thr Leu Glu Ile Leu Asp Ile Thr Pro Cys Ser Phe Gly
            580                 585                 590

Gly Val Ser Val Ile Thr Pro Gly Thr Asn Thr Ser Asn Gln Val Ala
        595                 600                 605

Val Leu Tyr Gln Asp Val Asn Cys Thr Glu Val Pro Val Ala Ile His
    610                 615                 620

Ala Asp Gln Leu Thr Pro Thr Trp Arg Val Tyr Ser Thr Gly Ser Asn
625                 630                 635                 640

Val Phe Gln Thr Arg Ala Gly Cys Leu Ile Gly Ala Glu His Val Asn
                645                 650                 655

Asn Ser Tyr Glu Cys Asp Ile Pro Ile Gly Ala Gly Ile Cys Ala Ser
            660                 665                 670

Tyr Gln Thr Gln Thr Asn Ser Arg Ser Val Ala Ser Gln Ser Ile Ile
        675                 680                 685

Ala Tyr Thr Met Ser Leu Gly Ala Glu Asn Ser Val Ala Tyr Ser Asn
    690                 695                 700

Asn Ser Ile Ala Ile Pro Thr Asn Phe Thr Ile Ser Val Thr Thr Glu
705                 710                 715                 720
```

```
Ile Leu Pro Val Ser Met Thr Lys Thr Ser Val Asp Cys Thr Met Tyr
                725                 730                 735

Ile Cys Gly Asp Ser Thr Glu Cys Ser Asn Leu Leu Leu Gln Tyr Gly
            740                 745                 750

Ser Phe Cys Thr Gln Leu Asn Arg Ala Leu Thr Gly Ile Ala Val Glu
        755                 760                 765

Gln Asp Lys Asn Thr Gln Glu Val Phe Ala Gln Val Lys Gln Ile Tyr
    770                 775                 780

Lys Thr Pro Pro Ile Lys Asp Phe Gly Gly Phe Asn Phe Ser Gln Ile
785                 790                 795                 800

Leu Pro Asp Pro Ser Lys Pro Ser Lys Arg Ser Phe Ile Glu Asp Leu
                805                 810                 815

Leu Phe Asn Lys Val Thr Leu Ala Asp Ala Gly Phe Ile Lys Gln Tyr
            820                 825                 830

Gly Asp Cys Leu Gly Asp Ile Ala Ala Arg Asp Leu Ile Cys Ala Gln
        835                 840                 845

Lys Phe Asn Gly Leu Thr Val Leu Pro Pro Leu Leu Thr Asp Glu Met
    850                 855                 860

Ile Ala Gln Tyr Thr Ser Ala Leu Leu Ala Gly Thr Ile Thr Ser Gly
865                 870                 875                 880

Trp Thr Phe Gly Ala Gly Ala Ala Leu Gln Ile Pro Phe Ala Met Gln
                885                 890                 895

Met Ala Tyr Arg Phe Asn Gly Ile Gly Val Thr Gln Asn Val Leu Tyr
            900                 905                 910

Glu Asn Gln Lys Leu Ile Ala Asn Gln Phe Asn Ser Ala Ile Gly Lys
        915                 920                 925

Ile Gln Asp Ser Leu Ser Ser Thr Ala Ser Ala Leu Gly Lys Leu Gln
    930                 935                 940

Asp Val Val Asn Gln Asn Ala Gln Ala Leu Asn Thr Leu Val Lys Gln
945                 950                 955                 960

Leu Ser Ser Asn Phe Gly Ala Ile Ser Ser Val Leu Asn Asp Ile Leu
                965                 970                 975

Ser Arg Leu Asp Lys Val Glu Ala Glu Val Gln Ile Asp Arg Leu Ile
            980                 985                 990

Thr Gly Arg Leu Gln Ser Leu Gln Thr Tyr Val Thr Gln Gln Leu Ile
        995                 1000                1005

Arg Ala Ala Glu Ile Arg Ala Ser Ala Asn Leu Ala Ala Thr Lys Met
    1010                1015                1020

Ser Glu Cys Val Leu Gly Gln Ser Lys Arg Val Asp Phe Cys Gly Lys
1025                1030                1035                1040

Gly Tyr His Leu Met Ser Phe Pro Gln Ser Ala Pro His Gly Val Val
                1045                1050                1055

Phe Leu His Val Thr Tyr Val Pro Ala Gln Glu Lys Asn Phe Thr Thr
            1060                1065                1070

Ala Pro Ala Ile Cys His Asp Gly Lys Ala His Phe Pro Arg Glu Gly
        1075                1080                1085

Val Phe Val Ser Asn Gly Thr His Trp Phe Val Thr Gln Arg Asn Phe
    1090                1095                1100

Tyr Glu Pro Gln Ile Ile Thr Thr Asp Asn Thr Phe Val Ser Gly Asn
1105                1110                1115                1120

Cys Asp Val Val Ile Gly Ile Val Asn Asn Thr Val Tyr Asp Pro Leu
                1125                1130                1135

Gln Pro Glu Leu Asp Ser Phe Lys Glu Glu Leu Asp Lys Tyr Phe Lys
```

```
            1140                1145                1150

Asn His Thr Ser Pro Asp Val Asp Leu Gly Asp Ile Ser Gly Ile Asn
        1155                1160                1165

Ala Ser Val Val Asn Ile Gln Lys Glu Ile Asp Arg Leu Asn Glu Val
    1170                1175                1180

Ala Lys Asn Leu Asn Glu Ser Leu Ile Asp Leu Gln Glu Leu Gly Lys
1185                1190                1195                1200

Tyr Glu Gln Tyr Ile Lys Trp Pro Trp Tyr Ile Trp Leu Gly Phe Ile
                1205                1210                1215

Ala Gly Leu Ile Ala Ile Val Met Val Thr Ile Met Leu Cys Cys Met
            1220                1225                1230

Thr Ser Cys Cys Ser Cys Leu Lys Gly Cys Cys Ser Cys Gly Ser Cys
        1235                1240                1245

Cys Lys Phe Asp Glu Asp Asp Ser Glu Pro Val Leu Lys Gly Val Lys
    1250                1255                1260

Leu His Tyr Thr
1265


<210> SEQ ID NO 10
<211> LENGTH: 1268
<212> TYPE: PRT
<213> ORGANISM: Artificial Sequence
<220> FEATURE:
<223> OTHER INFORMATION: Synthetic Construct

<400> SEQUENCE: 10

Phe Val Phe Leu Val Leu Leu Pro Leu Val Ser Ser Gln Cys Val Asn
1               5                   10                  15

Leu Thr Thr Arg Thr Gln Leu Pro Pro Ala Tyr Thr Asn Ser Phe Thr
            20                  25                  30

Arg Gly Val Tyr Tyr Pro Asp Lys Val Phe Arg Ser Ser Val Leu His
        35                  40                  45

Ser Thr Gln Asp Leu Phe Leu Pro Phe Phe Ser Asn Val Thr Trp Phe
    50                  55                  60

His Ala Ile His Val Ser Gly Thr Asn Gly Thr Lys Arg Phe Asp Asn
65                  70                  75                  80

Pro Val Leu Pro Phe Asn Asp Gly Val Tyr Phe Ala Ser Thr Glu Lys
                85                  90                  95

Ser Asn Ile Ile Arg Gly Trp Ile Phe Gly Thr Thr Leu Asp Ser Lys
            100                 105                 110

Thr Gln Ser Leu Leu Ile Val Asn Asn Ala Thr Asn Val Val Ile Lys
        115                 120                 125

Val Cys Glu Phe Gln Phe Cys Asn Asp Pro Phe Leu Gly Val Tyr Tyr
    130                 135                 140

His Lys Asn Asn Lys Ser Trp Met Glu Ser Glu Phe Arg Val Tyr Ser
145                 150                 155                 160

Ser Ala Asn Asn Cys Thr Phe Glu Tyr Val Ser Gln Pro Phe Leu Met
                165                 170                 175

Asp Leu Glu Gly Lys Gln Gly Asn Phe Lys Asn Leu Arg Glu Phe Val
            180                 185                 190

Phe Lys Asn Ile Asp Gly Tyr Phe Lys Ile Tyr Ser Lys His Thr Pro
        195                 200                 205

Ile Asn Leu Val Arg Asp Leu Pro Gln Gly Phe Ser Ala Leu Glu Pro
    210                 215                 220

Leu Val Asp Leu Pro Ile Gly Ile Asn Ile Thr Arg Phe Gln Thr Leu
```

```
225                 230                 235                 240

Leu Ala Leu His Arg Ser Tyr Leu Thr Pro Gly Asp Ser Ser Ser Gly
                245                 250                 255

Trp Thr Ala Gly Ala Ala Ala Tyr Tyr Val Gly Tyr Leu Gln Pro Arg
            260                 265                 270

Thr Phe Leu Leu Lys Tyr Asn Glu Asn Gly Thr Ile Thr Asp Ala Val
        275                 280                 285

Asp Cys Ala Leu Asp Pro Leu Ser Glu Thr Lys Cys Thr Leu Lys Ser
    290                 295                 300

Phe Thr Val Glu Lys Gly Ile Tyr Gln Thr Ser Asn Phe Arg Val Gln
305                 310                 315                 320

Pro Thr Glu Ser Ile Val Arg Phe Pro Asn Ile Thr Asn Leu Cys Pro
                325                 330                 335

Phe Gly Glu Val Phe Asn Ala Thr Arg Phe Ala Ser Val Tyr Ala Trp
            340                 345                 350

Asn Arg Lys Arg Ile Ser Asn Cys Val Ala Asp Tyr Ser Val Leu Tyr
        355                 360                 365

Asn Ser Ala Ser Phe Ser Thr Phe Lys Cys Tyr Gly Val Ser Pro Thr
    370                 375                 380

Lys Leu Asn Asp Leu Cys Phe Thr Asn Val Tyr Ala Asp Ser Phe Val
385                 390                 395                 400

Ile Arg Gly Asp Glu Val Arg Gln Ile Ala Pro Gly Gln Thr Gly Lys
                405                 410                 415

Ile Ala Asp Tyr Asn Tyr Lys Leu Pro Asp Asp Phe Thr Gly Cys Val
            420                 425                 430

Ile Ala Trp Asn Ser Asn Asn Leu Asp Ser Lys Val Gly Gly Asn Tyr
        435                 440                 445

Asn Tyr Leu Tyr Arg Leu Phe Arg Lys Ser Asn Leu Lys Pro Phe Glu
    450                 455                 460

Arg Asp Ile Ser Thr Glu Ile Tyr Gln Ala Gly Ser Thr Pro Cys Asn
465                 470                 475                 480

Gly Val Glu Gly Phe Asn Cys Tyr Phe Pro Leu Gln Ser Tyr Gly Phe
                485                 490                 495

Gln Pro Thr Asn Gly Val Gly Tyr Gln Pro Tyr Arg Val Val Val Leu
            500                 505                 510

Ser Phe Glu Leu Leu His Ala Pro Ala Thr Val Cys Gly Pro Lys Lys
        515                 520                 525

Ser Thr Asn Leu Val Lys Asn Lys Cys Val Asn Phe Asn Phe Asn Gly
    530                 535                 540

Leu Thr Gly Thr Gly Val Leu Thr Glu Ser Asn Lys Lys Phe Leu Pro
545                 550                 555                 560

Phe Gln Gln Phe Gly Arg Asp Ile Ala Asp Thr Thr Asp Ala Val Arg
                565                 570                 575

Asp Pro Gln Thr Leu Glu Ile Leu Asp Ile Thr Pro Cys Ser Phe Gly
            580                 585                 590

Gly Val Ser Val Ile Thr Pro Gly Thr Asn Thr Ser Asn Gln Val Ala
        595                 600                 605

Val Leu Tyr Gln Asp Val Asn Cys Thr Glu Val Pro Val Ala Ile His
    610                 615                 620

Ala Asp Gln Leu Thr Pro Thr Trp Arg Val Tyr Ser Thr Gly Ser Asn
625                 630                 635                 640

Val Phe Gln Thr Arg Ala Gly Cys Leu Ile Gly Ala Glu His Val Asn
                645                 650                 655
```

```
Asn Ser Tyr Glu Cys Asp Ile Pro Ile Gly Ala Gly Ile Cys Ala Ser
            660                 665                 670

Tyr Gln Thr Gln Thr Asn Ser Arg Ser Val Ala Ser Gln Ser Ile Ile
        675                 680                 685

Ala Tyr Thr Met Ser Leu Gly Ala Glu Asn Ser Val Ala Tyr Ser Asn
    690                 695                 700

Asn Ser Ile Ala Ile Pro Thr Asn Phe Thr Ile Ser Val Thr Thr Glu
705                 710                 715                 720

Ile Leu Pro Val Ser Met Thr Lys Thr Ser Val Asp Cys Thr Met Tyr
                725                 730                 735

Ile Cys Gly Asp Ser Thr Glu Cys Ser Asn Leu Leu Leu Gln Tyr Gly
            740                 745                 750

Ser Phe Cys Thr Gln Leu Asn Arg Ala Leu Thr Gly Ile Ala Val Glu
        755                 760                 765

Gln Asp Lys Asn Thr Gln Glu Val Phe Ala Gln Val Lys Gln Ile Tyr
    770                 775                 780

Lys Thr Pro Pro Ile Lys Asp Phe Gly Gly Phe Asn Phe Ser Gln Ile
785                 790                 795                 800

Leu Pro Asp Pro Ser Lys Pro Ser Lys Arg Ser Phe Ile Glu Asp Leu
                805                 810                 815

Leu Phe Asn Lys Val Thr Leu Ala Asp Ala Gly Phe Ile Lys Gln Tyr
            820                 825                 830

Gly Asp Cys Leu Gly Asp Ile Ala Ala Arg Asp Leu Ile Cys Ala Gln
        835                 840                 845

Lys Phe Asn Gly Leu Thr Val Leu Pro Pro Leu Leu Thr Asp Glu Met
    850                 855                 860

Ile Ala Gln Tyr Thr Ser Ala Leu Leu Ala Gly Thr Ile Thr Ser Gly
865                 870                 875                 880

Trp Thr Phe Gly Ala Gly Ala Ala Leu Gln Ile Pro Phe Ala Met Gln
                885                 890                 895

Met Ala Tyr Arg Phe Asn Gly Ile Gly Val Thr Gln Asn Val Leu Tyr
            900                 905                 910

Glu Asn Gln Lys Leu Ile Ala Asn Gln Phe Asn Ser Ala Ile Gly Lys
        915                 920                 925

Ile Gln Asp Ser Leu Ser Ser Thr Ala Ser Ala Leu Gly Lys Leu Gln
    930                 935                 940

Asp Val Val Asn Gln Asn Ala Gln Ala Leu Asn Thr Leu Val Lys Gln
945                 950                 955                 960

Leu Ser Ser Asn Phe Gly Ala Ile Ser Ser Val Leu Asn Asp Ile Leu
                965                 970                 975

Ser Arg Leu Asp Pro Pro Glu Ala Glu Val Gln Ile Asp Arg Leu Ile
            980                 985                 990

Thr Gly Arg Leu Gln Ser Leu Gln Thr Tyr Val Thr Gln Gln Leu Ile
        995                 1000                1005

Arg Ala Ala Glu Ile Arg Ala Ser Ala Asn Leu Ala Ala Thr Lys Met
    1010                1015                1020

Ser Glu Cys Val Leu Gly Gln Ser Lys Arg Val Asp Phe Cys Gly Lys
1025                1030                1035                1040

Gly Tyr His Leu Met Ser Phe Pro Gln Ser Ala Pro His Gly Val Val
                1045                1050                1055

Phe Leu His Val Thr Tyr Val Pro Ala Gln Glu Lys Asn Phe Thr Thr
            1060                1065                1070
```

```
Ala Pro Ala Ile Cys His Asp Gly Lys Ala His Phe Pro Arg Glu Gly
        1075                1080                1085

Val Phe Val Ser Asn Gly Thr His Trp Phe Val Thr Gln Arg Asn Phe
    1090                1095                1100

Tyr Glu Pro Gln Ile Ile Thr Thr Asp Asn Thr Phe Val Ser Gly Asn
1105                1110                1115                1120

Cys Asp Val Val Ile Gly Ile Val Asn Asn Thr Val Tyr Asp Pro Leu
                1125                1130                1135

Gln Pro Glu Leu Asp Ser Phe Lys Glu Glu Leu Asp Lys Tyr Phe Lys
            1140                1145                1150

Asn His Thr Ser Pro Asp Val Asp Leu Gly Asp Ile Ser Gly Ile Asn
        1155                1160                1165

Ala Ser Val Val Asn Ile Gln Lys Glu Ile Asp Arg Leu Asn Glu Val
    1170                1175                1180

Ala Lys Asn Leu Asn Glu Ser Leu Ile Asp Leu Gln Glu Leu Gly Lys
1185                1190                1195                1200

Tyr Glu Gln Tyr Ile Lys Trp Pro Trp Tyr Ile Trp Leu Gly Phe Ile
                1205                1210                1215

Ala Gly Leu Ile Ala Ile Val Met Val Thr Ile Met Leu Cys Cys Met
            1220                1225                1230

Thr Ser Cys Cys Ser Cys Leu Lys Gly Cys Cys Ser Cys Gly Ser Cys
        1235                1240                1245

Cys Lys Phe Asp Glu Asp Asp Ser Glu Pro Val Leu Lys Gly Val Lys
    1250                1255                1260

Leu His Tyr Thr
1265


<210> SEQ ID NO 11
<211> LENGTH: 1764
<212> TYPE: DNA
<213> ORGANISM: SARS-CoV-2

<400> SEQUENCE: 11

agtgtggctt ctcaaagcat tatagcatac actatgtctc ttggtgccga aaattccgtg      60

gcctattcta acaattcaat cgccatccca accaacttca caattagcgt gactaccgaa     120

atactgcctg tgagcatgac gaaaaccagc gtagactgca ctatgtatat ctgtggagac     180

tccactgagt gctccaacct tctcctgcag tacggtagct tctgtaccca attgaaccgc     240

gcccttacag gcatcgctgt tgagcaagat aagaataccc aggaagtttt tgcccaggtt     300

aagcagatat acaaaacacc gcccattaag gacttcggag gcttcaactt ctctcagata     360

ctgcctgacc cctccaagcc atcaaaacgc agcttcattg aggacctctt gttcaacaaa     420

gtgactctgg ctgatgctgg cttcattaag cagtacggag attgcctggg agatattgct     480

gccagggacc tcatctgcgc ccagaagttt aatggcctga cagtcttgcc cccacttctg     540

acagacgaga tgattgctca gtacacatct gccctcctcg ctggcaccat aacatccgga     600

tggacatttg gtgctggtgc tgccctccag attcccttcg caatgcagat ggcgtatcgc     660

tttaacggca tcggtgtcac acaaaacgtg ttgtatgaga accaaaagct catcgctaac     720

cagtttaatt ctgctattgg taagattcag gacagcctgt catcaaccgc gtctgccctt     780

ggtaagttgc aggacgtggt gaaccagaat gctcaggctt tgaatactct ggtgaagcaa     840

ctctcttcaa atttcggcgc tatctcttct gtgttgaacg acatcctgag tcgccttgat     900

aaggtggaag ctgaagttca aattgataga ttgattactg gcaggctcca gtctttgcag     960
```

```
acctacgtta cacagcagct gattagggcg gctgaaatta gagcttccgc caatctggct   1020
gcaaccaaga tgtccgaatg cgtcctgggt cagtcaaagc gcgttgactt ttgtggtaaa   1080
ggctaccacc tcatgtcatt tccccagtca gcacctcacg gagtagtgtt cctccacgtc   1140
acctacgttc cagcacagga aaagaatttt accactgcgc cggcaatctg tcacgacggt   1200
aaggcacact tcccccgcga gggcgtattc gtgtctaacg gaactcattg gttcgtcaca   1260
cagagaaact tctatgagcc tcagatcatt accaccgaca atacatttgt gtccggtaac   1320
tgcgacgttg tgattggaat cgtcaacaac actgtgtacg atccacttca gccagaactg   1380
gatagcttca aggaagaatt ggacaaatat ttcaaaaatc acacttcacc cgatgtggac   1440
ctgggtgaca ttagtggtat caatgcgtcc gtggtcaata ttcaaaaaga gattgacagg   1500
ctcaacgaag tggccaagaa cctgaacgaa agtcttatcg atctgcaaga attgggaaag   1560
tatgagcagt acatcaagtg gccgtggtac atttggttgg gttttatcgc cggtctgatc   1620
gccatcgtta tggttaccat tatgctttgc tgcatgacga gctgttgctc ctgtctgaag   1680
ggatgctgct cttgcggatc atgttgcaag ttcgatgaag acgatagcga accagttctg   1740
aagggcgtca agctgcatta caca                                          1764
```

```
<210> SEQ ID NO 12
<211> LENGTH: 1764
<212> TYPE: DNA
<213> ORGANISM: Artificial Sequence
<220> FEATURE:
<223> OTHER INFORMATION: Synthetic Construct

<400> SEQUENCE: 12
```

```
agtgtggctt ctcaaagcat tatagcatac actatgtctc ttggtgccga aaattccgtg     60
gcctattcta acaattcaat cgccatccca accaacttca caattagcgt gactaccgaa    120
atactgcctg tgagcatgac gaaaaccagc gtagactgca ctatgtatat ctgtggagac    180
tccactgagt gctccaacct tctcctgcag tacggtagct tctgtaccca attgaaccgc    240
gcccttacag gcatcgctgt tgagcaagat aagaataccc aggaagtttt tgcccaggtt    300
aagcagatat acaaaacacc gcccattaag gacttcggag gcttcaactt ctctcagata    360
ctgcctgacc cctccaagcc atcaaaacgc agcttcattg aggacctctt gttcaacaaa    420
gtgactctgg ctgatgctgg cttcattaag cagtacggag attgcctggg agatattgct    480
gccagggacc tcatctgcgc ccagaagttt aatggcctga cagtcttgcc cccacttctg    540
acagacgaga tgattgctca gtacacatct gccctcctcg ctggcaccat aacatccgga    600
tggacatttg gtgctggtgc tgccctccag attcccttcg caatgcagat ggcgtatcgc    660
tttaacggca tcggtgtcac acaaaacgtg ttgtatgaga accaaaagct catcgctaac    720
cagtttaatt ctgctattgg taagattcag gacagcctgt catcaaccgc gtctgccctt    780
ggtaagttgc aggacgtggt gaaccagaat gctcaggctt tgaatactct ggtgaagcaa    840
ctctcttcaa atttcggcgc tatctcttct gtgttgaacg acatcctgag tcgccttgat    900
cctccagaag ctgaagttca aattgataga ttgattactg gcaggctcca gtctttgcag    960
acctacgtta cacagcagct gattagggcg gctgaaatta gagcttccgc caatctggct   1020
gcaaccaaga tgtccgaatg cgtcctgggt cagtcaaagc gcgttgactt ttgtggtaaa   1080
ggctaccacc tcatgtcatt tccccagtca gcacctcacg gagtagtgtt cctccacgtc   1140
acctacgttc cagcacagga aaagaatttt accactgcgc cggcaatctg tcacgacggt   1200
aaggcacact tcccccgcga gggcgtattc gtgtctaacg gaactcattg gttcgtcaca   1260
```

```
cagagaaact tctatgagcc tcagatcatt accaccgaca atacatttgt gtccggtaac   1320

tgcgacgttg tgattggaat cgtcaacaac actgtgtacg atccacttca gccagaactg   1380

gatagcttca aggaagaatt ggacaaatat ttcaaaaatc acacttcacc cgatgtggac   1440

ctgggtgaca ttagtggtat caatgcgtcc gtggtcaata ttcaaaaaga gattgacagg   1500

ctcaacgaag tggccaagaa cctgaacgaa agtcttatcg atctgcaaga attgggaaag   1560

tatgagcagt acatcaagtg gccgtggtac atttggttgg gttttatcgc cggtctgatc   1620

gccatcgtta tggttaccat tatgctttgc tgcatgacga gctgttgctc ctgtctgaag   1680

ggatgctgct cttgcggatc atgttgcaag ttcgatgaag acgatagcga accagttctg   1740

aagggcgtca agctgcatta caca                                          1764
```

<210> SEQ ID NO 13
<211> LENGTH: 3816
<212> TYPE: DNA
<213> ORGANISM: SARS-CoV-2

<400> SEQUENCE: 13

```
ttcgttttcc ttgttctgtt gcctctcgtt agtagccaat gcgtcaacct tactactaga     60

acccagctcc ctccagcata taccaactct ttcaccaggg gcgtatatta cccggacaaa    120

gtgttccgct caagtgtgct gcattctacg caggaccttt tcttgccctt tttcagtaat    180

gttacttggt ttcatgctat ccatgtgtct ggaactaacg gaaccaagcg ctttgacaac    240

cccgtcctcc ctttcaacga tggcgtgtac ttcgcttcca cggaaaagtc aaacataatt    300

cgcggctgga tctttggtac aacactcgac tcaaagacgc agagcctgct gatcgttaat    360

aacgctacaa atgttgtgat aaaggtgtgt gaatttcagt tctgcaatga tcccttcctg    420

ggtgtgtact accataagaa taacaagagc tggatggaat ccgaatttag ggtttacagt    480

tccgctaaca actgcacatt cgaatacgta agccagccat ttcttatgga tcttgagggc    540

aagcaaggaa acttcaagaa cttgagggag ttcgtgttca aaaatatcga cggctatttt    600

aagatatata gcaagcacac tccaataaac ttggtgcgcg acctgcccca gggattctct    660

gctctggagc ccctggtgga tctgcccatt ggaataaaca taactcgctt tcaaacactg    720

ctcgccctgc atcgcagtta cctcacccct ggtgatagta gttcaggatg gacagcagga    780

gccgccgcat actacgtcgg ctacctgcag cctaggacct tcttgctgaa gtacaacgag    840

aacggtacaa taactgacgc tgtggactgc gctctggacc ctctgtccga gacgaagtgc    900

accctgaaga gctttactgt tgaaaaaggc atttaccaaa ccagcaactt ccgcgtccag    960

ccaaccgaga gcatcgtcag atttcccaac attacaaatc tgtgtccctt cggcgaggtg   1020

ttcaacgcca cacgcttcgc ttcagtgtac gcatggaacc gcaagcgcat atctaactgc   1080

gtcgcggatt attctgtcct ctacaactcc gcctctttct ccaccttcaa gtgctacgga   1140

gtgtcaccga ctaagctgaa cgatctctgc tttaccaacg tctacgcgga ctccttcgtg   1200

ataagaggtg atgaagtgag acaaatagcc ccaggtcaga ctggtaagat cgcagattac   1260

aactacaaat tgcctgatga tttcactggt tgcgttatcg cgtggaactc taataacctc   1320

gattctaagg tcggtggtaa ctacaattac ctgtaccgct tgtttaggaa gtcaaacctg   1380

aagcctttcg agagggatat ttcaaccgaa atctatcaag cgggttcaac accgtgtaac   1440

ggtgtggaag gatttaactg ctacttcccc ctgcagtctt acggattcca gccaaccaat   1500

ggcgtgggtt accaacctta tcgcgtggtg gttctgagtt tcgaactgtt gcacgctccc   1560
```

```
gccacggtat gcggtcccaa gaagagcact aacttggtga agaataagtg cgtgaatttc   1620
aatttcaatg gcctcactgg aactggagtg ctgaccgaat ccaataagaa gttcttgccc   1680
ttccagcagt tcggaagaga cattgctgac acaaccgacg cggtgcgcga tcctcagact   1740
ctggagatat tggacattac accatgttct ttcggcggtg tgtctgtcat tactccgggc   1800
acgaatacta gcaaccaggt agccgtgctg taccaagacg tgaattgcac agaggttccc   1860
gtcgcaattc acgctgacca gctgaccccc acgtggaggg tttacagcac tggtagtaac   1920
gtcttccaga cgagagccgg ttgcttgatc ggagcggaac atgtgaataa ctcctacgag   1980
tgcgacatcc ccatcggagc cggtatatgc gcctcttatc agacacaaac taactcaccc   2040
aggagagccc gcagtgtggc ttctcaaagc attatagcat acactatgtc tcttggtgcc   2100
gaaaattccg tggcctattc taacaattca atcgccatcc caaccaactt cacaattagc   2160
gtgactaccg aaatactgcc tgtgagcatg acgaaaacca gcgtagactg cactatgtat   2220
atctgtggag actccactga gtgctccaac cttctcctgc agtacggtag cttctgtacc   2280
caattgaacc gcgcccttac aggcatcgct gttgagcaag ataagaatac ccaggaagtt   2340
tttgcccagg ttaagcagat atacaaaaca ccgcccatta aggacttcgg aggcttcaac   2400
ttctctcaga tactgcctga cccctccaag ccatcaaaac gcagcttcat tgaggacctc   2460
ttgttcaaca aagtgactct ggctgatgct ggcttcatta agcagtacgg agattgcctg   2520
ggagatattg ctgccaggga cctcatctgc gcccagaagt ttaatggcct gacagtcttg   2580
cccccacttc tgacagacga gatgattgct cagtacacat ctgccctcct cgctggcacc   2640
ataacatccg gatggacatt tggtgctggt gctgccctcc agattccctt cgcaatgcag   2700
atggcgtatc gctttaacgg catcggtgtc acacaaaacg tgttgtatga gaaccaaaag   2760
ctcatcgcta accagtttaa ttctgctatt ggtaagattc aggacagcct gtcatcaacc   2820
gcgtctgccc ttggtaagtt gcaggacgtg gtgaaccaga atgctcaggc tttgaatact   2880
ctggtgaagc aactctcttc aaatttcggc gctatctctt ctgtgttgaa cgacatcctg   2940
agtcgccttg ataaggtgga agctgaagtt caaattgata gattgattac tggcaggctc   3000
cagtctttgc agacctacgt tacacagcag ctgattaggg cggctgaaat tagagcttcc   3060
gccaatctgg ctgcaaccaa gatgtccgaa tgcgtcctgg gtcagtcaaa gcgcgttgac   3120
ttttgtggta aaggctacca cctcatgtca tttccccagt cagcacctca cggagtagtg   3180
ttcctccacg tcacctacgt tccagcacag gaaaagaatt ttaccactgc gccggcaatc   3240
tgtcacgacg gtaaggcaca cttcccccgc gagggcgtat tcgtgtctaa cggaactcat   3300
tggttcgtca cacagagaaa cttctatgag cctcagatca ttaccaccga caatacattt   3360
gtgtccggta actgcgacgt tgtgattgga atcgtcaaca acactgtgta cgatccactt   3420
cagccagaac tggatagctt caaggaagaa ttggacaaat atttcaaaaa tcacacttca   3480
cccgatgtgg acctgggtga cattagtggt atcaatgcgt ccgtggtcaa tattcaaaaa   3540
gagattgaca ggctcaacga agtggccaag aacctgaacg aaagtcttat cgatctgcaa   3600
gaattgggaa agtatgagca gtacatcaag tggccgtggt acatttggtt gggttttatc   3660
gccggtctga tcgccatcgt tatggttacc attatgcttt gctgcatgac gagctgttgc   3720
tcctgtctga agggatgctg ctcttgcgga tcatgttgca agttcgatga agacgatagc   3780
gaaccagttc tgaagggcgt caagctgcat tacaca                              3816
```

<210> SEQ ID NO 14
<211> LENGTH: 3804

<212> TYPE: DNA
<213> ORGANISM: Artificial Sequence
<220> FEATURE:
<223> OTHER INFORMATION: Synthetic Construct

<400> SEQUENCE: 14
ttcgttttcc ttgttctgtt gcctctcgtt agtagccaat gcgtcaacct tactactaga 60
acccagctcc ctccagcata taccaactct ttcaccaggg gcgtatatta cccggacaaa 120
gtgttccgct caagtgtgct gcattctacg caggaccttt tcttgccctt tttcagtaat 180
gttacttggt ttcatgctat ccatgtgtct ggaactaacg gaaccaagcg ctttgacaac 240
cccgtcctcc ctttcaacga tggcgtgtac ttcgcttcca cggaaaagtc aaacataatt 300
cgcggctgga tctttggtac aacactcgac tcaaagacgc agagcctgct gatcgttaat 360
aacgctacaa atgttgtgat aaaggtgtgt gaatttcagt tctgcaatga tcccttcctg 420
ggtgtgtact accataagaa taacaagagc tggatggaat ccgaatttag ggtttacagt 480
tccgctaaca actgcacatt cgaatacgta agccagccat ttcttatgga tcttgagggc 540
aagcaaggaa acttcaagaa cttgagggag ttcgtgttca aaaatatcga cggctatttt 600
aagatatata gcaagcacac tccaataaac ttggtgcgcg acctgcccca gggattctct 660
gctctggagc ccctggtgga tctgcccatt ggaataaaca taactcgctt tcaaacactg 720
ctcgccctgc atcgcagtta cctcacccct ggtgatagta gttcaggatg gacagcagga 780
gccgccgcat actacgtcgg ctacctgcag cctaggacct tcttgctgaa gtacaacgag 840
aacggtacaa taactgacgc tgtggactgc gctctggacc ctctgtccga gacgaagtgc 900
accctgaaga gctttactgt tgaaaaaggc atttaccaaa ccagcaactt ccgcgtccag 960
ccaaccgaga gcatcgtcag atttcccaac attacaaatc tgtgtccctt cggcgaggtg 1020
ttcaacgcca cacgcttcgc ttcagtgtac gcatggaacc gcaagcgcat atctaactgc 1080
gtcgcggatt attctgtcct ctacaactcc gcctctttct ccaccttcaa gtgctacgga 1140
gtgtcaccga ctaagctgaa cgatctctgc tttaccaacg tctacgcgga ctccttcgtg 1200
ataagaggtg atgaagtgag acaaatagcc ccaggtcaga ctggtaagat cgcagattac 1260
aactacaaat tgcctgatga tttcactggt tgcgttatcg cgtggaactc taataacctc 1320
gattctaagg tcggtggtaa ctacaattac ctgtaccgct tgtttaggaa gtcaaacctg 1380
aagcctttcg agagggatat ttcaaccgaa atctatcaag cgggttcaac accgtgtaac 1440
ggtgtggaag gatttaactg ctacttcccc ctgcagtctt acggattcca gccaaccaat 1500
ggcgtgggtt accaacctta tcgcgtggtg gttctgagtt tcgaactgtt gcacgctccc 1560
gccacggtat gcggtcccaa gaagagcact aacttggtga agaataagtg cgtgaatttc 1620
aatttcaatg gcctcactgg aactggagtg ctgaccgaat ccaataagaa gttcttgccc 1680
ttccagcagt tcggaagaga cattgctgac acaaccgacg cggtgcgcga tcctcagact 1740
ctggagatat tggacattac accatgttct ttcggcggtg tgtctgtcat tactccgggc 1800
acgaatacta gcaaccaggt agccgtgctg taccaagacg tgaattgcac agaggttccc 1860
gtcgcaattc acgctgacca gctgaccccc acgtggaggg tttacagcac tggtagtaac 1920
gtcttccaga cgagagccgg ttgcttgatc ggagcggaac atgtgaataa ctcctacgag 1980
tgcgacatcc ccatcggagc cggtatatgc gcctcttatc agacacaaac taactcacgc 2040
agtgtggctt ctcaaagcat tatagcatac actatgtctc ttggtgccga aaattccgtg 2100
gcctattcta acaattcaat cgccatccca accaacttca caattagcgt gactaccgaa 2160
atactgcctg tgagcatgac gaaaaccagc gtagactgca ctatgtatat ctgtggagac 2220
tccactgagt gctccaacct tctcctgcag tacggtagct tctgtaccca attgaaccgc 2280
gcccttacag gcatcgctgt tgagcaagat aagaataccc aggaagtttt tgcccaggtt 2340
aagcagatat acaaaacacc gcccattaag gacttcggag gcttcaactt ctctcagata 2400
ctgcctgacc cctccaagcc atcaaaacgc agcttcattg aggacctctt gttcaacaaa 2460
gtgactctgg ctgatgctgg cttcattaag cagtacggag attgcctggg agatattgct 2520
gccagggacc tcatctgcgc ccagaagttt aatggcctga cagtcttgcc cccacttctg 2580
acagacgaga tgattgctca gtacacatct gccctcctcg ctggcaccat aacatccgga 2640
tggacatttg gtgctggtgc tgccctccag attcccttcg caatgcagat ggcgtatcgc 2700
tttaacggca tcggtgtcac acaaaacgtg ttgtatgaga accaaaagct catcgctaac 2760
cagtttaatt ctgctattgg taagattcag gacagcctgt catcaaccgc gtctgccctt 2820
ggtaagttgc aggacgtggt gaaccagaat gctcaggctt tgaatactct ggtgaagcaa 2880
ctctcttcaa atttcggcgc tatctcttct gtgttgaacg acatcctgag tcgccttgat 2940
aaggtggaag ctgaagttca aattgataga ttgattactg gcaggctcca gtctttgcag 3000
acctacgtta cacagcagct gattagggcg gctgaaatta gagcttccgc caatctggct 3060
gcaaccaaga tgtccgaatg cgtcctgggt cagtcaaagc gcgttgactt ttgtggtaaa 3120
ggctaccacc tcatgtcatt tccccagtca gcacctcacg gagtagtgtt cctccacgtc 3180
acctacgttc cagcacagga aaagaatttt accactgcgc cggcaatctg tcacgacggt 3240
aaggcacact tcccccgcga gggcgtattc gtgtctaacg gaactcattg gttcgtcaca 3300
cagagaaact tctatgagcc tcagatcatt accaccgaca atacatttgt gtccggtaac 3360
tgcgacgttg tgattggaat cgtcaacaac actgtgtacg atccacttca gccagaactg 3420
gatagcttca aggaagaatt ggacaaatat ttcaaaaatc acacttcacc cgatgtggac 3480
ctgggtgaca ttagtggtat caatgcgtcc gtggtcaata ttcaaaaaga gattgacagg 3540
ctcaacgaag tggccaagaa cctgaacgaa agtcttatcg atctgcaaga attgggaaag 3600
tatgagcagt acatcaagtg gccgtggtac atttggttgg gttttatcgc cggtctgatc 3660
gccatcgtta tggttaccat tatgctttgc tgcatgacga gctgttgctc ctgtctgaag 3720
ggatgctgct cttgcggatc atgttgcaag ttcgatgaag acgatagcga accagttctg 3780
aagggcgtca agctgcatta caca 3804

<210> SEQ ID NO 15
<211> LENGTH: 3804
<212> TYPE: DNA
<213> ORGANISM: Artificial Sequence
<220> FEATURE:
<223> OTHER INFORMATION: Synthetic Construct

<400> SEQUENCE: 15
ttcgttttcc ttgttctgtt gcctctcgtt agtagccaat gcgtcaacct tactactaga 60
acccagctcc ctccagcata taccaactct ttcaccaggg gcgtatatta cccggacaaa 120
gtgttccgct caagtgtgct gcattctacg caggaccttt tcttgccctt tttcagtaat 180
gttacttggt ttcatgctat ccatgtgtct ggaactaacg gaaccaagcg ctttgacaac 240
cccgtcctcc ctttcaacga tggcgtgtac ttcgcttcca cggaaaagtc aaacataatt 300
cgcggctgga tctttggtac aacactcgac tcaaagacgc agagcctgct gatcgttaat 360
aacgctacaa atgttgtgat aaaggtgtgt gaatttcagt tctgcaatga tcccttcctg 420

```
ggtgtgtact accataagaa taacaagagc tggatggaat ccgaatttag ggtttacagt    480
tccgctaaca actgcacatt cgaatacgta agccagccat ttcttatgga tcttgagggc    540
aagcaaggaa acttcaagaa cttgagggag ttcgtgttca aaaatatcga cggctatttt    600
aagatatata gcaagcacac tccaataaac ttggtgcgcg acctgcccca gggattctct    660
gctctggagc ccctggtgga tctgcccatt ggaataaaca taactcgctt tcaaacactg    720
ctcgccctgc atcgcagtta cctcacccct ggtgatagta gttcaggatg gacagcagga    780
gccgccgcat actacgtcgg ctacctgcag cctaggacct tcttgctgaa gtacaacgag    840
aacggtacaa taactgacgc tgtggactgc gctctggacc ctctgtccga gacgaagtgc    900
accctgaaga gctttactgt tgaaaaaggc atttaccaaa ccagcaactt ccgcgtccag    960
ccaaccgaga gcatcgtcag atttcccaac attacaaatc tgtgtccctt cggcgaggtg   1020
ttcaacgcca cacgcttcgc ttcagtgtac gcatggaacc gcaagcgcat atctaactgc   1080
gtcgcggatt attctgtcct ctacaactcc gcctctttct ccaccttcaa gtgctacgga   1140
gtgtcaccga ctaagctgaa cgatctctgc tttaccaacg tctacgcgga ctccttcgtg   1200
ataagaggtg atgaagtgag acaaatagcc ccaggtcaga ctggtaagat cgcagattac   1260
aactacaaat tgcctgatga tttcactggt tgcgttatcg cgtggaactc taataacctc   1320
gattctaagg tcggtggtaa ctacaattac ctgtaccgct tgtttaggaa gtcaaacctg   1380
aagcctttcg agagggatat ttcaaccgaa atctatcaag cgggttcaac accgtgtaac   1440
ggtgtggaag gatttaactg ctacttcccc ctgcagtctt acggattcca gccaaccaat   1500
ggcgtgggtt accaacctta tcgcgtggtg gttctgagtt tcgaactgtt gcacgctccc   1560
gccacggtat gcggtcccaa gaagagcact aacttggtga agaataagtg cgtgaatttc   1620
aatttcaatg gcctcactgg aactggagtg ctgaccgaat ccaataagaa gttcttgccc   1680
ttccagcagt tcggaagaga cattgctgac acaaccgacg cggtgcgcga tcctcagact   1740
ctggagatat tggacattac accatgttct ttcggcggtg tgtctgtcat tactccgggc   1800
acgaatacta gcaaccaggt agccgtgctg taccaagacg tgaattgcac agaggttccc   1860
gtcgcaattc acgctgacca gctgaccccc acgtggaggg tttacagcac tggtagtaac   1920
gtcttccaga cgagagccgg ttgcttgatc ggagcggaac atgtgaataa ctcctacgag   1980
tgcgacatcc ccatcggagc cggtatatgc gcctcttatc agacacaaac taactcacgc   2040
agtgtggctt ctcaaagcat tatagcatac actatgtctc ttggtgccga aaattccgtg   2100
gcctattcta acaattcaat cgccatccca accaacttca caattagcgt gactaccgaa   2160
atactgcctg tgagcatgac gaaaaccagc gtagactgca ctatgtatat ctgtggagac   2220
tccactgagt gctccaacct tctcctgcag tacggtagct tctgtaccca attgaaccgc   2280
gcccttacag gcatcgctgt tgagcaagat aagaataccc aggaagtttt tgcccaggtt   2340
aagcagatat acaaaacacc gcccattaag gacttcggag gcttcaactt ctctcagata   2400
ctgcctgacc cctccaagcc atcaaaacgc agcttcattg aggacctctt gttcaacaaa   2460
gtgactctgg ctgatgctgg cttcattaag cagtacggag attgcctggg agatattgct   2520
gccagggacc tcatctgcgc ccagaagttt aatggcctga cagtcttgcc cccacttctg   2580
acagacgaga tgattgctca gtacacatct gccctcctcg ctggcaccat aacatccgga   2640
tggacatttg gtgctggtgc tgccctccag attcccttcg caatgcagat ggcgtatcgc   2700
tttaacggca tcggtgtcac acaaaacgtg ttgtatgaga accaaaagct catcgctaac   2760
```

```
cagtttaatt ctgctattgg taagattcag gacagcctgt catcaaccgc gtctgccctt   2820

ggtaagttgc aggacgtggt gaaccagaat gctcaggctt tgaatactct ggtgaagcaa   2880

ctctcttcaa atttcggcgc tatctcttct gtgttgaacg acatcctgag tcgccttgat   2940

cctccagaag ctgaagttca aattgataga ttgattactg gcaggctcca gtctttgcag   3000

acctacgtta cacagcagct gattagggcg gctgaaatta gagcttccgc caatctggct   3060

gcaaccaaga tgtccgaatg cgtcctgggt cagtcaaagc gcgttgactt ttgtggtaaa   3120

ggctaccacc tcatgtcatt tccccagtca gcacctcacg gagtagtgtt cctccacgtc   3180

acctacgttc cagcacagga aaagaatttt accactgcgc cggcaatctg tcacgacggt   3240

aaggcacact tcccccgcga gggcgtattc gtgtctaacg gaactcattg gttcgtcaca   3300

cagagaaact tctatgagcc tcagatcatt accaccgaca atacatttgt gtccggtaac   3360

tgcgacgttg tgattggaat cgtcaacaac actgtgtacg atccacttca gccagaactg   3420

gatagcttca aggaagaatt ggacaaatat ttcaaaaatc acacttcacc cgatgtggac   3480

ctgggtgaca ttagtggtat caatgcgtcc gtggtcaata ttcaaaaaga gattgacagg   3540

ctcaacgaag tggccaagaa cctgaacgaa agtcttatcg atctgcaaga attgggaaag   3600

tatgagcagt acatcaagtg gccgtggtac atttggttgg gttttatcgc cggtctgatc   3660

gccatcgtta tggttaccat tatgctttgc tgcatgacga gctgttgctc ctgtctgaag   3720

ggatgctgct cttgcggatc atgttgcaag ttcgatgaag acgatagcga accagttctg   3780

aagggcgtca agctgcatta caca                                          3804
```

```
<210> SEQ ID NO 16
<211> LENGTH: 31
<212> TYPE: PRT
<213> ORGANISM: Artificial Sequence
<220> FEATURE:
<223> OTHER INFORMATION: Synthetic Construct

<400> SEQUENCE: 16

Asp Ala Met Lys Arg Gly Leu Cys Cys Val Leu Leu Leu Cys Gly Ala
1               5                   10                  15

Val Phe Val Ser Pro Ser Gln Glu Ile His Ala Arg Phe Arg Arg
            20                  25                  30


<210> SEQ ID NO 17
<211> LENGTH: 17
<212> TYPE: PRT
<213> ORGANISM: Homo sapiens

<400> SEQUENCE: 17

Asp Trp Thr Trp Ile Leu Phe Leu Val Ala Ala Ala Thr Arg Val His
1               5                   10                  15

Ser


<210> SEQ ID NO 18
<211> LENGTH: 634
<212> TYPE: PRT
<213> ORGANISM: Mus musculus

<400> SEQUENCE: 18

Met Leu Thr Phe Phe Ala Ala Phe Leu Ala Ala Pro Leu Ala Leu Ala
1               5                   10                  15

Glu Ser Pro Tyr Leu Val Arg Val Asp Ala Ala Arg Pro Leu Arg Pro
            20                  25                  30
```

```
Leu Leu Pro Phe Trp Arg Ser Thr Gly Phe Cys Pro Pro Leu Pro His
        35                  40                  45

Asp Gln Ala Asp Gln Tyr Asp Leu Ser Trp Asp Gln Gln Leu Asn Leu
    50                  55                  60

Ala Tyr Ile Gly Ala Val Pro His Ser Gly Ile Glu Gln Val Arg Ile
65                  70                  75                  80

His Trp Leu Leu Asp Leu Ile Thr Ala Arg Lys Ser Pro Gly Gln Gly
                85                  90                  95

Leu Met Tyr Asn Phe Thr His Leu Asp Ala Phe Leu Asp Leu Leu Met
            100                 105                 110

Glu Asn Gln Leu Leu Pro Gly Phe Glu Leu Met Gly Ser Pro Ser Gly
        115                 120                 125

Tyr Phe Thr Asp Phe Asp Asp Lys Gln Gln Val Phe Glu Trp Lys Asp
    130                 135                 140

Leu Val Ser Leu Leu Ala Arg Arg Tyr Ile Gly Arg Tyr Gly Leu Thr
145                 150                 155                 160

His Val Ser Lys Trp Asn Phe Glu Thr Trp Asn Glu Pro Asp His His
                165                 170                 175

Asp Phe Asp Asn Val Ser Met Thr Thr Gln Gly Phe Leu Asn Tyr Tyr
            180                 185                 190

Asp Ala Cys Ser Glu Gly Leu Arg Ile Ala Ser Pro Thr Leu Lys Leu
        195                 200                 205

Gly Gly Pro Gly Asp Ser Phe His Pro Leu Pro Arg Ser Pro Met Cys
    210                 215                 220

Trp Ser Leu Leu Gly His Cys Ala Asn Gly Thr Asn Phe Phe Thr Gly
225                 230                 235                 240

Glu Val Gly Val Arg Leu Asp Tyr Ile Ser Leu His Lys Lys Gly Ala
                245                 250                 255

Gly Ser Ser Ile Ala Ile Leu Glu Gln Glu Met Ala Val Val Glu Gln
            260                 265                 270

Val Gln Gln Leu Phe Pro Glu Phe Lys Asp Thr Pro Ile Tyr Asn Asp
        275                 280                 285

Glu Ala Asp Pro Leu Val Gly Trp Ser Leu Pro Gln Pro Trp Arg Ala
    290                 295                 300

Asp Val Thr Tyr Ala Ala Leu Val Val Lys Val Ile Ala Gln His Gln
305                 310                 315                 320

Asn Leu Leu Phe Ala Asn Ser Ser Ser Ser Met Arg Tyr Val Leu Leu
                325                 330                 335

Ser Asn Asp Asn Ala Phe Leu Ser Tyr His Pro Tyr Pro Phe Ser Gln
            340                 345                 350

Arg Thr Leu Thr Ala Arg Phe Gln Val Asn Asn Thr His Pro Pro His
        355                 360                 365

Val Gln Leu Leu Arg Lys Pro Val Leu Thr Val Met Gly Leu Met Ala
    370                 375                 380

Leu Leu Asp Gly Glu Gln Leu Trp Ala Glu Val Ser Lys Ala Gly Ala
385                 390                 395                 400

Val Leu Asp Ser Asn His Thr Val Gly Val Leu Ala Ser Thr His His
                405                 410                 415

Pro Glu Gly Ser Ala Ala Ala Trp Ser Thr Thr Val Leu Ile Tyr Thr
            420                 425                 430

Ser Asp Asp Thr His Ala His Pro Asn His Ser Ile Pro Val Thr Leu
        435                 440                 445

Arg Leu Arg Gly Val Pro Pro Gly Leu Asp Leu Val Tyr Ile Val Leu
```

```
    450                 455                 460

Tyr Leu Asp Asn Gln Leu Ser Ser Pro Tyr Ser Ala Trp Gln His Met
465                 470                 475                 480

Gly Gln Pro Val Phe Pro Ser Ala Glu Gln Phe Arg Arg Met Arg Met
                485                 490                 495

Val Glu Asp Pro Val Ala Glu Ala Pro Arg Pro Phe Pro Ala Arg Gly
            500                 505                 510

Arg Leu Thr Leu His Arg Lys Leu Pro Val Pro Ser Leu Leu Leu Val
        515                 520                 525

His Val Cys Thr Arg Pro Leu Lys Pro Pro Gly Gln Val Ser Arg Leu
    530                 535                 540

Arg Ala Leu Pro Leu Thr His Gly Gln Leu Ile Leu Val Trp Ser Asp
545                 550                 555                 560

Glu Arg Val Gly Ser Lys Cys Leu Trp Thr Tyr Glu Ile Gln Phe Ser
                565                 570                 575

Gln Lys Gly Glu Glu Tyr Ala Pro Ile Asn Arg Arg Pro Ser Thr Phe
            580                 585                 590

Asn Leu Phe Val Phe Ser Pro Asp Thr Ala Val Val Ser Gly Ser Tyr
        595                 600                 605

Arg Val Arg Ala Leu Asp Tyr Trp Ala Arg Pro Gly Pro Phe Ser Asp
    610                 615                 620

Pro Val Thr Tyr Leu Asp Val Pro Ala Ser
625                 630


<210> SEQ ID NO 19
<211> LENGTH: 653
<212> TYPE: PRT
<213> ORGANISM: Homo sapiens

<400> SEQUENCE: 19

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190
```

```
Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
```

```
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650


<210> SEQ ID NO 20
<211> LENGTH: 354
<212> TYPE: PRT
<213> ORGANISM: Mus musculus

<400> SEQUENCE: 20

Met Leu Ser Asn Leu Arg Ile Leu Leu Asn Asn Ala Ala Leu Arg Lys
1               5                   10                  15

Gly His Thr Ser Val Val Arg His Phe Trp Cys Gly Lys Pro Val Gln
            20                  25                  30

Ser Gln Val Gln Leu Lys Gly Arg Asp Leu Leu Thr Leu Lys Asn Phe
        35                  40                  45

Thr Gly Glu Glu Ile Gln Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Ser Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Thr Asp Ala Val Leu Ala Arg Val Tyr Lys
    130                 135                 140

Gln Ser Asp Leu Asp Thr Leu Ala Lys Glu Ala Ser Ile Pro Ile Val
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Gly Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Pro Asn Ile Val Lys Leu Ala Glu Gln Tyr Ala Lys Glu Asn
225                 230                 235                 240

Gly Thr Lys Leu Ser Met Thr Asn Asp Pro Leu Glu Ala Ala Arg Gly
                245                 250                 255

Gly Asn Val Leu Ile Thr Asp Thr Trp Ile Ser Met Gly Gln Glu Asp
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335
```

```
Val Met Val Ser Leu Leu Thr Asp Tyr Ser Pro Val Leu Gln Lys Pro
            340                 345                 350

Lys Phe


<210> SEQ ID NO 21
<211> LENGTH: 419
<212> TYPE: PRT
<213> ORGANISM: Mus musculus

<400> SEQUENCE: 21

Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
            20                  25                  30

Gly Val Ala Ile Gly Asp Gln Ile Leu Asp Leu Ser Val Ile Lys His
        35                  40                  45

Leu Phe Thr Gly Pro Ala Leu Ser Lys His Gln His Val Phe Asp Glu
    50                  55                  60

Thr Thr Leu Asn Asn Phe Met Gly Leu Gly Gln Ala Ala Trp Lys Glu
65                  70                  75                  80

Ala Arg Ala Ser Leu Gln Asn Leu Leu Ser Ala Ser Gln Ala Arg Leu
                85                  90                  95

Arg Asp Asp Lys Glu Leu Arg Gln Arg Ala Phe Thr Ser Gln Ala Ser
            100                 105                 110

Ala Thr Met His Leu Pro Ala Thr Ile Gly Asp Tyr Thr Asp Phe Tyr
        115                 120                 125

Ser Ser Arg Gln His Ala Thr Asn Val Gly Ile Met Phe Arg Gly Lys
    130                 135                 140

Glu Asn Ala Leu Leu Pro Asn Trp Leu His Leu Pro Val Gly Tyr His
145                 150                 155                 160

Gly Arg Ala Ser Ser Ile Val Val Ser Gly Thr Pro Ile Arg Arg Pro
                165                 170                 175

Met Gly Gln Met Arg Pro Asp Asn Ser Lys Pro Pro Val Tyr Gly Ala
            180                 185                 190

Cys Arg Leu Leu Asp Met Glu Leu Glu Met Ala Phe Phe Val Gly Pro
        195                 200                 205

Gly Asn Arg Phe Gly Glu Pro Ile Pro Ile Ser Lys Ala His Glu His
    210                 215                 220

Ile Phe Gly Met Val Leu Met Asn Asp Trp Ser Ala Arg Asp Ile Gln
225                 230                 235                 240

Gln Trp Glu Tyr Val Pro Leu Gly Pro Phe Leu Gly Lys Ser Phe Gly
                245                 250                 255

Thr Thr Ile Ser Pro Trp Val Val Pro Met Asp Ala Leu Met Pro Phe
            260                 265                 270

Val Val Pro Asn Pro Lys Gln Asp Pro Lys Pro Leu Pro Tyr Leu Cys
        275                 280                 285

His Ser Gln Pro Tyr Thr Phe Asp Ile Asn Leu Ser Val Ser Leu Lys
    290                 295                 300

Gly Glu Gly Met Ser Gln Ala Ala Thr Ile Cys Arg Ser Asn Phe Lys
305                 310                 315                 320

His Met Tyr Trp Thr Met Leu Gln Gln Leu Thr His His Ser Val Asn
                325                 330                 335

Gly Cys Asn Leu Arg Pro Gly Asp Leu Leu Ala Ser Gly Thr Ile Ser
            340                 345                 350
```

Gly Ser Asp Pro Glu Ser Phe Gly Ser Met Leu Glu Leu Ser Trp Lys
355 360 365

Gly Thr Lys Ala Ile Asp Val Glu Gln Gly Gln Thr Arg Thr Phe Leu
370 375 380

Leu Asp Gly Asp Glu Val Ile Ile Thr Gly His Cys Gln Gly Asp Gly
385 390 395 400

Tyr Arg Val Gly Phe Gly Gln Cys Ala Gly Lys Val Leu Pro Ala Leu
405 410 415

Ser Pro Ala

<210> SEQ ID NO 22
<211> LENGTH: 1983
<212> TYPE: PRT
<213> ORGANISM: Homo sapiens

<400> SEQUENCE: 22

Met Leu Trp Trp Glu Glu Val Glu Asp Cys Tyr Glu Arg Glu Asp Val
1 5 10 15

Gln Lys Lys Thr Phe Thr Lys Trp Val Asn Ala Gln Phe Ser Lys Phe
20 25 30

Gly Lys Gln His Ile Glu Asn Leu Phe Ser Asp Leu Gln Asp Gly Arg
35 40 45

Arg Leu Leu Asp Leu Leu Glu Gly Leu Thr Gly Gln Lys Leu Pro Lys
50 55 60

Glu Lys Gly Ser Thr Arg Val His Ala Leu Asn Asn Val Asn Lys Ala
65 70 75 80

Leu Arg Val Leu Gln Asn Asn Asn Val Asp Leu Val Asn Ile Gly Ser
85 90 95

Thr Asp Ile Val Asp Gly Asn His Lys Leu Thr Leu Gly Leu Ile Trp
100 105 110

Asn Ile Ile Leu His Trp Gln Val Lys Asn Val Met Lys Asn Ile Met
115 120 125

Ala Gly Leu Gln Gln Thr Asn Ser Glu Lys Ile Leu Leu Ser Trp Val
130 135 140

Arg Gln Ser Thr Arg Asn Tyr Pro Gln Val Asn Val Ile Asn Phe Thr
145 150 155 160

Thr Ser Trp Ser Asp Gly Leu Ala Leu Asn Ala Leu Ile His Ser His
165 170 175

Arg Pro Asp Leu Phe Asp Trp Asn Ser Val Val Cys Gln Gln Ser Ala
180 185 190

Thr Gln Arg Leu Glu His Ala Phe Asn Ile Ala Arg Tyr Gln Leu Gly
195 200 205

Ile Glu Lys Leu Leu Asp Pro Glu Asp Val Asp Thr Thr Tyr Pro Asp
210 215 220

Lys Lys Ser Ile Leu Met Tyr Ile Thr Ser Leu Phe Gln Val Leu Pro
225 230 235 240

Gln Gln Val Ser Ile Glu Ala Ile Gln Glu Val Glu Met Leu Pro Arg
245 250 255

Pro Pro Lys Val Thr Lys Glu Glu His Phe Gln Leu His His Gln Met
260 265 270

His Tyr Ser Gln Gln Ile Thr Val Ser Leu Ala Gln Gly Tyr Glu Arg
275 280 285

Thr Ser Ser Pro Lys Pro Arg Phe Lys Ser Tyr Ala Tyr Thr Gln Ala
290 295 300

```
Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Glu Thr Glu Ile Ala Val Gln Ala
            660                 665                 670

Lys Gln Pro Asp Val Glu Glu Ile Leu Ser Lys Gly Gln His Leu Tyr
        675                 680                 685

Lys Glu Lys Pro Ala Thr Gln Pro Val Lys Arg Lys Leu Glu Asp Leu
    690                 695                 700

Ser Ser Glu Trp Lys Ala Val Asn Arg Leu Leu Gln Glu Leu Arg Ala
705                 710                 715                 720

Lys Gln Pro Asp Leu Ala Pro Gly Leu Thr Thr Ile Gly Ala Ser Pro
```

```
                725                 730                 735

Thr Gln Thr Val Thr Leu Val Thr Gln Pro Val Val Thr Lys Glu Thr
            740                 745                 750

Ala Ile Ser Lys Leu Glu Met Pro Ser Ser Leu Met Leu Glu Val Pro
        755                 760                 765

Ala Leu Ala Asp Phe Asn Arg Ala Trp Thr Glu Leu Thr Asp Trp Leu
    770                 775                 780

Ser Leu Leu Asp Gln Val Ile Lys Ser Gln Arg Val Met Val Gly Asp
785                 790                 795                 800

Leu Glu Asp Ile Asn Glu Met Ile Ile Lys Gln Lys Ala Thr Met Gln
                805                 810                 815

Asp Leu Glu Gln Arg Arg Pro Gln Leu Glu Glu Leu Ile Thr Ala Ala
            820                 825                 830

Gln Asn Leu Lys Asn Lys Thr Ser Asn Gln Glu Ala Arg Thr Ile Ile
        835                 840                 845

Thr Asp Arg Ile Glu Arg Ile Gln Asn Gln Trp Asp Glu Val Gln Glu
    850                 855                 860

His Leu Gln Asn Arg Arg Gln Gln Leu Asn Glu Met Leu Lys Asp Ser
865                 870                 875                 880

Thr Gln Trp Leu Glu Ala Lys Glu Glu Ala Glu Gln Val Leu Gly Gln
                885                 890                 895

Ala Arg Ala Lys Leu Glu Ser Trp Lys Glu Gly Pro Tyr Thr Val Asp
            900                 905                 910

Ala Ile Gln Lys Lys Ile Thr Glu Thr Lys Gln Leu Ala Lys Asp Leu
        915                 920                 925

Arg Gln Trp Gln Thr Asn Val Asp Val Ala Asn Asp Leu Ala Leu Lys
    930                 935                 940

Leu Leu Arg Asp Tyr Ser Ala Asp Asp Thr Arg Lys Val His Met Ile
945                 950                 955                 960

Thr Glu Asn Ile Asn Ala Ser Trp Arg Ser Ile His Lys Arg Val Ser
                965                 970                 975

Glu Arg Glu Ala Ala Leu Glu Glu Thr His Arg Leu Leu Gln Gln Phe
            980                 985                 990

Pro Leu Asp Leu Glu Lys Phe Leu Ala Trp Leu Thr Glu Ala Glu Thr
        995                 1000                1005

Thr Ala Asn Val Leu Gln Asp Ala Thr Arg Lys Glu Arg Leu Leu Glu
    1010                1015                1020

Asp Ser Lys Gly Val Lys Glu Leu Met Lys Gln Trp Gln Asp Leu Gln
1025                1030                1035                1040

Gly Glu Ile Glu Ala His Thr Asp Val Tyr His Asn Leu Asp Glu Asn
                1045                1050                1055

Ser Gln Lys Ile Leu Arg Ser Leu Glu Gly Ser Asp Asp Ala Val Leu
            1060                1065                1070

Leu Gln Arg Arg Leu Asp Asn Met Asn Phe Lys Trp Ser Glu Leu Arg
        1075                1080                1085

Lys Lys Ser Leu Asn Ile Arg Ser His Leu Glu Ala Ser Ser Asp Gln
    1090                1095                1100

Trp Lys Arg Leu His Leu Ser Leu Gln Glu Leu Leu Val Trp Leu Gln
1105                1110                1115                1120

Leu Lys Asp Asp Glu Leu Ser Arg Gln Ala Pro Ile Gly Gly Asp Phe
                1125                1130                1135

Pro Ala Val Gln Lys Gln Asn Asp Val His Arg Ala Phe Lys Arg Glu
            1140                1145                1150
```

-continued

Leu Lys Thr Lys Glu Pro Val Ile Met Ser Thr Leu Glu Thr Val Arg
1155 1160 1165

Ile Phe Leu Thr Glu Gln Pro Leu Glu Gly Leu Glu Lys Leu Tyr Gln
1170 1175 1180

Glu Pro Arg Glu Leu Pro Pro Glu Glu Arg Ala Gln Asn Val Thr Arg
1185 1190 1195 1200

Leu Leu Arg Lys Gln Ala Glu Glu Val Asn Thr Glu Trp Glu Lys Leu
1205 1210 1215

Asn Leu His Ser Ala Asp Trp Gln Arg Lys Ile Asp Glu Thr Leu Glu
1220 1225 1230

Arg Leu Arg Glu Leu Gln Glu Ala Thr Asp Glu Leu Asp Leu Lys Leu
1235 1240 1245

Arg Gln Ala Glu Val Ile Lys Gly Ser Trp Gln Pro Val Gly Asp Leu
1250 1255 1260

Leu Ile Asp Ser Leu Gln Asp His Leu Glu Lys Val Lys Ala Leu Arg
1265 1270 1275 1280

Gly Glu Ile Ala Pro Leu Lys Glu Asn Val Ser His Val Asn Asp Leu
1285 1290 1295

Ala Arg Gln Leu Thr Thr Leu Gly Ile Gln Leu Ser Pro Tyr Asn Leu
1300 1305 1310

Ser Thr Leu Glu Asp Leu Asn Thr Arg Trp Lys Leu Leu Gln Val Ala
1315 1320 1325

Val Glu Asp Arg Val Arg Gln Leu His Glu Ala His Arg Asp Phe Gly
1330 1335 1340

Pro Ala Ser Gln His Phe Leu Ser Thr Ser Val Gln Gly Pro Trp Glu
1345 1350 1355 1360

Arg Ala Ile Ser Pro Asn Lys Val Pro Tyr Tyr Ile Asn His Glu Thr
1365 1370 1375

Gln Thr Thr Cys Trp Asp His Pro Lys Met Thr Glu Leu Tyr Gln Ser
1380 1385 1390

Leu Ala Asp Leu Asn Asn Val Arg Phe Ser Ala Tyr Arg Thr Ala Met
1395 1400 1405

Lys Leu Arg Arg Leu Gln Lys Ala Leu Cys Leu Asp Leu Leu Ser Leu
1410 1415 1420

Ser Ala Ala Cys Asp Ala Leu Asp Gln His Asn Leu Lys Gln Asn Asp
1425 1430 1435 1440

Gln Pro Met Asp Ile Leu Gln Ile Ile Asn Cys Leu Thr Thr Ile Tyr
1445 1450 1455

Asp Arg Leu Glu Gln Glu His Asn Asn Leu Val Asn Val Pro Leu Cys
1460 1465 1470

Val Asp Met Cys Leu Asn Trp Leu Leu Asn Val Tyr Asp Thr Gly Arg
1475 1480 1485

Thr Gly Arg Ile Arg Val Leu Ser Phe Lys Thr Gly Ile Ile Ser Leu
1490 1495 1500

Cys Lys Ala His Leu Glu Asp Lys Tyr Arg Tyr Leu Phe Lys Gln Val
1505 1510 1515 1520

Ala Ser Ser Thr Gly Phe Cys Asp Gln Arg Arg Leu Gly Leu Leu Leu
1525 1530 1535

His Asp Ser Ile Gln Ile Pro Arg Gln Leu Gly Glu Val Ala Ser Phe
1540 1545 1550

Gly Gly Ser Asn Ile Glu Pro Ser Val Arg Ser Cys Phe Gln Phe Ala
1555 1560 1565

```
Asn Asn Lys Pro Glu Ile Glu Ala Ala Leu Phe Leu Asp Trp Met Arg
    1570                1575                1580

Leu Glu Pro Gln Ser Met Val Trp Leu Pro Val Leu His Arg Val Ala
1585                1590                1595                1600

Ala Ala Glu Thr Ala Lys His Gln Ala Lys Cys Asn Ile Cys Lys Glu
                1605                1610                1615

Cys Pro Ile Ile Gly Phe Arg Tyr Arg Ser Leu Lys His Phe Asn Tyr
            1620                1625                1630

Asp Ile Cys Gln Ser Cys Phe Phe Ser Gly Arg Val Ala Lys Gly His
        1635                1640                1645

Lys Met His Tyr Pro Met Val Glu Tyr Cys Thr Pro Thr Thr Ser Gly
    1650                1655                1660

Glu Asp Val Arg Asp Phe Ala Lys Val Leu Lys Asn Lys Phe Arg Thr
1665                1670                1675                1680

Lys Arg Tyr Phe Ala Lys His Pro Arg Met Gly Tyr Leu Pro Val Gln
                1685                1690                1695

Thr Val Leu Glu Gly Asp Asn Met Glu Thr Pro Val Thr Leu Ile Asn
            1700                1705                1710

Phe Trp Pro Val Asp Ser Ala Pro Ala Ser Ser Pro Gln Leu Ser His
        1715                1720                1725

Asp Asp Thr His Ser Arg Ile Glu His Tyr Ala Ser Arg Leu Ala Glu
    1730                1735                1740

Met Glu Asn Ser Asn Gly Ser Tyr Leu Asn Asp Ser Ile Ser Pro Asn
1745                1750                1755                1760

Glu Ser Ile Asp Asp Glu His Leu Leu Ile Gln His Tyr Cys Gln Ser
                1765                1770                1775

Leu Asn Gln Asp Ser Pro Leu Ser Gln Pro Arg Ser Pro Ala Gln Ile
            1780                1785                1790

Leu Ile Ser Leu Glu Ser Glu Glu Arg Gly Glu Leu Glu Arg Ile Leu
        1795                1800                1805

Ala Asp Leu Glu Glu Glu Asn Arg Asn Leu Gln Ala Glu Tyr Asp Arg
    1810                1815                1820

Leu Lys Gln Gln His Glu His Lys Gly Leu Ser Pro Leu Pro Ser Pro
1825                1830                1835                1840

Pro Glu Met Met Pro Thr Ser Pro Gln Ser Pro Arg Asp Ala Glu Leu
                1845                1850                1855

Ile Ala Glu Ala Lys Leu Leu Arg Gln His Lys Gly Arg Leu Glu Ala
            1860                1865                1870

Arg Met Gln Ile Leu Glu Asp His Asn Lys Gln Leu Glu Ser Gln Leu
        1875                1880                1885

His Arg Leu Arg Gln Leu Leu Glu Gln Pro Gln Ala Glu Ala Lys Val
    1890                1895                1900

Asn Gly Thr Thr Val Ser Ser Pro Ser Thr Ser Leu Gln Arg Ser Asp
1905                1910                1915                1920

Ser Ser Gln Pro Met Leu Leu Arg Val Val Gly Ser Gln Thr Ser Asp
                1925                1930                1935

Ser Met Gly Glu Glu Asp Leu Leu Ser Pro Pro Gln Asp Thr Ser Thr
            1940                1945                1950

Gly Leu Glu Glu Val Met Glu Gln Leu Asn Asn Ser Phe Pro Ser Ser
        1955                1960                1965

Arg Gly Arg Asn Thr Pro Gly Lys Pro Met Arg Glu Asp Thr Met
    1970                1975                1980
```

<210> SEQ ID NO 23
<211> LENGTH: 3685
<212> TYPE: PRT
<213> ORGANISM: Homo sapiens

<400> SEQUENCE: 23

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380
```

```
Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
```

```
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
865                 870                 875                 880

Ser Asp Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu Glu
    1010                1015                1020

Ile Glu Gly Arg Trp Lys Lys Leu Ser Ser Gln Leu Val Glu His Cys
1025                1030                1035                1040

Gln Lys Leu Glu Glu Gln Met Asn Lys Leu Arg Lys Ile Gln Asn His
                1045                1050                1055

Ile Gln Thr Leu Lys Lys Trp Met Ala Glu Val Asp Val Phe Leu Lys
            1060                1065                1070

Glu Glu Trp Pro Ala Leu Gly Asp Ser Glu Ile Leu Lys Lys Gln Leu
        1075                1080                1085

Lys Gln Cys Arg Leu Leu Val Ser Asp Ile Gln Thr Ile Gln Pro Ser
    1090                1095                1100

Leu Asn Ser Val Asn Glu Gly Gly Gln Lys Ile Lys Asn Glu Ala Glu
1105                1110                1115                1120

Pro Glu Phe Ala Ser Arg Leu Glu Thr Glu Leu Lys Glu Leu Asn Thr
                1125                1130                1135

Gln Trp Asp His Met Cys Gln Gln Val Tyr Ala Arg Lys Glu Ala Leu
            1140                1145                1150

Lys Gly Gly Leu Glu Lys Thr Val Ser Leu Gln Lys Asp Leu Ser Glu
        1155                1160                1165

Met His Glu Trp Met Thr Gln Ala Glu Glu Glu Tyr Leu Glu Arg Asp
    1170                1175                1180

Phe Glu Tyr Lys Thr Pro Asp Glu Leu Gln Lys Ala Val Glu Glu Met
1185                1190                1195                1200

Lys Arg Ala Lys Glu Glu Ala Gln Gln Lys Glu Ala Lys Val Lys Leu
                1205                1210                1215

Leu Thr Glu Ser Val Asn Ser Val Ile Ala Gln Ala Pro Pro Val Ala
            1220                1225                1230
```

-continued

```
Gln Glu Ala Leu Lys Lys Glu Leu Glu Thr Leu Thr Thr Asn Tyr Gln
        1235                1240                1245

Trp Leu Cys Thr Arg Leu Asn Gly Lys Cys Lys Thr Leu Glu Glu Val
    1250                1255                1260

Trp Ala Cys Trp His Glu Leu Leu Ser Tyr Leu Glu Lys Ala Asn Lys
1265                1270                1275                1280

Trp Leu Asn Glu Val Glu Phe Lys Leu Lys Thr Thr Glu Asn Ile Pro
                1285                1290                1295

Gly Gly Ala Glu Glu Ile Ser Glu Val Leu Asp Ser Leu Glu Asn Leu
            1300                1305                1310

Met Arg His Ser Glu Asp Asn Pro Asn Gln Ile Arg Ile Leu Ala Gln
        1315                1320                1325

Thr Leu Thr Asp Gly Gly Val Met Asp Glu Leu Ile Asn Glu Glu Leu
    1330                1335                1340

Glu Thr Phe Asn Ser Arg Trp Arg Glu Leu His Glu Glu Ala Val Arg
1345                1350                1355                1360

Arg Gln Lys Leu Leu Glu Gln Ser Ile Gln Ser Ala Gln Glu Thr Glu
                1365                1370                1375

Lys Ser Leu His Leu Ile Gln Glu Ser Leu Thr Phe Ile Asp Lys Gln
            1380                1385                1390

Leu Ala Ala Tyr Ile Ala Asp Lys Val Asp Ala Ala Gln Met Pro Gln
        1395                1400                1405

Glu Ala Gln Lys Ile Gln Ser Asp Leu Thr Ser His Glu Ile Ser Leu
    1410                1415                1420

Glu Glu Met Lys Lys His Asn Gln Gly Lys Glu Ala Ala Gln Arg Val
1425                1430                1435                1440

Leu Ser Gln Ile Asp Val Ala Gln Lys Lys Leu Gln Asp Val Ser Met
                1445                1450                1455

Lys Phe Arg Leu Phe Gln Lys Pro Ala Asn Phe Glu Gln Arg Leu Gln
            1460                1465                1470

Glu Ser Lys Met Ile Leu Asp Glu Val Lys Met His Leu Pro Ala Leu
        1475                1480                1485

Glu Thr Lys Ser Val Glu Gln Glu Val Val Gln Ser Gln Leu Asn His
    1490                1495                1500

Cys Val Asn Leu Tyr Lys Ser Leu Ser Glu Val Lys Ser Glu Val Glu
1505                1510                1515                1520

Met Val Ile Lys Thr Gly Arg Gln Ile Val Gln Lys Lys Gln Thr Glu
                1525                1530                1535

Asn Pro Lys Glu Leu Asp Glu Arg Val Thr Ala Leu Lys Leu His Tyr
            1540                1545                1550

Asn Glu Leu Gly Ala Lys Val Thr Glu Arg Lys Gln Gln Leu Glu Lys
        1555                1560                1565

Cys Leu Lys Leu Ser Arg Lys Met Arg Lys Glu Met Asn Val Leu Thr
    1570                1575                1580

Glu Trp Leu Ala Ala Thr Asp Met Glu Leu Thr Lys Arg Ser Ala Val
1585                1590                1595                1600

Glu Gly Met Pro Ser Asn Leu Asp Ser Glu Val Ala Trp Gly Lys Ala
                1605                1610                1615

Thr Gln Lys Glu Ile Glu Lys Gln Lys Val His Leu Lys Ser Ile Thr
            1620                1625                1630

Glu Val Gly Glu Ala Leu Lys Thr Val Leu Gly Lys Lys Glu Thr Leu
        1635                1640                1645
```

```
Val Glu Asp Lys Leu Ser Leu Leu Asn Ser Asn Trp Ile Ala Val Thr
    1650                1655                1660

Ser Arg Ala Glu Glu Trp Leu Asn Leu Leu Leu Glu Tyr Gln Lys His
1665                1670                1675                1680

Met Glu Thr Phe Asp Gln Asn Val Asp His Ile Thr Lys Trp Ile Ile
                1685                1690                1695

Gln Ala Asp Thr Leu Leu Asp Glu Ser Glu Lys Lys Lys Pro Gln Gln
            1700                1705                1710

Lys Glu Asp Val Leu Lys Arg Leu Lys Ala Glu Leu Asn Asp Ile Arg
        1715                1720                1725

Pro Lys Val Asp Ser Thr Arg Asp Gln Ala Ala Asn Leu Met Ala Asn
    1730                1735                1740

Arg Gly Asp His Cys Arg Lys Leu Val Glu Pro Gln Ile Ser Glu Leu
1745                1750                1755                1760

Asn His Arg Phe Ala Ala Ile Ser His Arg Ile Lys Thr Gly Lys Ala
                1765                1770                1775

Ser Ile Pro Leu Lys Glu Leu Glu Gln Phe Asn Ser Asp Ile Gln Lys
            1780                1785                1790

Leu Leu Glu Pro Leu Glu Ala Glu Ile Gln Gln Gly Val Asn Leu Lys
        1795                1800                1805

Glu Glu Asp Phe Asn Lys Asp Met Asn Glu Asp Asn Glu Gly Thr Val
    1810                1815                1820

Lys Glu Leu Leu Gln Arg Gly Asp Asn Leu Gln Gln Arg Ile Thr Asp
1825                1830                1835                1840

Glu Arg Lys Arg Glu Glu Ile Lys Ile Lys Gln Gln Leu Leu Gln Thr
                1845                1850                1855

Lys His Asn Ala Leu Lys Asp Leu Arg Ser Gln Arg Arg Lys Lys Ala
            1860                1865                1870

Leu Glu Ile Ser His Gln Trp Tyr Gln Tyr Lys Arg Gln Ala Asp Asp
        1875                1880                1885

Leu Leu Lys Cys Leu Asp Asp Ile Glu Lys Lys Leu Ala Ser Leu Pro
    1890                1895                1900

Glu Pro Arg Asp Glu Arg Lys Ile Lys Glu Ile Asp Arg Glu Leu Gln
1905                1910                1915                1920

Lys Lys Lys Glu Glu Leu Asn Ala Val Arg Arg Gln Ala Glu Gly Leu
                1925                1930                1935

Ser Glu Asp Gly Ala Ala Met Ala Val Glu Pro Thr Gln Ile Gln Leu
            1940                1945                1950

Ser Lys Arg Trp Arg Glu Ile Glu Ser Lys Phe Ala Gln Phe Arg Arg
        1955                1960                1965

Leu Asn Phe Ala Gln Ile His Thr Val Arg Glu Glu Thr Met Met Val
    1970                1975                1980

Met Thr Glu Asp Met Pro Leu Glu Ile Ser Tyr Val Pro Ser Thr Tyr
1985                1990                1995                2000

Leu Thr Glu Ile Thr His Val Ser Gln Ala Leu Leu Glu Val Glu Gln
                2005                2010                2015

Leu Leu Asn Ala Pro Asp Leu Cys Ala Lys Asp Phe Glu Asp Leu Phe
            2020                2025                2030

Lys Gln Glu Glu Ser Leu Lys Asn Ile Lys Asp Ser Leu Gln Gln Ser
        2035                2040                2045

Ser Gly Arg Ile Asp Ile Ile His Ser Lys Lys Thr Ala Ala Leu Gln
    2050                2055                2060

Ser Ala Thr Pro Val Glu Arg Val Lys Leu Gln Glu Ala Leu Ser Gln
```

```
2065                2070                2075                2080

Leu Asp Phe Gln Trp Glu Lys Val Asn Lys Met Tyr Lys Asp Arg Gln
                2085                2090                2095

Gly Arg Phe Asp Arg Ser Val Glu Lys Trp Arg Arg Phe His Tyr Asp
            2100                2105                2110

Ile Lys Ile Phe Asn Gln Trp Leu Thr Glu Ala Glu Gln Phe Leu Arg
        2115                2120                2125

Lys Thr Gln Ile Pro Glu Asn Trp Glu His Ala Lys Tyr Lys Trp Tyr
    2130                2135                2140

Leu Lys Glu Leu Gln Asp Gly Ile Gly Gln Arg Gln Thr Val Val Arg
2145                2150                2155                2160

Thr Leu Asn Ala Thr Gly Glu Glu Ile Ile Gln Gln Ser Ser Lys Thr
                2165                2170                2175

Asp Ala Ser Ile Leu Gln Glu Lys Leu Gly Ser Leu Asn Leu Arg Trp
            2180                2185                2190

Gln Glu Val Cys Lys Gln Leu Ser Asp Arg Lys Lys Arg Leu Glu Glu
        2195                2200                2205

Gln Lys Asn Ile Leu Ser Glu Phe Gln Arg Asp Leu Asn Glu Phe Val
    2210                2215                2220

Leu Trp Leu Glu Glu Ala Asp Asn Ile Ala Ser Ile Pro Leu Glu Pro
2225                2230                2235                2240

Gly Lys Glu Gln Gln Leu Lys Glu Lys Leu Glu Gln Val Lys Leu Leu
                2245                2250                2255

Val Glu Glu Leu Pro Leu Arg Gln Gly Ile Leu Lys Gln Leu Asn Glu
            2260                2265                2270

Thr Gly Gly Pro Val Leu Val Ser Ala Pro Ile Ser Pro Glu Glu Gln
        2275                2280                2285

Asp Lys Leu Glu Asn Lys Leu Lys Gln Thr Asn Leu Gln Trp Ile Lys
    2290                2295                2300

Val Ser Arg Ala Leu Pro Glu Lys Gln Gly Glu Ile Glu Ala Gln Ile
2305                2310                2315                2320

Lys Asp Leu Gly Gln Leu Glu Lys Lys Leu Glu Asp Leu Glu Glu Gln
                2325                2330                2335

Leu Asn His Leu Leu Leu Trp Leu Ser Pro Ile Arg Asn Gln Leu Glu
            2340                2345                2350

Ile Tyr Asn Gln Pro Asn Gln Glu Gly Pro Phe Asp Val Lys Glu Thr
        2355                2360                2365

Glu Ile Ala Val Gln Ala Lys Gln Pro Asp Val Glu Glu Ile Leu Ser
    2370                2375                2380

Lys Gly Gln His Leu Tyr Lys Glu Lys Pro Ala Thr Gln Pro Val Lys
2385                2390                2395                2400

Arg Lys Leu Glu Asp Leu Ser Ser Glu Trp Lys Ala Val Asn Arg Leu
                2405                2410                2415

Leu Gln Glu Leu Arg Ala Lys Gln Pro Asp Leu Ala Pro Gly Leu Thr
            2420                2425                2430

Thr Ile Gly Ala Ser Pro Thr Gln Thr Val Thr Leu Val Thr Gln Pro
        2435                2440                2445

Val Val Thr Lys Glu Thr Ala Ile Ser Lys Leu Glu Met Pro Ser Ser
    2450                2455                2460

Leu Met Leu Glu Val Pro Ala Leu Ala Asp Phe Asn Arg Ala Trp Thr
2465                2470                2475                2480

Glu Leu Thr Asp Trp Leu Ser Leu Leu Asp Gln Val Ile Lys Ser Gln
                2485                2490                2495
```

```
Arg Val Met Val Gly Asp Leu Glu Asp Ile Asn Glu Met Ile Ile Lys
            2500                2505                2510

Gln Lys Ala Thr Met Gln Asp Leu Glu Gln Arg Arg Pro Gln Leu Glu
        2515                2520                2525

Glu Leu Ile Thr Ala Ala Gln Asn Leu Lys Asn Lys Thr Ser Asn Gln
    2530                2535                2540

Glu Ala Arg Thr Ile Ile Thr Asp Arg Ile Glu Arg Ile Gln Asn Gln
2545                2550                2555                2560

Trp Asp Glu Val Gln Glu His Leu Gln Asn Arg Arg Gln Gln Leu Asn
                2565                2570                2575

Glu Met Leu Lys Asp Ser Thr Gln Trp Leu Glu Ala Lys Glu Glu Ala
            2580                2585                2590

Glu Gln Val Leu Gly Gln Ala Arg Ala Lys Leu Glu Ser Trp Lys Glu
        2595                2600                2605

Gly Pro Tyr Thr Val Asp Ala Ile Gln Lys Lys Ile Thr Glu Thr Lys
    2610                2615                2620

Gln Leu Ala Lys Asp Leu Arg Gln Trp Gln Thr Asn Val Asp Val Ala
2625                2630                2635                2640

Asn Asp Leu Ala Leu Lys Leu Leu Arg Asp Tyr Ser Ala Asp Asp Thr
                2645                2650                2655

Arg Lys Val His Met Ile Thr Glu Asn Ile Asn Ala Ser Trp Arg Ser
            2660                2665                2670

Ile His Lys Arg Val Ser Glu Arg Glu Ala Ala Leu Glu Glu Thr His
        2675                2680                2685

Arg Leu Leu Gln Gln Phe Pro Leu Asp Leu Glu Lys Phe Leu Ala Trp
    2690                2695                2700

Leu Thr Glu Ala Glu Thr Thr Ala Asn Val Leu Gln Asp Ala Thr Arg
2705                2710                2715                2720

Lys Glu Arg Leu Leu Glu Asp Ser Lys Gly Val Lys Glu Leu Met Lys
                2725                2730                2735

Gln Trp Gln Asp Leu Gln Gly Glu Ile Glu Ala His Thr Asp Val Tyr
            2740                2745                2750

His Asn Leu Asp Glu Asn Ser Gln Lys Ile Leu Arg Ser Leu Glu Gly
        2755                2760                2765

Ser Asp Asp Ala Val Leu Leu Gln Arg Arg Leu Asp Asn Met Asn Phe
    2770                2775                2780

Lys Trp Ser Glu Leu Arg Lys Lys Ser Leu Asn Ile Arg Ser His Leu
2785                2790                2795                2800

Glu Ala Ser Ser Asp Gln Trp Lys Arg Leu His Leu Ser Leu Gln Glu
                2805                2810                2815

Leu Leu Val Trp Leu Gln Leu Lys Asp Asp Glu Leu Ser Arg Gln Ala
            2820                2825                2830

Pro Ile Gly Gly Asp Phe Pro Ala Val Gln Lys Gln Asn Asp Val His
        2835                2840                2845

Arg Ala Phe Lys Arg Glu Leu Lys Thr Lys Glu Pro Val Ile Met Ser
    2850                2855                2860

Thr Leu Glu Thr Val Arg Ile Phe Leu Thr Glu Gln Pro Leu Glu Gly
2865                2870                2875                2880

Leu Glu Lys Leu Tyr Gln Glu Pro Arg Glu Leu Pro Pro Glu Glu Arg
                2885                2890                2895

Ala Gln Asn Val Thr Arg Leu Leu Arg Lys Gln Ala Glu Glu Val Asn
            2900                2905                2910
```

```
Thr Glu Trp Glu Lys Leu Asn Leu His Ser Ala Asp Trp Gln Arg Lys
        2915                2920                2925

Ile Asp Glu Thr Leu Glu Arg Leu Arg Glu Leu Gln Glu Ala Thr Asp
    2930                2935                2940

Glu Leu Asp Leu Lys Leu Arg Gln Ala Glu Val Ile Lys Gly Ser Trp
2945                2950                2955                2960

Gln Pro Val Gly Asp Leu Leu Ile Asp Ser Leu Gln Asp His Leu Glu
                2965                2970                2975

Lys Val Lys Ala Leu Arg Gly Glu Ile Ala Pro Leu Lys Glu Asn Val
            2980                2985                2990

Ser His Val Asn Asp Leu Ala Arg Gln Leu Thr Thr Leu Gly Ile Gln
        2995                3000                3005

Leu Ser Pro Tyr Asn Leu Ser Thr Leu Glu Asp Leu Asn Thr Arg Trp
    3010                3015                3020

Lys Leu Leu Gln Val Ala Val Glu Asp Arg Val Arg Gln Leu His Glu
3025                3030                3035                3040

Ala His Arg Asp Phe Gly Pro Ala Ser Gln His Phe Leu Ser Thr Ser
                3045                3050                3055

Val Gln Gly Pro Trp Glu Arg Ala Ile Ser Pro Asn Lys Val Pro Tyr
            3060                3065                3070

Tyr Ile Asn His Glu Thr Gln Thr Thr Cys Trp Asp His Pro Lys Met
        3075                3080                3085

Thr Glu Leu Tyr Gln Ser Leu Ala Asp Leu Asn Asn Val Arg Phe Ser
    3090                3095                3100

Ala Tyr Arg Thr Ala Met Lys Leu Arg Arg Leu Gln Lys Ala Leu Cys
3105                3110                3115                3120

Leu Asp Leu Leu Ser Leu Ser Ala Ala Cys Asp Ala Leu Asp Gln His
                3125                3130                3135

Asn Leu Lys Gln Asn Asp Gln Pro Met Asp Ile Leu Gln Ile Ile Asn
            3140                3145                3150

Cys Leu Thr Thr Ile Tyr Asp Arg Leu Glu Gln Glu His Asn Asn Leu
        3155                3160                3165

Val Asn Val Pro Leu Cys Val Asp Met Cys Leu Asn Trp Leu Leu Asn
    3170                3175                3180

Val Tyr Asp Thr Gly Arg Thr Gly Arg Ile Arg Val Leu Ser Phe Lys
3185                3190                3195                3200

Thr Gly Ile Ile Ser Leu Cys Lys Ala His Leu Glu Asp Lys Tyr Arg
                3205                3210                3215

Tyr Leu Phe Lys Gln Val Ala Ser Ser Thr Gly Phe Cys Asp Gln Arg
            3220                3225                3230

Arg Leu Gly Leu Leu Leu His Asp Ser Ile Gln Ile Pro Arg Gln Leu
        3235                3240                3245

Gly Glu Val Ala Ser Phe Gly Gly Ser Asn Ile Glu Pro Ser Val Arg
    3250                3255                3260

Ser Cys Phe Gln Phe Ala Asn Asn Lys Pro Glu Ile Glu Ala Ala Leu
3265                3270                3275                3280

Phe Leu Asp Trp Met Arg Leu Glu Pro Gln Ser Met Val Trp Leu Pro
                3285                3290                3295

Val Leu His Arg Val Ala Ala Ala Glu Thr Ala Lys His Gln Ala Lys
            3300                3305                3310

Cys Asn Ile Cys Lys Glu Cys Pro Ile Ile Gly Phe Arg Tyr Arg Ser
        3315                3320                3325

Leu Lys His Phe Asn Tyr Asp Ile Cys Gln Ser Cys Phe Phe Ser Gly
```

3330 3335 3340

Arg Val Ala Lys Gly His Lys Met His Tyr Pro Met Val Glu Tyr Cys
3345 3350 3355 3360

Thr Pro Thr Thr Ser Gly Glu Asp Val Arg Asp Phe Ala Lys Val Leu
3365 3370 3375

Lys Asn Lys Phe Arg Thr Lys Arg Tyr Phe Ala Lys His Pro Arg Met
3380 3385 3390

Gly Tyr Leu Pro Val Gln Thr Val Leu Glu Gly Asp Asn Met Glu Thr
3395 3400 3405

Pro Val Thr Leu Ile Asn Phe Trp Pro Val Asp Ser Ala Pro Ala Ser
3410 3415 3420

Ser Pro Gln Leu Ser His Asp Asp Thr His Ser Arg Ile Glu His Tyr
3425 3430 3435 3440

Ala Ser Arg Leu Ala Glu Met Glu Asn Ser Asn Gly Ser Tyr Leu Asn
3445 3450 3455

Asp Ser Ile Ser Pro Asn Glu Ser Ile Asp Asp Glu His Leu Leu Ile
3460 3465 3470

Gln His Tyr Cys Gln Ser Leu Asn Gln Asp Ser Pro Leu Ser Gln Pro
3475 3480 3485

Arg Ser Pro Ala Gln Ile Leu Ile Ser Leu Glu Ser Glu Glu Arg Gly
3490 3495 3500

Glu Leu Glu Arg Ile Leu Ala Asp Leu Glu Glu Glu Asn Arg Asn Leu
3505 3510 3515 3520

Gln Ala Glu Tyr Asp Arg Leu Lys Gln Gln His Glu His Lys Gly Leu
3525 3530 3535

Ser Pro Leu Pro Ser Pro Pro Glu Met Met Pro Thr Ser Pro Gln Ser
3540 3545 3550

Pro Arg Asp Ala Glu Leu Ile Ala Glu Ala Lys Leu Leu Arg Gln His
3555 3560 3565

Lys Gly Arg Leu Glu Ala Arg Met Gln Ile Leu Glu Asp His Asn Lys
3570 3575 3580

Gln Leu Glu Ser Gln Leu His Arg Leu Arg Gln Leu Leu Glu Gln Pro
3585 3590 3595 3600

Gln Ala Glu Ala Lys Val Asn Gly Thr Thr Val Ser Ser Pro Ser Thr
3605 3610 3615

Ser Leu Gln Arg Ser Asp Ser Ser Gln Pro Met Leu Leu Arg Val Val
3620 3625 3630

Gly Ser Gln Thr Ser Asp Ser Met Gly Glu Glu Asp Leu Leu Ser Pro
3635 3640 3645

Pro Gln Asp Thr Ser Thr Gly Leu Glu Glu Val Met Glu Gln Leu Asn
3650 3655 3660

Asn Ser Phe Pro Ser Ser Arg Gly Arg Asn Thr Pro Gly Lys Pro Met
3665 3670 3675 3680

Arg Glu Asp Thr Met
3685

<210> SEQ ID NO 24
<211> LENGTH: 393
<212> TYPE: PRT
<213> ORGANISM: Homo sapiens

<400> SEQUENCE: 24

Met Glu Glu Pro Gln Ser Asp Pro Ser Val Glu Pro Pro Leu Ser Gln
1 5 10 15

```
Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 25
<211> LENGTH: 403
<212> TYPE: PRT
<213> ORGANISM: Homo sapiens

<400> SEQUENCE: 25

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val
```

<210> SEQ ID NO 26
<211> LENGTH: 117
<212> TYPE: PRT
<213> ORGANISM: SARS-CoV-2

<400> SEQUENCE: 26

Gln Val Gln Leu Val Glu Ser Gly Gly Gly Leu Val Gln Ala Gly Gly
1               5                   10                  15

Ser Leu Arg Leu Ser Cys Ala Val Ser Gly Ala Gly Ala His Arg Val
            20                  25                  30

Gly Trp Phe Arg Arg Ala Pro Gly Lys Glu Arg Glu Phe Val Ala Ala
        35                  40                  45

Ile Gly Ala Ser Gly Gly Met Thr Asn Tyr Leu Asp Ser Val Lys Gly
    50                  55                  60

Arg Phe Thr Ile Ser Arg Asp Asn Ala Lys Asn Thr Ile Tyr Leu Gln
65                  70                  75                  80

Met Asn Ser Leu Lys Pro Gln Asp Thr Ala Val Tyr Tyr Cys Ala Ala
                85                  90                  95

Arg Asp Ile Glu Thr Ala Glu Tyr Ile Tyr Trp Gly Gln Gly Thr Gln
            100                 105                 110

Val Thr Val Ser Ser
        115

<210> SEQ ID NO 27
<211> LENGTH: 117
<212> TYPE: PRT
<213> ORGANISM: SARS-CoV-2

<400> SEQUENCE: 27

Gln Val Gln Leu Val Glu Ser Gly Gly Gly Leu Val Gln Ala Gly Gly
1               5                   10                  15

Ser Leu Arg Leu Ser Cys Ala Val Ser Gly Leu Gly Ala His Arg Val
            20                  25                  30

Gly Trp Phe Arg Arg Ala Pro Gly Lys Glu Arg Glu Phe Val Ala Ala
        35                  40                  45

Ile Gly Ala Asn Gly Gly Asn Thr Asn Tyr Leu Asp Ser Val Lys Gly
    50                  55                  60

Arg Phe Thr Ile Ser Arg Asp Asn Ala Lys Asn Thr Ile Tyr Leu Gln
65                  70                  75                  80

Met Asn Ser Leu Lys Pro Gln Asp Thr Ala Val Tyr Tyr Cys Ala Ala
                85                  90                  95

Arg Asp Ile Glu Thr Ala Glu Tyr Thr Tyr Trp Gly Gln Gly Thr Gln
            100                 105                 110

Val Thr Val Ser Ser
        115

<210> SEQ ID NO 28
<211> LENGTH: 403
<212> TYPE: PRT
<213> ORGANISM: SARS-CoV-2

<400> SEQUENCE: 28

Gln Val Gln Leu Val Glu Ser Gly Gly Gly Leu Val Gln Ala Gly Gly
1               5                   10                  15

Ser Leu Arg Leu Ser Cys Ala Val Ser Gly Ala Gly Ala His Arg Val
            20                  25                  30

Gly Trp Phe Arg Arg Ala Pro Gly Lys Glu Arg Glu Phe Val Ala Ala
        35                  40                  45

```
Ile Gly Ala Ser Gly Gly Met Thr Asn Tyr Leu Asp Ser Val Lys Gly
    50                  55                  60

Arg Phe Thr Ile Ser Arg Asp Asn Ala Lys Asn Thr Ile Tyr Leu Gln
65                  70                  75                  80

Met Asn Ser Leu Lys Pro Gln Asp Thr Ala Val Tyr Tyr Cys Ala Ala
                85                  90                  95

Arg Asp Ile Glu Thr Ala Glu Tyr Ile Tyr Trp Gly Gln Gly Thr Gln
            100                 105                 110

Val Thr Val Ser Ser Lys Leu Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gln Val Gln Leu Val Glu Ser Gly Gly Gly Leu Val Gln Ala Gly Gly
145                 150                 155                 160

Ser Leu Arg Leu Ser Cys Ala Val Ser Gly Ala Gly Ala His Arg Val
                165                 170                 175

Gly Trp Phe Arg Arg Ala Pro Gly Lys Glu Arg Glu Phe Val Ala Ala
            180                 185                 190

Ile Gly Ala Ser Gly Gly Met Thr Asn Tyr Leu Asp Ser Val Lys Gly
        195                 200                 205

Arg Phe Thr Ile Ser Arg Asp Asn Ala Lys Asn Thr Ile Tyr Leu Gln
    210                 215                 220

Met Asn Ser Leu Lys Pro Gln Asp Thr Ala Val Tyr Tyr Cys Ala Ala
225                 230                 235                 240

Arg Asp Ile Glu Thr Ala Glu Tyr Ile Tyr Trp Gly Gln Gly Thr Gln
                245                 250                 255

Val Thr Val Ser Ser Gly Gly Gly Gly Ser Gly Gly Gly Gly Ser Gly
            260                 265                 270

Gly Gly Gly Ser Gly Gly Gly Gly Ser Gly Gly Gly Gly Ser Gln Val
        275                 280                 285

Gln Leu Val Glu Ser Gly Gly Gly Leu Val Gln Ala Gly Gly Ser Leu
    290                 295                 300

Arg Leu Ser Cys Ala Val Ser Gly Ala Gly Ala His Arg Val Gly Trp
305                 310                 315                 320

Phe Arg Arg Ala Pro Gly Lys Glu Arg Glu Phe Val Ala Ala Ile Gly
                325                 330                 335

Ala Ser Gly Gly Met Thr Asn Tyr Leu Asp Ser Val Lys Gly Arg Phe
            340                 345                 350

Thr Ile Ser Arg Asp Asn Ala Lys Asn Thr Ile Tyr Leu Gln Met Asn
        355                 360                 365

Ser Leu Lys Pro Gln Asp Thr Ala Val Tyr Tyr Cys Ala Ala Arg Asp
    370                 375                 380

Ile Glu Thr Ala Glu Tyr Ile Tyr Trp Gly Gln Gly Thr Gln Val Thr
385                 390                 395                 400

Val Ser Ser


<210> SEQ ID NO 29
<211> LENGTH: 404
<212> TYPE: PRT
<213> ORGANISM: SARS-CoV-2

<400> SEQUENCE: 29

Gln Val Gln Leu Val Glu Ser Gly Gly Gly Leu Val Gln Ala Gly Gly
1               5                   10                  15
```

```
Ser Leu Arg Leu Ser Cys Ala Val Ser Gly Leu Gly Ala His Arg Val
            20                  25                  30

Gly Trp Phe Arg Arg Ala Pro Gly Lys Glu Arg Glu Phe Val Ala Ala
        35                  40                  45

Ile Gly Ala Asn Gly Gly Asn Thr Asn Tyr Leu Asp Ser Val Lys Gly
    50                  55                  60

Arg Phe Thr Ile Ser Arg Asp Asn Ala Lys Asn Thr Ile Tyr Leu Gln
65                  70                  75                  80

Met Asn Ser Leu Lys Pro Gln Asp Thr Ala Val Tyr Tyr Cys Ala Ala
                85                  90                  95

Arg Asp Ile Glu Thr Ala Glu Tyr Thr Tyr Trp Gly Gln Gly Thr Gln
            100                 105                 110

Val Thr Val Ser Ser Lys Leu Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Ser Gln Val Gln Leu Val Glu Ser Gly Gly Gly Leu Val Gln Ala Gly
145                 150                 155                 160

Gly Ser Leu Arg Leu Ser Cys Ala Val Ser Gly Leu Gly Ala His Arg
                165                 170                 175

Val Gly Trp Phe Arg Arg Ala Pro Gly Lys Glu Arg Glu Phe Val Ala
            180                 185                 190

Ala Ile Gly Ala Asn Gly Gly Asn Thr Asn Tyr Leu Asp Ser Val Lys
        195                 200                 205

Gly Arg Phe Thr Ile Ser Arg Asp Asn Ala Lys Asn Thr Ile Tyr Leu
    210                 215                 220

Gln Met Asn Ser Leu Lys Pro Gln Asp Thr Ala Val Tyr Tyr Cys Ala
225                 230                 235                 240

Ala Arg Asp Ile Glu Thr Ala Glu Tyr Thr Tyr Trp Gly Gln Gly Thr
                245                 250                 255

Gln Val Thr Val Ser Ser Gly Gly Gly Gly Ser Gly Gly Gly Gly Ser
            260                 265                 270

Gly Gly Gly Gly Ser Gly Gly Gly Gly Ser Gly Gly Gly Gly Ser Gln
        275                 280                 285

Val Gln Leu Val Glu Ser Gly Gly Gly Leu Val Gln Ala Gly Gly Ser
    290                 295                 300

Leu Arg Leu Ser Cys Ala Val Ser Gly Leu Gly Ala His Arg Val Gly
305                 310                 315                 320

Trp Phe Arg Arg Ala Pro Gly Lys Glu Arg Glu Phe Val Ala Ala Ile
                325                 330                 335

Gly Ala Asn Gly Gly Asn Thr Asn Tyr Leu Asp Ser Val Lys Gly Arg
            340                 345                 350

Phe Thr Ile Ser Arg Asp Asn Ala Lys Asn Thr Ile Tyr Leu Gln Met
        355                 360                 365

Asn Ser Leu Lys Pro Gln Asp Thr Ala Val Tyr Tyr Cys Ala Ala Arg
    370                 375                 380

Asp Ile Glu Thr Ala Glu Tyr Thr Tyr Trp Gly Gln Gly Thr Gln Val
385                 390                 395                 400

Thr Val Ser Ser
```

<210> SEQ ID NO 30
<211> LENGTH: 119
<212> TYPE: PRT

<213> ORGANISM: SARS-CoV-2

<400> SEQUENCE: 30

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Tyr Ile Phe Gly Arg Asn
            20                  25                  30

Ala Met Gly Trp Tyr Arg Gln Ala Pro Gly Lys Glu Arg Glu Leu Val
        35                  40                  45

Ala Gly Ile Thr Arg Arg Gly Ser Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Ala Ser Pro Ala Tyr Gly Asp Tyr Trp Gly Gln Gly
            100                 105                 110

Thr Gln Val Thr Val Ser Ser
        115
```

<210> SEQ ID NO 31
<211> LENGTH: 397
<212> TYPE: PRT
<213> ORGANISM: SARS-CoV-2

<400> SEQUENCE: 31

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Tyr Ile Phe Gly Arg Asn
            20                  25                  30

Ala Met Gly Trp Tyr Arg Gln Ala Pro Gly Lys Glu Arg Glu Leu Val
        35                  40                  45

Ala Gly Ile Thr Arg Arg Gly Ser Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Ala Ser Pro Ala Tyr Gly Asp Tyr Trp Gly Gln Gly
            100                 105                 110

Thr Gln Val Thr Val Ser Ser Gly Gly Gly Gly Ser Gly Gly Gly Gly
        115                 120                 125

Ser Gly Gly Gly Gly Ser Gly Gly Gly Gly Ser Gln Val Gln Leu Val
    130                 135                 140

Glu Ser Gly Gly Gly Leu Val Gln Ala Gly Gly Ser Leu Arg Leu Ser
145                 150                 155                 160

Cys Ala Ala Ser Gly Tyr Ile Phe Gly Arg Asn Ala Met Gly Trp Tyr
                165                 170                 175

Arg Gln Ala Pro Gly Lys Glu Arg Glu Leu Val Ala Gly Ile Thr Arg
            180                 185                 190

Arg Gly Ser Ile Thr Tyr Tyr Ala Asp Ser Val Lys Gly Arg Phe Thr
        195                 200                 205

Ile Ser Arg Asp Asn Ala Lys Asn Thr Val Tyr Leu Gln Met Asn Ser
    210                 215                 220

Leu Lys Pro Glu Asp Thr Ala Val Tyr Tyr Cys Ala Ala Asp Pro Ala
```

```
225                 230                 235                 240

Ser Pro Ala Tyr Gly Asp Tyr Trp Gly Gln Gly Thr Gln Val Thr Val
                245                 250                 255

Ser Ser Gly Gly Gly Gly Ser Gly Gly Gly Gly Ser Gly Gly Gly Gly
            260                 265                 270

Ser Gly Gly Gly Gly Ser Gln Val Gln Leu Val Glu Ser Gly Gly Gly
        275                 280                 285

Leu Val Gln Ala Gly Gly Ser Leu Arg Leu Ser Cys Ala Ala Ser Gly
    290                 295                 300

Tyr Ile Phe Gly Arg Asn Ala Met Gly Trp Tyr Arg Gln Ala Pro Gly
305                 310                 315                 320

Lys Glu Arg Glu Leu Val Ala Gly Ile Thr Arg Arg Gly Ser Ile Thr
                325                 330                 335

Tyr Tyr Ala Asp Ser Val Lys Gly Arg Phe Thr Ile Ser Arg Asp Asn
            340                 345                 350

Ala Lys Asn Thr Val Tyr Leu Gln Met Asn Ser Leu Lys Pro Glu Asp
        355                 360                 365

Thr Ala Val Tyr Tyr Cys Ala Ala Asp Pro Ala Ser Pro Ala Tyr Gly
    370                 375                 380

Asp Tyr Trp Gly Gln Gly Thr Gln Val Thr Val Ser Ser
385                 390                 395


<210> SEQ ID NO 32
<211> LENGTH: 455
<212> TYPE: PRT
<213> ORGANISM: SARS-CoV-2

<400> SEQUENCE: 32

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Ala Phe Thr Thr Tyr
            20                  25                  30

Ala Met Asn Trp Val Arg Gln Ala Pro Gly Arg Gly Leu Glu Trp Val
        35                  40                  45

Ser Ala Ile Ser Asp Gly Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Arg Gly Arg Gly Leu Tyr Asp Tyr Val Trp Gly Ser Lys
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

```
Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 33
<211> LENGTH: 219
<212> TYPE: PRT
<213> ORGANISM: SARS-CoV-2

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gly Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 34
<211> LENGTH: 167
<212> TYPE: PRT
<213> ORGANISM: Artificial Sequence
<220> FEATURE:
<223> OTHER INFORMATION: Synthetic Construct

<400> SEQUENCE: 34

Ser Ala Glu Ile Asp Leu Gly Lys Gly Asp Phe Arg Glu Ile Arg Ala
1               5                   10                  15

Ser Glu Asp Ala Arg Glu Ala Ala Glu Ala Leu Ala Glu Ala Ala Arg
            20                  25                  30

Ala Met Lys Glu Ala Leu Glu Ile Ile Arg Glu Ile Ala Glu Lys Leu
        35                  40                  45

Arg Asp Ser Ser Arg Ala Ser Glu Ala Ala Lys Arg Ile Ala Lys Ala
    50                  55                  60

Ile Arg Lys Ala Ala Asp Ala Ile Ala Glu Ala Ala Lys Ile Ala Ala
65                  70                  75                  80

Arg Ala Ala Lys Asp Gly Asp Ala Ala Arg Asn Ala Glu Asn Ala Ala
                85                  90                  95

Arg Lys Ala Lys Glu Phe Ala Glu Glu Gln Ala Lys Leu Ala Asp Met
            100                 105                 110

Tyr Ala Glu Leu Ala Lys Asn Gly Asp Lys Ser Ser Val Leu Glu Gln
        115                 120                 125

Leu Lys Thr Phe Ala Asp Lys Ala Phe His Glu Met Glu Asp Arg Phe
    130                 135                 140

Tyr Gln Ala Ala Leu Ala Val Phe Glu Ala Ala Glu Ala Ala Ala Gly
145                 150                 155                 160

Gly Ser Gly Trp Gly Ser Gly
                165


<210> SEQ ID NO 35
<211> LENGTH: 344
<212> TYPE: PRT
<213> ORGANISM: Artificial Sequence
<220> FEATURE:
<223> OTHER INFORMATION: Synthetic Construct

<400> SEQUENCE: 35

Ser Ala Glu Ile Asp Leu Gly Lys Gly Asp Phe Arg Glu Ile Arg Ala
1               5                   10                  15

Ser Glu Asp Ala Arg Glu Ala Ala Glu Ala Leu Ala Glu Ala Ala Arg
            20                  25                  30

Ala Met Lys Glu Ala Leu Glu Ile Ile Arg Glu Ile Ala Glu Lys Leu
```

```
        35                  40                  45

Arg Asp Ser Ser Arg Ala Ser Glu Ala Ala Lys Arg Ile Ala Lys Ala
    50                  55                  60

Ile Arg Lys Ala Ala Asp Ala Ile Ala Glu Ala Ala Lys Ile Ala Ala
65                  70                  75                  80

Arg Ala Ala Lys Asp Gly Asp Ala Ala Arg Asn Ala Glu Asn Ala Ala
                85                  90                  95

Arg Lys Ala Lys Glu Phe Ala Glu Glu Gln Ala Lys Leu Ala Asp Met
            100                 105                 110

Tyr Ala Glu Leu Ala Lys Asn Gly Asp Lys Ser Ser Val Leu Glu Gln
        115                 120                 125

Leu Lys Thr Phe Ala Asp Lys Ala Phe His Glu Met Glu Asp Arg Phe
    130                 135                 140

Tyr Gln Ala Ala Leu Ala Val Phe Glu Ala Ala Glu Ala Ala Ala Gly
145                 150                 155                 160

Gly Gly Gly Ser Gly Gly Ser Gly Ser Gly Gly Ser Gly Gly Gly Ser
                165                 170                 175

Pro Gly Ser Ala Glu Ile Asp Leu Gly Lys Gly Asp Phe Arg Glu Ile
            180                 185                 190

Arg Ala Ser Glu Asp Ala Arg Glu Ala Ala Glu Ala Leu Ala Glu Ala
        195                 200                 205

Ala Arg Ala Met Lys Glu Ala Leu Glu Ile Ile Arg Glu Ile Ala Glu
    210                 215                 220

Lys Leu Arg Asp Ser Ser Arg Ala Ser Glu Ala Ala Lys Arg Ile Ala
225                 230                 235                 240

Lys Ala Ile Arg Lys Ala Ala Asp Ala Ile Ala Glu Ala Ala Lys Ile
                245                 250                 255

Ala Ala Arg Ala Ala Lys Asp Gly Asp Ala Ala Arg Asn Ala Glu Asn
            260                 265                 270

Ala Ala Arg Lys Ala Lys Glu Phe Ala Glu Glu Gln Ala Lys Leu Ala
        275                 280                 285

Asp Met Tyr Ala Glu Leu Ala Lys Asn Gly Asp Lys Ser Ser Val Leu
    290                 295                 300

Glu Gln Leu Lys Thr Phe Ala Asp Lys Ala Phe His Glu Met Glu Asp
305                 310                 315                 320

Arg Phe Tyr Gln Ala Ala Leu Ala Val Phe Glu Ala Ala Glu Ala Ala
                325                 330                 335

Ala Gly Gly Ser Gly Trp Gly Ser
            340
```

<210> SEQ ID NO 36
<211> LENGTH: 9
<212> TYPE: RNA
<213> ORGANISM: Artificial Sequence
<220> FEATURE:
<223> OTHER INFORMATION: Synthetic Construct

<400> SEQUENCE: 36 gccaccaug 9

<210> SEQ ID NO 37
<211> LENGTH: 51
<212> TYPE: DNA
<213> ORGANISM: Artificial Sequence
<220> FEATURE:
<223> OTHER INFORMATION: Synthetic Construct

<400> SEQUENCE: 37
gaaaaacaaa aaacaaaaaa aacaaaaaaa aaaccaaaaa aacaaaacac a 51

<210> SEQ ID NO 38
<211> LENGTH: 27
<212> TYPE: DNA
<213> ORGANISM: Artificial Sequence
<220> FEATURE:
<223> OTHER INFORMATION: Synthetic Construct

<400> SEQUENCE: 38
acgagtcctg gactgaaacg gacttgt 27

<210> SEQ ID NO 39
<211> LENGTH: 52
<212> TYPE: RNA
<213> ORGANISM: Artificial Sequence
<220> FEATURE:
<223> OTHER INFORMATION: Synthetic Construct

<400> SEQUENCE: 39
aaaauccguu gaccuuaaac ggucgugugg guucaagucc cuccaccccc ac 52

<210> SEQ ID NO 40
<211> LENGTH: 16
<212> TYPE: RNA
<213> ORGANISM: Artificial Sequence
<220> FEATURE:
<223> OTHER INFORMATION: Synthetic Construct

<400> SEQUENCE: 40
gagacgcuac ggacuu 16

<210> SEQ ID NO 41
<211> LENGTH: 33
<212> TYPE: RNA
<213> ORGANISM: Artificial Sequence
<220> FEATURE:
<223> OTHER INFORMATION: Synthetic Construct

<400> SEQUENCE: 41
gggagacccu cgaccgucga uuguccacug guc 33

<210> SEQ ID NO 42
<211> LENGTH: 35
<212> TYPE: RNA
<213> ORGANISM: Artificial Sequence
<220> FEATURE:
<223> OTHER INFORMATION: Synthetic Construct

<400> SEQUENCE: 42
accaguggac aaucgacgga uaacagcaua ucuag 35

<210> SEQ ID NO 43
<211> LENGTH: 19
<212> TYPE: RNA
<213> ORGANISM: Artificial Sequence
<220> FEATURE:
<223> OTHER INFORMATION: Synthetic Construct

<400> SEQUENCE: 43
uaauacgacu cacuauagg 19

<210> SEQ ID NO 44
<211> LENGTH: 54

<212> TYPE: RNA
<213> ORGANISM: Artificial Sequence
<220> FEATURE:
<223> OTHER INFORMATION: Synthetic Construct

<400> SEQUENCE: 44
gagggcagag gaagucuucu aacaugcggu gacguggagg agaaucccgg cccu 54

<210> SEQ ID NO 45
<211> LENGTH: 57
<212> TYPE: RNA
<213> ORGANISM: Artificial Sequence
<220> FEATURE:
<223> OTHER INFORMATION: Synthetic Construct

<400> SEQUENCE: 45
gcuacuaacu ucagccugcu gaagcaggcu ggagacgugg aggagaaccc uggaccu 57

<210> SEQ ID NO 46
<211> LENGTH: 131
<212> TYPE: RNA
<213> ORGANISM: Artificial Sequence
<220> FEATURE:
<223> OTHER INFORMATION: Synthetic Construct

<400> SEQUENCE: 46
aacaauagau gacuuacaac uaaucggaag gugcagagac ucgacgggag cuacccuaac 60
gucaagacga ggguaaagag agaguccaau ucucaaagcc aauaggcagu agcgaaagcu 120
gcaagagaau g 131

<210> SEQ ID NO 47
<211> LENGTH: 116
<212> TYPE: RNA
<213> ORGANISM: Artificial Sequence
<220> FEATURE:
<223> OTHER INFORMATION: Synthetic Construct

<400> SEQUENCE: 47
aaauaauuga gccuuaaaga agaaauucuu uaaguggaug cucucaaacu cagggaaacc 60
uaaaucuagu uauagacaag gcaauccuga gccaagccga aguaguaauu aguaag 116

<210> SEQ ID NO 48
<211> LENGTH: 3819
<212> TYPE: DNA
<213> ORGANISM: SARS-CoV-2

<400> SEQUENCE: 48
atgttcgttt tccttgttct gttgcctctc gttagtagcc aatgcgtcaa ccttactact 60
agaacccagc tccctccagc atataccaac tctttcacca ggggcgtata ttacccggac 120
aaagtgttcc gctcaagtgt gctgcattct acgcaggacc ttttcttgcc ctttttcagt 180
aatgttactt ggtttcatgc tatccatgtg tctggaacta acggaaccaa gcgctttgac 240
aaccccgtcc tccctttcaa cgatggcgtg tacttcgctt ccacggaaaa gtcaaacata 300
attcgcggct ggatctttgg tacaacactc gactcaaaga cgcagagcct gctgatcgtt 360
aataacgcta caaatgttgt gataaaggtg tgtgaatttc agttctgcaa tgatcccttc 420
ctgggtgtgt actaccataa gaataacaag agctggatgg aatccgaatt tagggtttac 480
agttccgcta acaactgcac attcgaatac gtaagccagc catttcttat ggatcttgag 540
ggcaagcaag gaaacttcaa gaacttgagg gagttcgtgt tcaaaaatat cgacggctat 600

```
tttaagatat atagcaagca cactccaata aacttggtgc gcgacctgcc ccagggattc    660
tctgctctgg agcccctggt ggatctgccc attggaataa acataactcg ctttcaaaca    720
ctgctcgccc tgcatcgcag ttacctcacc cctggtgata gtagttcagg atggacagca    780
ggagccgccg catactacgt cggctacctg cagcctagga ccttcttgct gaagtacaac    840
gagaacggta caataactga cgctgtggac tgcgctctgg accctctgtc cgagacgaag    900
tgcaccctga agagctttac tgttgaaaaa ggcatttacc aaaccagcaa cttccgcgtc    960
cagccaaccg agagcatcgt cagatttccc aacattacaa atctgtgtcc cttcggcgag   1020
gtgttcaacg ccacacgctt cgcttcagtg tacgcatgga accgcaagcg catatctaac   1080
tgcgtcgcgg attattctgt cctctacaac tccgcctctt tctccacctt caagtgctac   1140
ggagtgtcac cgactaagct gaacgatctc tgctttacca acgtctacgc ggactccttc   1200
gtgataagag gtgatgaagt gagacaaata gccccaggtc agactggtaa gatcgcagat   1260
tacaactaca aattgcctga tgatttcact ggttgcgtta tcgcgtggaa ctctaataac   1320
ctcgattcta aggtcggtgg taactacaat tacctgtacc gcttgtttag gaagtcaaac   1380
ctgaagcctt tcgagaggga tatttcaacc gaaatctatc aagcgggttc aacaccgtgt   1440
aacggtgtgg aaggatttaa ctgctacttc cccctgcagt cttacggatt ccagccaacc   1500
aatggcgtgg gttaccaacc ttatcgcgtg gtggttctga gtttcgaact gttgcacgct   1560
cccgccacgg tatgcggtcc caagaagagc actaacttgg tgaagaataa gtgcgtgaat   1620
ttcaatttca atggcctcac tggaactgga gtgctgaccg aatccaataa gaagttcttg   1680
cccttccagc agttcggaag agacattgct gacacaaccg acgcggtgcg cgatcctcag   1740
actctggaga tattggacat tacaccatgt tctttcggcg gtgtgtctgt cattactccg   1800
ggcacgaata ctagcaacca ggtagccgtg ctgtaccaag acgtgaattg cacagaggtt   1860
cccgtcgcaa ttcacgctga ccagctgacc cccacgtgga gggtttacag cactggtagt   1920
aacgtcttcc agacgagagc cggttgcttg atcggagcgg aacatgtgaa taactcctac   1980
gagtgcgaca tccccatcgg agccggtata tgcgcctctt atcagacaca aactaactca   2040
cccaggagag cccgcagtgt ggcttctcaa agcattatag catacactat gtctcttggt   2100
gccgaaaatt ccgtggccta ttctaacaat tcaatcgcca tcccaaccaa cttcacaatt   2160
agcgtgacta ccgaaatact gcctgtgagc atgacgaaaa ccagcgtaga ctgcactatg   2220
tatatctgtg gagactccac tgagtgctcc aaccttctcc tgcagtacgg tagcttctgt   2280
acccaattga accgcgccct tacaggcatc gctgttgagc aagataagaa tacccaggaa   2340
gtttttgccc aggttaagca gatatacaaa acaccgccca ttaaggactt cggaggcttc   2400
aacttctctc agatactgcc tgacccctcc aagccatcaa aacgcagctt cattgaggac   2460
ctcttgttca acaaagtgac tctggctgat gctggcttca ttaagcagta cggagattgc   2520
ctgggagata ttgctgccag ggacctcatc tgcgcccaga agtttaatgg cctgacagtc   2580
ttgcccccac ttctgacaga cgagatgatt gctcagtaca catctgccct cctcgctggc   2640
accataacat ccggatggac atttggtgct ggtgctgccc tccagattcc cttcgcaatg   2700
cagatggcgt atcgctttaa cggcatcggt gtcacacaaa acgtgttgta tgagaaccaa   2760
aagctcatcg ctaaccagtt taattctgct attggtaaga ttcaggacag cctgtcatca   2820
accgcgtctg cccttggtaa gttgcaggac gtggtgaacc agaatgctca ggctttgaat   2880
actctggtga agcaactctc ttcaaatttc ggcgctatct cttctgtgtt gaacgacatc   2940
ctgagtcgcc ttgataaggt ggaagctgaa gttcaaattg atagattgat tactggcagg   3000
```

ctccagtctt tgcagaccta cgttacacag cagctgatta gggcggctga aattagagct 3060
tccgccaatc tggctgcaac caagatgtcc gaatgcgtcc tgggtcagtc aaagcgcgtt 3120
gacttttgtg gtaaaggcta ccacctcatg tcatttcccc agtcagcacc tcacggagta 3180
gtgttcctcc acgtcaccta cgttccagca caggaaaaga attttaccac tgcgccggca 3240
atctgtcacg acggtaaggc acacttcccc cgcgagggcg tattcgtgtc taacggaact 3300
cattggttcg tcacacagag aaacttctat gagcctcaga tcattaccac cgacaataca 3360
tttgtgtccg gtaactgcga cgttgtgatt ggaatcgtca acaacactgt gtacgatcca 3420
cttcagccag aactggatag cttcaaggaa gaattggaca aatatttcaa aaatcacact 3480
tcacccgatg tggacctggg tgacattagt ggtatcaatg cgtccgtggt caatattcaa 3540
aaagagattg acaggctcaa cgaagtggcc aagaacctga acgaaagtct tatcgatctg 3600
caagaattgg gaaagtatga gcagtacatc aagtggccgt ggtacatttg gttgggtttt 3660
atcgccggtc tgatcgccat cgttatggtt accattatgc tttgctgcat gacgagctgt 3720
tgctcctgtc tgaagggatg ctgctcttgc ggatcatgtt gcaagttcga tgaagacgat 3780
agcgaaccag ttctgaaggg cgtcaagctg cattacaca 3819

<210> SEQ ID NO 49
<211> LENGTH: 669
<212> TYPE: DNA
<213> ORGANISM: Artificial Sequence
<220> FEATURE:
<223> OTHER INFORMATION: Synthetic Construct

<400> SEQUENCE: 49
cgcgtccagc caaccgagag catcgtcaga tttcccaaca ttacaaatct gtgtcccttc 60
ggcgaggtgt tcaacgccac acgcttcgct tcagtgtacg catggaaccg caagcgcata 120
tctaactgcg tcgcggatta ttctgtcctc tacaactccg cctctttctc caccttcaag 180
tgctacggag tgtcaccgac taagctgaac gatctctgct ttaccaacgt ctacgcggac 240
tccttcgtga taagaggtga tgaagtgaga caaatagccc caggtcagac tggtaagatc 300
gcagattaca actacaaatt gcctgatgat ttcactggtt gcgttatcgc gtggaactct 360
aataacctcg attctaaggt cggtggtaac tacaattacc tgtaccgctt gtttaggaag 420
tcaaacctga agcctttcga gagggatatt tcaaccgaaa tctatcaagc gggttcaaca 480
ccgtgtaacg gtgtggaagg atttaactgc tacttccccc tgcagtctta cggattccag 540
ccaaccaatg gcgtgggtta ccaaccttat cgcgtggtgg ttctgagttt cgaactgttg 600
cacgctcccg ccacggtatg cggtcccaag aagagcacta acttggtgaa gaataagtgc 660
gtgaatttc 669

<210> SEQ ID NO 50
<211> LENGTH: 96
<212> TYPE: DNA
<213> ORGANISM: Artificial Sequence
<220> FEATURE:
<223> OTHER INFORMATION: Synthetic Construct

<400> SEQUENCE: 50
ggaagcggct acatcccaga agcccctaga gacggacagg cttacgtgcg aaaagacggc 60
gagtgggtgc tgctgagcac attcctggga aggagc 96

<210> SEQ ID NO 51

<211> LENGTH: 99
<212> TYPE: DNA
<213> ORGANISM: Artificial Sequence
<220> FEATURE:
<223> OTHER INFORMATION: Synthetic Construct

<400> SEQUENCE: 51
cgaatgaagc agattgagga taaaattgag gagattctca gcaaaattta ccacatagaa 60
aatgagatcg ctcggattaa aaaactgatc ggagaaaga 99

<210> SEQ ID NO 52
<211> LENGTH: 30
<212> TYPE: DNA
<213> ORGANISM: Artificial Sequence
<220> FEATURE:
<223> OTHER INFORMATION: Synthetic Construct

<400> SEQUENCE: 52
ggcggaggag gcagcggcgg aggaggcagc 30

<210> SEQ ID NO 53
<211> LENGTH: 741
<212> TYPE: DNA
<213> ORGANISM: Artificial Sequence
<220> FEATURE:
<223> OTHER INFORMATION: Synthetic Construct

<400> SEQUENCE: 53
ttaaaacagc ctgtgggttg atcccaccca caggcccatt gggcgctagc actctggtat 60
cacggtacct ttgtgcgcct gttttatacc ccctccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggcccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatcccttt gttgggttta taccacttag cttgaaagag gttaaaacat tacaattcat 720
tgttaagttg aatacagcaa a 741

<210> SEQ ID NO 54
<211> LENGTH: 419
<212> TYPE: PRT
<213> ORGANISM: Homo sapiens

<400> SEQUENCE: 54

Met Ser Phe Ile Pro Val Ala Glu Asp Ser Asp Phe Pro Ile His Asn
1 5 10 15

Leu Pro Tyr Gly Val Phe Ser Thr Arg Gly Asp Pro Arg Pro Arg Ile
20 25 30

Gly Val Ala Ile Gly Asp Gln Ile Leu Asp Leu Ser Ile Ile Lys His
35 40 45

Leu Phe Thr Gly Pro Val Leu Ser Lys His Gln Asp Val Phe Asn Gln
50 55 60

Pro Thr Leu Asn Ser Phe Met Gly Leu Gly Gln Ala Ala Trp Lys Glu
65 70 75 80

Ala Arg Val Phe Leu Gln Asn Leu Leu Ser Val Ser Gln Ala Arg Leu
85 90 95

Arg Asp Asp Thr Glu Leu Arg Lys Cys Ala Phe Ile Ser Gln Ala Ser
100 105 110

Ala Thr Met His Leu Pro Ala Thr Ile Gly Asp Tyr Thr Asp Phe Tyr
115 120 125

Ser Ser Arg Gln His Ala Thr Asn Val Gly Ile Met Phe Arg Asp Lys
130 135 140

Glu Asn Ala Leu Met Pro Asn Trp Leu His Leu Pro Val Gly Tyr His
145 150 155 160

Gly Arg Ala Ser Ser Val Val Val Ser Gly Thr Pro Ile Arg Arg Pro
165 170 175

Met Gly Gln Met Lys Pro Asp Asp Ser Lys Pro Pro Val Tyr Gly Ala
180 185 190

Cys Lys Leu Leu Asp Met Glu Leu Glu Met Ala Phe Phe Val Gly Pro
195 200 205

Gly Asn Arg Leu Gly Glu Pro Ile Pro Ile Ser Lys Ala His Glu His
210 215 220

Ile Phe Gly Met Val Leu Met Asn Asp Trp Ser Ala Arg Asp Ile Gln
225 230 235 240

Lys Trp Glu Tyr Val Pro Leu Gly Pro Phe Leu Gly Lys Ser Phe Gly
245 250 255

Thr Thr Val Ser Pro Trp Val Val Pro Met Asp Ala Leu Met Pro Phe
260 265 270

Ala Val Pro Asn Pro Lys Gln Asp Pro Arg Pro Leu Pro Tyr Leu Cys
275 280 285

His Asp Glu Pro Tyr Thr Phe Asp Ile Asn Leu Ser Val Asn Leu Lys
290 295 300

Gly Glu Gly Met Ser Gln Ala Ala Thr Ile Cys Lys Ser Asn Phe Lys
305 310 315 320

Tyr Met Tyr Trp Thr Met Leu Gln Gln Leu Thr His His Ser Val Asn
325 330 335

Gly Cys Asn Leu Arg Pro Gly Asp Leu Leu Ala Ser Gly Thr Ile Ser
340 345 350

Gly Pro Glu Pro Glu Asn Phe Gly Ser Met Leu Glu Leu Ser Trp Lys
355 360 365

Gly Thr Lys Pro Ile Asp Leu Gly Asn Gly Gln Thr Arg Lys Phe Leu
370 375 380

Leu Asp Gly Asp Glu Val Ile Ile Thr Gly Tyr Cys Gln Gly Asp Gly
385 390 395 400

Tyr Arg Ile Gly Phe Gly Gln Cys Ala Gly Lys Val Leu Pro Ala Leu
405 410 415

Leu Pro Ser

<210> SEQ ID NO 55
<211> LENGTH: 354
<212> TYPE: PRT
<213> ORGANISM: Homo sapiens

<400> SEQUENCE: 55

Met Leu Phe Asn Leu Arg Ile Leu Leu Asn Asn Ala Ala Phe Arg Asn
1 5 10 15

Gly His Asn Phe Met Val Arg Asn Phe Arg Cys Gly Gln Pro Leu Gln
20 25 30

Asn Lys Val Gln Leu Lys Gly Arg Asp Leu Leu Thr Leu Lys Asn Phe
35 40 45

Thr Gly Glu Glu Ile Lys Tyr Met Leu Trp Leu Ser Ala Asp Leu Lys
50 55 60

Phe Arg Ile Lys Gln Lys Gly Glu Tyr Leu Pro Leu Leu Gln Gly Lys
65 70 75 80

Ser Leu Gly Met Ile Phe Glu Lys Arg Ser Thr Arg Thr Arg Leu Ser
85 90 95

Thr Glu Thr Gly Leu Ala Leu Leu Gly Gly His Pro Cys Phe Leu Thr
100 105 110

Thr Gln Asp Ile His Leu Gly Val Asn Glu Ser Leu Thr Asp Thr Ala
115 120 125

Arg Val Leu Ser Ser Met Ala Asp Ala Val Leu Ala Arg Val Tyr Lys
130 135 140

Gln Ser Asp Leu Asp Thr Leu Ala Lys Glu Ala Ser Ile Pro Ile Ile
145 150 155 160

Asn Gly Leu Ser Asp Leu Tyr His Pro Ile Gln Ile Leu Ala Asp Tyr
165 170 175

Leu Thr Leu Gln Glu His Tyr Ser Ser Leu Lys Gly Leu Thr Leu Ser
180 185 190

Trp Ile Gly Asp Gly Asn Asn Ile Leu His Ser Ile Met Met Ser Ala
195 200 205

Ala Lys Phe Gly Met His Leu Gln Ala Ala Thr Pro Lys Gly Tyr Glu
210 215 220

Pro Asp Ala Ser Val Thr Lys Leu Ala Glu Gln Tyr Ala Lys Glu Asn
225 230 235 240

Gly Thr Lys Leu Leu Leu Thr Asn Asp Pro Leu Glu Ala Ala His Gly
245 250 255

Gly Asn Val Leu Ile Thr Asp Thr Trp Ile Ser Met Gly Gln Glu Glu
260 265 270

Glu Lys Lys Lys Arg Leu Gln Ala Phe Gln Gly Tyr Gln Val Thr Met
275 280 285

Lys Thr Ala Lys Val Ala Ala Ser Asp Trp Thr Phe Leu His Cys Leu
290 295 300

Pro Arg Lys Pro Glu Glu Val Asp Asp Glu Val Phe Tyr Ser Pro Arg
305 310 315 320

Ser Leu Val Phe Pro Glu Ala Glu Asn Arg Lys Trp Thr Ile Met Ala
325 330 335

Val Met Val Ser Leu Leu Thr Asp Tyr Ser Pro Gln Leu Gln Lys Pro
340 345 350

Lys Phe

<210> SEQ ID NO 56
<211> LENGTH: 1163
<212> TYPE: PRT
<213> ORGANISM: Homo sapiens

<400> SEQUENCE: 56

Met Met Ser Phe Val Gln Lys Gly Ser Trp Leu Leu Leu Ala Leu Leu
1 5 10 15

His Pro Thr Ile Ile Leu Ala Gln Gln Glu Ala Val Glu Gly Gly Cys
20 25 30

```
Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350

Val Gly Pro Ala Gly Ser Pro Gly Ser Asn Gly Ala Pro Gly Gln Arg
        355                 360                 365

Gly Glu Pro Gly Pro Gln Gly His Ala Gly Ala Gln Gly Pro Pro Gly
    370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
            420                 425                 430

Glu Pro Gly Lys Asn Gly Ala Lys Gly Glu Pro Gly Pro Arg Gly Glu
        435                 440                 445
```

```
Arg Gly Glu Ala Gly Ile Pro Gly Val Pro Gly Ala Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
            500                 505                 510

Gly Pro Ala Gly Pro Arg Gly Ala Ala Gly Glu Pro Gly Arg Asp Gly
        515                 520                 525

Val Pro Gly Gly Pro Gly Met Arg Gly Met Pro Gly Ser Pro Gly Gly
    530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
                565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Pro
        595                 600                 605

Gly Lys Asn Gly Glu Thr Gly Pro Gln Gly Pro Pro Gly Pro Thr Gly
    610                 615                 620

Pro Gly Gly Asp Lys Gly Asp Thr Gly Pro Pro Gly Pro Gln Gly Leu
625                 630                 635                 640

Gln Gly Leu Pro Gly Thr Gly Gly Pro Pro Gly Glu Asn Gly Lys Pro
                645                 650                 655

Gly Glu Pro Gly Pro Lys Gly Asp Ala Gly Ala Pro Gly Ala Pro Gly
            660                 665                 670

Gly Lys Gly Asp Ala Gly Ala Pro Gly Glu Arg Gly Pro Pro Gly Leu
        675                 680                 685

Ala Gly Ala Pro Gly Leu Arg Gly Gly Ala Gly Pro Pro Gly Pro Glu
    690                 695                 700

Gly Gly Lys Gly Ala Ala Gly Pro Pro Gly Pro Pro Gly Ala Ala Gly
705                 710                 715                 720

Thr Pro Gly Leu Gln Gly Met Pro Gly Glu Arg Gly Gly Leu Gly Ser
                725                 730                 735

Pro Gly Pro Lys Gly Asp Lys Gly Glu Pro Gly Gly Pro Gly Ala Asp
            740                 745                 750

Gly Val Pro Gly Lys Asp Gly Pro Arg Gly Pro Thr Gly Pro Ile Gly
        755                 760                 765

Pro Pro Gly Pro Ala Gly Gln Pro Gly Asp Lys Gly Glu Gly Gly Ala
    770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Lys Asp
        835                 840                 845

Gly Thr Ser Gly His Pro Gly Pro Ile Gly Pro Pro Gly Pro Arg Gly
    850                 855                 860

Asn Arg Gly Glu Arg Gly Ser Glu Gly Ser Pro Gly His Pro Gly Gln
```

-continued 865 870 875 880

Pro Gly Pro Pro Gly Pro Pro Gly Ala Pro Gly Pro Cys Cys Gly Gly
885 890 895

Val Gly Ala Ala Ala Ile Ala Gly Ile Gly Gly Glu Lys Ala Gly Gly
900 905 910

Phe Ala Pro Tyr Tyr Gly Asp Glu Pro Met Asp Phe Lys Ile Asn Thr
915 920 925

Asp Glu Ile Met Thr Ser Leu Lys Ser Val Asn Gly Gln Ile Glu Ser
930 935 940

Leu Ile Ser Pro Asp Gly Ser Arg Lys Asn Pro Ala Arg Asn Cys Arg
945 950 955 960

Asp Leu Lys Phe Cys His Pro Glu Leu Lys Ser Gly Glu Tyr Trp Val
965 970 975

Asp Pro Asn Gln Gly Cys Lys Leu Asp Ala Ile Lys Val Phe Cys Asn
980 985 990

Met Glu Thr Gly Glu Thr Cys Ile Ser Ala Asn Pro Leu Asn Val Pro
995 1000 1005

Arg Lys His Trp Trp Thr Asp Ser Ser Ala Glu Lys Lys His Val Trp
1010 1015 1020

Phe Gly Glu Ser Met Asp Gly Gly Phe Gln Phe Ser Tyr Gly Asn Pro
1025 1030 1035 1040

Glu Leu Pro Glu Asp Val Leu Asp Val Gln Leu Ala Phe Leu Arg Leu
1045 1050 1055

Leu Ser Ser Arg Ala Ser Gln Asn Ile Thr Tyr His Cys Lys Asn Ser
1060 1065 1070

Ile Ala Tyr Met Asp Gln Ala Ser Gly Asn Val Lys Lys Ala Leu Lys
1075 1080 1085

Leu Met Gly Ser Asn Glu Gly Glu Phe Lys Ala Glu Gly Asn Ser Lys
1090 1095 1100

Phe Thr Tyr Thr Val Leu Glu Asp Gly Cys Thr Lys His Thr Gly Glu
1105 1110 1115 1120

Trp Ser Lys Thr Val Phe Glu Tyr Arg Thr Arg Lys Ala Val Arg Leu
1125 1130 1135

Pro Ile Val Asp Ile Ala Pro Tyr Asp Ile Gly Gly Pro Asp Gln Glu
1140 1145 1150

Phe Gly Val Asp Val Gly Pro Val Cys Phe Leu
1155 1160

<210> SEQ ID NO 57
<211> LENGTH: 1038
<212> TYPE: PRT
<213> ORGANISM: Homo sapiens

<400> SEQUENCE: 57

Met Thr Ser Ser Leu Gln Arg Pro Trp Arg Val Pro Trp Leu Pro Trp
1 5 10 15

Thr Ile Leu Leu Val Ser Thr Ala Ala Ala Ser Gln Asn Gln Glu Arg
20 25 30

Leu Cys Ala Phe Lys Asp Pro Tyr Gln Gln Asp Leu Gly Ile Gly Glu
35 40 45

Ser Arg Ile Ser His Glu Asn Gly Thr Ile Leu Cys Ser Lys Gly Ser
50 55 60

Thr Cys Tyr Gly Leu Trp Glu Lys Ser Lys Gly Asp Ile Asn Leu Val
65 70 75 80

```
Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
```

```
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925
```

```
Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly Thr
    1010                1015                1020

Ala Thr Thr Met Val Ser Lys Asp Ile Gly Met Asn Cys Leu
1025                1030                1035


<210> SEQ ID NO 58
<211> LENGTH: 1195
<212> TYPE: PRT
<213> ORGANISM: Homo sapiens

<400> SEQUENCE: 58

Met Pro Thr Ala Glu Ser Glu Ala Lys Val Lys Thr Lys Val Arg Phe
1               5                   10                  15

Glu Glu Leu Leu Lys Thr His Ser Asp Leu Met Arg Glu Lys Lys Lys
            20                  25                  30

Leu Lys Lys Lys Leu Val Arg Ser Glu Glu Asn Ile Ser Pro Asp Thr
        35                  40                  45

Ile Arg Ser Asn Leu His Tyr Met Lys Glu Thr Thr Ser Asp Asp Pro
    50                  55                  60

Asp Thr Ile Arg Ser Asn Leu Pro His Ile Lys Glu Thr Thr Ser Asp
65                  70                  75                  80

Asp Val Ser Ala Ala Asn Thr Asn Asn Leu Lys Lys Ser Thr Arg Val
                85                  90                  95

Thr Lys Asn Lys Leu Arg Asn Thr Gln Leu Ala Thr Glu Asn Pro Asn
            100                 105                 110

Gly Asp Ala Ser Val Glu Glu Asp Lys Gln Gly Lys Pro Asn Lys Lys
        115                 120                 125

Val Ile Lys Thr Val Pro Gln Leu Thr Thr Gln Asp Leu Lys Pro Glu
    130                 135                 140

Thr Pro Glu Asn Lys Val Asp Ser Thr His Gln Lys Thr His Thr Lys
145                 150                 155                 160

Pro Gln Pro Gly Val Asp His Gln Lys Ser Glu Lys Ala Asn Glu Gly
                165                 170                 175

Arg Glu Glu Thr Asp Leu Glu Glu Asp Glu Glu Leu Met Gln Ala Tyr
            180                 185                 190

Gln Cys His Val Thr Glu Glu Met Ala Lys Glu Ile Lys Arg Lys Ile
        195                 200                 205

Arg Lys Lys Leu Lys Glu Gln Leu Thr Tyr Phe Pro Ser Asp Thr Leu
    210                 215                 220

Phe His Asp Asp Lys Leu Ser Ser Glu Lys Arg Lys Lys Lys Lys Glu
225                 230                 235                 240

Val Pro Val Phe Ser Lys Ala Glu Thr Ser Thr Leu Thr Ile Ser Gly
                245                 250                 255

Asp Thr Val Glu Gly Glu Gln Lys Lys Glu Ser Ser Val Arg Ser Val
```

```
            260                 265                 270

Ser Ser Asp Ser His Gln Asp Asp Glu Ile Ser Ser Met Glu Gln Ser
        275                 280                 285

Thr Glu Asp Ser Met Gln Asp Asp Thr Lys Pro Lys Pro Lys Lys Thr
    290                 295                 300

Lys Lys Lys Thr Lys Ala Val Ala Asp Asn Asn Glu Asp Val Asp Gly
305                 310                 315                 320

Asp Gly Val His Glu Ile Thr Ser Arg Asp Ser Pro Val Tyr Pro Lys
                325                 330                 335

Cys Leu Leu Asp Asp Asp Leu Val Leu Gly Val Tyr Ile His Arg Thr
            340                 345                 350

Asp Arg Leu Lys Ser Asp Phe Met Ile Ser His Pro Met Val Lys Ile
        355                 360                 365

His Val Val Asp Glu His Thr Gly Gln Tyr Val Lys Lys Asp Asp Ser
    370                 375                 380

Gly Arg Pro Val Ser Ser Tyr Tyr Glu Lys Glu Asn Val Asp Tyr Ile
385                 390                 395                 400

Leu Pro Ile Met Thr Gln Pro Tyr Asp Phe Lys Gln Leu Lys Ser Arg
                405                 410                 415

Leu Pro Glu Trp Glu Glu Gln Ile Val Phe Asn Glu Asn Phe Pro Tyr
            420                 425                 430

Leu Leu Arg Gly Ser Asp Glu Ser Pro Lys Val Ile Leu Phe Phe Glu
        435                 440                 445

Ile Leu Asp Phe Leu Ser Val Asp Glu Ile Lys Asn Asn Ser Glu Val
    450                 455                 460

Gln Asn Gln Glu Cys Gly Phe Arg Lys Ile Ala Trp Ala Phe Leu Lys
465                 470                 475                 480

Leu Leu Gly Ala Asn Gly Asn Ala Asn Ile Asn Ser Lys Leu Arg Leu
                485                 490                 495

Gln Leu Tyr Tyr Pro Pro Thr Lys Pro Arg Ser Pro Leu Ser Val Val
            500                 505                 510

Glu Ala Phe Glu Trp Trp Ser Lys Cys Pro Arg Asn His Tyr Pro Ser
        515                 520                 525

Thr Leu Tyr Val Val Arg Gly Leu Lys Val Pro Asp Cys Ile Lys Pro
    530                 535                 540

Ser Tyr Arg Ser Met Met Ala Pro Gln Glu Glu Lys Gly Lys Pro Val
545                 550                 555                 560

His Cys Glu Arg His His Glu Ser Ser Ser Val Asp Thr Glu Pro Gly
                565                 570                 575

Leu Glu Glu Ser Lys Glu Val Ile Lys Trp Lys Arg Leu Pro Gly Gln
            580                 585                 590

Ala Cys Arg Ile Pro Asn Lys His Leu Phe Ser Leu Asn Ala Gly Glu
        595                 600                 605

Arg Gly Cys Phe Cys Leu Asp Phe Ser His Asn Gly Arg Ile Leu Ala
    610                 615                 620

Ala Ala Cys Ala Ser Arg Asp Gly Tyr Pro Ile Ile Leu Tyr Glu Ile
625                 630                 635                 640

Pro Ser Gly Arg Phe Met Arg Glu Leu Cys Gly His Leu Asn Ile Ile
                645                 650                 655

Tyr Asp Leu Ser Trp Ser Lys Asp Asp His Tyr Ile Leu Thr Ser Ser
            660                 665                 670

Ser Asp Gly Thr Ala Arg Ile Trp Lys Asn Glu Ile Asn Asn Thr Asn
        675                 680                 685
```

```
Thr Phe Arg Val Leu Pro His Pro Ser Phe Val Tyr Thr Ala Lys Phe
    690                 695                 700

His Pro Ala Val Arg Glu Leu Val Val Thr Gly Cys Tyr Asp Ser Met
705                 710                 715                 720

Ile Arg Ile Trp Lys Val Glu Met Arg Glu Asp Ser Ala Ile Leu Val
                725                 730                 735

Arg Gln Phe Asp Val His Lys Ser Phe Ile Asn Ser Leu Cys Phe Asp
            740                 745                 750

Thr Glu Gly His His Met Tyr Ser Gly Asp Cys Thr Gly Val Ile Val
        755                 760                 765

Val Trp Asn Thr Tyr Val Lys Ile Asn Asp Leu Glu His Ser Val His
    770                 775                 780

His Trp Thr Ile Asn Lys Glu Ile Lys Glu Thr Glu Phe Lys Gly Ile
785                 790                 795                 800

Pro Ile Ser Tyr Leu Glu Ile His Pro Asn Gly Lys Arg Leu Leu Ile
                805                 810                 815

His Thr Lys Asp Ser Thr Leu Arg Ile Met Asp Leu Arg Ile Leu Val
            820                 825                 830

Ala Arg Lys Phe Val Gly Ala Ala Asn Tyr Arg Glu Lys Ile His Ser
        835                 840                 845

Thr Leu Thr Pro Cys Gly Thr Phe Leu Phe Ala Gly Ser Glu Asp Gly
    850                 855                 860

Ile Val Tyr Val Trp Asn Pro Glu Thr Gly Glu Gln Val Ala Met Tyr
865                 870                 875                 880

Ser Asp Leu Pro Phe Lys Ser Pro Ile Arg Asp Ile Ser Tyr His Pro
                885                 890                 895

Phe Glu Asn Met Val Ala Phe Cys Ala Phe Gly Gln Asn Glu Pro Ile
            900                 905                 910

Leu Leu Tyr Ile Tyr Asp Phe His Val Ala Gln Gln Glu Ala Glu Met
        915                 920                 925

Phe Lys Arg Tyr Asn Gly Thr Phe Pro Leu Pro Gly Ile His Gln Ser
    930                 935                 940

Gln Asp Ala Leu Cys Thr Cys Pro Lys Leu Pro His Gln Gly Ser Phe
945                 950                 955                 960

Gln Ile Asp Glu Phe Val His Thr Glu Ser Ser Ser Thr Lys Met Gln
                965                 970                 975

Leu Val Lys Gln Arg Leu Glu Thr Val Thr Glu Val Ile Arg Ser Cys
            980                 985                 990

Ala Ala Lys Val Asn Lys Asn Leu Ser Phe Thr Ser Pro Pro Ala Val
        995                 1000                1005

Ser Ser Gln Gln Ser Lys Leu Lys Gln Ser Asn Met Leu Thr Ala Gln
    1010                1015                1020

Glu Ile Leu His Gln Phe Gly Phe Thr Gln Thr Gly Ile Ile Ser Ile
1025                1030                1035                1040

Glu Arg Lys Pro Cys Asn His Gln Val Asp Thr Ala Pro Thr Val Val
                1045                1050                1055

Ala Leu Tyr Asp Tyr Thr Ala Asn Arg Ser Asp Glu Leu Thr Ile His
            1060                1065                1070

Arg Gly Asp Ile Ile Arg Val Phe Phe Lys Asp Asn Glu Asp Trp Trp
        1075                1080                1085

Tyr Gly Ser Ile Gly Lys Gly Gln Glu Gly Tyr Phe Pro Ala Asn His
    1090                1095                1100
```

Val Ala Ser Glu Thr Leu Tyr Gln Glu Leu Pro Pro Glu Ile Lys Glu
1105 1110 1115 1120

Arg Ser Pro Pro Leu Ser Pro Glu Glu Lys Thr Lys Ile Glu Lys Ser
1125 1130 1135

Pro Ala Pro Gln Lys Gln Ser Ile Asn Lys Asn Lys Ser Gln Asp Phe
1140 1145 1150

Arg Leu Gly Ser Glu Ser Met Thr His Ser Glu Met Arg Lys Glu Gln
1155 1160 1165

Ser His Glu Asp Gln Gly His Ile Met Asp Thr Arg Met Arg Lys Asn
1170 1175 1180

Lys Gln Ala Gly Arg Lys Val Thr Leu Ile Glu
1185 1190 1195

<210> SEQ ID NO 59
<211> LENGTH: 558
<212> TYPE: PRT
<213> ORGANISM: Homo sapiens

<400> SEQUENCE: 59

Met Ala Gln Asp Ser Val Asp Leu Ser Cys Asp Tyr Gln Phe Trp Met
1 5 10 15

Gln Lys Leu Ser Val Trp Asp Gln Ala Ser Thr Leu Glu Thr Gln Gln
20 25 30

Asp Thr Cys Leu His Val Ala Gln Phe Gln Glu Phe Leu Arg Lys Met
35 40 45

Tyr Glu Ala Leu Lys Glu Met Asp Ser Asn Thr Val Ile Glu Arg Phe
50 55 60

Pro Thr Ile Gly Gln Leu Leu Ala Lys Ala Cys Trp Asn Pro Phe Ile
65 70 75 80

Leu Ala Tyr Asp Glu Ser Gln Lys Ile Leu Ile Trp Cys Leu Cys Cys
85 90 95

Leu Ile Asn Lys Glu Pro Gln Asn Ser Gly Gln Ser Lys Leu Asn Ser
100 105 110

Trp Ile Gln Gly Val Leu Ser His Ile Leu Ser Ala Leu Arg Phe Asp
115 120 125

Lys Glu Val Ala Leu Phe Thr Gln Gly Leu Gly Tyr Ala Pro Ile Asp
130 135 140

Tyr Tyr Pro Gly Leu Leu Lys Asn Met Val Leu Ser Leu Ala Ser Glu
145 150 155 160

Leu Arg Glu Asn His Leu Asn Gly Phe Asn Thr Gln Arg Arg Met Ala
165 170 175

Pro Glu Arg Val Ala Ser Leu Ser Arg Val Cys Val Pro Leu Ile Thr
180 185 190

Leu Thr Asp Val Asp Pro Leu Val Glu Ala Leu Leu Ile Cys His Gly
195 200 205

Arg Glu Pro Gln Glu Ile Leu Gln Pro Glu Phe Phe Glu Ala Val Asn
210 215 220

Glu Ala Ile Leu Leu Lys Lys Ile Ser Leu Pro Met Ser Ala Val Val
225 230 235 240

Cys Leu Trp Leu Arg His Leu Pro Ser Leu Glu Lys Ala Met Leu His
245 250 255

Leu Phe Glu Lys Leu Ile Ser Ser Glu Arg Asn Cys Leu Arg Arg Ile
260 265 270

Glu Cys Phe Ile Lys Asp Ser Ser Leu Pro Gln Ala Ala Cys His Pro
275 280 285

```
Ala Ile Phe Arg Val Val Asp Glu Met Phe Arg Cys Ala Leu Leu Glu
    290                 295                 300

Thr Asp Gly Ala Leu Glu Ile Ile Ala Thr Ile Gln Val Phe Thr Gln
305                 310                 315                 320

Cys Phe Val Glu Ala Leu Glu Lys Ala Ser Lys Gln Leu Arg Phe Ala
                325                 330                 335

Leu Lys Thr Tyr Phe Pro Tyr Thr Ser Pro Ser Leu Ala Met Val Leu
            340                 345                 350

Leu Gln Asp Pro Gln Asp Ile Pro Arg Gly His Trp Leu Gln Thr Leu
        355                 360                 365

Lys His Ile Ser Glu Leu Leu Arg Glu Ala Val Glu Asp Gln Thr His
    370                 375                 380

Gly Ser Cys Gly Gly Pro Phe Glu Ser Trp Phe Leu Phe Ile His Phe
385                 390                 395                 400

Gly Gly Trp Ala Glu Met Val Ala Glu Gln Leu Leu Met Ser Ala Ala
                405                 410                 415

Glu Pro Pro Thr Ala Leu Leu Trp Leu Leu Ala Phe Tyr Tyr Gly Pro
            420                 425                 430

Arg Asp Gly Arg Gln Gln Arg Ala Gln Thr Met Val Gln Val Lys Ala
        435                 440                 445

Val Leu Gly His Leu Leu Ala Met Ser Arg Ser Ser Ser Leu Ser Ala
    450                 455                 460

Gln Asp Leu Gln Thr Val Ala Gly Gln Gly Thr Asp Thr Asp Leu Arg
465                 470                 475                 480

Ala Pro Ala Gln Gln Leu Ile Arg His Leu Leu Leu Asn Phe Leu Leu
                485                 490                 495

Trp Ala Pro Gly Gly His Thr Ile Ala Trp Asp Val Ile Thr Leu Met
            500                 505                 510

Ala His Thr Ala Glu Ile Thr His Glu Ile Ile Gly Phe Leu Asp Gln
        515                 520                 525

Thr Leu Tyr Arg Trp Asn Arg Leu Gly Ile Glu Ser Pro Arg Ser Glu
    530                 535                 540

Lys Leu Ala Arg Glu Leu Leu Lys Glu Leu Arg Thr Gln Val
545                 550                 555


<210> SEQ ID NO 60
<211> LENGTH: 1274
<212> TYPE: PRT
<213> ORGANISM: Homo sapiens

<400> SEQUENCE: 60

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Ala Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
                85                  90                  95

Ala Glu Glu Ala Glu Pro Met Leu Ala Pro Ala Pro Ala Pro Ala Glu
```

```
            100                 105                 110

Ala Thr Gly Ala Pro Gly Glu Ala Pro Ala Pro Ala Ala Glu Leu Gly
        115                 120                 125

Glu Ser Ala Pro Ser Pro Lys Gly Ser Ser Ser Ala Ala Leu Asn Gly
    130                 135                 140

Pro Thr Pro Gly Ala Pro Asp Asp Pro Ile Gly Leu Phe Val Met Arg
145                 150                 155                 160

Pro Gln Asp Gly Glu Val Thr Val Gly Gly Ser Ile Thr Phe Ser Ala
                165                 170                 175

Arg Val Ala Gly Ala Ser Leu Leu Lys Pro Pro Val Val Lys Trp Phe
            180                 185                 190

Lys Gly Lys Trp Val Asp Leu Ser Ser Lys Val Gly Gln His Leu Gln
        195                 200                 205

Leu His Asp Ser Tyr Asp Arg Ala Ser Lys Val Tyr Leu Phe Glu Leu
    210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
                245                 250                 255

His Glu Ala Met Gly Thr Gly Asp Leu Asp Leu Leu Ser Ala Phe Arg
            260                 265                 270

Arg Thr Ser Leu Ala Gly Gly Gly Arg Arg Ile Ser Asp Ser His Glu
        275                 280                 285

Asp Thr Gly Ile Leu Asp Phe Ser Ser Leu Leu Lys Lys Arg Asp Ser
    290                 295                 300

Phe Arg Thr Pro Arg Asp Ser Lys Leu Glu Ala Pro Ala Glu Glu Asp
305                 310                 315                 320

Val Trp Glu Thr Leu Arg Gln Ala Pro Pro Ser Glu Tyr Glu Arg Ile
                325                 330                 335

Ala Phe Gln Tyr Gly Val Thr Asp Leu Arg Gly Met Leu Lys Arg Leu
            340                 345                 350

Lys Gly Met Arg Arg Asp Glu Lys Lys Ser Thr Ala Phe Gln Lys Lys
        355                 360                 365

Leu Glu Pro Ala Tyr Gln Val Ser Lys Gly His Lys Ile Arg Leu Thr
    370                 375                 380

Val Glu Leu Ala Asp His Asp Ala Glu Val Lys Trp Leu Lys Asp Gly
385                 390                 395                 400

Gln Glu Ile Gln Met Ser Gly Ser Lys Tyr Ile Phe Glu Ser Ile Gly
                405                 410                 415

Ala Lys Arg Thr Leu Thr Ile Ser Gln Cys Ser Leu Ala Asp Asp Ala
            420                 425                 430

Ala Tyr Gln Cys Val Val Gly Gly Glu Lys Cys Ser Thr Glu Leu Phe
        435                 440                 445

Val Lys Glu Pro Pro Val Leu Ile Thr Arg Pro Leu Glu Asp Gln Leu
    450                 455                 460

Val Met Val Gly Gln Arg Val Glu Phe Glu Cys Glu Val Ser Glu Glu
465                 470                 475                 480

Gly Ala Gln Val Lys Trp Leu Lys Asp Gly Val Glu Leu Thr Arg Glu
                485                 490                 495

Glu Thr Phe Lys Tyr Arg Phe Lys Lys Asp Gly Gln Arg His His Leu
            500                 505                 510

Ile Ile Asn Glu Ala Met Leu Glu Asp Ala Gly His Tyr Ala Leu Cys
        515                 520                 525
```

```
Thr Ser Gly Gly Gln Ala Leu Ala Glu Leu Ile Val Gln Glu Lys Lys
    530                 535                 540

Leu Glu Val Tyr Gln Ser Ile Ala Asp Leu Met Val Gly Ala Lys Asp
545                 550                 555                 560

Gln Ala Val Phe Lys Cys Glu Val Ser Asp Glu Asn Val Arg Gly Val
                565                 570                 575

Trp Leu Lys Asn Gly Lys Glu Leu Val Pro Asp Ser Arg Ile Lys Val
            580                 585                 590

Ser His Ile Gly Arg Val His Lys Leu Thr Ile Asp Asp Val Thr Pro
        595                 600                 605

Ala Asp Glu Ala Asp Tyr Ser Phe Val Pro Glu Gly Phe Ala Cys Asn
    610                 615                 620

Leu Ser Ala Lys Leu His Phe Met Glu Val Lys Ile Asp Phe Val Pro
625                 630                 635                 640

Arg Gln Glu Pro Pro Lys Ile His Leu Asp Cys Pro Gly Arg Ile Pro
                645                 650                 655

Asp Thr Ile Val Val Val Ala Gly Asn Lys Leu Arg Leu Asp Val Pro
            660                 665                 670

Ile Ser Gly Asp Pro Ala Pro Thr Val Ile Trp Gln Lys Ala Ile Thr
        675                 680                 685

Gln Gly Asn Lys Ala Pro Ala Arg Pro Ala Pro Asp Ala Pro Glu Asp
    690                 695                 700

Thr Gly Asp Ser Asp Glu Trp Val Phe Asp Lys Lys Leu Leu Cys Glu
705                 710                 715                 720

Thr Glu Gly Arg Val Arg Val Glu Thr Thr Lys Asp Arg Ser Ile Phe
                725                 730                 735

Thr Val Glu Gly Ala Glu Lys Glu Asp Glu Gly Val Tyr Thr Val Thr
            740                 745                 750

Val Lys Asn Pro Val Gly Glu Asp Gln Val Asn Leu Thr Val Lys Val
        755                 760                 765

Ile Asp Val Pro Asp Ala Pro Ala Ala Pro Lys Ile Ser Asn Val Gly
    770                 775                 780

Glu Asp Ser Cys Thr Val Gln Trp Glu Pro Pro Ala Tyr Asp Gly Gly
785                 790                 795                 800

Gln Pro Ile Leu Gly Tyr Ile Leu Glu Arg Lys Lys Lys Lys Ser Tyr
                805                 810                 815

Arg Trp Met Arg Leu Asn Phe Asp Leu Ile Gln Glu Leu Ser His Glu
            820                 825                 830

Ala Arg Arg Met Ile Glu Gly Val Val Tyr Glu Met Arg Val Tyr Ala
        835                 840                 845

Val Asn Ala Ile Gly Met Ser Arg Pro Ser Pro Ala Ser Gln Pro Phe
    850                 855                 860

Met Pro Ile Gly Pro Pro Ser Glu Pro Thr His Leu Ala Val Glu Asp
865                 870                 875                 880

Val Ser Asp Thr Thr Val Ser Leu Lys Trp Arg Pro Pro Glu Arg Val
                885                 890                 895

Gly Ala Gly Gly Leu Asp Gly Tyr Ser Val Glu Tyr Cys Pro Glu Gly
            900                 905                 910

Cys Ser Glu Trp Val Ala Ala Leu Gln Gly Leu Thr Glu His Thr Ser
        915                 920                 925

Ile Leu Val Lys Asp Leu Pro Thr Gly Ala Arg Leu Leu Ser Arg Val
    930                 935                 940
```

```
Arg Ala His Asn Met Ala Gly Pro Gly Ala Pro Val Thr Thr Thr Glu
945                 950                 955                 960

Pro Val Thr Val Gln Glu Ile Leu Gln Arg Pro Arg Leu Gln Leu Pro
                965                 970                 975

Arg His Leu Arg Gln Thr Ile Gln Lys Lys Val Gly Glu Pro Val Asn
            980                 985                 990

Leu Leu Ile Pro Phe Gln Gly Lys Pro Arg Pro Gln Val Thr Trp Thr
        995                 1000                1005

Lys Glu Gly Gln Pro Leu Ala Gly Glu Glu Val Ser Ile Arg Asn Ser
    1010                1015                1020

Pro Thr Asp Thr Ile Leu Phe Ile Arg Ala Ala Arg Arg Val His Ser
1025                1030                1035                1040

Gly Thr Tyr Gln Val Thr Val Arg Ile Glu Asn Met Glu Asp Lys Ala
                1045                1050                1055

Thr Leu Val Leu Gln Val Val Asp Lys Pro Ser Pro Pro Gln Asp Leu
            1060                1065                1070

Arg Val Thr Asp Ala Trp Gly Leu Asn Val Ala Leu Glu Trp Lys Pro
        1075                1080                1085

Pro Gln Asp Val Gly Asn Thr Glu Leu Trp Gly Tyr Thr Val Gln Lys
    1090                1095                1100

Ala Asp Lys Lys Thr Met Glu Trp Phe Thr Val Leu Glu His Tyr Arg
1105                1110                1115                1120

Arg Thr His Cys Val Val Pro Glu Leu Ile Ile Gly Asn Gly Tyr Tyr
                1125                1130                1135

Phe Arg Val Phe Ser Gln Asn Met Val Gly Phe Ser Asp Arg Ala Ala
            1140                1145                1150

Thr Thr Lys Glu Pro Val Phe Ile Pro Arg Pro Gly Ile Thr Tyr Glu
        1155                1160                1165

Pro Pro Asn Tyr Lys Ala Leu Asp Phe Ser Glu Ala Pro Ser Phe Thr
    1170                1175                1180

Gln Pro Leu Val Asn Arg Ser Val Ile Ala Gly Tyr Thr Ala Met Leu
1185                1190                1195                1200

Cys Cys Ala Val Arg Gly Ser Pro Lys Pro Lys Ile Ser Trp Phe Lys
                1205                1210                1215

Asn Gly Leu Asp Leu Gly Glu Asp Ala Arg Phe Arg Met Phe Ser Lys
            1220                1225                1230

Gln Gly Val Leu Thr Leu Glu Ile Arg Lys Pro Cys Pro Phe Asp Gly
        1235                1240                1245

Gly Ile Tyr Val Cys Arg Ala Thr Asn Leu Gln Gly Glu Ala Arg Cys
    1250                1255                1260

Glu Cys Arg Leu Glu Val Arg Val Pro Gln
1265                1270


<210> SEQ ID NO 61
<211> LENGTH: 369
<212> TYPE: PRT
<213> ORGANISM: Homo sapiens

<400> SEQUENCE: 61

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45
```

Ser Leu Ser Val Ser Thr Leu Pro Leu Pro Glu Val Gln Cys Phe Val
50 55 60

Phe Asn Val Glu Tyr Met Asn Cys Thr Trp Asn Ser Ser Ser Glu Pro
65 70 75 80

Gln Pro Thr Asn Leu Thr Leu His Tyr Trp Tyr Lys Asn Ser Asp Asn
85 90 95

Asp Lys Val Gln Lys Cys Ser His Tyr Leu Phe Ser Glu Glu Ile Thr
100 105 110

Ser Gly Cys Gln Leu Gln Lys Lys Glu Ile His Leu Tyr Gln Thr Phe
115 120 125

Val Val Gln Leu Gln Asp Pro Arg Glu Pro Arg Arg Gln Ala Thr Gln
130 135 140

Met Leu Lys Leu Gln Asn Leu Val Ile Pro Trp Ala Pro Glu Asn Leu
145 150 155 160

Thr Leu His Lys Leu Ser Glu Ser Gln Leu Glu Leu Asn Trp Asn Asn
165 170 175

Arg Phe Leu Asn His Cys Leu Glu His Leu Val Gln Tyr Arg Thr Asp
180 185 190

Trp Asp His Ser Trp Thr Glu Gln Ser Val Asp Tyr Arg His Lys Phe
195 200 205

Ser Leu Pro Ser Val Asp Gly Gln Lys Arg Tyr Thr Phe Arg Val Arg
210 215 220

Ser Arg Phe Asn Pro Leu Cys Gly Ser Ala Gln His Trp Ser Glu Trp
225 230 235 240

Ser His Pro Ile His Trp Gly Ser Asn Thr Ser Lys Glu Asn Pro Phe
245 250 255

Leu Phe Ala Leu Glu Ala Val Val Ile Ser Val Gly Ser Met Gly Leu
260 265 270

Ile Ile Ser Leu Leu Cys Val Tyr Phe Trp Leu Glu Arg Thr Met Pro
275 280 285

Arg Ile Pro Thr Leu Lys Asn Leu Glu Asp Leu Val Thr Glu Tyr His
290 295 300

Gly Asn Phe Ser Ala Trp Ser Gly Val Ser Lys Gly Leu Ala Glu Ser
305 310 315 320

Leu Gln Pro Asp Tyr Ser Glu Arg Leu Cys Leu Val Ser Glu Ile Pro
325 330 335

Pro Lys Gly Gly Ala Leu Gly Glu Gly Pro Gly Ala Ser Pro Cys Asn
340 345 350

Gln His Ser Pro Tyr Trp Ala Pro Pro Cys Tyr Thr Leu Lys Pro Glu
355 360 365

Thr

<210> SEQ ID NO 62
<211> LENGTH: 1272
<212> TYPE: PRT
<213> ORGANISM: Artificial Sequence
<220> FEATURE:
<223> OTHER INFORMATION: Synthetic Construct

<400> SEQUENCE: 62

Phe Val Phe Leu Val Leu Leu Pro Leu Val Ser Ser Gln Cys Val Asn
1 5 10 15

Leu Thr Thr Arg Thr Gln Leu Pro Pro Ala Tyr Thr Asn Ser Phe Thr
20 25 30

```
Arg Gly Val Tyr Tyr Pro Asp Lys Val Phe Arg Ser Ser Val Leu His
        35                  40                  45

Ser Thr Gln Asp Leu Phe Leu Pro Phe Phe Ser Asn Val Thr Trp Phe
    50                  55                  60

His Ala Ile His Val Ser Gly Thr Asn Gly Thr Lys Arg Phe Asp Asn
65                  70                  75                  80

Pro Val Leu Pro Phe Asn Asp Gly Val Tyr Phe Ala Ser Thr Glu Lys
                85                  90                  95

Ser Asn Ile Ile Arg Gly Trp Ile Phe Gly Thr Thr Leu Asp Ser Lys
            100                 105                 110

Thr Gln Ser Leu Leu Ile Val Asn Asn Ala Thr Asn Val Val Ile Lys
        115                 120                 125

Val Cys Glu Phe Gln Phe Cys Asn Asp Pro Phe Leu Gly Val Tyr Tyr
    130                 135                 140

His Lys Asn Asn Lys Ser Trp Met Glu Ser Glu Phe Arg Val Tyr Ser
145                 150                 155                 160

Ser Ala Asn Asn Cys Thr Phe Glu Tyr Val Ser Gln Pro Phe Leu Met
                165                 170                 175

Asp Leu Glu Gly Lys Gln Gly Asn Phe Lys Asn Leu Arg Glu Phe Val
            180                 185                 190

Phe Lys Asn Ile Asp Gly Tyr Phe Lys Ile Tyr Ser Lys His Thr Pro
        195                 200                 205

Ile Asn Leu Val Arg Asp Leu Pro Gln Gly Phe Ser Ala Leu Glu Pro
    210                 215                 220

Leu Val Asp Leu Pro Ile Gly Ile Asn Ile Thr Arg Phe Gln Thr Leu
225                 230                 235                 240

Leu Ala Leu His Arg Ser Tyr Leu Thr Pro Gly Asp Ser Ser Ser Gly
                245                 250                 255

Trp Thr Ala Gly Ala Ala Ala Tyr Tyr Val Gly Tyr Leu Gln Pro Arg
            260                 265                 270

Thr Phe Leu Leu Lys Tyr Asn Glu Asn Gly Thr Ile Thr Asp Ala Val
        275                 280                 285

Asp Cys Ala Leu Asp Pro Leu Ser Glu Thr Lys Cys Thr Leu Lys Ser
    290                 295                 300

Phe Thr Val Glu Lys Gly Ile Tyr Gln Thr Ser Asn Phe Arg Val Gln
305                 310                 315                 320

Pro Thr Glu Ser Ile Val Arg Phe Pro Asn Ile Thr Asn Leu Cys Pro
                325                 330                 335

Phe Gly Glu Val Phe Asn Ala Thr Arg Phe Ala Ser Val Tyr Ala Trp
            340                 345                 350

Asn Arg Lys Arg Ile Ser Asn Cys Val Ala Asp Tyr Ser Val Leu Tyr
        355                 360                 365

Asn Ser Ala Ser Phe Ser Thr Phe Lys Cys Tyr Gly Val Ser Pro Thr
    370                 375                 380

Lys Leu Asn Asp Leu Cys Phe Thr Asn Val Tyr Ala Asp Ser Phe Val
385                 390                 395                 400

Ile Arg Gly Asp Glu Val Arg Gln Ile Ala Pro Gly Gln Thr Gly Lys
                405                 410                 415

Ile Ala Asp Tyr Asn Tyr Lys Leu Pro Asp Asp Phe Thr Gly Cys Val
            420                 425                 430

Ile Ala Trp Asn Ser Asn Asn Leu Asp Ser Lys Val Gly Gly Asn Tyr
        435                 440                 445

Asn Tyr Leu Tyr Arg Leu Phe Arg Lys Ser Asn Leu Lys Pro Phe Glu
```

```
    450                 455                 460

Arg Asp Ile Ser Thr Glu Ile Tyr Gln Ala Gly Ser Thr Pro Cys Asn
465                 470                 475                 480

Gly Val Glu Gly Phe Asn Cys Tyr Phe Pro Leu Gln Ser Tyr Gly Phe
                485                 490                 495

Gln Pro Thr Asn Gly Val Gly Tyr Gln Pro Tyr Arg Val Val Val Leu
            500                 505                 510

Ser Phe Glu Leu Leu His Ala Pro Ala Thr Val Cys Gly Pro Lys Lys
        515                 520                 525

Ser Thr Asn Leu Val Lys Asn Lys Cys Val Asn Phe Asn Phe Asn Gly
    530                 535                 540

Leu Thr Gly Thr Gly Val Leu Thr Glu Ser Asn Lys Lys Phe Leu Pro
545                 550                 555                 560

Phe Gln Gln Phe Gly Arg Asp Ile Ala Asp Thr Thr Asp Ala Val Arg
                565                 570                 575

Asp Pro Gln Thr Leu Glu Ile Leu Asp Ile Thr Pro Cys Ser Phe Gly
            580                 585                 590

Gly Val Ser Val Ile Thr Pro Gly Thr Asn Thr Ser Asn Gln Val Ala
        595                 600                 605

Val Leu Tyr Gln Asp Val Asn Cys Thr Glu Val Pro Val Ala Ile His
    610                 615                 620

Ala Asp Gln Leu Thr Pro Thr Trp Arg Val Tyr Ser Thr Gly Ser Asn
625                 630                 635                 640

Val Phe Gln Thr Arg Ala Gly Cys Leu Ile Gly Ala Glu His Val Asn
                645                 650                 655

Asn Ser Tyr Glu Cys Asp Ile Pro Ile Gly Ala Gly Ile Cys Ala Ser
            660                 665                 670

Tyr Gln Thr Gln Thr Asn Ser Pro Arg Arg Ala Arg Ser Val Ala Ser
        675                 680                 685

Gln Ser Ile Ile Ala Tyr Thr Met Ser Leu Gly Ala Glu Asn Ser Val
    690                 695                 700

Ala Tyr Ser Asn Asn Ser Ile Ala Ile Pro Thr Asn Phe Thr Ile Ser
705                 710                 715                 720

Val Thr Thr Glu Ile Leu Pro Val Ser Met Thr Lys Thr Ser Val Asp
                725                 730                 735

Cys Thr Met Tyr Ile Cys Gly Asp Ser Thr Glu Cys Ser Asn Leu Leu
            740                 745                 750

Leu Gln Tyr Gly Ser Phe Cys Thr Gln Leu Asn Arg Ala Leu Thr Gly
        755                 760                 765

Ile Ala Val Glu Gln Asp Lys Asn Thr Gln Glu Val Phe Ala Gln Val
    770                 775                 780

Lys Gln Ile Tyr Lys Thr Pro Pro Ile Lys Asp Phe Gly Gly Phe Asn
785                 790                 795                 800

Phe Ser Gln Ile Leu Pro Asp Pro Ser Lys Pro Ser Lys Arg Ser Phe
                805                 810                 815

Ile Glu Asp Leu Leu Phe Asn Lys Val Thr Leu Ala Asp Ala Gly Phe
            820                 825                 830

Ile Lys Gln Tyr Gly Asp Cys Leu Gly Asp Ile Ala Ala Arg Asp Leu
        835                 840                 845

Ile Cys Ala Gln Lys Phe Asn Gly Leu Thr Val Leu Pro Pro Leu Leu
    850                 855                 860

Thr Asp Glu Met Ile Ala Gln Tyr Thr Ser Ala Leu Leu Ala Gly Thr
865                 870                 875                 880
```

```
Ile Thr Ser Gly Trp Thr Phe Gly Ala Gly Ala Ala Leu Gln Ile Pro
                885                 890                 895

Phe Ala Met Gln Met Ala Tyr Arg Phe Asn Gly Ile Gly Val Thr Gln
            900                 905                 910

Asn Val Leu Tyr Glu Asn Gln Lys Leu Ile Ala Asn Gln Phe Asn Ser
        915                 920                 925

Ala Ile Gly Lys Ile Gln Asp Ser Leu Ser Ser Thr Ala Ser Ala Leu
    930                 935                 940

Gly Lys Leu Gln Asp Val Val Asn Gln Asn Ala Gln Ala Leu Asn Thr
945                 950                 955                 960

Leu Val Lys Gln Leu Ser Ser Asn Phe Gly Ala Ile Ser Ser Val Leu
                965                 970                 975

Asn Asp Ile Leu Ser Arg Leu Asp Pro Pro Glu Ala Glu Val Gln Ile
            980                 985                 990

Asp Arg Leu Ile Thr Gly Arg Leu Gln Ser Leu Gln Thr Tyr Val Thr
        995                 1000                1005

Gln Gln Leu Ile Arg Ala Ala Glu Ile Arg Ala Ser Ala Asn Leu Ala
    1010                1015                1020

Ala Thr Lys Met Ser Glu Cys Val Leu Gly Gln Ser Lys Arg Val Asp
1025                1030                1035                1040

Phe Cys Gly Lys Gly Tyr His Leu Met Ser Phe Pro Gln Ser Ala Pro
                1045                1050                1055

His Gly Val Val Phe Leu His Val Thr Tyr Val Pro Ala Gln Glu Lys
            1060                1065                1070

Asn Phe Thr Thr Ala Pro Ala Ile Cys His Asp Gly Lys Ala His Phe
        1075                1080                1085

Pro Arg Glu Gly Val Phe Val Ser Asn Gly Thr His Trp Phe Val Thr
    1090                1095                1100

Gln Arg Asn Phe Tyr Glu Pro Gln Ile Ile Thr Thr Asp Asn Thr Phe
1105                1110                1115                1120

Val Ser Gly Asn Cys Asp Val Val Ile Gly Ile Val Asn Asn Thr Val
                1125                1130                1135

Tyr Asp Pro Leu Gln Pro Glu Leu Asp Ser Phe Lys Glu Glu Leu Asp
            1140                1145                1150

Lys Tyr Phe Lys Asn His Thr Ser Pro Asp Val Asp Leu Gly Asp Ile
        1155                1160                1165

Ser Gly Ile Asn Ala Ser Val Val Asn Ile Gln Lys Glu Ile Asp Arg
    1170                1175                1180

Leu Asn Glu Val Ala Lys Asn Leu Asn Glu Ser Leu Ile Asp Leu Gln
1185                1190                1195                1200

Glu Leu Gly Lys Tyr Glu Gln Tyr Ile Lys Trp Pro Trp Tyr Ile Trp
                1205                1210                1215

Leu Gly Phe Ile Ala Gly Leu Ile Ala Ile Val Met Val Thr Ile Met
            1220                1225                1230

Leu Cys Cys Met Thr Ser Cys Cys Ser Cys Leu Lys Gly Cys Cys Ser
        1235                1240                1245

Cys Gly Ser Cys Cys Lys Phe Asp Glu Asp Asp Ser Glu Pro Val Leu
    1250                1255                1260

Lys Gly Val Lys Leu His Tyr Thr
1265                1270
```

<210> SEQ ID NO 63
<211> LENGTH: 223

```
<212> TYPE: PRT
<213> ORGANISM: SARS-CoV-2

<400> SEQUENCE: 63

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Asn Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
                165                 170                 175

Tyr Gly Phe Gln Pro Thr Tyr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 64
<211> LENGTH: 669
<212> TYPE: DNA
<213> ORGANISM: SARS-CoV-2

<400> SEQUENCE: 64

cgcgtccagc caaccgagag catcgtcaga tttcccaaca ttacaaatct gtgtcccttc      60

ggcgaggtgt tcaacgccac acgcttcgct tcagtgtacg catggaaccg caagcgcata     120

tctaactgcg tcgcggatta ttctgtcctc tacaactccg cctctttctc caccttcaag     180

tgctacggag tgtcaccgac taagctgaac gatctctgct ttaccaacgt ctacgcggac     240

tccttcgtga taagaggtga tgaagtgaga caaatagccc caggtcagac tggtaacatc     300

gcagattaca actacaaatt gcctgatgat ttcactggtt gcgttatcgc gtggaactct     360

aataacctcg attctaaggt cggtggtaac tacaattacc tgtaccgctt gtttaggaag     420

tcaaacctga agcctttcga gagggatatt tcaaccgaaa tctatcaagc gggttcaaca     480

ccgtgtaacg gtgtgaaagg atttaactgc tacttccccc tgcagtctta cggattccag     540

ccaacctatg gcgtgggtta ccaaccttat cgcgtggtgg ttctgagttt cgaactgttg     600

cacgctcccg ccacggtatg cggtcccaag aagagcacta acttggtgaa gaataagtgc     660

gtgaatttc                                                             669
```

<210> SEQ ID NO 65
<211> LENGTH: 18
<212> TYPE: PRT
<213> ORGANISM: SARS-CoV-2

<400> SEQUENCE: 65

Gly Ile Tyr Gln Thr Ser Asn Phe Arg Val Gln Pro Thr Glu Ser Ile
1 5 10 15

Val Arg

<210> SEQ ID NO 66
<211> LENGTH: 17
<212> TYPE: PRT
<213> ORGANISM: SARS-CoV-2

<400> SEQUENCE: 66

Arg Val Gln Pro Thr Glu Ser Ile Val Arg Phe Pro Asn Ile Thr Asn
1 5 10 15

Leu

<210> SEQ ID NO 67
<211> LENGTH: 17
<212> TYPE: PRT
<213> ORGANISM: SARS-CoV-2

<400> SEQUENCE: 67

Ile Val Arg Phe Pro Asn Ile Thr Asn Leu Cys Pro Phe Gly Glu Val
1 5 10 15

Phe

<210> SEQ ID NO 68
<211> LENGTH: 18
<212> TYPE: PRT
<213> ORGANISM: SARS-CoV-2

<400> SEQUENCE: 68

Thr Asn Leu Cys Pro Phe Gly Glu Val Phe Asn Ala Thr Arg Phe Ala
1 5 10 15

Ser Val

<210> SEQ ID NO 69
<211> LENGTH: 18
<212> TYPE: PRT
<213> ORGANISM: SARS-CoV-2

<400> SEQUENCE: 69

Val Phe Asn Ala Thr Arg Phe Ala Ser Val Tyr Ala Trp Asn Arg Lys
1 5 10 15

Arg Ile

<210> SEQ ID NO 70
<211> LENGTH: 17
<212> TYPE: PRT
<213> ORGANISM: SARS-CoV-2

<400> SEQUENCE: 70

Ser Val Tyr Ala Trp Asn Arg Lys Arg Ile Ser Asn Cys Val Ala Asp
1 5 10 15

Tyr

<210> SEQ ID NO 71
<211> LENGTH: 17
<212> TYPE: PRT
<213> ORGANISM: SARS-CoV-2

<400> SEQUENCE: 71

Lys Arg Ile Ser Asn Cys Val Ala Asp Tyr Ser Val Leu Tyr Asn Ser
1 5 10 15

Ala

<210> SEQ ID NO 72
<211> LENGTH: 18
<212> TYPE: PRT
<213> ORGANISM: SARS-CoV-2

<400> SEQUENCE: 72

Ala Asp Tyr Ser Val Leu Tyr Asn Ser Ala Ser Phe Ser Thr Phe Lys
1 5 10 15

Cys Tyr

<210> SEQ ID NO 73
<211> LENGTH: 17
<212> TYPE: PRT
<213> ORGANISM: SARS-CoV-2

<400> SEQUENCE: 73

Ser Ala Ser Phe Ser Thr Phe Lys Cys Tyr Gly Val Ser Pro Thr Lys
1 5 10 15

Leu

<210> SEQ ID NO 74
<211> LENGTH: 18
<212> TYPE: PRT
<213> ORGANISM: SARS-CoV-2

<400> SEQUENCE: 74

Lys Cys Tyr Gly Val Ser Pro Thr Lys Leu Asn Asp Leu Cys Phe Thr
1 5 10 15

Asn Val

<210> SEQ ID NO 75
<211> LENGTH: 18
<212> TYPE: PRT
<213> ORGANISM: SARS-CoV-2

<400> SEQUENCE: 75

Lys Leu Asn Asp Leu Cys Phe Thr Asn Val Tyr Ala Asp Ser Phe Val
1 5 10 15

Ile Arg

<210> SEQ ID NO 76
<211> LENGTH: 18
<212> TYPE: PRT
<213> ORGANISM: SARS-CoV-2

<400> SEQUENCE: 76

Asn Val Tyr Ala Asp Ser Phe Val Ile Arg Gly Asp Glu Val Arg Gln
1 5 10 15

Ile Ala

<210> SEQ ID NO 77

<211> LENGTH: 18
<212> TYPE: PRT
<213> ORGANISM: SARS-CoV-2

<400> SEQUENCE: 77

Ile Arg Gly Asp Glu Val Arg Gln Ile Ala Pro Gly Gln Thr Gly Lys
1 5 10 15

Ile Ala

<210> SEQ ID NO 78
<211> LENGTH: 16
<212> TYPE: PRT
<213> ORGANISM: SARS-CoV-2

<400> SEQUENCE: 78

Ile Ala Pro Gly Gln Thr Gly Lys Ile Ala Asp Tyr Asn Tyr Lys Leu
1 5 10 15

<210> SEQ ID NO 79
<211> LENGTH: 18
<212> TYPE: PRT
<213> ORGANISM: SARS-CoV-2

<400> SEQUENCE: 79

Gly Lys Ile Ala Asp Tyr Asn Tyr Lys Leu Pro Asp Asp Phe Thr Gly
1 5 10 15

Cys Val

<210> SEQ ID NO 80
<211> LENGTH: 18
<212> TYPE: PRT
<213> ORGANISM: SARS-CoV-2

<400> SEQUENCE: 80

Lys Leu Pro Asp Asp Phe Thr Gly Cys Val Ile Ala Trp Asn Ser Asn
1 5 10 15

Asn Leu

<210> SEQ ID NO 81
<211> LENGTH: 18
<212> TYPE: PRT
<213> ORGANISM: SARS-CoV-2

<400> SEQUENCE: 81

Cys Val Ile Ala Trp Asn Ser Asn Asn Leu Asp Ser Lys Val Gly Gly
1 5 10 15

Asn Tyr

<210> SEQ ID NO 82
<211> LENGTH: 18
<212> TYPE: PRT
<213> ORGANISM: SARS-CoV-2

<400> SEQUENCE: 82

Asn Leu Asp Ser Lys Val Gly Gly Asn Tyr Asn Tyr Leu Tyr Arg Leu
1 5 10 15

Phe Arg

<210> SEQ ID NO 83
<211> LENGTH: 17
<212> TYPE: PRT
<213> ORGANISM: SARS-CoV-2

<400> SEQUENCE: 83

Asn Tyr Asn Tyr Leu Tyr Arg Leu Phe Arg Lys Ser Asn Leu Lys Pro
1 5 10 15

Phe

<210> SEQ ID NO 84
<211> LENGTH: 18
<212> TYPE: PRT
<213> ORGANISM: SARS-CoV-2

<400> SEQUENCE: 84

Leu Phe Arg Lys Ser Asn Leu Lys Pro Phe Glu Arg Asp Ile Ser Thr
1 5 10 15

Glu Ile

<210> SEQ ID NO 85
<211> LENGTH: 13
<212> TYPE: PRT
<213> ORGANISM: SARS-CoV-2

<400> SEQUENCE: 85

Pro Phe Glu Arg Asp Ile Ser Thr Glu Ile Tyr Gln Ala
1 5 10

<210> SEQ ID NO 86
<211> LENGTH: 18
<212> TYPE: PRT
<213> ORGANISM: SARS-CoV-2

<400> SEQUENCE: 86

Arg Asp Ile Ser Thr Glu Ile Tyr Gln Ala Gly Ser Thr Pro Cys Asn
1 5 10 15

Gly Val

<210> SEQ ID NO 87
<211> LENGTH: 18
<212> TYPE: PRT
<213> ORGANISM: SARS-CoV-2

<400> SEQUENCE: 87

Tyr Gln Ala Gly Ser Thr Pro Cys Asn Gly Val Glu Gly Phe Asn Cys
1 5 10 15

Tyr Phe

<210> SEQ ID NO 88
<211> LENGTH: 17
<212> TYPE: PRT
<213> ORGANISM: SARS-CoV-2

<400> SEQUENCE: 88

Asn Gly Val Glu Gly Phe Asn Cys Tyr Phe Pro Leu Gln Ser Tyr Gly
1 5 10 15

Phe

<210> SEQ ID NO 89
<211> LENGTH: 18
<212> TYPE: PRT
<213> ORGANISM: SARS-CoV-2

<400> SEQUENCE: 89

Cys Tyr Phe Pro Leu Gln Ser Tyr Gly Phe Gln Pro Thr Asn Gly Val
1               5                   10                  15

Gly Tyr

<210> SEQ ID NO 90
<211> LENGTH: 18
<212> TYPE: PRT
<213> ORGANISM: SARS-CoV-2

<400> SEQUENCE: 90

Gly Phe Gln Pro Thr Asn Gly Val Gly Tyr Gln Pro Tyr Arg Val Val
1               5                   10                  15

Val Leu

<210> SEQ ID NO 91
<211> LENGTH: 17
<212> TYPE: PRT
<213> ORGANISM: SARS-CoV-2

<400> SEQUENCE: 91

Gly Tyr Gln Pro Tyr Arg Val Val Val Leu Ser Phe Glu Leu Leu His
1               5                   10                  15

Ala

<210> SEQ ID NO 92
<211> LENGTH: 18
<212> TYPE: PRT
<213> ORGANISM: SARS-CoV-2

<400> SEQUENCE: 92

Val Val Leu Ser Phe Glu Leu Leu His Ala Pro Ala Thr Val Cys Gly
1               5                   10                  15

Pro Lys

<210> SEQ ID NO 93
<211> LENGTH: 17
<212> TYPE: PRT
<213> ORGANISM: SARS-CoV-2

<400> SEQUENCE: 93

His Ala Pro Ala Thr Val Cys Gly Pro Lys Lys Ser Thr Asn Leu Val
1               5                   10                  15

Lys

<210> SEQ ID NO 94
<211> LENGTH: 18
<212> TYPE: PRT
<213> ORGANISM: SARS-CoV-2

<400> SEQUENCE: 94

Gly Pro Lys Lys Ser Thr Asn Leu Val Lys Asn Lys Cys Val Asn Phe
1               5                   10                  15

Asn Phe

<210> SEQ ID NO 95
<211> LENGTH: 18
<212> TYPE: PRT
<213> ORGANISM: SARS-CoV-2

```
<400> SEQUENCE: 95

Val Lys Asn Lys Cys Val Asn Phe Asn Phe Asn Gly Leu Thr Gly Thr
1               5                   10                  15

Gly Val
```